United States Patent
Kristopeit et al.

(10) Patent No.: US 12,060,583 B2
(45) Date of Patent: Aug. 13, 2024

(54) SCALABLE CHROMATOGRAPHY PROCESS FOR PURIFICATION OF HUMAN CYTOMEGALOVIRUS

(71) Applicant: Merck Sharp & Dohme LLC, Rahway, NJ (US)

(72) Inventors: Adam Kristopeit, Lansdale, PA (US); Janelle Konietzko, Lansdale, PA (US); Wanli Ma, Lansdale, PA (US); Katherine Phillips, Audubon, PA (US); Andrew Swartz, Chalfont, PA (US); Sheng-Ching Wang, Eagleville, PA (US); Marc D. Wenger, Allentown, PA (US); Matthew Woodling, Lansdale, PA (US); Tiago Matos, Philadelphia, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 885 days.

(21) Appl. No.: 17/046,871

(22) PCT Filed: Apr. 19, 2019

(86) PCT No.: PCT/US2019/028216
§ 371 (c)(1),
(2) Date: Oct. 12, 2020

(87) PCT Pub. No.: WO2019/209632
PCT Pub. Date: Oct. 31, 2019

(65) Prior Publication Data
US 2021/0047626 A1 Feb. 18, 2021

Related U.S. Application Data

(60) Provisional application No. 62/661,928, filed on Apr. 24, 2018.

(51) Int. Cl.
*B01D 15/36* (2006.01)
*A61K 39/12* (2006.01)
*A61K 39/245* (2006.01)
*C12N 5/079* (2010.01)
*C12N 7/02* (2006.01)

(52) U.S. Cl.
CPC ............. *C12N 7/02* (2013.01); *B01D 15/362* (2013.01); *B01D 15/363* (2013.01); *C12N 5/0621* (2013.01); *C12N 2710/16111* (2013.01)

(58) Field of Classification Search
CPC ........ A61P 31/20; A61P 31/22; B01D 15/363; B01D 15/362; C12N 2710/16111
See application file for complete search history.

(56) References Cited

U.S. PATENT DOCUMENTS

| | | |
|---|---|---|
| 4,452,734 A | 6/1984 | Larson et al. |
| 7,999,085 B2 | 8/2011 | Gagnon |
| 8,124,106 B2 | 2/2012 | Weggeman et al. |
| 9,249,427 B2 | 2/2016 | Picker et al. |
| 9,546,355 B2 | 1/2017 | Fu et al. |
| 9,663,766 B2 | 5/2017 | Fitchmun |
| 2007/0167612 A1 | 7/2007 | Hua Zhou |
| 2009/0215169 A1 | 8/2009 | Wandless et al. |
| 2010/0143889 A1 | 6/2010 | Federspiel et al. |
| 2010/0279385 A1 | 11/2010 | Oriordan et al. |
| 2011/0207202 A1 | 8/2011 | Luitjens et al. |
| 2011/0263823 A1 | 10/2011 | Gagnon |
| 2014/0220062 A1 | 8/2014 | Fu et al. |
| 2015/0259387 A1 | 9/2015 | Schiedner et al. |
| 2016/0354461 A1 | 12/2016 | Picker et al. |
| 2017/0022479 A1 | 1/2017 | Fitchmun |
| 2017/0349634 A1 | 12/2017 | Anderson et al. |

FOREIGN PATENT DOCUMENTS

| | | |
|---|---|---|
| WO | 1998010311 A1 | 3/1998 |
| WO | 2003097797 A2 | 11/2003 |
| WO | 2011045381 A1 | 4/2011 |
| WO | 2013106398 A1 | 7/2013 |
| WO | 2016156613 A1 | 10/2016 |
| WO | 2017173283 A1 | 10/2017 |
| WO | 2018183426 A1 | 10/2018 |

OTHER PUBLICATIONS

Adler, et al., Human CMV vaccine trials: What if CMV caused a rash?, Journal of Clinical Virology, 2008, 231-236, 41.
Arvin, et al., Vaccine Development to Prevent Cytomegalovirus Disease: Report from the National Vaccine Advisory Committee, Clinical Infectious Diseases, 2004, 233-239, 39.
Britt, William J., Human Cytomegalovirus: Propagation, Quantification, and Storage, Current Protocols in Microbiology, 2010, 14E.3.1-14E.3.17, Unit 14E.3 (S18).
Chambers, R.W. et al., Propagation and Purification of High-Titer Human Cytomegalovirus, Applied Microbiology, 1971, 914-918, 22(5).
Clackson, et al., Redesigning an FKBP-ligand interface to generate chemical dimerizers with novel specificity, Proc Natl Acad Sci USA, 1998, 10437-10442, 95.
Crough, Tania et al., Immunobiology of Human Cytomegalovirus: from Bench to Bedside, Clinical Microbiology Reviews, 2009, 76-98, 22(1).
Dhugga, Kanwarpal S., Plant Golgi cell wall synthesis: From genes to enzyme activities, Proc. Natl. Acad. Sci. USA, 2005, 1815-1816, 102(6).

(Continued)

*Primary Examiner* — Barry A Chestnut
(74) *Attorney, Agent, or Firm* — Nichole M. Valeyko; Alysia Finnegan

(57) ABSTRACT

The present invention relates to a scalable process for the purification of human cytomegalovirus particles from cell culture medium. In particular, the process involves a two step chromatography process starting with an anion exchange chromatography step followed by a polishing chromatography step selected from mixed mode chromatography or cation exchange chromatography.

4 Claims, No Drawings

Specification includes a Sequence Listing.

(56) References Cited

OTHER PUBLICATIONS

Effio, C. Ladd, Next Generation Vaccines and Vectors: Designing Downstream Processes for Recombinant Protein-based Virus-like Particles, Biotechnology Journal, 2015, 37-64, 10.
Gagnon, Pete, The Emerging Generation of Chromatography Tools for Virus Purification, BioProcess International, 2008, 24-30, vol. 6, No. 6.
GE Healthcare Life Sciences, Capto Core 700, Multimodal chromatography, 2012, 1-4, Data file 28-9983-07 AA.
GE Healthcare Life Sciences, Purification of influenza A/H1N1 using Capto Core 700, Vaccines, 2012, 1-8, 29-0003-34 AA.
Huang, Eng-Shang et al., Human Cytomegalovirus, Journal of Virology, 1973, 1473-1481, 12(6).
James, Kevin T., Novel High-throughput Approach for Purification of Infectious Virions, Scientific Reports, 2016, 1-11, 6.
Langfield et al., Manufacture of measles viruses, Methods in Molecular Biology, 2011, 345-366, 737.
Lee, Micky Fu Xiang et al., Negative chromatography of hepatitis B virus-like particle: Comparative study of different adsorbent designs, Journal of Chromatography A, 2016, 1-9, 1445.
Lilja, Anders E. et al., The next generation recombinant human cytomegalovirus vaccine candidates—Beyond gB, Vaccine, 2012, 6980-6990, 30.
Marzi, Andrea et al., Cytomegalovirus-based vaccine expressing Ebola virus glycoprotein protects nonhuman primates from Ebola virus infection, Scientific Reports, 2016, 1-10, 6:21674.
Mocarski, et al., Cytomegaloviruses, Fields Virology, 2007, 2701-2772, Editors: Knipe, David M.; Howley, Peter M.
Mundle, Sophia T. et al., Core bead chromatography for preparation of highly pure, infectious respiratory syncytial virus in the negative purification mode, Vaccine, 2016, 3690-3696, 34.
Puig et al., Canine adenovirus downstream processing protocol, Methods in Molecular Biology, 2014, 197-210, 1089.
Revello, et al., Molecular Epidemiology of Primary Human Cytomegalovirus Infection in Pregnant Women and Their Families, Journal of Medical Virology, 2008, 1415-1425, 80.
Ryckman, et al., Characterization of the Human Cytomegalovirus gH/gL/UL128-131 Complex That Mediates Entry into Epithelial and Endothelial Cells, Journal of Virology, 2008, 60-70, 82(1).
Schneider-Ohrum, Kirsten et al., Production of Cytomegalovirus Dense Bodies by Scalable Bioprocess Methods Maintains Immunogenicity and Improves Neutralizing Antibody Titers, Journal of Virology, 2016, 10133-10144, 90(22).
Talbot, P. et al., Human Cytomegalovirus: Purification of Enveloped Virions and Dense Bodies, J. gen. Virol., 1977, 345-349, 36.
Tierney, Rob et al., A single-dose cytomegalovirus-based vaccine encoding tetanus toxin fragment C induces sustained levels of protective tetanus toxin antibodies in mice, Vaccine, 2012, 3047-3052, 30.
Tseng, Yu-Fen et al., A fast and efficient purification platform for cell-based influenza viruses by flow-through chromatography, Vaccine, 2018, 3146-3152, 36.
Vicente, Tiago et al., Fully aseptic single-use cross flow filtration system for clarification and concentration of cytomegalovirus-like particles, Engineering in Life Sciences, 2014, 318-326, 14.
Wang, Dai et al., A replication-defective human cytomegalovirus vaccine for prevention of congenital infection, Science Translational Medicine, 2016, 1-8, 8:362ra145.

SEQUENCE LISTING

<160> NUMBER OF SEQ ID NOS: 1

<210> SEQ ID NO 1
<211> LENGTH: 230966
<212> TYPE: DNA
<213> ORGANISM: Artificial Sequence
<220> FEATURE:
<223> OTHER INFORMATION: rdCMV - Destabilized IE 1/2 and UL51

<400> SEQUENCE: 1

```
gggccgcgtg gtgggtcctc gaggggcggg ggggtgtttt tagcgggggg gtgaaacttg      60
gagttgcgtg tgtggacggc gactagttgc gtgtggtgcg gaggacggcg acggcgaata     120
aaagcgacgt gcggcgcgca cggcgaaaag aagacgcgtg tctgtgtctg tgtgattccc     180
cggggaaaag aggaagttcc cggggacgg cagcatgggt ccctgggac acacgaaaag      240
caacgcccgg gggcgaggga cgacggcccct ggggaccgcg ggggaaataa cggccgcgag     300
gccacacact cgttcctgcg aagccgcaca ccccgaggcc gcgcacaccg ccgacacacc     360
ccgccaccac accccgccgg cacacccgcc acacgcccgc gacacacccg gcacgacaca     420
cccggcacac gcccgcgaca cccctgaca caccctgcca acacaccccc gacacaccca     480
acacacgccc gcgacacacc cggcacacac ccaccccggcc gcgccccgac acacccaaaa     540
caccgccggt gcggggccgc gtggtgggtc ctcgagggag tgttgagggc cgtaagcgtg     600
ttgtgtccga cgctgcctgc gcactgccgg tgcgtgtcgt cccacggtat ttgttgtcgg     660
cacccgggctt cgggacggtg tttcggcgcg ctgccggtgc gttccacggt ccttgcctgt     720
gtcgtttcgg cgctgcgctt gtcgggggtt ttcgagcgtt ctggccgccg gcgatgccgg     780
ggtgttgcgg agacgggggg tgtgcgggac ggtgttgggg ccggggacgg gggttgcgct     840
ggggccgggg ctgttcgcgc cgcgtagggg aggttacgtt ggggacgggg acagtttgcg     900
gcgcggacca gggaacccac ctcacctatt taacctccac ccactacaac acacacatgc     960
cgcacaatca tgccagccac agacacaaac agcacccaca ccacgccgct tcacccagac    1020
gcccaacaca cgttcacccctt acaccacagc aacacacaac cgcatgtcca aacctcggac    1080
aaacacgccg acgaagaaca ccgcacacag atggagctcg acgccgcaga ctacgctgct    1140
tgcgcacagg cccgccaaca cctctacgat caaacacaac ccctactact cgcatacccc    1200
aacaccaacc cacaggacag cgctcatttt cccacagaga atcaacatca actcacgcat    1260
ccacttcaca acattggcga gggcgcagca ctcggctacc ccgtccccg cgcggaaatc    1320
cgccgcggcg gtggcgactg ggccgacagc gcaagcgact ttgacgccga ctgctggtgc    1380
atgtggggac gcttcggaac catgggccgc caacctgtcg tcaccttact gttggcgcgc    1440
caacgcgacg gcctcgctga ctggaacgtc gtacgctgcc gcggcacagg ctttcgcgca    1500
cacgattccg aggacggcgt ctctgtctgg cgtcagcacc tggtttttttt actcggaggc    1560
cacggccgcc gtgtacagtt agaacgtcca tccgcgggag aagcccaagc tcgaggcctc    1620
ttgccacgca tccggatcac ccccatctcc acatctccac gtcggaaacc gccgcacccc    1680
gccacatcca ccgcatcgca ccaccacat gcttcgcctc ggtcagatca cacgcttttt    1740
cctgtcccat ctacaccctc agccacggtt cacaatcccc gaaactacgc cgtccaactt    1800
cacgccgaaa cgacccgcac atggcgctgg gcacaacgcg gtgaacgtgg cgcgtggatg    1860
ccggccgaga catttacgtg tccaaaggat aaacgtccct ggtagacggg gtaggggggat    1920
ctaccagccc agggatcgcg tctttcgccg ccacgctgct tcaccgatat ccaataaacc    1980
catcccctcg ccacgacgtc tccgcgtatc tttgtagcct caagaatccg tccccacgtc    2040
```

```
cacccatccc gagcactcca cacgccataa caaaccacgg acacgacaaa tgcatgcaaa    2100
cttctcattt attgtgtcta ctactctgtg ttgctacagg gagtgaagag ggtgaaggca    2160
aagaaaaaaa aaaggaacaa aataatagat tagcagaagg aataatccgt gcgaccgagc    2220
ttgtgcttct tttcttataa ggaggcaaat atactaggga aaacataaga ataggaagaa    2280
accgaggttt gggagaaaag ctgagataaa atagcgcatt ttccatacag aggttgttgt    2340
ttttgtggat cctaagaggt ttcaagtgcg aatctcaaag ttctcacgag aatattgtct    2400
tcaagtatcg acaactgtgg tccaagattt tttttggtc ttttaggtt ctgcgaggga     2460 catcacgatg gatcgttgcg atgaagtcac gcgtacgcct ctggtgtggc gcggtgtcgt    2520
gacaggagag tgtgttttca gtgcagagct gtcttgattc ctatatccga gtatctgttt    2580
tctcgtaagg acggtaatct tctttggtgt aagtacatct aaaagctgca aactatattt    2640
taagggctgt ctctaggtgt actttgatgc tggagttttt cgctgtgttg atgtgaataa    2700
atctactact actattatat gcagaaagag tgattatgcc gagacaagat tgcattggct    2760
gaactgtttc aaaaacgcct acactctact tatccgtaaa cctaaggtaa tactatgtgt    2820
aagttgtttt ttttcttttt tgtagtaaaa tggtgatacg tgcaattaaa actgtattcc    2880
atgtttccat ccttttcattt caactttaaa ggcggctttg agagcgaaga agtgcgagga    2940
taaaaatgga tgactccttc gtgtccaggg agtcgactac tgcaacgctg attgattaaa    3000
agatggtctc cgatgatgat gttgttattg atcgaatcat ggtgcagaac ggcgacggag    3060
aggagcgtgt ccgccgccgg gaaggtggtc tctttctctt ttcttttttc aagaaatctt    3120
ccatgtgttt atcgtagtga tcgaaatcga ctgatctcgg gttcttttg ttggtttctt     3180 ttcggttaat catgtattgt tttcttttt tacagaaaga acttttttt catgagcaat      3240 tcctcgcccg gcgccggcat gccgaggtgg ggccactgcg atcagcggca tgccgacgcc    3300
gacccgggga tcttggattc accgtttct ctcttctctc tctacataca gaccgggtgg     3360
caggagcggt aaggaatcat cgtcgtcttt cattcttcga tgattatggt aatactaaat    3420
cttatctagg agcatataca tctaagattg gagtactagt agtcgtttgt ggtttctatt    3480 ttttttata tttatctatg acagttttc tgttttcgt tttgataata atataataaa       3540
aactcatgga cgtgaaatct ggcttggttg tggtgatttc attctcatta ttgttgtttt    3600
ctttccgtct gcggatgaa gatgttgcga tgcggttgtt gttggtgttg ctatacaccg     3660
agagagatga tcttttttgtt cttctggttc atttcctatg attgtttggc tgctgaccga   3720
cgcgtcagga tgtgcagggc atgcggggaa tcaggaccgg acacgggata atttcatcta    3780
cctatacgga gatcgcggtc ctcgccatga ggatcgcgac aggcgcgtcg aggggggcagg   3840 aacacccttg cggattgaca ttcttggtgg tgtttcgttg ttgtcggtag ttgttgttga    3900
cgatgaggat aaataaaaat gaccttgttt ttgttctgtt ttctcttgtt gggaatcgtc    3960
gactttgaat tcttcgagtt atcggaaagc tgaggtaccc aaatgtctgt agctttttc     4020 tttttacccct cttgtttatc atctgcgatt cgtggtaggt aggagaggga aatgataatc   4080
cgagattaag gaaaggagaa gataaaaaat aaaaaaaat aataaaacag aagccgaccg     4140
gccgccgacc cgttccccag gaccagccta cgaggaacga ataacgcggt ggcgacggca    4200
gcggtggtgg cgctgggggt ggcggcagtg gtactgctga tggtagtcgg gacggaggag    4260
aggcgatgca tacatacacg cgtgcatgct gcatgggtgg atggtacggc cgggagacgc    4320
ggaagagaaa ctcacataaa aaggtgacaa aaagagcggt tgaaaaaaga aaacaagatt    4380
```

```
cgaccagaca gaagagaagg accggggctt ggcgacccctt ccacgactgc tgttgtcatc    4440
tcggctcctc cgtcttctcc cggccacggg cggctaagtc accgccgttc tccccatccg    4500
tccgagcgcc gaccgaccag ccggccgatt cgcccgccgg ggcttctgga gaacgccggg    4560
gcagcagcga tctggggaag ctgctaaacc cctgcgtttt tatatggtag ctctgccgag    4620
cgcgggctga cgcgttgggt aagcggaaag acgtgtgtga cgaaaagggg tcccatggta    4680
tttcacgtga cgatgaggag atacggtttg gagcacatac ggtttagaaa aagggagttg    4740
tcgtgacaag ggctgaggga cctctgtctc catgtgtgta taaaaagcaa ggcacgttca    4800
taatgtaaaa aagaacacgt tgtaaacaag ctattgctgt atcattcggc tgactatgct    4860
tcattcggac tgattttctt ttcctaacgg cgtaacttaa agtgattaac gtatgatatt    4920
tgttccccag agttatacta tagtcatcat cctaaaattc agatataaat gaacacatgt    4980
cgtatgggat tattaagaaa ccgaaactct ccacagttca ccatcttctt cgtcattcaa    5040
ccgatgaccc actccgtaca acgaatcagt ctgctgcgtc atattgcaaa gcacaagcga    5100
cgtatgcgaa caacttgaaa cacaggctgt tgtattgacg accgttgtac cattattagt    5160
caccaccgtt atcccatgtt tcccacccga tggaaaaccg tcttctatca tcaactgtgg    5220
taagatttcg accctgcgag gtattcagtt tcctcatatc cataacctgg attttatcat    5280
taaaccccaa tattaaacac ttttttagta ccccccaccc accaaaaaat gtgactggac    5340
cggttcctag cagctctggg agccatgttc aggttgaacc acagctacag cgaaaccgag    5400
tccagtgacc ggtaaccacg tccagccccct gcgtatgtac cagtccaagc acgtccggtc    5460
attgttctac acaggaaatc taactaggtc aacgcaattt tattccaccg ttacgcagaa    5520
tactaacaaa aaacacaca aatttaacga attacacgta gtttattaca tgaaaactgt    5580
aagaacacca attcactaag cgatacaaca tttagctgac ttccaagtgc cacacatcac    5640
cactgtattc atccatgttt tcaccgaacc aacgagacag atcgaagaag ccagaatctc    5700
ccgactttaa attacataaa tccaacgtat tatgaccaca gctcgacaca caaatagttg    5760
cgttactatt cacagtagca ttacctatac ccgtaacgtt gcacaaccac tgatcaccat    5820
tgttaccaaa aacggttttc cacttagttg tcaacggatc tttcctatgc gtaatggtaa    5880
aattactacc agtcgtcgct tttagctcat tacgagtatt atccgcatcc acatatatca    5940
acgtcatagc taggcacgct ataagtaccc cccccccaca atggaatgtt gccaaaccgg    6000
ttctttcccg ttatagccat agcgttccca ggcaaaagca aacgccaaac ctaatgcagt    6060
gaaaagcgct tgcagccaga accagcttat gtaccagcca caatcacatc cggttattgt    6120
ttccacagga atcctacca ggcaaagccc cgcttgtttt gttcctatct tgtttagcaa    6180
ttcgtaaact gtcagcctag cgacgtccgt ttagatcaaa agtcacgtat atagcgacgc    6240
tgtttccatc cgtttccccg tccgccgtt tccgaacaac ccacccgggt tcagacaacc    6300
gaccaccaac agaaatatac acacagacca ctgggagttc agttaaagat ttcatcaggt    6360
ttattttggc tgctgctagt cttttgcttc ttagaaaaaa aatacccata tagagaaata    6420
atgatagttt gacaacacat atggcaggga tttcttcttc atcaataaga tatgcaattc    6480
ccccagggag agactttcaa caattgaatt tacaaaaaca aaattacatc aggagaaaga    6540
gaggatacat taataaatat attatatctg gtgtatatac tgaatgctgc tggttcataa    6600
ggtaacgatg ctacttttttt taattccaag atggttttc tttgttagtc ttttgttgac    6660
ttgctggttc ctaaaagttc gcaaaaacga ttgtgtgaag attttatgac gttggttgac    6720
tagttcatga gattctgctg tacgtgtgat ggttattcgc tggttcgttc taagatgagt    6780
```

```
atcgtactgt gtctgcgatg gtcgtctctt actggcattc tctcggctgc ctcttgcttt    6840
catgattgaa aaggaaaaaa ggactccgag ggcgcggtca tcttttactt ttcggttttc    6900
tcgttggcgg gtcagaggta gtcagatcat gagactgtcg tggtcgatga aactgtgtct    6960
gctcaagtga cgtccatttc ttgtacggag aaaaaagtca tcgggataaa taaggctata    7020
caaggcgttg tcaagcgtgc ggctctaaac aaattaagcg atacaaaatt acagtaatac    7080
gaataataaa ttaccccct cccctgtgg tccccgaga cgagagccac ccatcgtgta    7140
ctctcgcacc acccacgacc acagagggag acgggacgaa gagacgacgc acagcgccat    7200
ctcctcctgg aggccggcga cgttaactgc tacagctgcg gcggcgaaga cagctgcgat    7260
ttgtcggccg acatgccgat ggtatgggcg gcggcggcaa tggccgcggc agcggggagg    7320
agaggagaga gaagaggagc ggggcgtccg aaggcgagga tggcatggtc tcgccggagc    7380
gcccggcttt tatggaacac tcgcgtccgg ttgggtatca cccacaggaa gatgagtcac    7440
aacttccaaa ccatcttgag acccgagtaa cggtttacag gtcgcacgcc agtcagctaa    7500
aaacagcgga cagtcccacg ctgtttctgt tgtggctctc tccagtttcc tcatcaccgt    7560
cccggtctcc gtcgtcatcg gaagaatacc acccgctctc atgcggcagt cgatcggcct    7620
cgacgaacga gacgcggcga cgcctctcca cggccgactg gttgtggtgg tgaaagaaga    7680
gcaccagcaa tcccaggagg agcaacaagc cctcacatgt ccaggaggtc ggggagaggg    7740
cctgtcggag atggccgtga ggcatcacgt acggcagctg aggagaaacg gagaagaaag    7800
gaaaattacc gtcaggggcc ggggttctta ttagagaaac agcacgtagg tcaggatcca    7860
gatgctaatg gcaatcatga tgacgatgat catgcaggcc aagacgcggc gcaccaatgc    7920
cgaatccaat agccgccgtg cctccggttg gtggccggcg gcatctagag acatgatttg    7980 gggggaccg gcggcgcaaa aagacaggga gatggacagt gtcacggtgt tttgttataa    8040
ttaggacatg gggaccggaa gccgagacag agtactacag ggtgttgaag ggtaacgtga    8100
gggagatcat gtcatgggcg ggctgaagac cgtgcgggga ggattgacgt gtgcggtgct    8160
tgtggaacac ggtgttttaa tatgtatccg cgtgtaatgc acgcggtgtg ctttctggca    8220
ctcagcttgg taagctatgt ggccgtctgc gccgaaacca aagtcgccac caactgtctc    8280
gtgaaatcag aagatacca tttgacgtgc aagtgcagtc cgaataacac atcatctaat    8340
accggcaatg gcagcaagtg ccacgcgatg tgcaaatgcc ggatcacaga acccattacc    8400
atgctaggcg catactcggc ctggggcgcg ggctcgttcg tggctacgct gatagtcctg    8460
ctggtggtct tctttgtaat ttacgcgcgc gaggaggaga aaaacaacac gggcaccgag    8520
gtagatcaat gtctggccta tcggagcctg acacgcaaaa agctggaaca acacgcggct    8580
aaaaagcaga acatctacga acggattcca taccgaccct ccagacagaa agataactcc    8640
ccgttgatcg aaccgacggg cacagacgac gaagaggacg aggacgacaa cgtctgataa    8700
ggaaggcgag aacgtgtttt gcaccatgca gacctacagc ccccctca cgcttgtcat    8760 agtcacgtcg ctgttttgt tcacaactca gggaagttca tcgaacgccg tcgaaccaac    8820 caaaaaccc ctaaagctcg ccaactaccg tgccacctgc gaggaccgta cacgcacgct    8880
ggttaccagg cttaacacta gccatcacag cgtagtctgg cagcgttatg atatctacag    8940
cagatacatg cgtcgtatgc cgccactttg tatcattaca gacgcctata aagaaaccac    9000
gcgtcagggc ggtgcggcgt tcgcgtgcac gcgccaaaat ctgacgctgt acaatctcac    9060
ggttaaagat acgggagtct acctcctgca ggatcagtat accggcgatg tcgaggcttt    9120
```

```
ctacctcatc atccacccac gtagcttctg ccgagccttg gaaacgcgtc gatgctttta    9180
tccgggacca gggagagttg tggttacgga ttcccaagag gcagaccggg caattatctc    9240
ggatttaaaa cgccagtggt ccggcctctc actccattgc gcctgggttt cgggaatgat    9300
gatctttgtt ggcgcgctgg tcatctgctt cctgcgatcg caacgaatcg gggaacagga    9360
cgctgaacat ctgcggacgg acctagatac ggaacctttg ttgttgacgg tggacgggga    9420
tttacagtaa aagatgcgtg tcgcctgccg aagacctcac catctcacgt acaggcatac    9480
ggcgtataca atcataatat tctatattct gcatagagtt acatgcaaca gtactactac    9540
caatactgca tccatcacat cacccaacac tgcttctacc acctttgtga ccagcgtatt    9600
ttctactccg aataacaaca catcaacgac gccacacaca tctgtcacct cacaagcgtc    9660
aaccattggc aacatcacca acgttacctc cgacttgagt actttcacaa ccgtatattc    9720
tacattcaat acatcatatg ctaatatatc caatacggct gccactacag aattgatttc    9780
aacaaatacc aacactatat tatcttttac caacgtaaca gcaaacgcta catcatctta    9840
taacacaaca atcaccgtaa ctatcacgtc agatgaaact tcgcacaacg tatccactaa    9900
tactgcactt ataagcacgc catggcttac aaattgcagc gccacaacgt acaccacgta    9960
caaccgtact aactcttcca acgcttgtca cacagagaca acaatcatac gtttcaaaga   10020
aactaataca acaggaatag aagggagtaa tgtcaccata aaaggtaatt ctacgtggga   10080
ttgtctttca gtcgcctgga tacgacatta caatcgatcc acacacggac atcatctagg   10140
tcatcgtaag aacgcacata cccaatcttg gtattggtta cgcatcctta cctctcatac   10200
tgtatgtcat tctcaacatg aaagaccttc actgtaccat gacttatgtc gttcgtgcaa   10260
caacacagaa ctacatctgt acgatctaaa tatcaccaat tccggcaggt acagcagacg   10320
ttgttttaaa gaaaattact tcacaggaca tcacgaagat gaaaatttct acctattagt   10380
aacaccaaaa aatcatactg aagctattaa tgctactttc gtttgcccta gatacaacac   10440
cgatatcgaa aatgaagata gagagaaagg aagtcaacat actaacaata cacatccacca   10500 caaacgtaat ctctatcata gctcgcaaag aagccgcacc gtatggacca tcgtgttggt   10560
ttgtatggcc tgcatagttc tgttttttgc acgacgagcc tttaacaaaa agtaccatat   10620
gttgcaagac accgtcagtg aatcagaatt cattgttcga tatcacacag aacatgaaga   10680
ttgagctacg tttccgggca gacatcttat gaagctgaac aataaactaa acattctgt   10740 aaggctcagc gttcaaagga atattaatgc ccattgagcg agaactaata ttgcaatgga   10800
ctggcgattt acggttatgt ggacgatact aaatatccgc gttatcagaa gctgcaatca   10860
aacctgttcc tgtcaatgtc cctgtagtac taccgttaac tattccacta gtactgagac   10920
agccacatca acatacagta caacagttat cagcaataaa agcacttcag aatctataaa   10980
ttgctctact gcaactgcac cagcaaccac cgtttctaca aaaccgtcga aaacaaccac   11040
acagatatcc acaacgacaa atacaaacgt tgagactacc acatgtacca acaccaccac   11100
gaccgttact tgtgatggtt tcaattatac agtccataaa agatgcgacc gcagttacga   11160
ggtaatcaac gtaacaggat acgttggtgg caacataact ctaaaaaatg caatcagact   11220
gagaaatggc acaatgtaga ctggattcat tatgagtacc ccacgcataa aatgtgcgaa   11280
ttaggcaact atcaccaaac aacaccacgg cacgacatat gtttttgactg caacgacacc   11340 tccctaacta tctacaactt aaccacaaga aacgctggaa aatataccag gcatcaccgt   11400
gataacggtc aagaagaaaa ttactacgta acggtgttaa ttggagacac aacgttatcc   11460
actcttggca catgccctgt aagatataaa gaatctagga acactgaaaa caccattgga   11520
```

```
agtaacatca taaaaaccat tgagaaagct aacattcccc tgggaattca tgctgtatgg  11580
gcaggcgtag tggtatcagt ggcgcttata gcgttgtaca tgggtagcca tcgcattccc  11640
aaaaaaccgc attacaccaa acttcccaaa tatgatccag atgaattttg gactaaggct  11700
taacatgcac atcaataaac ttttttttaac caataacatg tctctgtttt tttttgttaa  11760
caacctatga tataaagcgg tatattcaat cattactaaa caaaaaaaca tgggcatgca  11820
atgcaacact aaattgttat tgccagtcgc actaataccg gttgtaatca tcctaattgg  11880
tactctagtg cccatacttt tacatgaaca aaaaaaggcg ttttactggc gacttttttct  11940 gcaaagtcaa catgtagaag cacccattac agtaacgcag ggagacacag tctacctaga  12000
tgctagcaat aatccctgta attattccag cttttggtac cacggtaatt gcgaactttg  12060
tggatggaac ggatatctac gcaatgttac acattactac acaaacacat cgtgttcccc  12120
gcaattcatg tgcataaacg aaactaaagg tctgcagtta taatgtaa cattaaacga  12180 ttcaggtgct tatactgaac acgtttacga atgtgatctt tcatgtaaca ttactactta  12240
taacgaatat gaaatactca attacttcga taactgtaac tacaccataa atagcaccaa  12300
gcatattatc accgtggtgt cttcacgtca ttctaaacaa acaaattccc acgtatccac  12360
tcacgctggt tgggcagccg ccgtggtgac ggtaattatg atctacgttt tgatccactt  12420
taacgttccg gcaactctga gacacaaact acgaactaga aacaacgtaa atcgcatagc  12480
gtgattacaa agtatcgaca ctaatttatc caagataaaa tttgattact ccgtgcggtt  12540
ctcaaaaact gtaaggtccc gcttttctac tccatcatga aggatcgcaa tagaatactg  12600
ctatgtatca tctttatttg catcatgtgc ctcatttgta tttactttaa acgtcgttgt  12660
gttcttactc cgtctccaga caaagcggat ctgcgagtgg aatttccctc gttaccccg   12720 tgtatcggca tacaatgtgc tgcatgagaa cacgcgtgac acatagcgta cccctggacg  12780
gtacagttta tgataacgtc attcagggga agtatacatt actatcgacg tgttatcaca  12840
gaacacacag attttctgcg tgtttttataa aagagcgtct cgaagcagct tgagccacac  12900
tacggtccag atgacgagcg taatcaaaaa tatgccgcgc agtagtcgaa agccgtactg  12960
agcgtgcgag gcgggtaggg tgccgaacga cggatatgcg tcgttgtcat cttcgactat  13020
aaggatcgcg accgagtctt cggccatggt aaacgtcacc ctgtgtggct ggtatgtagc  13080
gtatccggtt tggaattgtt ctgctccagc tcggggata gtgaggaatt ctcaagggat   13140
acgggaccca atgactggat aagagaaggg ttttttcccg taagatgatc ctcgtatcac  13200
atgaggtctg gatatgtata aatgaagagt gaaataggca cagggaatca gatgccagcc  13260
tcgtgatgca gccgctggtt ctctcggcga agaaattgtc gtctctgttg gcttgcaaat  13320
acatcccacc ttaagcgatg agtccataaa gcaccgttgt ccgggtacgg tgaaagtgac  13380
tcggattgta gcacgtccct tttttttgtt tttgtatcgc ttatcgccac tgacagtgca  13440
atattttgat cgtgaggctg agtatggtta tgatgcttag aacgtggaga ttattaccaa  13500
tggtactact tgccgcgtac tgttattgtg tttttgggac ttgttcaatc ggcacgacga  13560
ctgctcccgt ggaatggaag tctcccgacc gtcagattcc taagaatatt acttgcgcta  13620
actactcagg gaccatcaac ggcaacgtta catttcgagg tcttcagaac aaaacggaag  13680 acttttttgca ctggttgtta gggtggggtc ataagtccat ctgttcgttc ttcccgaaac  13740
tccagggcaa ctataacgaa caacattaca gatatgaagt agcgaacctg acgtataact  13800
gcacctataa ccgcttgacg ttgctaaatc tgacgacgga aaacagcgga aagtactatt  13860
```

```
ttaaaaggga agatgcgaat ttcaccttttt attactcttg ttacaacctg accgtgtcct    13920
aaagaacgca cgtgaagttc cacagagccg cgtggctgta gctattgtgt ttacgttgct    13980
tttgaaatgt taagcgtccc tacggcgcta acatgtttct aggctactct gactgtgtag    14040
atcccggcct tgctgtgtat cgtgtatcta gatcacgctt aaagctcgtg ttgtcttttg    14100
tgtggttggt cggtttgcgt ctccatgatt gtgccgcgtt cgagtcctgc tgttacgaca    14160
tcaccgaggc ggagagtaac aaggctatat caagggacaa agcagcattc acctccagcg    14220
tgagcacccg tacaccgtcc ctggcgatcg cgcctcctcc tgatcgatcg atgctgttgt    14280
cgcgggagga agaactcgtt ccgtggagtc gtctcatcat cactaagcag ttctacggag    14340
gcctgatttt ccacaccacc tgggtcaccg gcttcgtctt actaggactt tgacgcttt    14400 tcgccagcct gtttcgcgta ccgcaatcca tctgtcgttt ctgcatagac cgtctccggg    14460
acatcgcccg tcctctgaaa taccgctatc aacgtctcgt cgctaccgtg tagctagtta    14520
gccagctgtg tatagtttgt tgtgttttgc ttttgcatat ttgttttcag tcagagagtc    14580
tgaaacgggg tgggagggac ttttacgggt aatgcatgct aagatgaacg ggtgggctgg    14640
ggtgcgcttg gtaactcact gtttgaatac gcgctcacgc acatatgtag cactcaacat    14700
gttagctttt gcccgcacgc cccggggcgt gccgagctgc cttttaata aagtctgggt    14760 ttccagatac gcgctggttc tgattttgat ggtttgtgcc tctgaaagct ctacgagctg    14820
ggccgtgaca tccaatcgac tgcctaactg tagcacgata actacaacag cgggtcaaga    14880
cgctgaattg cacggtccgg caccgttaag ctgtaatgtg acccagtggg gacgttacga    14940
gaatggaagc acaccgtat tatggtgcac tttatgggga tcacgcacgc gagtctcatt    15000
aggacaccgt gtagcgtttg gctgttcttg gaaaacattt tttatttata acgtttctga    15060
aagtagtggt ggcacttatt atcaaaaagg ttacaactgc accgacaaac atataacact    15120
atcttgtttc aacctaacgg tggttcctcg agcggttcaa agcacaacca ccgtaatgac    15180
acccacggtg gttacaaaact ccacattcag tgtgtcactt gttgcgtcga gactgacgac    15240
aaattccagc gcgtttagac acgctagtta tcaacggcaa cagcgtgtcg gaaacgggac    15300
gttatccaag aacataacta acttggcatt cacctacggc agctggggcg tcgcgatgct    15360
gctgttcgcc gccgtgatgg tgctcgttga tttgggtttg cctcaatcgg cttggcgacg    15420
ctggcgaagc cacgtggacg atgaagaacg tggtttgtta atgtaggaaa taaaaggcac    15480
tgtttgagca tgactgtttc caaaccgtaa cgtggtaaat aaatcatggc ttccgacgtg    15540
agctcccatc ttctaacggt tacacaatcc cgttggacaa tacatcatat gtacaataaa    15600
ctgttgattt tggcgttgtt taccccgtg attctggaat ccatcatcta cgtgtctggg    15660
ccacagggag ggaacgttac cctggtatcc aacttcactt caaacatcag cgcacggtgg    15720
tttcgctggg acggcaacga tagtcatctc atttgctttt acaaacgtgg agagggtctt    15780
tctacgccct atgtgggttt aagcctaagt tgtgcggcta accagatcac tatcttcaac    15840
ctcacgttaa acgactccgg tcgttacgga gcagaaggtt ttacgagaag cggcgaaaat    15900
gaaacgttcc tgtggtataa tttgaccgtg aaaccgaaac ctttggaaac tactacagct    15960
agtaacgtaa caaccatcgt cacgacgaca ccaacggtga tcggcacgaa aagtaacgtt    16020
acggggaacg ccagtttagc accacaacta cgtgccgtcg ctggattctt aaatcagacg    16080
cctcgggaaa acaacacgca cctggccttg gtaggtgtta tcgtatttat agctctaata    16140
gttgtttgta ttatgggatg gtggaagttg ttatgtagta aaccaaagtt atagtgatgt    16200 gcttttatc agggagaagg ttttgtgcca acaatgacta accctgggct atatgcatcg    16260
```

-continued

```
gaaaattata acggaaatta tgaacttacg gaagccgcca atacagcacg tacaaatagc  16320
agtgactggg taacgttagg aaccagtgcg tcgctgttga gaagcacgga gactgcggtt  16380
aaccctagca acgcgactac ggttactcca caacctgtgg aatacccagc tggggaagta  16440
caatatcaaa gaacgaaaac acattattct tggatgctaa ttattgccat aattctcatc  16500 attttatta tcatctgtct gcgagcacct caaaaagtct acgatcgctg gaaagacaat  16560
aaacagtacg gacaagtatt tatgacggac acggagctgt gatgaactac aatgtataga  16620
tacacgtggc tgctttggtg gataacaata ttgcttcgta tacaacagtt ctatcaatgg  16680
tggaaaccag atacaacgtc atgcattcag aaaacgggat atgaaggtca aaacctcagt  16740
ctgcctccta gtaatgcatt atcatctaaa gactatactt tttcatggta taagattca  16800 cttaaagccc ttaacatgtt atgttattat actgaaaaac ttgaagaaat agatagcaag  16860
ccagatacta tacgacgatg ttttttgaat catacattgt ttcttattaa tttaacaagt  16920
cactatagcg ggatttacta cttcgattct ctatacacat atggttgggt attacggaca  16980
cctctatgtt acaatgtcac tgtatattcc atatatcaaa cacacatcca cacaactata  17040
ttgctctatc cgcctacgtc cacatataat tcattaacta tatcatcatt tacctcaacc  17100
aacttaacac ataccgcggt ccactatgcc gccggtaacg ttgaagcaca acacgatact  17160
gccaccccac atacaatgtg gatcataccc ttagttatcg ttacaacaat tatcgtttta  17220
atttgtttca aatttcccca gaaagcttgg aataaattca cacaataccg atacaacagt  17280
atgctcaccg ccgcttaaag aatcaccgtc gagaaaacta aaacgtaaaa agaatggcca  17340
tgtacgttta ttttcagct cactgtttga ataccgtaaa cataatgacg tacatatacg  17400
tgattataca acaggtgttt gtgttatgcg gcgactgatt aaccatatcg tgaaccatga  17460
tcttttccga tggtccgtca tgaccgcaat gatatttac aggtattccg aaacctgtat  17520
ggaggtcact gtcagagtag gtgatccagt taccctcggt agtggacatg gttatcatcc  17580
aggacaaaaa gtacactggt ataaccagtc atgcgtcggc attagcaacg gcgaaaatac  17640
gcatcctatc tgcacctacg accctcctaa acctggtaga cgaaagacaa tgaaaaccac  17700
tccgttacca tcaccactgt tgtacgagtg tcacaattcc acattaagca ttcttcatgt  17760
aaacgtctca gatcccaaaa actattgcag gcgaaaatgt ccaccaaacg gtaactgtga  17820
atttcccaca tgttttacgt tatcactgat ttccagaacg acaaccacca gaaaacccgg  17880
acaaaaaact acgttgtcgc gattaaaaac cacgccaaat aaacatacgc agcacaaaag  17940
atccacgcga agaacgtcac ctagagatta caatgtaacg ggtctgccga aaggctttgc  18000
ggactcgttt accggtaacg tagaggcaca tagagccaaa gatgccgcac acagcgcatg  18060
gatcctcatt gtcatcatca ttatcatagt cgtcattta tttttcttca agattcctca  18120
aagactcaga gagaaatggg acaccagagg ataccttac aaaggaaccg acggcctgcc  18180
cactacggac tacttatcgt gagcggacgg atatctccgg tttcaaaccc actgtttgaa  18240
tatagggaca gtccctacgg aacctgagaa catgtggaaa tcacctgtgg tagaatgctg  18300
ctcaggtaca ttacctttca tcgtgaaaag gtactttacc tagcgatcgc atgcttcttt  18360
ggtatctaca tcagtttcca cgacgcatgc attctgtac ctgctaaagt aggtactaac  18420
gtcacattga acgcggtaca tgtgcatgac ggtgactatg tgtactggtc ttttggtgga  18480
ggtggagcta atagattaat gtgtcgctat acaccaaggc tagacgaaat tcacaaaaac  18540
accaatcgaa gtttttcatg tcttacaaat cacagtctcc ttctcatcaa tgtaacggaa  18600
```

```
gaatatactg attactatcg caccatgacc acattcgtac atcagtccca taattggcac   18660
aaccacggca acaaatggac tttagacaca tgttattatg tatacgttac ccaaaacgga   18720
acacttccca ctaccaccac caaaaaaccc actacgacca cgagaacgac aactaccacc   18780
acaacaaaga aaacaaccac cacgagcacg acaacgacca ccactaccac caagaagacg   18840
acgacaagca ctacccatca tcgacactcc aatcccaaag aatccaccac ccctaaaacc   18900
cacgtagaac ttcacgtcgg tttaggagcc acagcagcgg aaacaccgtt acaaccaagc   18960
ccacagtacc aacacgtggc tacacacgcc ctctgggttt tagcggtcgt aatcgttatt   19020
atcatcatta tcattttcta ctttcgaata ccgcaaaagc tgtggctgct ctggcagcat   19080
gacaagcacg gcatcgtgct catccctcaa accgatctgt gagcaagtcg cgtaggaaat   19140
gattgcatga aatcactgtg aaacgccaac tccgtgccag ctggcgcggc ggacaggcct   19200
ttgacgtatt tgaagccagg cgcgctctcg ataccgaaag gatccgaggg ggctttccaa   19260
agccgacgtc cctgattccc ttcataaagc tgttgaccgg ccctagaaag accaagagca   19320
tgctgtgggc ccactgcggt cgcttcttgc gttatcatct gctcccgctg ctgctgtgta   19380
gactgccatt cttactcctt ttccagcggc cgcagtgggc ccacggcttg acattgtcg   19440 aggaggacga gtggctacgg gagatacaag gagcgacgta ccagctgtcc atagtgcgcc   19500
aagccatgca gcacgccgga ttccaagtca gagcagcgtc ggtcatgacg cggcgaaacg   19560
ccgttgacct ggaccgaccg ccgctttggt cgggatcgct cccgcatttg cccgtctacg   19620
atgtgcgttc cccgcggccg ttgagaccgc cgtcatcaca gcatcacgcc gtatcacccg   19680
aactgccgtc gcgagacggg atacgttggc agtaccaaga gctgcagtat ctggtggaag   19740
aacaacggcg gcgaaatcag tcgcgcaatg cgattccgag accctcgttc cccctccgg   19800 atccaccatc gcagccggca gaggatgcac gagacgcgga cgcagaacgt accgaatcac   19860
cacatagtgc agaaagcacc gtcaggcacg acgcgagtga aacgcagtg cggcgacggc   19920 acgaaagacg gcgctataac gctctgacgg tccgcagccg ggactcgctg ctcctgacgc   19980
gaatacgctt ctccaaccaa cggtgtttcg gacgcgggcg tctgagacat cccgcgggaa   20040
gcggtcccaa caccggcgga ccgcgacccg cggtgcggg actccgtcaa ctacgccaac   20100
aactgacggt ccgctggcag ctgttccgcc tacggtgcca cggttggaca cagcaggtct   20160
ctagccagat cagaacccgc tgggaggaaa gcaacgtcgt gagccagacg gccacgcgag   20220
tacgtacgtg gttcgtggaa agaaccacgt tttggcgtcg cacgtgggtt ccgagacaga   20280
acccggcggc cgaagcgcaa gaactggccg tcataccgcc ggcacccacg gtgctccggc   20340
agaacgagga accacgtcaa cagcttacgg gagaggagac aagaaattca acgcacactc   20400
aacgtgaaga agtggaggac gtttcgagag agggcgcgag agaagggaat gatgggagcc   20460
gagcaagtgg aaacgacgag agaaggaata atgcgggaag atatgatgat gatcatgagg   20520
ttcaagagcc gcaggtcact tatccagcgg gacaaggaga actgaatagg aggtcacagg   20580
aggagaacga ggaaggtgga ccgtgtgaat cgccgccaat gacgacaaat acgctgaccg   20640
tggcctgtcc gccccgagaa ccccgcatc gtgccctgtt tcgtctatgc ttaggactgt   20700
gggtctcgag ctacctggtt cgacggccca tgacgattta gaatacaccg agccattcct   20760
ttatttcccc ccatccccgg tcgcttatgc gtgttaaaca ctaccaataa agataatctg   20820
ccaatcgcac cttatatata atatgtggtc gcgtgtggtc ttttaagga gctctgaaac   20880 acagacaggt atgggcggtg gtcggctgcc gccgctgtgg ctgccgctac tgatcgcctg   20940
gagcgagtgg ggcaactgct gcctcgatgc gcctccggtg gtgcgttcgc cctgtctgca   21000
```

```
gccggtgcgc gaccgcaacc gcgagcggaa cccgggctca ccgcagttgc tgccttacgg    21060
cgaccgtctg gaggtggcct gcatcttccc cgcgcacgac tggccagagg tctctatccg    21120
agtccacctc tgctactggc ccgagatcgt gcgttcgctg gtggtggacg cacgcagcgg    21180
tcaggtgtta cacaacgacg ccagctgtta catcgccggc gggcgctggc gcttcgagga    21240
cggcggcgcg gcgcagcggc tgagcctctc gtttcggctc atcaccgaga ccgcgggcac    21300
ctacacctgc gtgctgggca acgagaccca cagcctggcg accgagacca cggcgctggt    21360
ggccgacgtg cacgacctgc gccactcgga ccgctcctgc gacctggctt cggatcgcg    21420 ctcacagacg cggtacctgt ggacgcccga tccctccagg ttgcgcagta aaactgcgg    21480 ttgggagggt gaacggcacc gcgtagtcca ctacatcccc ggcacctcgg gtttgctgcc    21540
ctcgtgcgag gaggacgagc gcgaactgtg cgtgcccttc atcagccaga gcattgcgga    21600
caacaactgc agccgccggc atcgagttga cggcgctagg cggcgctatc atctacggag    21660
ggattactgg ctgacggatc cgaagatcgg gttgctggcc gcgggatcgg tggccctgac    21720
ctccctctgc cacctgctgt gctactggtg ttccgaatcg taccggcgtc tgaacaccga    21780
ggaggaaagc gaggcggcgg aggaaactgc cgcgggagaa gcctctgcgg tagcggcggc    21840
ggccgtctct gaggaagagc agcggcggga gtaaacgagg agagccatga agcggatgat    21900
tcgcagtcac ggcaggaaaa cggaatgtca gatgacgagc gccggcgagc gacgcggctc    21960
cgccgtcggt gcgcccatct gcggcagcgg tacccgacgc ggcagcggcg ccaacgaacg    22020
ccgcgactcc gacgtcggtc ccatcgccca cagtagcggt accagacgcg gttcggcgaa    22080
tgaaacgtcc gcctgtacgc ggaccgatca ccagaaggcg gacattgggc tgtggttcat    22140
gtttctggtt tttggactgt gttcgtggtt ggcgatgcgg tatcgcgcac aataaatttt    22200
gaatcgatgt caaggaacgc gtgttttgta ttttattggg aatattggcg gggataaacc    22260
tgtttcggat gtttacccct aatcttaccg gggacctcgt tgtcctctcc tccttcttcc    22320
tcggacaccg ggctccatgc tgacgtaggt accgactggg gtcaaaagcc tgggtactta    22380
tgaggagcgc gcacaaagga ccgttaggcg ccggcatgga gcgtcgccga ggtacggtac    22440
cgctgggatg ggtgtttttt gttctttgct tatctgcctc ttcctcgtgt gctgttgacc    22500
tgggtagcaa gtcctccaac tcgacctgcc gcttgaatgt gacggagttg gcctcgatcc    22560
atcctgggga aacgtggacg ttacacggga tgtgtatttc tatctgctac tacgagaatg    22620
tgaccgagga cgagatcatc ggcgtggctt ttacttggca gcataacgag tctgtggttg    22680
acctgtggtt gtaccagaac gacacggtga tccgcaattt cagcgacatc accactaaca    22740
tcttgcaaga cggactgaaa atgcgaaccg tccctgtgac taaactgtac accagccgca    22800
tggtcactaa tcttaccgtg ggccgctatg actgtttacg ctgcgagaac ggtacgacga    22860
aaataatcga gcgcctctac gtccgattgg gctcgctata tccgagaccg cccggatccg    22920
ggctcgccaa acacccctcc gtaagcgccg acgaggaact gtccgcgacc ttggcgagag    22980
acatcgtgtt ggtctcagcc atcactctgt tcttcttctt gttggcccta cggatccccc    23040
agcgactgtg tcagcggctg cgcattcgcc tgccgcatcg ataccagcgg ttacgcaccg    23100
aggactgaac ggataaccgc aaaggccacg tgcaacgttc acgctgctat aagaaggcca    23160
tgtcccccgt ggacgggtct ctttgacacg agcgcggcac gccgttgcca cgagcatgga    23220
tcacgcgctc ttcacacact tcgtcggccg accccgtcac tgtcggttgg aaatgttgat    23280
tctggacgaa caggtgtcta agagatcctg ggacaccacg gtttaccaca ggcgccgcaa    23340
```

```
acatctacct cgacgtcgcg ctccgtgcgg cccccagagg cccgccgaga ttcccaaaag    23400
aagaaaaaag gcggccgtcc ttctattttg gcacgatttg tgctggctgt ttcgacgact    23460
tttctttcct cgggaggact cagagccact gatgtcggat ccggcacggt ctcccgaaga    23520
ggaggagtaa acaacacacg gctaagagga tacatcatca aagaagatag gaggggtcaa    23580
aacgcggact gaaagtatat aacgccgatc atgtccgagg aactgttaat aaaacgccat    23640
gatgacaatg tggtgtctga cgttgtttgt gctgtggatg ttgagagtgg tgggaatgca    23700
cgtgttgcgt tacgggtaca cggggatttt cgatgataca tcgcatatga cgttgaccgt    23760 tgtgggatt tttgacgggc aacacttttt tacctatcac gttaattcca gcgataaagc    23820
gtcaagtcgg gccaacggta ccatttcttg gatggctaac gtctcggcgg cctaccccac    23880
ctacctggac ggggaaagag ccaaaggtga ccttatttt aaccaaaccg agcaaaacct    23940
gttagagctg gaaattgcgt tgggttaccg gtcacagagc gtgctgacgt ggacgcacga    24000
gtgtaatacc acggaaaacg gtagttttgt agccggttac gagggatttg ggtgggacgg    24060
ggaaacttta atggagctca aggataacct gacactatg acgggcccca attacgaaat    24120
tagttggttg aagcaaaaca aaacgtacat cgacggtaaa attaaaaaca tcagcgaggg    24180
ggatactaca atacaaagga actatctcaa gggtaattgc actcaatggt ccgtcattta    24240
tagcgggttt caacccccg tcacccaccc agtggtaaag gcggtgtcc gaaaccagaa    24300 tgacaacaga gctgaagcat tctgtacatc ttacgggttc tttccagggg aaattaatat    24360 tactttatt cattacggtg ataaggtgcc cgaggatagc gagcctcaat gcaatccgct    24420
acttcccacc ttggatggga cttcccatca gggatgttac gtagccatct tttgcaatca    24480
aaactacacc tgccgcgtta cacacggtaa ttggacggtg gaaatcccca tcagcgttac    24540
ctcacctgac gacagttcct cggggaggt ccctgatcac ccgacagcta acaaacgcta    24600
taacaccatg accatcagca gtgtcctcct agccctgctt ttatgcgctt tgctattcgc    24660
gttcctgcac tactttacca ccttgaaaca ataccctacgt aacctggcct ttgcgtggcg    24720
ctatcgcaag gtccggtcgt catgaccagc aacgccctgt atgagctgtt tcgacgtagg    24780
ttaccgcgtg cccccgtcaa cacggtcatg tttctcacgc gacgcactcg tgatgggttc    24840
tgcggtcggt tgacgtccat cgccacgaat tcccactaca ctatgttcgt gttagatcac    24900
gggtccgtgc gcatcgagcg accgagtcag tcagaagtgg attgcgccag tttaatggaa    24960
acgctgaagc ggattcggtt acgaaattcg tgggtagcgt cagaagacga gctagatgtg    25020
agtcgcgggg acgcgtgaca caaaacgcgt tcaggattaa cgtaggtttt cgaaataacc    25080
tacgtccgtg agtgacgcgg tttcgtgttg aaacccgcgc cggttctcac ggtggtttat    25140
gatgaaaccg gcgttgggga tctacgcggg ttcctcattc aacctgcgaa agaggaagt    25200 tgcggtaaaa ccacgtcaat aaagacgtca atgacacctc aatgttgcgt tggaacggtc    25260
tttatatata caaacgccgt tatgttcagt gtccggcaag atgctcggga tacgggctat    25320
gctggtgatg ctggattact actggataca gttgataaca acaatgaca ctcgaagcaa    25380 caataccgat accatctttg tatctctcct taccggggcc aacggagtta ctcgcacagc    25440
catcgggggt ctgcattcaa actacaccaa cttaaccgag gcattcagat tcactccagc    25500
aaacacaaca actaactctt ccacggaggg taattggagc gtgactaacc taacggagag    25560
ttgcatcaac cgcggtgagt cctatctaac taccatctgg cttctgaact gcgctgacaa    25620
caatacttat tggtactctg gaaatgccta taaccataca attgacactt gtaaaaatac    25680
agtttcggga tatctcttct tcggcatgtg ccagctatgg aaagattggg ttactaatgc    25740
```

```
ttctcacgac actgtcagaa ttcagtcgtt gggaaatgaa atacgctgca tgctgctccc   25800
tagacagtat accctcaacg ccacggtgga atggtacaac aaatctgaag gtgacgtacc   25860
agaagaattt atggactatg ttatcctgac ccccttggca gtgcttacat gcggactgca   25920
ggaagcttat atactcgaca agggtcgtag atacatgtat ttgttttccg tgtcctgcgc   25980
gggaatcaca ggtaccgtat ctattatact cgtctcccta tcgctgctca tcctcatctg   26040
ttactatcgc tgtggccggc ttctgatatg cccacgcggc tttgaactct tgccagaatt   26100
cactgaggaa gaggaggaaa aagaaaaatt gttaacgtac aaggacattg aagtccaggt   26160
gcctatccgc acgcggcggc tgctcgtccc ttggatccgg gagagcaaaa tgtgggtact   26220 accaccccg ctgcctccac gacctcccca cttaatagaa ttcccgccgt ctcctccgcc   26280
gtcgcctggg cccatgcaca tggtggtctg catgccagca tgacggactt tgaactttga   26340
gccccaagcg gtacggacta catattttcc ataaatctac actgaacttg agcacaaaaa   26400
tactgacaat ggactgaata tacagacttt tatatgatcc ttgtacagat gtaaataaaa   26460 tgttttatt taaaactggt cccaatgttc ttcgggaatc atggggtggg gacggggggac   26520 gcggtaagga gcaaaaccgg gtacatgggg ggaacatcg tccagcagta gcaccagcgg   26580
attgggtagg ggttgctgcg gaggtcggtc gatgacgatg tcgatctcca tcggcagatc   26640
cggcaacatc tcttcgtctc cctcaccgac cagcactcgg cgctgttctg gatgtatatg   26700
attttggaaa agcctccgac gagctcgcgg cgcgtagaaa gccaagcggc gcaagggccg   26760
gcgagcccga aagtccatgc gcacagatgg catgagtcct tgagtgacgg tggtgagctg   26820
gggaacaggg ctacctccca tcgcgacggt gacagtggat ccatgagaga ggcgccgcac   26880
gctgcatggc taaataccgt gaatccctg acgtcgtctt tcgtcccgaa cgcgtcatgt   26940
tgggggcgag gcgtaaaccg tcgaggttga aaaaccgcgt atctgcgacc cgtccggact   27000 acgttgttt tcagaagcgg ccacatgacc tcgagatgtc gtcacccaag gtatttaacg   27060
gcacacagcc agacgcgttc gtcagcagcg acgccgacaa gacctcagca tggctcggag   27120
gctatggatc ttgagcttac tagccgtgac cttgacggtg gctttggcgg caccttctca   27180
gaaatcgaag cgcaggtaaa cggaatctgg ggaattcaac acaggtaaga aatacaaaaa   27240
ataacgtgat tgtgaacgcg gttatcgtgt ttttgcagcg tgacggtgga acaacccagt   27300
accagcgctg atggtagtaa taccaccccc agcaagaacg taactctcag tcagggggg   27360 tccaccaccg acggagacga agattactcc ggggagtatg acgttttgat tacagacgga   27420
gatggcagcg aacatcagca accacaaaag actgatgaac acaaagaaaa tcaagccaaa   27480
gaaaatgaaa agaagattca gtaacagcag accccaaggg ttaacgatta tgttgactac   27540 cttgttttt attaaaaagc tgtaaggttt tgctctaaaa acacccgcc tccggtcttt   27600 tttcttttgt attcggcacg cgaaacacgg tttcttccca tagcctgtct aactagcctt   27660
cccgtgagag tttatgaaca tgtatctcac cagaatgcta gtttgtagag gctatgcggg   27720
atgctgcggc ggcgcgacct tccctctcca cccagccccg tcaaaacaca cgcgactcga   27780
gcggttcgta tgaaaaataa aaaacagctt tttatttaca ggaacgggga aaaaaaggc   27840 acacggtccg tgggagacgc gggttcacgc gtcgtcaaaa agttggtggt ccactccgta   27900
aggacaggta ggcttatta gcttccgcat gctcctggtt ccgtaataaa tgccgttttc   27960
gtggcagcgt gtcatgccgc gagtcacaaa ctccatcaaa ctgtcggcca cgatgcaaac   28020
gtgctgattg ttggcagcaa agacgcgcat acagtcgtcc acgaagaggt tgatcacgtc   28080
```

```
gtaggggctc accaaccagc ctaaaggttc cacgtggtta ctgccgacca tgaccctcca   28140
gtcgttaatc tcgctccagt cgtacagccg aatcgtggag acgcgaatga cgctgtaatc   28200
acccatgacc atgagtcggc cgcgatacgt agcacgccac tgcgcgaacg cgtggatgtg   28260
catgcagccg gccagcgctc taagcgaggc ggtgtgcggc agctcctctg ggacggtgat   28320
gaagttgcag cgtcgcaaac cgatgttgag aaattcagtg atgctctcgg ccacaaaggt   28380
caacgagtca gagtagatgt ggtcggtcca caggtacatg gcgcccgagg cgcccaggta   28440
cagttcagac ggcacgttgt gatcgccctt gtgtttaaga aagttgtagg tgcagatgct   28500
gccgacgaaa cgcagcggct cggggcagca gaggtagctg ccagacgct gtgcatcccg    28560 tccttcgtcg cgcaccaagc gccagcgacg ccggataacg aggcagcggt ctttgggcca   28620
gaccagggcc acgcgttgcc cgggtttcca cggtcgcgac gtcttaggag gcctccagcg   28680
gtcgagcaga ttgagaaaac agtccttgat taccgacatc gcggtcgcgc gtcggtggac   28740
aaaaagaaat cgggccgatc cggaaaaaaa aaacgacggc aaaacaccgc cgtgctcgag   28800
cgaagggtgg cggagggcca aagaggcgg ccttgacggg gttggcagcg aaaaaattgg    28860
cacgcgagtc aaacgggaag tagcgtcggt gttttatgcc ccaagcagcg tcgtcgtcac   28920
tcgtggcgtc acagtcaacg gtgctgacgt cctttgggc agtcgggcac gcgatcgtag    28980
atgccgttgt ggccgctgaa acgtcggttt tcaaacagca ggttaagtcc cagacacatg   29040
aacgtgttga gattatctcc caccccggatg tagcggtcgt cgcgcacgtc gcaggcgtag  29100
acggccccgg tataggcgac gacgatgggg ataaggtcga cgggccagcg caagtgagga   29160
aagggcgcgt tctcgcccctt gaggctgacg gttcccaggc cgagaacgcg cattccgaaa  29220
gcggttttga tgttgcgcag caagtgaccg ccttccacgc tgttttcgaa acacctgagg   29280
ttgcatagac gcagttccgt tcccggcggg tacgtcaacg gcatgaactg cccgtggtgg   29340
cggatgatga atcgcgccat ggtatccaaa ccgaggctcc aggcgcgcaa cagcgggcga   29400
aagtagcgct taaccaacga cgaggtcagg tagcgcatgc agtgcagggt ctcgacggcg   29460
cgcagcccga cgcgcgcaaa ctccatgagg ttgcgggcca ggtagtagac ggcggtgtcc   29520
tcgcgtacat agcaaaaaac atagccctcg tccgagatga ggcacacagc ggtcttcttc   29580
tgctgatccg gcgacaacac gccctcgttc acgaagcgac ccacgaaggc caggcgcgtc   29640
tggcaacaca ggtagtgact ccaagccttc acgtcctccg gtttgaagtc ctcgtccgtc   29700
tcgatctcct gcagcactag gttccagccc ggcggccaga ccacgggcaa cacctggcct   29760
gcgttgatgc gcacgtaagc ttccagacag cccaggccga actcggccgt gagcgccagg   29820
ctagccagat cgctcatgtg acgcgccgag tcagtgggcg agcccggggg cccgtcgcac   29880
accacgctcc gtcttcttgt cctcaccgcg gccagcgtgg cgaggacact ttccgcgccc   29940
gaggctgtat cttcggtttg cccgccggag ccggccctca ctatataacg tcccgcccgg   30000
gtctcctcca tgtatgcagg taagcaactg agccgaacgc acctcagcag acgagaggat   30060
gtcgtcgcgg cgtcgcagct cgtcacgtcg ctctggcgaa ccctcgacgg tgatttatat   30120
cccctcgagc aacgaggaca cgccggcgga tgaggaggcg gaggacagcg ttttcacgag   30180
cacgcgggcg cgcagcgcca cggaagatct ggatcgcatg gaggccggtt tgtcgcccta   30240
cagcgtctcc tcggacgctc cgtcgtcctt cgagctcgtg cgcgagaccg gcggcaccgg   30300
cgccgccaag aaaccgagcg aaaagaaacg atcgtcgtcg cgtcggcaac cgcagatcgc   30360
agcgggcgcg cctcggggct cgccggcgac acccaaggcc ggcaagtcgc ctaaagtctc   30420
gcgaccgcct agtgtgccct cgctgcccga gaacggcgcc ggcggcggtg gcgacgataa   30480
```

```
cagcagcagc ggcggtagca gcagtcgcac caccagtaac agtagcagaa gtaccagtcc   30540
cgtggcgcca ggtgagccgt ccgctgccga gggcgatgag ttttccttct gcgacagcga   30600
catcgaagac tttgagcgcg aatgttaccg ggtcagcgtg gccgacaatc tgggcttcga   30660
gcccagcgtg gtcgcgccgc agcacgtcga gtatctcaaa ttcgtgctgc aagactttga   30720
cgtgcagcac ctccgccgcc tcaacgaatg catacccatg ccggccttcg cgctcaccag   30780
cctcgtcgac cccgtcttaa caacgtagc gcctggcgag cgcgatctca cgcgtcggat   30840
aatcacgcac gcggtgatca tcaactatta ctacgtggcg caaaagaaag cgcgccacat   30900
ggtggaggcc atacgga cca ccgtgcgggg cgacacggta cgccgggtag ccgcgcaggt   30960
caacaaccag agccgttcgg ggcgtgcggc cgcgctagcg cttcattttc tcacgtcacg   31020
aaaaggagtg acggacggcc agtacgccac gtctctgcgg cggctggacg aagagctgcg   31080
gcatcgcggc acgcccgaat cgccgcggct caccgaggtt taccagacgc tacgcgatta   31140
caacgtgctc ttctataccg cccactacac ctcgcgcggc gcgctctacc tctatcggca   31200
aaacctgcag cggctcaacg agaaccaccg gggcatgctc cggctgcttt cggtcgaaga   31260
gatatgcgaa gagcacacgc tcaacgatct ggcgttccta gtaggcgtcg agcttatgat   31320
cacgcacttt caacgcacca ttcgcgtgct gcgctgctat ctccagcacc agctgcagag   31380
catctcggag ctgtgttacc tcatctatgt acaactgccg tcgttgcgcg aagactacgc   31440
gcagcttagt gacgtgatct actgggccgt cagtcaaaac tacgactacg cgctctacgc   31500
gagcacgccg gcgttgtttg acttttt acg cgtcgtgcgt cagcaggacg ccttcatttg   31560
caccgactac gtgtactgcg ccctgcgtct gctggcctgt cccgacagac ctattatcgg   31620
tgacaccggc ggcagcagta gctcccaacg cctcgtaggc gagtttatgg tgcgcgatcc   31680
gctgttgcgc gacccgcgcg ccacccacct gcgccagaaa ctcatcaccc gcgacatatg   31740
cgtggcgcgg ttgcaagcgc agccctcgag tcgacacatt ccggtcgaac acacgggtgt   31800
ctcctccgtc accctgctca aaatctttag ccaagtcccc cccgacgaac gcgaagaaga   31860
cacgttacgc gagatggctc ttaaagcgtt tatggaagcg aacggtaatc accccgaaca   31920
aatctgccga tccccaccac ccccgctgcc accgcgcgat tatcctcaac gcgacgagcg   31980
ggaccgtcac cgtcgcgacc gccgcgacag cggggaatac tgttgctgat ggtgggacga   32040
aacagcaggg cggaacagtt tatgatagaa agtcacagga agtatgtgt tgttttttt   32100 ttaatgtacc aagaataaaa agtgcgtcta cgaccaaagc ggtgtgtgga cgctcgtcct   32160
ctctgtcttc tccgggtttt ttttcacgt gttttttcct tcctattttg ttacggcaac   32220
agcgctgatg gcacgttgcc ggcttcgaac atcgcgtcgg tgatttcttg cttgcccggc   32280
gtcacacggt gacgtagcag cacgcggctc acgtagcagg ccgactcgcg gatgacctgg   32340
ccgtcggcgt cgcgtcgcag gcccgagcgg ttgccgtgac gcagtctgcc ctgcgcagcg   32400
cgctccacgt cttcaaagta gctgtgtagc aggccgcgct ccagcagctg cggcagcgag   32460
tcggcggcgc gcactacaaa gttctcacgg ctgatctcgt agcacagcac gctgccgtcg   32520
gccgccacgc cggccacgct gcggtcccaa ctgaaaaggt tggcgagtcc gatggtgccg   32580
atgacgcgca actgaccctg ggtcaccacc agcagcttcc agtattctac gtcgcgcggg   32640
gtgaggatgg tctcctccac gtcgcagaca acaacgtgt agccgcgcgg atagggcaga   32700
tccaggtggc gaccgcgctg gcggcgcata aaatcgtcta aattcaaacc gccgtcgggt   32760
gcgcgcctac tcgtcatcgc cgcgccttgt cggtcgatga ccccacggtg cttataacgc   32820
```

```
gccgccgcgg cttcatgtgg cgtgacctcc gacctcgtga ggccgaaaac ggcgtacatg   32880
aagacgctca aacttttgaa tgtgggcccg gtagcgcacc gagggccccg gggcggcgac   32940
gacggcgggc ccgagttcca gcggggcctt gcggcggcag cggttggcgt ggttgctcag   33000
ctcggcgtcc gagagcgccg agctgaactg cggcagccgc gtgcgatcct gcggcgcgtc   33060
cccgtgtcgc agcgagtgcc agagcaggcg ctggacgcgc gccgtctcgg gcgtcggcgg   33120
cgcgcgacag ccccggcgca gcttgaaaac gtgcaggcac agcagctcgc gcttgatgcg   33180
cagcgacacg ctgcggtagt cgggaatccg ctgcaccagc tcgagaaagt cgcagaaggt   33240
ctccacgaac gtgtcctcgg tgaagcgaat gcgcttcaga tcgtggacgt gtttgcgaaa   33300
ccgcgacagt tctcgacgtt gcacggggtt ctgagcgagt cccttgcgca gcagcgcagc   33360
ctcgccttta aacagcctga tgagccgctg cacgtccccg ctcaacatac gtatacacgc   33420
cgtgtactcg tgacgtatac tggcgcgcag cagccgaatg atacgcaggg ccagcacggc   33480
gttagaggcc aggtacatgg cgtagccgcg acgcggggttg gcacaggccc agcccgcggg   33540
gagcagaaag tagtcgtcga tcagcgtctg cgaccagtcg gcgaagccca ggtcacgtga   33600
tacgctgtcc tggacgcggg ccacgtcgcc ggccgtgagg tggcggatcg ccggcaggtg   33660
aaacgcgccc aggtgtcggt tgcgctccag cctcagctcg gcgtgctcca aacgggaatg   33720
gtgggacgcc accgcggagg gcgacaaaga ggagtggtca ttgccgtcgt ggttaccgtc   33780
gtggttaccg ccgttgtcgc gcccgtcgcc gcactcgcaa aaggccgcgt agaggtcctt   33840
caatgccgct tcggctcgcg ccataaacgt ggcgtggaaa aaaacggcgg cgcggtgcgt   33900
ccggtacttg acgggcaacc cgcggcacag ggccgccggc aggcagcggc cgatgagttc   33960
gcgctcctcg ggctccagaa acaggcacag ggtgccgtcc aggcgcaggt acagctcctc   34020
ggtcatcgag catagctgcc gcaagtaatg ggtgcgcgtc ccaaaggtct tgtaatcgag   34080
caacgtgcac accacgtatt gccccgtggc cacggccaga gcgatgcgtt tggcggcacg   34140
actgatctct ggcaagtact gcgcctcgtg caccagacgg cggaaagcgc cggcgttgag   34200
ccagcgaaaa tgctgcggat cgggcggcaa gggcacgcct cgaagcgcgg cccagacagc   34260
gaggtccgac tcgagcgtca gaccgcggat gtcgtacttg ccgtgcgccg tagcgcaggc   34320
tgaatggacc agacagctgc ggcgaatgta caccatggcg tgcttgggat gtttgggcgc   34380
cggcgttttc ttttttctgac cgccggcggc cgccagatcc tcgggcgtgc gacacaacag   34440
gccggcgcgc acagcctcct gtcgattacg aatcggcgtc aggtaggcgc gcaggaactg   34500
gtgacaaaac tcctcatcat cacgacagtc gtcgagatac tcgtacgtgg tgagcggatc   34560
gcgaaatagg cgctcgtcac cgtcgtcatg gtcttcttta gcctgctcct ccggctgctg   34620
ggttggcagt ggaggcggcg gctgatccac ggggttcatg actgagagga agaagaaggt   34680
ggcggcgaag cgacgcggag cgacggcggt aaagccagac accggctata tagctagtca   34740
tcacagtctc ctccttcacg acgccccgt gccgctcacg ctatccagca cgctacggcc   34800
cgaaaacacg tactcgctga cgtcgtacgc gggcgatgta tggctgctca ccggtttcgc   34860
ggcgacggtt gcgctcgagt ccaacggcga gaagcaaaaa cgccgtgggc aacgaaacca   34920
gaaggagccc tgacggataa aaccgcgcag cgtctcggcc aacttaacca gcatcgtacc   34980
gtacagcagt acgtgaatgc cgccatgcgc gtccataaat acggctttgt tcacgggttc   35040
catccatccg atgactacaa aatgggccty ttctagcacg ccgatcacga aattgttggc   35100
ctcgtcggcc tcggccacgt tccacgagcc gaaagtgaaa gtacaagcgg gcgagccgcc   35160
caggcggatc ttgctaccgg cgtggagctg acatacgcgc agcagattgg cgcggtcgtg   35220
```

```
cagtatctgg gagagttcgt acatgcccgc aaaggtgtgc ttaaaccacg cgccctctac   35280
gatctcatcc acgtagtcgc gctcaaagaa gctgtacacg gcaaagaggc cgttctcaaa   35340
aaactcgccg aacgagagcc ccagcacgta caccttgtcc tcgccgggca ggtacgcaaa   35400
ggcgtgcccg tgcccggaga cccagatctc gggcgccgtg tttgcgtccg cacgcattc    35460 gtacacactg acgaggccga taaagtacaa gcggccagcc tggcgcaggc acgagaagcg   35520
ccggtaggtc ttgtgatcgc gcaccacccc aaagtactga gtctgccca gcatgatgcc    35580 gtgcagcggc ggccagcaca gcgggagcca acgacccgcc gtggcgcgca cgtagcgctg   35640
caggtgaacc ccgctcgcac gctcgcgcgg cttcgggcgc ttgtgggtcc aggcatcacg   35700
cagaccgcgc cagatgctgc tgaacttggg ctgcccgcgc agatagagcg acgagagcga   35760
gtcaaagtag cccacgacga gcctgtcggg agacacaaga gcgcgaaaat caaacctaga   35820
gcgacgacgg tgaaaaaacc gaccagaagc gcgtgtctca acacgctac tttcggttat    35880 aaaaacaccg tcgccctatt tctgggcgcg tgtacactga tgactcacct acgctttttg   35940
aacggcagtc tcagctcggg attggcctcg tacagcgagc tgcggtccac ggggccgatg   36000
ctctcgtagc gaaagtcgtc gatgagcagc gccagcccca cgcgcacgaa gcccctgagg   36060
tcgcgcgcca gccgcaccaa cttatcctgc cccaccagcg ccgcgtacac ggtgcccgtg   36120
tcgccgcaga gaatccgcac gcggtgaaag aaggtcttgt cctcggcgcc ctcaatttcg   36180
cccagcggca tgacgggctc gcgcgtgtac aacgaacgtt gaaagcggcg cagcatcgag   36240
gccgagagcc ccagatcgcg cgccgtgcgc agcactaggg aatgcttctc gggccagatg   36300
agggtcagtt gcgcctcgcg gtgcgcctct acgtaggcgc aacgagcggc ggtgtcctcg   36360
caggccagca actcgcggaa agccagcagc gaacgtaggt agcggccgcg agcggaggcg   36420
cgcgagcggc ggcacagctc ggcccgatgg tcggatgca ccaagggcac gttaggttgc     36480
agacgcgcgc agatggattc gtgcaccggg tcgcagcgga tcatgcccct tggcaaaaaat  36540 ccggccagat ccgaggccaa ctcgtacagg cagtcctctt gcgcgtcgta ggcgaacacg   36600
gcgccgtacg cgtccacgaa cacctggtac cggcaggtgg cgtgcgagac cgtgccaatg   36660
agatgcagag ctcggaattc gccgaaaaag tcgttctggc agtgctccag atcgatctcg   36720
gtcagcgagt gcggcgaatg ctcgccccg accacgtaga tgcactgcga gggccagccc   36780
agcgacacgc acgagccctc gaagcgccgc aagtaacgcc gcaggccctc atagtcgcgt   36840
cgcacgcaca ggtcggccaa gtcgcgcgtg caaaagacct cgggtaccaa gcagcgtttg   36900
cgacgcggcc gacgcgcgtg cccaggcaga ggaggaaggc gcgacggcgg cgacgacgag   36960
gaggaagacg ccgtggccgc cgagcagccc ttgcgacggc cggacatgcc ggcagtccgc   37020
gacgatccac aggagacaaa aaagcagaag cagcagtagc ctcggcgacc cgctccaccc   37080
cgtcctccac acgctcagcc gcgactgaac gccggggcgc gccgctactt gggtttttat   37140
agccatctgc cccccgtctc gggcaccccgg gagcgatcta cggagacctg acagcagttg   37200
ggcaacacaa gatagggaaa tacaaagaca cttttaataa aaaacgagac tactttgtgt   37260
gtgtgctccg taaactgttt attctccccc tccgcttcgc tctggatggg ctccgggtcc   37320
gtcaacacgc gactcgcgcg gcaaaaggca cgctgttgac ggcgcgagag cccgtcgtga   37380
tagtccatca tgccccggag atcgtgcaca aagcagctgt cgccgcgcag aaaccgacgc   37440
agcgtctcca cgtgctgcag ctgccggcgc gtatcaggag ccgtcatcgc tgatgtcgtc   37500
atcgccctga caggcgcgta gatggcttcg cgagatcatg cgcgttttca accgccgtga   37560
```

```
cacatcaggt ccatcttgag ctggcgccgg gcctcgcgca ggtgttgcac gcgttgtgag    37620
cgggaggcga gttcggcttc ttgctcgaac tcctgctgct cactgtccga gagggtgcga    37680
taaaaggcgg caaagtcctc caagtcggct acatgcgccc tgggtctgac gctccaaagc    37740
gtacgcagtc tgatgaagcg gacccatcga gcgtcacggc acgccgtctt gaacgcgggg    37800
cccgggaaga ggttcttctc cccggcgcgc tcgggccggc gaggccgacg cggtttatat    37860
acaccgtctc ggacggcggg acgccgagcc cgcgccgcgg ccgctcatcc ggagacggcg    37920
gaaaccgcga cgccggagga acggggacc ggcaacgacg gcggtggcgg cgaccagatt    37980
atggggggaca aacccacgct tgtgaccctg ttgaccgtcg ccgtgtcgtc gccgccaccg    38040
tcgtcgccgc tgccgctcgt cagcttcacg gagctgttgt taccgccgcc gtccgtcgcc    38100
gccgctgcgg tggcggcgac agcgacgagc gaggtgggcg agaaaaccgc ggagcaagag    38160
gtagcggctg cggatccgga gaccgggaat gagagaagag aaaacaggga gaacgaagga    38220
ggggagacga ggacgacagg caccaccgcg gtcaaaaggt cgcacgacgg tatccctcgc    38280
caactggcag agcgcctgcg gctgtgccgc acatggacc ccgagcagga ctatcgtctg    38340
ccggcgcagg acgtggtgac ctcgtggatc gaagcgctac gcgacgcgga ccgcgacaac    38400
tacggtcgct gcgtgcgcca cgccaagatt caccgttcgg cctcgcacct gacggcctac    38460
gagtcgtact tggtgtccat caccgagcag tacaacacgg cctcgaacgt gacggagaaa    38520
gcttcgtacg tgcagggctg catctttctc tcgtttcccg tcatttacaa caacacgcag    38580
ggctgcggct acaagtacga ctggtccaac gtggtgacgc ccaaggcggc gtacgccgag    38640
ctcttctttc tgctctgctc caccagcgag agctccgtgg tgctgcaacc gctcatcacc    38700
aagggcgggc tctgctcgtc catggcggtt tacgacgagg aaaccatgcg gcagtcgcag    38760
gcggtgcaga tcggttttct gcacacacaa ctggtcatgg tgcccttcgt gccgcacgcc    38820
tgcccgcatt acgccgtgcc tttcacgacg ccgggaaagc cgggctgcgg cggtgctccg    38880
agcggcgttg cggggttgga ggaggcggcg ccctttggac gggtcagcgt cacgcggcat    38940
ggcgcgacgc tgctatgtcg cgtggaccat ctgacctgga tcagtaagcg cgtaaccacg    39000
tacggacaca aaaaaattac gcgctacctc gcgcagttcc gcggcacgat ggacgacgac    39060
gaggcagcgc tacccggcga ggacgaagcg tggatcgcgt ccaaaaacgt gcagtacgaa    39120
ttcatgggtc tcattttcac cgtcaacgtg gattcactat gcgtggacgc ggaacagcgc    39180
caactgctgg gcaccgtggc cacctccttc tgtcaccgcg tctcggacaa gatcacggcg    39240
cgcaacatgc cgcgcgcttt ttccttctac ctgctgacga gcgcgcagcg cgggtacgac    39300
ctgcgattca gccgcaaccc gtcactcttt tttagcggcg acgcgctcaa ctgtccgctt    39360
ctcaatgagc ccaacgtgtt ttcgctcacg gtgcacgcgc cttacgatat ccacttcggg    39420
gtgcaaccgc ggcagacggt ggagttggac ttgcgctacg tgcagatcac agaccggtgt    39480
ttcttggtgg ccaacttgcc acacgaggac gccttttaca cggggctcag cgtgtggcgc    39540
ggcggcgagc cgctcaaagt cacgctgtgg acgcgcacgc gttccatcgt gatcccgcag    39600
ggcaccccca tcgccacgtt gtatcaaatt accgagggcg acggtaacgt gtactcgtac    39660
aaccaccaca cggtgtttcg gcagatgcac gccgccggaa caaccacgtt ctttctgggc    39720
gacatgcaat tgcccgcgga caactttctc acgtctcccc atccctgacc ctccgtccgt    39780
cctccttttcc cgacacgtca ctatccgatg gtttcattaa aaagtacgtc tgcgtgtgtg    39840
tttcttaact attcctccgt gttcttaatc ttctcgatct tttggaggat gttctgcacg    39900
gcgtccgacg gcgttttggc gccccccatg ccggcagaac ccggttgcgg ccccgtaccg    39960
```

```
ctcttctggg gcgacgatag gtcgaaagcc accgttttca tgcccgtcgt gctcttgacg   40020
ggggaaccta cggcggcggt ccccgtcgag cggcgtgatt gcaaagccgc gctcgccccc   40080
ggtttcagga tggaggggga ggccacaggc ggcgcattcg atacgctgct tttggccgta   40140
gacgacggtg ggtaaacggt ggttaccgcg ggatacgtcg gcgtggtcga ggcggcccgg   40200
ctgctgccgg acaggcgacc cggcgcgcta ccgctcacgg ggaccgaggg cggtcgacct   40260
accaccgcct tgccgcccaa agtaggtttc aaggaaggaa caccgacgcg gctgccccgg   40320
cctttcaccg gagacggggg ggcactcttg gccggggacg gagaggctga cgaaagcatg   40380
gacagcggcg atgtggcggg ggacacgaca tcatcctccg tgggcgacaa aacgacgcc    40440 gaggctgacg gctgtcgagc cgaagaagcg gaagaggttc ccgcgccaga agtcacgttc   40500
cttgatgacg tcgttttaga cgaagccggt tgaggttgca acagcgtggc gggtaccgtc   40560
gacggcgtgc ccgacacctg tttctctagc cttccctgaa ccggcgtcga cgtcaccgtc   40620
tgcgctcggg cggacgcgtg cggcgtcgcg actcgcttgc ccagcaccgg tttctggctc   40680
gtggatgtcg tcgtcattgg agacgataac ttagctttac gtattctgga cggcgtcgac   40740
tgctcgggcg tctgactggg aggcgaaatg acgtcgttgt tgtaatcgga cgacggtgtt   40800
gtgtgtccca ggctgacgac ggagccggtg tccgaggagt cgtcgtcttc ctcctcgctg   40860
tcttcgaccg gtgactctgc agtttggtcc cttaaagccc aaacctcatc agcggcgtcc   40920
cgagacgctg tttgtgtcac cgcggcgcgt ggagtcgacg gcctccgagg ggtggtggac   40980
acggtgtttt gagaagccgt ggaagtcgta ggcatcctga agggattgta agccaggtga   41040
ggattcttga gggcccacgc gcgttcgcgc ggccagttgg cggggttcat atccccgggc   41100
aacggcgccg tcggagccca gggcgagtta ccgttgaccg gggtttgggt acccgcgaag   41160
gtaggtgtcg gggccggagc gggggccgtg gaaggattga caggcgtcgg cgtgaggatg   41220
gcagcgccgg cgccagcagg aacgttaact ccggcgccga acgtcaacgt cggttgctcg   41280
aacttgtacg cggtggtgac gggcggtttg gcgctcgtct cggtatccgt gatgtccacc   41340
agcgtgtcgg tgaaacgcgg atcttgacgg ttgggggggat agccatccga gctgtcggaa   41400
tcctcgtcgc ccgagaaaag atcccctctg gtctccgtga gcggcctcac gtcccacgcg   41460
ctgtcccgac ggaccctcc cgggctggcc ttggtcacct gcggggagac gagactgaaa    41520
gccgcgtgac gctgttgttg ttgcgggatg ttcaagggac cgctggtcgg tttctgactg   41580
cccgaggata acaggccgct gaaaatgctg gaaacaccgc caccactagc ggcgcccttg   41640
ccgctagttc ccggtttctt gatgggcgta aagatgtttt tctcgtcatc atcatcgtcg   41700
tcgtcctcat cggcactgga gccaaagagc ctccgggagg cgctcggttt acgtgccggg   41760
ggcggtggtt gctgctgacg ttgctgcagg ttctgctgcc tctcctccca agccttcagc   41820
tgctgtttct cacgctgcac cacctcgtcg tccacccgtt tctgccgctc gcgacgcttt   41880
tcctcttcgt cgtaatagcc gacggccgcc gaacgggcag cgtgggcttc ggcggccggt   41940
gccagagaac catgggcctc gaagcggaac ggtttgtgtc ccttccaggg actggcgatc   42000
cagctccagc cgtccagcgg ctgcgtgggg acatgtttct tgggtaccga cgagaaggcc   42060
gaaccgccgc cgagcgagag gagattggcg tcatcgtcaa actccaacga cggcgagcgc   42120
gcgcccaaaa acgtgtgcgc cgactgtggg aagctgtcca cgtagatatc aaagtcctcg   42180
atgagcagct ccaacagcgt gtcggccgag tcgccgtttt ccacggcgtg cttgaggata   42240
ttgcgacagt agttggaatc aaaggaaagg cacatgcgca gctccttgac cagcagcttg   42300
```

```
cagcgctcct gaatgcgcgc cagacatttg cgctccagct cctcccaaga cctgcgcacg    42360
ttcatgatga dacggcccgt gtacacgagc ttgttgacgg cgttgaccag cgccgtgttg    42420
gcgtgccggt ccaggttaag gtcgagcggt ttcacgcaga acatgttacg gcgcacaccc    42480
tccaggtttt cttcaatgcg ctgcacctcc gtatccttga ggtgcacaaa ggcgatgggt    42540
tccgtctggc cgatggctgt gaccagcgtc tcgcgcaccg acatcttggc cagaatgacc    42600
gcgcttacga gcgcgcgttc cacgatcctg gcatcgtggc gcacgtccgt atcgaattcg    42660
gtacggtcta gcacagccag gtggtcacgc gccttaccac gatcaccgaa cgggtaagtg    42720
tagccgcgac gcgccacggc cacgcaacgc acctcgaact cctcgagcac tgaggagagg    42780
tcggggttgt gaaaacgcag ctcgcggtag tatcccaacc aaagcatgag ctcgttgaac    42840
agcaccgtac gccggtgcag gcgttttttcg ccacattttt tcaggatctt ggggtgtgcc    42900
tcgagatcca cgtcgggctt ttgcgtgaga tggcgcagaa agttgaccag ggctaccaca    42960
tcgcgccgct gtagaccgat aaactgcaaa ctcatgctgg cttttctcca gaacccggaa    43020
gcgtcgtcgc cccggactgc gcccgcggtc tgctattcgc ccacgatgga caccatcatc    43080
cacaactcgg tgagcgcccc acctagaggg aggggggta gtttaatagc ggaggcggat    43140
acgcggtttt cttttaagcg ccgctgactt gtttcttctg ttttttcgcc ccgtgtgctg    43200
ttccgcccag acccgcaaca acactcctcc gcacatcaat gacacttgca acatgacagg    43260
gccgctattc gccattcgaa ccaccgaagc cgtactcaac acattcatca tcttcgtggg    43320
cggtccactt aacgccatag tgttgatcac gcagctgctc acgaatcgcg tgcttggcta    43380
ttcgacgccc accatttaca tgaccaacct ctactctact aattttctca cgcttactgt    43440
gctacccttt atcgtactca gcaaccagtg gctgttgccg gccggcgtgg cctcgtgtaa    43500
atttctatcg gtgatctact actcaagctg cacagtgggc tttgccaccg tagctctgat    43560
cgccgccgat cgttatcgcg tccttcataa acgaacatac gcacgccaat cataccgttc    43620
aacctatatg attttgctat tgacatggct cgctggacta attttttccg tgcccgcagc    43680
tgtttacacc acggtggtga tgcatcacga tgccaacgat accaataata ctaatgggca    43740
cgccacctgt gtactgtact tcgtagctga agaagtgcac acagtgctgc tttcgtggaa    43800
agtgctgctg acgatggtat ggggtgccgc acccgtgata atgatgacgt ggttctacgc    43860
attcttctac tcaaccgtac agcgcacgtc acagaaacaa aggagtcgta ccttaacctt    43920
tgttagcgtg ctactcatct ccttcgtggc gctacaaact ccctacgtct ctctcatgat    43980
cttcaacagt tatgccacaa ccgcctggcc catgcagtgt gaacacctca cactgcgacg    44040
caccattggc acgctggcgc gtgtggtgcc ccacctacac tgcctcatta atcccatcct    44100
gtacgcgctg ctgggtcatg attttctgca acgcatgcgg cagtgttttcc gcggtcagtt    44160 gctggaccgc cgcgctttcc tgagatcgca gcagaatcag cgagctacag cggagacaaa    44220
tctagcggct ggcaacaatt cacaatcagt ggctacgtca ttagacacca atagcaaaaa    44280
ctacaatcag cacgccaaac gcagcgtgtc tttcaattttt cccagcggta cgtggaaagg    44340
cggccagaaa accgcgtcca acgacacatc cacaaaaatc ccccatcgac tctcacaatc    44400
gcatcataac ctcagcgggg tatgagcttt cctgttactt tattcagaaa gcaccagaac    44460
ccgtcgccat ttcccctcat atacggtaca cgtcccctg atctgtcatc acggtacaca    44520
gatttcgccc gactgcggac gccgacggcc aatcgcgtgg cgtaggagtg gcgcccggc    44580 ttcattataa cgccacgtcg gagccctgc gcgcacaac gccgtccggc gcaacttctg    44640
tctcggcacg gtacgataaa aacaacgtcc cccgtcgacg ttgttttctc cgagcggtga    44700
```

```
tcgttcccgt ccctctcctc cctccgcggc ccccacggcg gcggcctgct cgcacggacc   44760
tatactatta ccgccccacc gccgtcgtcg tcatgaactt catcatcacc acccgagact   44820
tctccaacga cgattcagtc ctgcgagccg ccgagatgcg tgacaacgtg gcaggctcga   44880
tttccaaagc gtacaagggc acggtacgcg ccgaaggcaa aagaagctg ctgctgaagc    44940 acttgcccgt gccgcccggc ggctgctcgc gccgcaacag caacctcttc gttttctgca   45000
ccgagcgcga ctaccgcaag ttccaccagg gcatcgcaca gctcaagcgc gcgccggccg   45060
aactggaccc ccacgagatc cagcaagtca cggccagtat ccgctgccgc ctgcagccca   45120
gtctccgcga gccgcccacg ccggccgacg agctgcagac ggctgtgtcg cgcgtgtgcg   45180
cgctcttcaa ccagctggtt ttcacggccc agctgcgcca ctactgcgag caccaggaca   45240
aggtggtgag ctacgcgcgc gacgagctga ctaaacgctg cggcgaaaaa tcggcgctgg   45300
gcgtggaagt gcatcaactg gtagccctgc tgccacacga gcgccaccgc gaactgtgcc   45360
acgtcctcat cggcttgttg caccagacgc cgcacatgtg ggcgcgctcc atccgtctca   45420
tcggacacct gcgccactac ctgcagaaca gcttcctaca cctgttgatg aactcaggtt   45480
tggatatcgc acaagttttc gacggctgtt accacagcga ggcctaccgc atgctcttcc   45540
agatcggtca tacggactcg gtgtcggcgg ccctggaact ctcacacggc gcggcggccg   45600
ggccgcccga ggccgatgaa acaacgacg agggagagga ggacgacgac gagctccgtc    45660
acagcgaccc ggcgccgctt cacgagtcca agaagcccg caacgcccgt cgtccccgca    45720
cacgcgtgcc gcctcacgag caaaagcccg aagaaacga ggaggaagaa gaggagctgt    45780
ttccctcctg caaggcaacc gcagcattcc tgcgggcaga accctccgtc tccaacgacg   45840
acggcaacgg cggcgaacgc tgcgacacgc tagcgaccgc cctgcggcat cgcgccgacg   45900
aagaagacgg acctctagcc agccagaccg ctgtgcgggt cgccgcgacc ccctcacctt   45960
cagtcacccc agcccttacc cccgtcacgt cccccataac cccgttgtgt atttaacgtc   46020
actggagaac aataaagcgt tgatttctca agttccgctc tggttttggt ttcgttttca   46080
aagggagccc catcatggcc caaggatcgc gagcccatc gggcccgcca ctgcccgttc    46140
tccccgtgga cgactggctc aactttcggg ttgatctatt tggggacgag caccggcgcc   46200
tgctgctcga aatgttgacc cagggctgct ccaactttgt ggggctgctc aactttggcg   46260
tgcccagccc cgtatacgcg ctggaggccc tggtggactt ccaggtgcgc aacgctttta   46320
tgaaggtaaa gcccgtggcc caggagatta tccgtatctg catactcgct aaccactacc   46380
gcaacagccg cgacgtgttg cgggacctgc gcacgcagct cgacgtgctg tactcggatc   46440
cgcttaagac gcggctgctt agagggctca tccggctctg ccgcgctgcg caaaccggcg   46500
tcaagcccga ggacatcagc gtgcacctag gcgccgacga tgtgacattc ggcgtgctaa   46560
aacgagcgct ggtccggctg caccgggtac gcgacgcgct ggggctgcgc gcgtctcccg   46620
aggccgaggc gcgctatccg cgcctcacca cctacaacct gctgttccac ccaccgccct   46680
tcaccacggt cgaggcggtg gatctgtgcg ccgagaacct gtccgacgta acacaacgtc   46740
gtaaccgacc gttgcgctgc ctcacctcca tcaaacgccc gggctcacgc accctggagg   46800
acgcgctaaa cgacatgtat ctgttgttga cgctgcgaca cttgcagctg cgacacgcgc   46860
tggagctaca aatgatgcag gactgggtgg tggaacgctg caaccggctt tgcgacgcgc   46920
tttacttttg ttacacgcaa gccccgagaa gcggcagac tttcgtcacg ctggtgcgtg    46980
ggctggaact tgcgcggcaa cacagcagtc cggccttcca gccgatgctg tacaatctgt   47040
```

```
tgcagctact gacgcaactg cacgaggcca acgtgtacct ctgcccggga tatttacatt    47100
tcagcgcgta caagctgctg aaaaagatcc aatcggtctc ggacgcccgc gagcgcggcg    47160
agttcgggga cgaggacgaa gagcaggaga acgacggcga gccgcgcgag gcccagctcg    47220
atctcgaagc cgatcccacg gcgcgcgagg gcgagctctt tttcttctcc aagaacctgt    47280
acggcaacgg tgaggttttc cgcgtgccag aacagcccag ccgctacctg cgccgacgta    47340
tgttcgtgga acgcccgaa  accctgcaga tcttttataa cttccacgaa ggcaagatca    47400
ccaccgagac gtatcacctc cagcgcatct atagcatgat gatcgagggc gcctctcggc    47460
agacgggcct gacacccaag cgcttcatgg aactcctcga cagagcgcct ctgggccagg    47520
agtcggaacc cgagatcaca gaacatcgcg atttatttgc cgatgttttt cgccgtcctg    47580
tgaccgacgc ggcttcttcg tcgtccgcgt cttcgtcgtc gtcctcagca tctccgaatt    47640
ctgtttcgct gccgtctgcc aggtcgtcat ccacacgaac caccacgccc gcgtccacgt    47700
acacctcggc cgggacttct tctaccacag gtctcttgct ctcttcttcc ttgtcgggt     47760 cgcacggcat tagctccgcg gacctggagc agccgccccg gcaacgacgc cgcatggtca    47820
gcgtgaccct cttttcgccc tactcggtag cctacagcca ccaccgacgt caccgaaggc    47880
gacgcagccc gccaccccgca ccccgagggc cggcccacac acgcttccag ggacccgaca    47940
gcatgccgag cactagctac ggcagcgacg tcgaagaccc gcgggacgat ctggccgaaa    48000 acctacgca  tctctgaaag cggtttttcc tcttttcta  cgtgtctgtc tcaagatgag    48060
acgtcgatat caataaaaat accgtcgacg tggttttttt aacagtgtgg ttttctttat    48120
tgactagcga agtacacagt ttacgagtag aaaagacagg gaaaggttat ataaaatgct    48180
gtattatata caaaaacatg cacataaaca acgggaccag tcgtgctcat catcccctcc    48240
ttgatcagtt gttcatgtaa acgtgtggcg gggtgagggg cggcatgccg ttggcggcgc    48300
cgggaataat gtgccgtcga ccgacgtcgc acaccttgaa acgccgtcgg cgcacgcagc    48360
ggtcgcagga cgggatatcc cagaggaagc ccatgtaggt ctcggggtcc tcgtcgtgaa    48420
agcggtagga gagttcaaag tggtgcaacg agcccgtccg agctcgcagc ttctggcgaa    48480
caccctccac gtcatcggtg cacagcgaca gtgctgggct gtcacacagg gcctgaagct    48540
cctgcggcca caggtgcgtg gccaggggcg agtccgtcgt caccagtttg acgcagtgca    48600
tcaggttctc ggtgatggcg tcgtacaggc gactctcagc ctcctcgtgc gtcatcacgt    48660
ttcgaggcag cgacagctcg tcgtcgtcat cctcgtcaaa catgatcatg ggtcagggg    48720 ttttttggg  atgttgacag gtgggtgtct tttccagacg cacgatggcc tcacgccggc    48780
cgctgaaacg gtggtttcgg tgtcccttct ttcccatgac gcaggtgaac ataaccacgt    48840
cctcggccaa acggtagacg gcgtccatgg cggggtcgta gccgtagacg acgccgaaag    48900
tgtccaccaa gacgtactgg cgtacgagga actctttgcg ttctggcacc tcgtggccca    48960
gcgcgcccaa caactggtgg taacaggtga tgcgcggcac ggtacggatc atgagctcca    49020
tggtctggat gctgccgccc gcgcggacga cgctgaagga tgtttccttg aacttcataa    49080
cctctgtgtt gtgggtccag aaggcgaaat gggtgtcggg acactcatcg aaagggtcgt    49140
cgatggtgta ggaagcgtag cctcgcttgg tcacctcggc cgacaggctc tccacgtcac    49200
gcgggtagag catgacggcg ttccagtagt cgtcgtactg caccatgggc cgctggtagt    49260
cgcgcatagt gtggaagtgg tcgcggtgac gaaagccgtt ccgcagaaag tccttcatgg    49320
tgggtgccag ctcgtagacg cagtcgcgca ggtcatcgta gcagtagatg ccgccgcgct    49380
gcccgatgag cacgatgagt tggtagcgca taaagcccgg accctcgacg aagccaaagg    49440
```

```
ggtgcaggta ctcctgacag cagacgtaag cacctggtag agaatagaaa aaatccacgc    49500
acgttgaaaa cacctggaaa gaacgtgccc gagcgaacgt cctctttcca ggtgtcttca    49560
acgacgtggg gcttaccttg cgaacagacg gtgcccatct tgcccacgaa gggccccagg    49620
gcgctgcgcg aacggagctg gatgaagcag cgttcgggcc aggccacgtg cagccgggtg    49680
ccgcattcct gctccagaaa gtcgttgaga ccgttaaagt ccccggctcg gatggcgatg    49740
cagccgtagg ccatcagcgt gtcccgtagg tcgtccatga cggactcctc taccttcgct    49800
cgccgacgct gcgcttctcc agccaccgct gcggtcgaca gactcctccg tccgccttcg    49860
gagaactacg cgcggcggc acggccttta tagacactat cagcgttgac gtcagacgat    49920
ccgatgaacg tcgttttttg tgctggaact ccctcgtcc cgacaaatgt agcggaaatc    49980
ttcaagcaaa tcgcgacgaa gtccgatgag gaggatgcaa agaggctga gcaacgcgat    50040 gctgcccgcc gccacagtac atatgctcaa caacgcccag tgtcccaagg cgcgactttt    50100
ggctcggaga gagccgaac ggcggtttct ccacatgacg gacaacgtgg tccagtacgt    50160
ccatcctttg cattccggtg tccagacggg aagcgttgtc atgttatttc ccgtaactgt    50220
cacgttatgt tttgttttgt ttctcgtgag cttaacggtc ctcttgagaa atcgcgggca    50280
catgtcttgt agaaagatat aatcactttc cgcgtatttc gtcagtgttg acatcacggt    50340
ggtagtgttt tctgaagaag tagcgttgtc agtgacgttt gtttcttccc aacgtacgta    50400
tgattcgaac ggactcgtgt gcgctattgc ccgcaacacg tagctgtggc cggtgaagtt    50460
gagcgtcagt tgtcccacgg tcacgttcgt gtcattccta aaacatgcta cttctccgtg    50520
aacttccgtg acgtttatct cacgactctc gttcaagaca cgcaggggaa accagccttc    50580
caggtgatac tgaaaaccaa atttaagcat gacgctgtgc catttccgtc gtgattgatt    50640
aaacgttaca ttcaagggca gtctggcttc ggtcccgaga caggggccgt tgtagatttg    50700
cgtgtgattg cgtgtgcagt ttaggtggca gttcatgctc gtggtgttgg aagtgcgatt    50760
aacgtccgta ccgtggtacg tacatcggac cgaaacaccg tgtcccgtgc tccaaagcag    50820
cgtcaacaac agccacacag aaacctacgg ggagacgaca cgggactttt tattgacgga    50880
gactcacgtt tctaccctcc cctttcccgt aggtaaaaac ccacgtttat cacacacgtt    50940
gtttttacct gaaacccgcg cagcccgtgg acgcgacaaa aaaccgcggc actagaaaga    51000
aaatgaaaca agtatgttta ttaagcagca tgtggggcta ataggggga taactgaggt    51060 atagcaacta tgaaaaaata ctacaaaaaa aaaagctgaa catggtcatc tagcagcaaa    51120
gttctccttc tagaccacga ccaccatctg taccacgtcg ccctccccgg ccgtgtacac    51180
gacatccttc accacgaccg gcggcagcgg cggcgacgag gacaactcgc tctcgacgga    51240 ggcccgggacg acagaggacg ggggggtggt ggcggcggag gacgaagggg tggcggcggc    51300
agcgggatct tcttccgaca cgggcaacgg caggctcggc ggcgcggaca gcacccgttg    51360
cgccggggcg tgagaaggct gagccccggt ggcctggatg tgggccaacg aattggctcg    51420
cagcgagtcg cgatccacga aggtcatagg aattttccct tcgcggatcc gccgctcaga    51480
ttccaggatg gcgcgcacgt agctgttcac cgacttggca aaagtgcgcg gcccctccgt    51540
attcttgtcg cgacgcgctt ccagcacctg cttttcgtag tccagctggt ggaagaccat    51600
caccaggtcg tccatagtgt gcgcgtgctg acggacgtgg gagcgcacct ccaccgggaa    51660
caaagcgttc caatactcca gcacgatagc accgtgccag aactgcgcca tgctgggcgc    51720
caggaaaaac aggataccgg agtcgtaggc gaacacgtcc cacttgggcg tcatgaacaa    51780
```

```
caccagctga cgcgtgggcc gcaccgaagc ttcctcccag gcctcgatga ccccgaacat   51840
gatgagctcc tggtccaacg gggggcagtg tcgctccagc caactgatct tgctcaggtt   51900
catctgcaga aactcgtacg aagggtcgca gatgcacacg tagagacccg agtcgtgccg   51960
cagcctggct ccgcgcttca tcagtttcct caccgcgtag cgaagcgcca ccttgcccaa   52020
cgccgacgcc tggatcagtc cccccacgtc catctgcgtc tgtcgccact cggcctcgtc   52080
cagcaggctc atgatagcgg cagtgctatg cgtggtcgta gtcatccttt ctatccttct   52140
ctatgaatag cagcaatagc ggtaaagtcc cttcttatac tatcccggag tctgtggttt   52200
ttttgtttac ccctgcttac tggtgagact gctgggggcc gttgtgctgc agcatccgag   52260
ctcgttgccg ccgttgccac aggaaccggt gtctccgcag ggccttttg agggcttcgc    52320
aggcttctcg cgcaagtcct gagaggccct cggcgtcgat ggggttcacc tcgggcgtcc   52380
gagcctcgtt ttcttcttct tcatcctccc tttcctcctc cgtgtcctcc cgctctgtgt   52440
cctccgttac gctctcctcc ccggcctcgg ccaagagcgc ggccaccaag tccacggacc   52500
gctcggtctc cgagttctca ccgtcaatta cgccatgttg cgcgcgtaac cggtgccgag   52560
aacgccgggt gagcgcacat gcttttttct ttcttaacca aggcgggaga ggatcttcaa   52620
ggcgttttcg ctggatccag cggtagctaa agtaccaaaa ggccagcagg cccacgctac   52680
ctaacagatt cacgtagact ggagacataa ttaaagaaag aagtgaaacc cgcgtgtggg   52740
tctcacgtcg tcttgaaaca ccgtcttata tacatgaaga tgccgacat gacgcgccca    52800
agacacgtgg ggttttcccc ttaggcgacc cggtttctta agatgttttt catcttcgca   52860
cgcgatgtac tacatcaaag ggtcggctga ccgaccgcat tgacgcacag tttccgagta   52920
cgcgcgtctc ggagcacctg acggtgagcc acccaactca cgcggatagg ggacaacact   52980
gacgtgaggg gcgattcacg tcactgacgg gaataagacg ggtgagggat ttccaccttt   53040
ttcttaagtg tgactctctt tacggtaaat cgcacctgtg acctcttaac ccctcctccc   53100
tggtacccga taaccgtgaa aaacacacac cacacgtcac gacaccgatc gattttcttt   53160
attcttagtg tgatgatagg taagggcact cgtgaggatg tgcaattatc attatcaagc   53220
cttttttcaag gcgtagtgat gatcgttggg cagaaccccc aggctcctag cgatctggga   53280
atagaaggag gagaacgagc ccagggccag aatgcccaca gtgtacatgg cccaggtctc   53340
cagaccgaac gtggcgggtc gcagcttcag atggtaggcc acccgctccg agagttgtga   53400
atgctcgttc aggcaacagg actgcaggtg ggtgagccca aaagcgcttt cgtttacgcc   53460
gcgcacgtgc accgtctggg ccgggcaatc ctggtgttgc gcgcgaaagt ggtcctgaca   53520
ggaaattccg tctacgtggc ggcgcgtgtt gttacccact tcgatcaaca acgtgttatc   53580
ggcaggatga tgcgagaacg cgacgacggt gttgttggag gtctggcggc aacagtacac   53640
gtcgagcgtc atgagggcca tgtcgccttg gtggtacacg gcgtacgccc aaccctggaa   53700
cacgagcgga cataacggac cgtgagcgga cgtcacggcg gcggttgtta ccgtcgtctc   53760
ggcaggagaa cacaataaac tcctgatcct catacacagg agtccaaccg tcagaattaa   53820
agtccgcgga gccataaccg cgcaagtgaa gccgatacga gtgttgctga atttgttcat   53880
tctgccgact gttgctcacg agcgttcgga ggcggtgcca caggctgttg gccattaaaa   53940
agtcctggcc cgaatgacga caagacagag cccgaggcga agaaaaaggc gcccgtcatg   54000
aagacgtagg caggggaatt cccatatttt tatggcttct tttaaaagtc tgtatccgac   54060
tccatccggc gcttttccca aaccgtggtc tcctcgtcgt ccgactcggt acccaggagg   54120
tggtaagtct tttgccgcac gtagaaagct ttcaacgtgg agcaaaagat gagaataaag   54180
```

```
accccgaaaa cgaaacaaac cacgccgatc atgccgatgc agacgttcat gtcgacgtag    54240
ccggcggtgc tgttggcggt gcggcaaaag agtgtcatgt cgtgcgtgca caaaaaacaa    54300
cacacaccac aggccaggtc gtagcgtagt tattattccg tagcagcaat gatggtacag    54360
tcaagcacat gctctatccc cgttaccccg atgatgcttg cgtccccgtt gttatattgg    54420
cactgtcccg gttaatcacc acggtgaaca ccacggccaa gaaaatgatc cctaatatag    54480
cgaccactaa gagagcaaaa gtccatttcc agccgttgtc aaagtacgcc cccgtggtgg    54540
gatgcatggt ggcgggcatt tccatcatgt ccatgtcgaa cgtgtgtcgc ggcgacggcg    54600
aactaaccag gcagtacggg ggtcgatagg gcggtgggct gcagtcgggt ggtggcggcg    54660
gtggcgtgga aaccgtcgtc gggcacagac ccatggcctg ctcgtaggtg ggggcgcgt    54720 cgtcgtgatc ccggtcgcgg agcatcgcg tgggctccat gtcggtggca gtgacggcga     54780
cggtggtaac tgtggtggag acggtaccga cggcgtccgc ggttcacctt cgagcaaaga    54840
gccccttctt tttgcgcaaa cgacggcaaa acagttctct gggacaaccg gtggcgcggt    54900
aagcgggtgc cacgctttca gggtgggtaa acagtcgcg ggcgaagcag tagttgttgc     54960
agaaccgcaa gaacccgacg cgaaagaagc ccaggagtcc gcgcgccaga aagtgcgcct    55020
gccgcgtctc gggatgcacg ccgaagacgg cgccgctctc gttcaccagt atggagatgt    55080
ccaggcgctg ctgcgactcc accggcacgg cccgcaccac aaatacctgc agcacgttca    55140
gcgagcacgt ctcttttaac cagttgccgt gggccggatc ctcgtaagtc tggctcccgt    55200
tcaagacgac cgtcgtcagc gcctcattac cgtctcgcca gctgaagatg gaaccctcgc    55260
gcttcatgca caggcgccac aaggccagca ggtcgcgcgc caacatgaac tcgcgaccca    55320
cgtcgccgcc ggtctcgaag cggacatagc ccagttcttc gcgcagcggc gcgtagttgc    55380
gcaggccctc ctgcacgaag ccgcggaaac cggaccgcga caccaggtac agcgattcca    55440
ccacgggcga gtagacgtag acgcgaccgc cttcgccgat gagtacgggt agcggtgggc    55500
ggccgatggc ttcgcaacga ctcacagtgc ccaccggcag caggaacttg tcgcagcaca    55560
ggaaggtctt ctccaaacct ttaatattga gatgtccaaa gtaaccaacg cgtaacaggt    55620
cgcagtaggt gaagaaccaa ccgtttggcc agctgagacg cagcaccgtg ccgctgacgc    55680
gacgaaccag cttctgcagg tccttgcgag cgtcggaggt gacagagcag cggaaggtct    55740
cgttaaccag ctcgacagcc agcgcgtcct ccagcgtgcg ttccttcatc tcgtcgttga    55800
tgctctgacg gcgccgccgg atttcgtcga acgggccgc ggaggcggcg accgacgcgg      55860
aggtcgtccg aacgccctct gtgacgctgc cgtccggcca gtcaagaaag ctaaggctgg    55920
cgctgcgccg cctaaagtgt ccgatccgcg cgggacgtcg ctgagggacg gtggctggtc    55980
tgctggggcg ggtacggccg cgggtgtccg cggacacgtt agttatacac ggaattgagt    56040
cacgtggcac gttgccagct gaaaccgccg tcgtctccgc cggcgttttc tccatcacgg    56100
gaccgcgccg tgcgcgcgtt ccaggcacg cggcccgcgc tctagccgca cttttgcttc     56160
ttggtgttag ggacgaactc gaacgttaca gaatcctcgc tgtcgctctc ctctttcgcg    56220
tcgttgaagt aattgccgga gttgcgatcc aaaccgccgc ctcctcctcc tccgccgccg    56280
cccgatccac ctttggacgt caggtagctg gtgatcttgt gctgctcgta tttttccttg    56340
gaggaaagac cgtggtcgtg atcaccgccg ccgccaccgc tgctcatttt ccgcgtaccg    56400
gaaccaccgc cgccaccgcg gtcgtgcttc ttgccgccac cgccgccacc tcctcccaga    56460
ccgccgagac ccatgggctc gttcatgaga tcgttatcca gacccgggcc gtcgtcatgc    56520
```

```
agaccgccgg cattggccag cgaagagagg ctgccgccac caccgccgcc gccacgcgac   56580
ttgccgctgt tcccgacgta attttttgtcg aagggatcgc cacgctggaa aggttcctcg   56640
gtgagaaaat tctccacggc gaacagaccg ttgcggctgg ccacgtacaa cagcgtgtcg   56700
tgctccgtaa ctatacgcaa cgtgcacggc agtttggtga cggcgcaatt gagcagcgtc   56760
tggtagaagt tcttcagctg cacgttgata cgcatgtttt tcacgccgtg gaaactgacg   56820
cggttattgg ctgtgaattc cagctcgctg ccgttggtca ggataaactt gatgccggt   56880 ggaccggcgt gcaccagaat ctgcacggtg cccgtagggc agggcgcttt tttaacgtta   56940
cgcttgacgc gggtatgcgg cccgatccac ttaagcaggt cggccaccac gccgaaatct   57000
agatccacgt gcacggccga attctcgctt tcgcgcacaa tgtcttggcc gtgcacgcag   57060
gccgagctga actccatatt gaaatcgggc gcgcacatgg agatcttggc cgacaggtcc   57120
gagatgtcct gcacgtagaa cttggtcagg tccttgctgg aagtcaggta catgaaatta   57180
cccagcagcg gcgtggaatt gttaatggtc ttgggctgaa cgacttgtc agtgatgtag   57240 aggcatgagc tgttaaaagt gattttttgac acgcagtgac tgcgtaccgt ttgcaagata   57300
agcgacggcg tgggcaagaa ggtaaccgtg gtgttctcct tgagcgcacg gatcacagat   57360
cgcagctgct ggatagccgt cttgtacggc ttcagccgca gcgccagcgt cggcggctcc   57420
gagaggcgcg tcttgcgatc catcccggac agcgtgcaag tctcgactaa ggagcgggcg   57480
cgagcgagcg aaagttttat agagagcaca cacgacgacc gggaacgctg cgaagacgcc   57540
cggcgtctaa taatacagcc gcgccgagcc agcgggcccc cgactaagag gcacagtact   57600
tatatactcc gaccttaaag cgccagtggt accacttgag catcctggcc agaagcacgt   57660
cgggcgtcat ccccgagtca tagtagaaaa ccagggccac gcactggtcc acaaacacgc   57720
tcaggttcac ggccgccatt tccacgtcgt tttggatcgc cggtgccgcc tggaacagac   57780
actgcgtcgc cttgccctcc tcctggtgct gctccaacca cgcgtaattc accacgggca   57840
cgcgcagcgg cctccgcacc acggtgggga agtaacactc acggttgggc gggcacaatg   57900
accacaccgt ctcctcctcg aacacggtgc cgcgcgaagc ccacactgac ggcgtcacgc   57960
cccacagatg cgccacctcg tcgtcgggac ccaccgccag aaactgacag ttgcgcaatc   58020
cgaactcgag catgtcggcg cgcagcgctt cccagcgcgc gctggcgatg gagagccgcg   58080
gcaaccgata caattcgaaa atgaatttgc cctcttgata gatggtgcgt tcgaaccact   58140
cgcagcgcgg caaacccgac ttgcacaaat cgacgctagc gcgcaccgcg gcaaagtaca   58200
tgtgctcaaa gatgcgctcg atcaagtccc aagaggcaaa gtacgtgaac cctaaccgca   58260
tgagcgccgt gtgcaagcca gccacgccga tgtgcagcgg acgcagttttt tccagcgcgc   58320 tctctaccca ccattcggac gccgacatta gcgcgtccaa gcgcgcgttg ccccaaacca   58380
ccgcctcggt caccaactcg cgcagcacgc tcaaatcaaa gtaacgtcgc gtgttcccca   58440
aaaccacgtc gggtagatgc agcttctgct cgtcgctacg cgcaaacacg cagcgagcca   58500
cgttcaccgt cagccgctgc accggcatgt cacactcgcc aaagtggcac gacgccatat   58560
cgggactcaa gcacggcggc aggcacacgc tgtcggccat aatcgagtac ttgactacgt   58620
gatggacaaa gaccaccgag gcacggccct tgagcgcgca cagcaacatc ttttttcagaa   58680 aatcgtccgt gttcacgacc accttggggc acgattgctc gcagcgcgaa tactctttct   58740
cgaaagccga ctcctgaccc aggtccgaga gccgccggga gacaggccgc ccaaacagcg   58800
agtagcgctg ctcacgcgca cggtagcgct tcattaacac gctaggcacg ttgaaagcgt   58860
agcaaacccc cgtcaactcc gacgtgcttt ctttgagaat aaagttaatc acgcggatag   58920
```

```
cggccacgtc ccacatgtcc acaaacacac gtaccacggg tcgatgcacc tccttctcgc    58980
gtatcaaatc gcagtatccc cccaggcaac gaatcacgct gttcacatcg gcgttaagtc    59040
gcgttacgtt caccgacaca gaaacgccgc aactcaaggt actcatccac ttgcacatgg    59100
ccgcccaact ggcgtcacgc gagaaagggt cggccgagat cagaaagtcg tactgcggca    59160
cgcgatcgaa acccacggta gacatggtga aggtggacag cgacagctgc ccatcgcgac    59220
agcgcttcaa caccgattcc aacacctcgc cctcgaaacg cgcatccaga tggaaacgat    59280
agatgcgcga gtgcctactg ttctcgatag cggccgtcaa cgccacggcg atgcgcaaaa    59340
acacgccgcc cgggctctcg tcctgtccgt gcagttggcg acacaccta tccaaacaca    59400 aaatggccgc gtacaagccc cagcaaccgg ccaattccac aaaacgcgcc gtctcctcgg    59460
ccagcttggg tagatcctcc atgtgacgca gcacaaaacg cgcaccgac tcatcgcaca    59520 gctccgaagc gtaacacagt ggcgtgcggc tttcacgcgc ccagttggct ttgaaataaa    59580
agcgacccaa cagcaggtcg caacgcgcg agtgacgaat cagacaggga ccgtggcgca    59640
taatgagctg aaatagcctg aaactgccca accggcact gtgccgcgac acggtgtcca    59700
tctcgcgcca cagcgcgttc ctgtcggacg gcagctcccg cgccggctcc tgtacgccgc    59760
aaaagcgaaa cttgccccag tagccgtgac aatgacactt tttgcccatc aacatgcgcg    59820
tagcttgtat cggcggcgat actttgcaga gcgaagcccc gaaatcgtcc tcctcctcga    59880
cactgtccag ctccatcctg gtcgcgccgg ccggattaaa ggtgctcaga ccgctactca    59940
cgcgtccacc gcgactgggc acggcgggac cgctgtcacg cgtcaacgac agcacagacg    60000
gcgtgccgtc gggagacggc gactcgggac gccaactgac gacgccgcca ccactcgtaa    60060
aacccgctac acatgctaca ccgctcgata cgttggtatt tccagcggac gcttccttgt    60120
cacccccggg cagcggcccc tcctcgagct cgctgtcatc tcccccgata gtatcagcgg    60180
cgacctctgc cgacgattcc tccgtctcgg tttccgcgct gcggcttgga atcctacctg    60240
gccggcaccg atgtgcgggc accgaggaca cccgctgttc ctcgtccgcg tcagccggat    60300
tcataagttt acgaggaaaa taacaaagaa atcaggtaga tttcaataaa gtgagtctag    60360
atggcgccga caactacggt ttataaagtc tgtgtgcgat gtgttttttt cttctgtgtc    60420
tcctccccgt atgctgtcag cgccgctcag acgaattctc gaaagtctcc caattcgacg    60480
ctaaagttgt ccaaacggac gacggacagt ttgagttctt tgtgtaccag gaacgaggtg    60540
tgaatgtcgt cagccaggca ccagcccagc ttttgtatga ccccggtaca cagagggatc    60600
tggcgcgggc gcgtgatgcg acggttgaca aagctacagc gctcgcgggc gaactttccg    60660
cgtgcaacgt cgaccaaggt ctgccagtgt gcgatgctgg aggtgagcac gtagatgccg    60720
ggacgtgttt cgggcccgtc atagtcatag acgatgatta aatacacgta ttgcagccgt    60780
ccccgggtct cttcccacgt caggtacatg tctttcggta tcatcaacgc gaacacctcc    60840
gttttgagcg tgttgtaaag gtagccgcgc atgacgcagg tgagcaacga ggtgatgccc    60900
agcgagacgg tcttgacgca gcccagcgtc tcgaggcggc ggtgcagcag atgcgggccc    60960
aggtccagcc actgcagcgc ggcgcgcgcg gccgaggccg tgtacacgct ttcgagcagg    61020
cagcgcgtgc tggccgagac gttggaggcg cgaatgccta acaggtaaag gctaatgtag    61080
aggtgtcgcg gcgagtcgca acccgtctcc atgcggatga gcagcgcgcc cggctgcgcc    61140
tcgaactcta ccaggccctc gggcacgaag aaacgcgccg tgagcgcctg gtgatcggcc    61200
tggtagagat agcgaaccga tatagtattt acctcgcgtt tggctttgag cgccgtcact    61260
```

-continued

```
agttcattgt cctcgtcggc cgggtcgcgc ggccgtttgg ccaccgcgcg cgcgtccatg   61320
atggcgaggc gcacggtaga tttcaaaaag ttgatagagc agctgcgggc acgggccacg   61380
gacaaagcgg aggcgttaaa taccgtgagc caattggaga tcggcgcggt ggatgcccag   61440
gacgtgaccg cgagcgccgt gcgcgccttc gtgggtgcgt tgccgagctc gggctaccac   61500
tttggcttcg tgcgtcagaa cgtggtctt tacctcctaa gccacgccac ggtacagacg   61560
gcgcgcgacc cgctgtacgc cgccgagcag ttgcacgaac agctggaccg cttcctgcga   61620
caccagcacg acggcggcgg agacgaggac cggttgccgt tctaccacaa cggggccacg   61680
ctgacggctt tccagaagct gttgcagacc ctgcgcgaga tccagaccgt aatagccgaa   61740
cagagcggcg gcaccgcggc ggcggcggac ttgatcgcca gtaacaacgc gtcgaccgag   61800
cgccgcggca agaagggcgg ttcgagttcc gggggccagc agccgctggt ccgccgggtg   61860
atcacgcagc tggaaacggc tgccacggag gcgcggccct acgtcaattg tcgcgccgtg   61920
gccgaactcc tggacctgac ctaccagcgg ctcatctact gggcctgcac gctcatgccc   61980
tacgtgttgt ttcggcgcga caccgacacc gaactggaca cggtgcttct gatgcatttt   62040
ttttacacac actaccgttc ggttaacggc gatttggccg tggagtttca aaactacgtc   62100
aagaacagcg tgcggcacat gagctctttc gtcagttccg atatcgacgg cgaccagaag   62160
cccggtgccg aacacatgcg tgacgtcagc tacaagctgt tcgtgggtaa tctgcaagcg   62220
cgtgacgcca gcggcctcat gtttcccatc attagcacgc gcatctccac cgtgaacctt   62280
tacctgtcgc ccgaacgtat gttttttccac ccgggtctga tctcgcgtct gttgagtgag   62340
gaagtttcgc cgcgcgccaa cctagacgct tacgcgcgcg tgtgcgatcg cgtgctggaa   62400
gaccacttgc atacgccgcg acgcgtgcaa cggctactag atctgacgca gatggtaatg   62460
cgactggtgg aactgggttt caatcacgat acctgcgcgg cctacgcaca aatgcgctg   62520 atccagccgg ccagtcagaa gagctcgctc tttgtcagcg agattcgcga gaaactcata   62580
cagatcatct acaattttta cacgttttc atgtgcctct atgtgtacag ccccacgttc   62640
ctgttcgacc accggcggcg gttgattttg gagcagcatc gatccacgtt gatcggctcc   62700
aaggaggaac tacagcacgt ctggagcaac gtgacactga acgtcaatac gcactttgcg   62760
gttcagtaca cggaagaaga cttttgaggca catacgaagg gtgccacgga ggcggagcgc   62820
gagtacctgt atcgggacct gcacagcaag tggggcgtgc acctgtttac cttgcgtccg   62880
tctcgcggcg cggccggcgc ggcctcgcct ttgcctccgc ttgacggcgt cacacgctcc   62940
gacatcttac gcgaatgcgc gctcgttaat ctgaacgaag gccgcgtcaa ctacgcctcc   63000
ctgctagcct tcagccatca tcccgagttc cccagcatct tcgcgcagtt ggtggtggta   63060
actgagttct cggagatctt tggtatcccg cagggcctgt ttcaagccgt gggttcgccg   63120
cgtcttttcg cactcattca gctgtgccgt gtattgttgc ccgagcaggt gacgctgtac   63180
cagaacctgg tctccatcta caacctgacc accttcgtca agcacatcga cgccgcggtt   63240
tttaagacgg tacgcgattg cgtcttcgac atcgccacga ctctcgagca cctcagcggt   63300
gtacccgtca cgcccaatgt ggacctgctg gccgagctca tggcgcgctc cgtagcgcat   63360
aacctgtaca ccaccgtcaa cccgctgatc gaggacgtga tgcgcagcag cgccggcagt   63420 ctgagaaaact atctgcgaca tacgcgactc tgtttcggtc tggcgcgtgg ccgggcgcgc   63480
ctctcggagg acggcgtgac ggtgtacgtg gaggtacaag gtcaatacgg actacgcgta   63540
cccaccacgc gtttcgtaga acagttgcgc gagctggttc gccgcgatcg gctgttggcc   63600
gagaatctgc gcggcttgaa cgagcgcctg ctgagtgttc gcgtgcgcgt acgtcagatc   63660
```

-continued

```
agcagcgaca cagaggaagt aagccgacac gccaagggtc accgcacggt ggcccagatg   63720
agcaaggcgc tcaaaaagac ggcctccaaa atcaaagtgt tggaaacacg cgtgacattg   63780
gcgctcgagc aggcgcaacg ttccaatggc gccgtcgtta ccgcggtgca acgcgcgcta   63840
gccgtctttg acgtactaag tcgcgagaac ttggaacgcc gcggcgcaca gctctgtctg   63900
acggaagcga cgagcctact gcaccgacat cgcgcgctag cgccgatgac ctggcccgcg   63960
ggcacgggcg ttgcggcggc ggccgaagcg gatcgcgcct tacgcgagtt cttggaggcg   64020
ccctgggaat cggcgcccca accgccgcga ctccgcatga cgcccgacac cgatcacgaa   64080
gaatcaacgg caggcgcgac gtccgtaccg gaggtcctgg gtgcgcgcta cgaacccgca   64140
cacctggccg cgagcgacct attaaactgg tacatcgtcc ccgtaagcca ggcgcagcag   64200
gacatcttgt cttcgatcga cccgcccgcc ggctcgacat cggtgtccct gccgccggcc   64260
tcgccatgaa agtcacacag gccagctgcc accagggcga catcgctcgc tttggagcgc   64320
gagcgggcaa tcaatgcgtc tgcaacggca tcatgttcct acacgccttg cacctgggtg   64380
gaacgagcgc cgtcctgcag accgaggcgc tggacgccat catggaagag ggcgcgcgtc   64440
tggacgcgcg gctagagcgc gagttgcaaa agaagctgcc cgccggcggg cggctgccgg   64500
tctacagact gggcgacgaa gtgccgcgcc gcctggagtc gcggttcggc cggaccgtgc   64560
acgcgctctc gcggcccttc aacggcacca ccgagacgtg cgacctggac ggctacatgt   64620
gtccgggcat cttcgacttt ctgcggtacg cgcacgccaa accgcgtccc acctacgtac   64680
tcgtcaccgt caactcgttg gcgcgcgccg tggtcttcac cgaggaccac atgttggtct   64740
ttgatccgca cagctccgcg gaatgtcaca acgccgccgt gtatcactgc gagggtctcc   64800
atcaggtgct gatggtgctc acgggcttcg gcgtgcagct gtcgcccgct ttctactatg   64860 aggcccttttt tctctacatg ctggatgtgg cgaccgtacc agaggctgag atcgccgcgc   64920
gtttggtctc cacctatcgc gaccgcgata tcgacctcac cggcgtcgtc cgagaaagcg   64980
cggacacggc agcgacaacg accaccgccg caccttcctt acctccgctg cccgaccccca   65040 tcgtcgaccc gggttgccct cctggcgtgg cgcccagcat tcccgtctac gatccctcgt   65100
cctcacccaa aaaacacccc gagaaacgcc gcaaggacct cagcggtagc aaacacggag   65160
gcaaaaagaa accccgtcc acgacgtcca aaacactggc caccgcctcc tcctccccct   65220
cagcgatagc ggcggcctct tcttcgtccg cggtaccacc gtcctacagc tgcggcgaag   65280
gggccctgcc ggccctgggc cgctaccaac agctggtcga cgaggtagag caggagttga   65340
aggctctgac gctgccgccg ttgcctgcca acaccagcg ctggacgttg cacgcggcgg   65400
gtaccgaaag cggcgctaac gcggcaacgg ccacggcgcc gtccttcgac gaagctttcc   65460
tcaccgatcg tctccagcag ctcatcatcc atgccgtcaa tcagcgctcg tgtctgcgtc   65520
gcccctgcgg tccgcaatcg gcggcgcagc aggcggtacg cgcctatctg ggcctatcca   65580
agaaactgga tgcctttctg ctcaactggc tgcaccacgg cctggatctg cagcgcatgc   65640
acgactacct gagccacaag accaccaaag gcacgtactc gacgctggat cgcgcactgc   65700
tggagaaaat gcaagtcgtc ttcgatccct acggacgtca gcacggcccg gcgctcatcg   65760
cctgggtgga ggagatgctg cgctacgtgg aaagcaagcc cactaacgaa ctgtctcaac   65820
gactgcaacg tttcgtaacc aagcgaccga tgcccgttag cgacagcttc gtctgcctgc   65880
gacccgtaga ctttcagcgt ctgacgcagg tcatcgaaca gcgacgtcgg gtgttgcaac   65940
gtcaacgcga ggaataccac ggcgtttacg agcacttggc cggcctcatc accagcatcg   66000
```

```
acattcacga cctagacgcc agcgatctga accgacgcga aattctgaaa gcgctgcagc    66060
cgttggacga caacgccaag caggaactct ttcgcctggg caacgccaaa atgctagagt    66120
tgcagatgga cctggaccgt ctgagcacgc agctgctgac gcgcgtgcac aatcacatcc    66180
ttaacggctt tttgccggta gaggacctga agcagatgga acgcgtcgtc gagcaggtac    66240
tgagactctt ttacgacctg cgcgacctga aactgtgtga cggcagctac gaagagggat    66300
tcgtcgtcat acgcgaacaa ctgagctacc tcatgacggg cactgtgcgc gacaacgtac    66360
cgctactgca agagatcctg cagctgcgac acgcgtacca gcaagccacg cagcaaaacg    66420
agggtcgcct cacgcagatc cacgacctgc ttcatgtcat cgagacgctg gtgcgcgacc    66480
cgggcagccg cggctcggcg ctgacactgg ccttggtaca ggagcagcta gctcagctgg    66540
aagcgctagg cggcctgcag ctacccgaag tgcagcagcg cctacagaac gcgcaactcg    66600
cgctaagccg cctctacgaa gaggaagagg aaacgcagcg tttcctcgac ggactctcgt    66660
acgacgatcc gcccaacgaa cagaccatca agcgacaccc acaattacgc gagatgttac    66720
gtcgcgacga acagacgcgt ctgcgactca tcaacgccgt actgagcatg ttccacacat    66780
tagtgatgcg actggcgcgc gacgagtcgc cgcgaccgac gttttttgac gccgtcagtt    66840
tgttgttgca gcaactgcca cccgactcgc acgaacgtga ggatctgcgt gccgccaacg    66900
ccacgtacgc gcagatggtc aagaaactgg agcagatcga gaaagccggt accggcgcat    66960
ccgaaaaacg tttccaagcg ttacgggagt tggtttactt tttccgtaat catgaatatt    67020
tctttcaaca tatggtcgga cgactgggcg tcggacctca ggtaacggaa ctctacgagc    67080
gatatcaaca cgagatggaa gaacagcacc tggaacggct agaacgtgaa tggcaagaag    67140
aggccggcaa gctcacggta acttctgtgg aggacgtgca gcgtgtcttg gcccgggcac    67200
cgagccatcg tgtcatgcat caaatgcaac aaacgttaac caccaagatg caagactttt    67260
tagacaagga gaaacgtaaa caggaagaac agcaacggca gctactggac ggctaccaaa    67320
aaaaggtgca gcaggatttg caacgcgtgg tggacgccgt taagggcgag atgctctcca    67380
ccatcccgca ccaaccactg gaggccacac tcgagctgct cttgggccta gatcaacgcg    67440
cccaaccgct actagacaag ttcaaccagg acttgctgtc ggcgctgcag cagctgagca    67500
aaaaactaga cgggcgaatc aacgagtgtc tgcacggcgt gctgacgggt gatgtagagc    67560
ggcgctgtca cccgcaccga gaagcggcta tgcaaaccca agcctcgcta aaccacttgg    67620
accaaatttt gggtccgcaa cttctgatcc atgagacgca gcaggccctg caacacgccg    67680
tccatcaagc gcagttcatc gagaagtgtc aacaggcgca tccaactaca gccatcacgg    67740
gcagcgagtt cgagggcgac tttgcacgct accgcagcag tcaacagaag atggaggaac    67800
aattacaaga gactagacaa cagatgaccg agactagcga gcggctagat cgctcgctgc    67860
gccaggatcc cgggagcagc tccgtcacgc gtgtacccga gaaacccttc aagggtcagg    67920
agctggcggg tcggatcacg cccccgcccg ccgacttcca gcagcccgtt ttcaaaacgc    67980
tgctagatca gcaggccgac gcggcccgga aagcgctcag cgacgaggcc gatctgctga    68040
atcagaaagt acagacgcag ttgcgacaac gcgacgagca gctgagcacg gcgcagaacc    68100
tgtggactga tctggtcacg cgccacaaaa tgagcggcgg actggacgtg accacccccg    68160
acgccaaggc gctgatggaa aagccgctgg agacacttcg cgagctgttg ggcaaagcca    68220
cgcaacaact gccgtacctg tcggcggaac gcacagtgcg ctggatgctg gcctttctgg    68280
aggaagccct tgcgcaaatc accgcggacc ctacgcaccc gcatcacgga agcaggaccc    68340
actaccggaa cctgcaacag caagctgtcg agagcgccgt gacgctagcg catcaaatcg    68400
```

```
aacaaaacgc ggcctgtgaa aattttattg cacagcatca agaggcgact gccaacggcg   68460
cgtccacgcc gcgggtcgac atggtccagg cggtggaagc ggtctggcag cgactggaac   68520
ccggacgcgt agccggcggc gccgcgcgtc atcaaaaagt gcaggaactg ttgcagcgct   68580
tgggtcagac gctaggcgac ctagaactgc aggaaacgtt ggcgacggaa tactttgcgc   68640
tgttacacgg aatccagacc ttcagctacg ggctggactt tcggtcgcag ttggaaaaga   68700
tccgcgatct gcggactcgt tttgcggaac tggccaagcg acgcggcacg cgtctctcca   68760
acgagggagt cctgcccaac ccccggaaac cgcaggcgac gacttcactg ggcgccttta   68820
cacgcgggtt gaacgcgctg gaacgacacg tccagctggg tcaccagtat ctgctcaaca   68880
agctcaacgg ctcatcgcta gtctataggc tggaagacat tcctagcgtg cttccggcaa   68940
cacacgagac cgaccccgcg ctgataatgc gcgaccgcct gcgtcgccta tgcttcgcgc   69000
gtcaccacga caccttcctt gaagtggtag acgtcttcgg catgcggcaa atcgtcacgc   69060
aggccggcga acccattcac ctggtcaccg attatggcaa cgtagccttt aagtacttgg   69120
cgctgcgaga cgatggtcgg cccctggcat ggcggcgccg ctgtagcggc ggaggactca   69180
agaacgtcgt caccacacgt tataaagcca tcacggtagc cgtggccgtc tgtcagacat   69240
tgcgcacttt ctggccacag atctcgcagt acgacctacg accctacctc acgcagcatc   69300
agagccacac gcaccccgcg gagactcaca cgttgcataa ccttaagctc ttttgttatc   69360
tggtgagcac cgcctggcac cagcgcatcg acacgcagca ggagctgacg gccgccgatc   69420
gcgtaggcag cggcgagggt ggtgacgtag gggaacagag accgggccgc ggtaccgtgc   69480
tgcgcctgag tctgcaagag ttttgtgtac tcatagcggc tctgtacccc gagtacatct   69540
acaccgtcct caaatacccg gtgcagatgt cactaccctc cctcacagct cacctacatc   69600
aggatgtgat acacgcggta gtcaataaca cacacaaaat gcccccgac cacctccccg   69660 aacaggtcaa ggccttctgt atcaccccca cccaatggcc cgccatgcag ctcaataaac   69720
tgttttggga aaataaactg gtacagcaac tgtgccaggt aggcccgcaa aaaagcacac   69780
cgcccttagg caagctatgg ctctacgcca tggccacgct ggtctttcca caagacatgc   69840
tgcagtgtct gtggctagaa ctgaaacccc agtacgccga catacgcc tcggtgtccg   69900 aattggtaca gacgttgttt cagattttca cgcaacaatg cgaaatggtg accgaggggt   69960
acacgcaacc gcagctcccc accggagagc cggtgcttca gatgatccgc gtgccacgtc   70020
aggacacaac caccacagac acaaacacga ccacggagcc gggacttta gatgttttta   70080 ttcaaacaga aaccgcccta gactacgcgc tgggctcctg gcttttcggc ataccgtgt   70140 gtctcggcgt gcatgtagcc gacctgctga aaggccaacg tatactagta gcgcgccacc   70200
tcgaatacac gtcgcgagac cgcgacttcc tccgcatcca acgctcccgg gatctcaatc   70260
tcagtcaact gctccaggac acgtggaccg aaacgccgct ggagcactgc tggctacaag   70320
cccaaatcag acggctacgc gattacctgc gtttccccac ccgcttagag tttattcccc   70380
tagtcattta caacgcacag gaccacaccg tcgtacgcgt gctgcgaccg ccctccacgt   70440
tcgaacagga ccacagtcgg ctggtgttgg acgaggcctt ccccacccttc ccgctgtatg   70500 accaagatga taactcatcc gcggacaaca tcgctgcgtc tggcgccgct ccaacaccgc   70560
cggtaccttt caaccgcgtg ccagtcaata ttcagtttct gcgtgaaaac ccgccaccca   70620
tcgcgcgagt tcagcagccg ccgcgccgac atcgtcatcg agcggccgcg gccgcagacg   70680
acgacggaca gatagatcac gtacaagacg atacatcaag gacagccgac tctgcattag   70740
```

```
tctctaccgc ctttggcggg tccgtctttc aagaaaaccg attgggagaa acaccactat   70800
gccgagatga acttgtggcc gtggcgcccg gcgccgccag caccagtttc gcctcgccgc   70860
ctatcacggt gcttacgcag aacgtcctca gtgctctaga aatactgcgg ctagtgcgat   70920
tggacctgcg acaactggcg caatccgtac aggacactat tcaacacatg cggtttctct   70980
atcttttgta accgacactg acagtagcgg gtaataaaaa caataggatt tttatcgttt   71040
ttttatgtta caaaacaacg tatcactttc acggtgattt attcttgcta ttccttttcc   71100
ccttgggctg tcagcgccgg gtgcgcgaca cggctaccat gcgcaacagg tccagcttaa   71160
aggcgcactt gtcattaaac aggctggaca tgcgcgtgta cttgctcagc atggtggcca   71220
acaccgggtg ggtggcctct gatatctcgg tcggcagctc caaaacgacg ttaacgacgt   71280
gacggtgttt ttcgtcccgc ttgttggcca ccgtgggtcc cggcgcggtg ttagacatgg   71340
ggcaggccgt gggggagga cgaagaggaa gccgctgcta aaccgccgcg cgcctgctgc   71400
acaatgtggc cgccgacgtg gcaggcggtc tgtttaacca gcgcgcagcc ccgacacagc   71460
ggggcgccgt cctcgctttc caaacagctg tcgcggtact cgcccgtctg acagcgcgcg   71520
cacagcaggc cgtgcccgtg cgaagtgagg cgcaggagac gcgggaccgt cacgtcgcgt   71580
accaccacag tggagtcgca ggtgcgtgcc gcgcagggca gaatgacgtc gaaagccagc   71640
cggtgatcgt acacggcaca agccgcgttg aggcccagca cggctttcca gcccacgcgt   71700
acgcagcgct gtccaaagag cgtctcggag acgagctcgt agacgcgctg ccgcaccacc   71760
cgctgactgc cgcagagcga gcagtgcacg agctcggcgt gcgtgttgaa gatgacgctc   71820
ttttcttgac ggtcccgata atagaacatc gagttgagcg gaaagttttg ctggcagtgt   71880
agcttttcct tacccaggtt gaggcagtgt ccgcactgcc gacagaccac ggccaccagc   71940
gagcgcgcgt ccagatggcg ctcgcacttg agtcgacaca gaccagag cggcaggtcg   72000 atgacgctgc cgatgaggcc gccgcgcagc gcggcgctga gtgcaaagag gacgatcttg   72060
gtgggctcta cgtgacgcgc ctgctgtccg gcgcccgcgt gtcctaccgc cgcagctgcc   72120
gccgtcgagc ctcctccgcg cgtctcgtcg tgcagaccca gtgcccgcaa cggcaccagg   72180
tatcgcggac acgtgtcgca aaacgtctgc accgcttgtc gggccagtac gtagagcggg   72240
tttccgcagg gtaccttccc ggcgtaccgg cgcaaggctg cgatgaggcc ccgcaactgc   72300
ggcgaccgcg gctgccgttg gtgacaccac tggttacggt ggtatacggc caaatcagcg   72360
cgggcgtcga agcgcttggc gcgtagtaat gctaggcacg gcgagctggt ggggtgaagc   72420
acgggcagcc gaaggtccac cccgaaaagg aaacggtgaa ggtcacctag cagcgaggcg   72480
gtgacaccgt ccaacaacgc gtgcagccgc tcgggcgggt agagccgcag acggcgcagc   72540
aggtagtcgg tgtcgtagcg ttcgaaacgc agaaaggcca tcgtgcggac ggccacggtg   72600
tgcagacagt ccatgctgta gacgtaagcg agaaacacaa gtagggctt ggtcataacc   72660 atacgctgaa agagcgccgt caccgcctcc cgctcggctt gccgacacac cagccattcg   72720
cgcaggaagc gttggtagag acggtcgccc agctcgcgat tcagaaagcg cttatccgtc   72780
acgaagagat gaaggacgca agaacgtggc acgtgatgca ccagctgctg ctggaggacc   72840
gccgacgtct cgcgccgcaaa ctgcgccggt ggctgcgacg tttctaccgc cgcttcctcc   72900
ggctgcagcg caccgcggcc gatcaccagc tgcacatgga aatggtcctc gtgaacgcag   72960
aggggcgcga agagacggcg cagagcctgg tggaactcat cagtcgcggt gtgcggagcg   73020
tgtcggagac gacgactggc catgaccgcg ccacagcaga gccagcacca gcagaagagc   73080
cagcaccagc gggcccagag tcgcaaagcg cgcgggcagc cacggcccag actgcggtcg   73140
```

```
cgatggcccg gagcgcgctc gccaccacga tgacggtgcc caacgataac cagtccgctc   73200
caaggacggc gcgcacggcg gagacggcgg atgacggtga tgggtcgaca cccctcgccg   73260
acgactcacg tgctcctcca gaggccgacg cgcggaccct ccgacgtcct ggcccgccgc   73320
tgccgctgcc gccttccctt ctcccgccag agccagcaac tcctcctcct cttcatcagc   73380
gtctccctcg cttgcgcatc cgcatcgtcc catacaggcc tcacaacgac acagccgcca   73440
cgaccccgcc gccatgggtg gcggcggcgg ccgaggcccg gcagcggcgc cgccagcggc   73500
gaccatggtg ggagagcaac tcggatgacg aggaggagga gggggagatg cggtccgaga   73560
ggaccgcttt cccgccgttc gcgtaagcgc ggccgacatg cgggcgcgcc acagggacgg   73620
accgctgccg ctgtgactgc ttacggtgac gtggttccgg accgccaacg acgtcgacgc   73680
ggctttcttg gcgtacagct cgcgcagcag attctcgtac tcgccctcgt tttcgggtcc   73740
gaaggcgatg agctcgatgt tgaagaccga cgccgaattg gatttgcgca ccacgcactt   73800
cgtcagcact ccgtaggccg agggcttgat ctcctcgatg tccttgagcg tgacgatgag   73860
cgactcgttc accttaagca cattgaactc acctacgtgg cgcgccggcg aaacgagctt   73920
gacgggcgct cgtacaaaac agcagaggga gacggcgcag ccagtgtttt taaagataaa   73980
acaaggcacg tggtctgtgc ggctctccca gtagctgagt agatactcga cacaatagac   74040
cgtgtctgtc ttgagcatgg cgtcgcacac cgagtaattg gggttttttac agatgaggcc   74100 ggcatcggtg acgcgcagct cgctgggacc caacttgagg atacgccgcg tggcctgcac   74160
cagatcctga tggagaacct tgttcatctc catcgcaccg acgccaccgc cgatttattt   74220
acccggcgcc gactcgtctt ttccctccag gattccgtta atgtccatga gcttgctgac   74280
gatcgccgtt aatagttgcg tcttctcacg gaggatctct ccgtgactgc aggtcgcgca   74340
gtcgccgtgc acgtacttga ggaaggcggc gtacttctga cccgcgttca cgaaatttaa   74400
gcgcgcgtcc agagagggca gcaacagatc gtagacgcgc ggcagcatcg gctcgaactg   74460
taatagcaga tcgtcgtcaa gatcgggtag cgcgtgtccg tcttcaccgt cctcgtcgtc   74520
accacctccc ccctcgagcc caccgctcgt accagccgcg ggctccgcgt cctcgtcgat   74580
caccagcggt cgcgtcggca ccggagaatc cacgtcatcc tgcacgtcgt tttcctcctc   74640
tccgtcgtca tcgtccagaa acggcacccg ctgcttagcc caggattccg gttttagaag   74700
ctccacatcg aagacgagag tggcatgtgg tgggatgatg cctgggtgcc cagtggcacc   74760
ataggcataa tctggagata tagtcagttt ggctctctga cccacactca tctgggcaac   74820
cccttcttcc cagcctcgga tcacctcctg cttgcctagc ataaacttaa agggcttgtt   74880
tctgtcccgg gaggaatcga ctttctttcc atcttcaagc atcccggtgt agtgcaccac   74940
acaggtctgg ccgcgcttgg ggaaggtgcg cccgtctcct ggggagatgg tttccacctg   75000
cactcccatt ctttttttccg cgtcctcaat cagcggcgcc gatcgccatg aatccgagta   75060
cccacgtgag cagtaacggc ccaacgactc ccctcacgg gccccacacc acgtttcttc   75120
ccccgaccag cccggccccg tccaccagct ccgtcgccgc cgctaccttg tgcagtccgc   75180
aacgacaggc cgtttcgcgt tacagcggct ggagcaccga gtacccccag tggcactcgg   75240
acttgacaac tgagctgcta tggcacgcgc acccgcgtca agtacctatg gacgaagcgc   75300
tggccgccgc ggcggccgcc tcataccagg taaatcctca acaccccgcc aaccgttacc   75360
gtcattacga attccagacg ctcagcctcg gcacctcgga ggtagacgaa ctgctcaact   75420
gttgtgcgga agaaaccacg tgcggcggca cgcaatccac cgtactcacc aatgcgacca   75480
```

```
acaccactag ctgcggcgga gccgtcgccg gcagtagcaa cgtaggaccc gccggcgctt    75540
cggccgcctg cgacctagat gcagaactgg ccggcctcga aacctcggcg gccgactttg    75600
aacaactgcg gcgactgtgc gcgccgctgg ccatcgacac gcgctgtaac ctatgcgcca    75660
tcatcagcat ctgcctcaaa caggactgcg accagagctg gctcctcgag tacagcttgc    75720
tgtgcttcaa atgcagttac gcgccccgtg cggcgctcag cacgctcatc atcatgtccg    75780
agtttacgca tctgctgcag cagcactttt ccgatctgcg catcgacgac ctgttccgac    75840
accacgttct cacggtcttc gatttccacc tgcactttt catcaatcgt tgctttgaaa     75900
aacaagtggg cgacgcggtt gataacgaga atgtcaccct gaaccatctg gccgtggtgc    75960
gggccatggt catgggtgaa gacacggtgc cttacaacaa gcctcggcgc cacccgcaac    76020
agaagcaaaa aaacaaccct tatcacgtcg aagtgccgca agaactgatc gacaactttc    76080
tagaacacag ctcacctagc cgcgaccgct tcgtgcagct gcttttctat atgtgggccg    76140
gcaccggcgt catgagcacc acgccactca cggaactcac gcacactaag ttcgcgcgac    76200
tagacgcgtt atccacggcc tcggaaagag aagacgcaag gatgatgata gaagaagagg    76260
aggatgaaga aggaggagaa aaaggaggag acgatccggg ccgtcacaac ggcggtggca    76320
ccagcggggg gttcagcgag agcacgctaa aaaaaaacgt gggtcccatt tacctatgtc    76380
ccgtacccgc ttttttttacc aagaaccaaa ccagtaccgt gtgtctgctg tgcgaactca    76440
tggcctgctc ctattacgat aacgtcgtcc tgcgcgagct gtaccgccgc gtcgtctcgt    76500
attgtcagaa caatgtgaag atggtggacc gcattcagct ggtattggcc gatctgttgc    76560
gcgaatgcac gtcgccgctc ggcgcggcac acgaggacgt ggcgcgctgt ggactcgaag    76620
cacccacctc gcccggaggc gactcggact accacggcct gagcggcgtc gacggcgcac    76680
tggcgcgacc cgacccggta ttttgccacg tcctgcgtca ggcaggcgtc acgggcatct    76740
acaagcactt tttctgcgac ccgcagtgcg ccggcaacat ccgcgtcacc aacgaggccg    76800
tgctcttcgg acgcctgcac ccccaccacg tccaggaggt gaaactggcc atctgtcacg    76860
acaattacta tataagtcga cttccgcgac gtgtgtggct ctgcatcaca ctcttcaagg    76920
cctttcagat tacaaaacgc acctacaaag gcaaagtgca cctggcggac tttatgcgcg    76980
atttcacgca gctgttggag agttgcgaca tcaagctggt ggaccccacg tacgtgatag    77040
acaagtatgt ctagcgtgag cggcgtgcgc acgccgcgcg aacgacgctc ggccttgcgc    77100
tccctgctcc gcaagcgccg ccaacgcgag ctggccagca aagtggcgtc gacggtgaac    77160
ggcgctacgc cggccaacaa ccacggcgaa ccgccgtcgc cggccgacgc gcgcccgcgc    77220
ctcacgctgc acgacctgca cgacatcttc cgcgagcacc ccgaactgga gctcaagtac    77280
cttaacatga tgaagatggc catcacgggc aaagagtcca tctgcttacc cttcaatttc    77340
cactcgcacc ggcagcacac ctgcctcgac atctcgccgt acgcaacga gcaggtctcg     77400 cgcatcgcct gcacctcgtg cgaggacaac cgcatcctgc ccaccgcctc cgacgccatg    77460
gtggccttca tcaatcagac gtccaacatc atgaaaaata gaaacttttta ttacgggttc   77520 tgtaagagca gcgagctact caagctctcc accaaccagc cgcccatctt ccaaatttat    77580
tacctgctgc acgccgccaa ccacgacatc gtgcccttta tgcacgccga ggacggccgg    77640
ttgcacatgc acgtcatctt cgaaaaccc gacgtgcaca tccctgcga ctgcatcacg      77700 cagatgctca cggcggcgcg cgaagactac agcgtcacgc tcaacatcgt gcgcgaccac    77760
gtcgttatca gcgtgctgtg tcacgccgtc tcggccagca gcgtcaagat cgacgtgact    77820
attttgcaac gcaagattga cgagatggac attcccaacg acgtgagcga gtcctttgag    77880
```

```
cgctacaaag agctcattca ggagctgtgt cagtccagcg gcaacaacct atacgaggag    77940
gccacgtcgt cctacgcgat acggtctccc ttaaccgcgt cgccgttgca cgtagtttcc    78000
accaacggct gcggcccctc ctcctcgtcc cagtccacgc cgcctcatct ccacccgccg    78060
tcgcaggcga cgcagcccca ccactactct caccaccagt ctcagtctca gcagcatcat    78120
caccgtcccc agtcaccacc gccgccgctg tttctcaaca gcattcgtgc gccttgacac    78180
tgtacggcag aaaagccggc tccaagtgca agcgccgcgg cagcaccatg tgcaaaaact    78240
tgtccttgcg cgcggtttcg ccgccgggaa agacgggcga cagcacgtta gttacagcct    78300
tgagaacctg ctcaaagtac ttgtcggcgt gaatgggcac gccgtgctcg cgcacgtagc    78360
tcggatcttc ggctacctcg tagttgcaca cggccgacgg tggtttccgc gccctcttct    78420
ttgccggctc tcctcctctc ctgttgctct cctctacccc gccgccgtca gcgtcgtcgt    78480
ccgtgccatc aatcgcgtcc gaccgggaaa ccacgccggc ggttacagaa tcaccgttgt    78540
cggaggaacc ctgcggcgcc gtccggacac cgggcgccgt cagaacgtaa aagacccgat    78600
ccccgaccga gggtagctcc tcagaacggg ccgccaatcg cttaatgacg gcaatgtgcg    78660
gcaggttaga ttgacggtac agcgagatgt ccttagagag caccgacgaa agcaccaggt    78720
cctcgacacg cacacggtgc aggtacagat cgtcgcgggc ctgcaccaag cggcgtaaga    78780
tacgccagaa accgcgtggc acgccgtact tcttgacttc atcgagtgag aggcgcgaca    78840
ggcgcacggc tgcttccgag acctcgcgat cctcaaagag cagcgagagg acgtcacgcg    78900
tgacgccctt gacgaactcg caggccgtct tgcgcaccag atccacgccc ttcatgctca    78960
gacccgaggc gccctccact ttgccgatgt aacgtttctt gcagatcatc ataagagaga    79020
cgaagacctt ttcaaactcc agcttgacgg gctccacaaa aagacaggcc gtcacgtagt    79080
gcgccaggct gggcccacgc gccaccagag cctgcggcgt caggccacga aagcggacaa    79140
acacgctgtc cgtgtccccg tagatgaccc gcgcctccac ccgccgttcg ttcgagcccc    79200
ctgacgatgt ttcgagcccc tccggtaacg cgctgctctc ctccgaatcc ccctcccgcg    79260
ttcccactac atagtcttcc tgattaaaaa aattgtgcaa aaaacacggc tctgaaaagt    79320
tgtctttgat gaaccgcgcc gtgcgctcta gcatgtcgcg accgatgcgc gtgatgctgg    79380
cggcgatggg cagacacggc atcataccgt tgaccacgcc ggtaaaaccg tagaaagcgt    79440
tgcacgttac tttgagcgcc atctgttcct tgtcgagcag catacggcgc acagggtctt    79500
gacactcgcg catgcattcg cgcacggcac gccgctgcga aacccacttg ttgagcagtt    79560
ccgagagcac cgagacgcgc accgaagcac gcacaaagcg gtgggtcacg ccgttctcta    79620
gcgtgacgct gtatacgtcg gcggggtcca cagggtactc gccacccggc accagcaggg    79680
tggagtagca gaggttgtgg gccatgatga tggaagggta gaggctggca aagtcgaaca    79740
cggccacggg gtcgttgtag taacccacct cgggctcaaa caccgtggcg ccctggtacg    79800
aaaccgccgc agtaccgccg gcgccgtgat tgtcgttgga aacgccgacg ccgccactac    79860
tgccggagcc gacgctgaaa acgccgacgc tgctactact gttactgccg gagccgggtg    79920
aaacgccgtc ctgactggac ggcgcagatt gcaagggcgg cgacatctga acatagccg    79980 ccacagaacc cgcgtcgccg ggcacagcgg cggtagagat gatagcagcg ttaggtgaca    80040
cagcaacgct attcgtttcg ggcaccgtcg tacctttgct gtagtggttg ggcaggataa    80100
aatcgcggca ggcgcactcg tccagcagcg aggtgtagat acggatctgc tgtccgtcaa    80160
agatgacacg ccgcaacgga attttagcca gccgcgcgat ggccccggcc tcgtagtgaa    80220
```

```
aattaatggt gttgaacaga tcgcgcacca atacggcgtc ctgcagacag taacggccta    80280
cctgggcgcg gccctcggca ttagccacga aacaacgcgg gatgtccttg taagacaggt    80340
catccttgcg ttgccgcagg taaagctcgg ccatagtgtt gagcttatag ttgggcgagt    80400
tagtcttggc catgcataca gggtacatgt cgataaccac cgaacccgca atatacacct    80460
tggtggcggc cgtgctggcc ggattgttgt gagaagccga gggaaaagcg gcggcgtact    80520
gccgcttaaa acccacggcg gggctgtgta aaagaaacg gccgccctgc gccgtaggca     80580
acttgcagaa gcgctgcgag tccaccttat acaggtactc gagacgcgtg aggatgtact    80640
tcaagtcaaa agagttgatg ttgtaaccgg tcacaaaggc cggcgcgtac cgttgaaaga    80700
aaagcataaa gcccagcagc agctcgtatt cggaagggaa ctcgtagacg tccacgtctg    80760
ggcccacctg cccgcaggtg ccgatcgtaa agagatgaag acccgagtgc ccaaagatca    80820
caccctccga agtgcagccc cgaccatcgt tcccgtttgg gatccctga tccacggcgg     80880 tgtttccccc cgtctcgtag cacacgcacg agatctgaat gacaatgtca tcggacttct    80940
cggcgcaggg aaaaccaccc tcgccgctca tgcactcgat atcgaaggac aggcatcgat    81000
agcgcggcca cgagctgtcg tcgggcacag ccaccaggtc agagacatcg cagtctacct    81060
cgatatcaca agtcgacgcg cgaccctgct gccgccagtc gtaacgattc acggagcacc    81120
agccgaacgt ggtgatccgc cgatcgatga ccaaacgcgt cagcggatcc acacggacct    81180
cgtacacggg aaaaccctgc tccagcagat actcgccgat ttttctggcc atggtccagt    81240
tgctgataga cacacactgc aaatcgggca cgggtcgcgt cccgtaccca tagatggagg    81300
tcttggtggc cggcgtgaca gacacggcgt atggcgtccg cggttcgggc actagttcgc    81360
ccacgctggc aatgaccctca cgcagcctat cggtgtcgct gtactcacag taaaagtagc    81420
tgcgctgccc gaaaacgttg acgcagatac tgtagccgtg ttctgtggcc ccgaagaaac    81480
gcaacacgtt ccccgaaggc accagatgct gacgatagcg cggcgacacg ttttcgggcg    81540
agtcgaagaa gagcacggcg tccgtctgat cgtaggtgtg aaaacgaata ggtcccacca    81600
cgcgacccac cagggtctcg cgccaaggac acggccaaac catgtcatga ctcaacaaat    81660
gtttaatctc tcgatagaac atgagaggca gccgtcccgt cttatgcttg atcaaccccg    81720
tctgaccgtc gaacatgaca cctcgcggca cgatctgcaa aaactgtttc tgtggcggcc    81780
gcttgcccga gccctgcgcg gagccgggct gcgaacgctg acgccggcca cccgcgaccg    81840
caccgccggt cacgccgccg ctcagatacg ggttgaaaaa catagcggac cgtgagaggc    81900
tgacagctta cgaagcaaaa tcacaaagaa aatacacatg cagcacctag atatccagtt    81960
taaccccgta tatcacaagt ctctgtgtca atatttttg tctagttttt ttttcctcct     82020
ggttcagacg ttctcttctt cgtcggagtc tttcaagtgt ctgtagccgt ttttgcgatg    82080
tcgcagccgg tctagcaggt taggcttctg tcccttgtcc tgcgtgccag tctgtccgtc    82140
caaagaatct gtaccgttct gctgcgctcg ctgctctgcg tccagacggg ccagggccag    82200
aagcatctgg taagcctgct cgttggtgta aggcggagcc gccgtggatg catcagacga    82260
cggtggtccc ggtcctttgc gaccagaatt ataaacactt tcctcgtagg aaggcggagc    82320
ctgtaacgac gtgtctttgg tgctgcccga cgtcacggtg gtcccgtcgg cggacaccag    82380
atagggaaag aggttctgca gcggctgcgt gcacagacgc cgctgtcgag tatagatcaa    82440
ataagtgata atgactacgg ctatggccac gaggatgatg gtgaaggctc gaagggggtt    82500
tttgaggaag gtgcaacgc cttcgaccac ggaggccacc gcgccaccca cggccccaat     82560
ggctacgcca acggcctttc ccgcggcgcc caggccgctc atgaggtcgt ccagacccctt    82620
```

```
gaggtagggc ggtagcgggt cgactacctt gtcctccacg tactttaccc gctgcttgta    82680
cgagttgaat tcgcgcatga tctcttcgag gtcaaaaacg ttgctggaac gcagctcttt    82740
ctgcgagtaa agttccagta ccctgaagtc ggtattttcc agcgggtcga tatccagggc    82800
gatcatgctg tcgacggtgg agatactgct gaggtcaatc atgcgtttga agaggtagtc    82860
cacgtactcg taggccgagt tcccggcgat gaagatcttg aggctgggaa gctgacattc    82920
ctcagtgcgg tggttgccca acaggatttc gttgtcctcg cccagttgac cgtactgcac    82980
gtacgagctg ttggcgaaat taaagatgac cacgggtcgt gagtagcagc gtcctggcga    83040
ttccttcacg ttcatatcac gcagcacctt gacgctggtt tggttgatgg tcacgcagct    83100
ggccaggccc aagacatcac ccatgaaacg cgcggcaatc ggtttgttgt aaatggccga    83160
gagaatggct gacgggttga tcttgctgag ttccttgaag acctctaggg tgcgccgttg    83220
atccacacac caggcttctg cgatttgcgc cagcgcccgg ttgatgtaac cgcgcaacgt    83280
gtcataggtg aactgcagct gggcgtagac cagattgtgc accgattcca tgctggacaa    83340
atgagttgta ttattgtcac tcgtacttct tctggtccta tgagtgatat tcagactgga    83400
tcgattggcc aaacgttcca attccaccaa agatttttgc ttgatgcctt gccagaacac    83460
caccagaccg ccgctggttt cgaagacgga cacgtttccg tatttttcat atgtttgatt    83520
gtatgaagta ttgaaaatct gctgtaactt atttatagcc tcatcacgta cgcagtccag    83580
cgcggagtcg gacatgttca cttcttgttt cttagacaga aaagttgcag tcattttggc    83640
agaagaaaag tggtacgagt cttcggcttc ggaacggata gtacgttccg aggcttccca    83700
gaaggtgagc tggcaggtga cattcttctc gtcctgtata tcccaagaga tcaccgagtc    83760
ggcacgttcg agaaaagcca ccaacctatg ggtttctggc gcagcgttgg gtcttccaaa    83820
gtcggaaacg atggtgtagt tcgggaaaat gaaaaacttg tcggcgtttt ctccaaagta    83880
gctggcattg cgattggttc cgttgtagaa aggagaaatg taaaccacat cacccgtgga    83940
agttgcaaaa aaatgataag gatacttgga gcgcgcagta gtgatggtca gcatacagtt    84000
cagattacag gtctcacgat agagccaggt gctgccgcgg ctgtgccact gatccttgac    84060
cgtcacgtaa cgggtactgt gggtgttgga ataatcgtcg ggaattaatt gcatggtttt    84120
gttttcataa ctgtccctat gatatgccac gaaaaccgtg cctcctataa cgcggctgta    84180
ggaactgtag cattgagcaa acttgttgat gtgatgaatc tcccacatag gaggcgccac    84240
gtattccgta ttgctgccca gcagataagt ggtgtagatg taagcgtagc tacgacgaaa    84300
cgtcaaaacc ttttggtaga cccgtacctt aaaggtgtgc gccacgatgt tgcgcttgta    84360
gaccaccatg atgccctcat ccaagtcttc attgataggc ttcatcgagg tgcagatgat    84420
attacgttca aagcgaataa gatccgtacc ctgggccata aacacacgc gatagggta    84480
cttggtagtg ttgactccca ccacatctcc gtacttgagg gtagtgttgt agatagtctc    84540
gttggctcta tgactgacgg cttcagaaga cgttacgtgt tgagaataga ctgaccgggt    84600
ttgagcagac gtcgtacgag aagtatggct tccattgtga gtagaagaag ttgcatggga    84660
agtactagaa gaggaaaccg cagcacccag acagacgata cacaggttaa cgcagactac    84720
caggcaccag atcctggatt ccatgttcgt cgcgggccaa atccagcagc gatgaggcgc    84780
gtcgtggtct cttgcgtgtc gcgcggaccc tccgggaaac acccgcagtc gaggaggagg    84840
gatacggact tggcagccaa ggtcggtccg gctccctgaa gacacccgag acggccgcgg    84900
cggccgtcag ggtggagggc ttggccacgg gagctgttgg cacgtcgcca ctctcatccg    84960
```

```
gtctggacag atgcctgtag aggaggagat atagatcttt ggacttataa agacttcctt    85020
cgtgacgaag cagcagcggc cactctttgt tatacgtgag aatcacatct ctgtccgggt    85080
gcagttcgtc gcgcaggcac gcgatcgaga gttgtttccc gaaagtttca ttatatagtg    85140
cgacggagag cacgagctcc cgcacgtgca tccacatctc cttctgcagc acgtttaggt    85200
cctgacagtc cgaaaaattg aaaaaaccca tatacttcac caccatccac tcactgggat    85260
acacggtacc ttccgcgcat ttgaccaaat cgtccttgac gtggggtagt acgcccgcgt    85320
tgtcgcaggc ataggccatg tccacattgt gagagagggg ataacgatcg gtgcagtggg    85380
tgaagagggg cccgttacac aactcgtaga tctgctgacc cagtagcggg agggattcca    85440
caggcagact cttgtggatc aggttattga ccacatacag gtgctcatcg taggtgaact    85500
gatcacccac gtccaccacg tcttggtcct ggtggtattg gctgcggtac agaaacccat    85560
tcatgagctt agagataaag tccagacaca agggccccac tagattgaca tcgatgagct    85620
tgctagtcag acgctcctgc gttttgatgc aacggatcac cttgccatag cccacctccg    85680
agaccttctg caggtaggcg cgtttgcgca cgttcacctc gcgagtgacg ttgtggatgc    85740
gggagcgcgc gtccaccaag tcgagagcct cgtgttcgtc gcagttgcgc acccgtaagc    85800
cgttctcgct gccgtcgccg tcctgccccat tcaccctcc ccctaccact ttcttgcctc    85860
ctccacgagc ccggccgccg ccaccgttat tcctctgact gtgagtactg ctgttgctgc    85920
tgttgctggc cgtcatcaaa gtcgtacccg tccccgacat cgcctcccgt ccacgcaggt    85980
gaatagcctc gccctcgggg ccgtcgcccc ccgtgccatc tggcagcgga cgtcgaatct    86040
cctcgagaat atgcttgatt ttggtgtaca tctcgttgct ttcgtggagc ttgttgaaca    86100
ccgggttgtc ctcgaaagct tgaatgctga gggatgtgat gaggtcgatg atcctgttgg    86160
gggcggcaaa gaccgacccc acgaacatgc gctcctcccc gtccaacgcc ttttccccga    86220
gcacgaagat gtcctccacg tcctccccgt acagatggcg actgatgccg ttcatgagcg    86280
cccggcacag ctggtgatac acatttagct gctggatggt gatgcccacc cgcttgacga    86340
taacctccga ggtacgggac cagtaggtaa aatccgacaa ggaatatatt cgttccggta    86400
tatccgtaaa caggttgtac tccctcagcg cctcctccgc ctcctggatg tagctgtggt    86460
aggccgatga agaagagaat aggcttttga gggccgaaag gactccagcc aagtggggga    86520
tgcgcgttgt caggtccagc aggtcctgct ccaccgtctg gatattcaca tcggactggc    86580
ttgacggacg gtggaccgct atatggttgc acagcaagcc ctgcagccgc ttgttcagcg    86640
agcggccctg attcgggatg atggtcagct cctcgtagca ttgggcgcat gtcgtccctt    86700
cgacgtacac ttcctgacgc gccaccggcg agatgccgca taggcgacgg aggagctcca    86760
gcaactgcgc gcagacctcc aggccggcct ccggcgccag gatcccgtac acgtagttca    86820
ttttgcacag gaagcgctcg atgtcgttga gtgtggccag actgacgctg aaacggacgt    86880
tgtccgtaaa ctggagctcc acggtgtgat ggcgatcgca gcgatccaaa cggaggacgg    86940
tacggtagaa ggccgcccgg tccggctggc gcgagtaggc catcagcgcc cgatccagca    87000
aagccgtatc ctcgtgcagc gccttcagca gcatctccag gtagagcgtc agcaacgaac    87060
tctgcgtacg attctgcgcc accacctccg ggtagatctt ccggtacaga tacactatag    87120
ccgccgcgtt tctcttgaac ggcgtggact ccgccagtaa cacgttcgga tcgcagtact    87180
ttagacactc cagctccatg gcgtattcgt tgcatttcga acacactacg catagtttct    87240
gtaacaaatt catctccatg actcgactcg ctcacgtacg agacgctgtc gtccggtctg    87300
gcgccggcca gagacatgga gtcggtgcac aaataactcg cgggccgctc gctatgccga    87360
```

```
ctgacgttga cgttaatata taacgacgtc gtcgacgacg cggggttctgc tcccgaagct   87420 gttgccgccg cttgcggcgc aacctcctcc accaccgccg ccgccggctc ctccgcctcg   87480
ggcgacgggg gctcggagat gaccggctgt gtctgacact cctcccctc ctcaggcggc     87540 ccgggcgccg acgcgaatgt cggagtttgc cagcgcggcg gcggtctctg tctctggtgc   87600
cgcggcgcta accttcgggg ctgttgctgc tgttgatgat gcgacgccgt ctgtcgccgc    87660
tgttgcggcg gtagctgata cggtgtcgcc tggtgctgct gtgtcggtgg ctgctgttgc    87720
tgctgttgtt gcggtctgaa aagcggccac gggggctgcg actgttgttg ctgttgttgc    87780
gatgctcgtg gctgcggcgg ccgttgtcgc ggcgtttgct ggcggttaca accggctgcg    87840
tttggccggc aataacccgc tgcccccgcc gccccgctg ctcccgccga cgccgccagc     87900
ctcgtcttcg ccggcgttca cgagaaagca gccacctccc gtctcgccgg gcacgccgaa    87960
gcaaatggag ttgcccgcga cggactcgcc gagaagaaga ccgccacccc cgacgccgga    88020
cgccgcgccg acgccactgg gcgcgaagag cgccgacagg tcgtgcacct cccccccggc    88080
ggcgtccgtt aatcgctggg cgtcggcgtc cagcacgcgt cgcaagttct ccagcgaaaa    88140
gtcctccacg ccctgctcct gcaacgcggc aaacttgtcc atcagcgacg cggccagcgc    88200
ctcgcagcca tccacgaaga agagcacatc gtcggacgcg gggatctcct cgcgcacgct    88260
cagaatctcg tacacggcca tcacttcggg gtcgcaatcc aagttctcgg cgtccagcgc    88320
cagcatgacg cggttttta taagatccgc gtcaaaaagc acgttctcgc ggcgcgagcg    88380
tttgatgagc acgtcggcca gacgcgtagc caagaggtag cgctggcgca tgaaacgata    88440
atcttggccg ctcatagagc tcacgttaag gctgcgttcc acaccgttgc ccgaaaagta    88500
gccgatctgc ccaaactgat agatctcctt gctgttgttg ataccgcat attttccac      88560 gctcacgggc acggtcacca aggaacgatg ctcaaaaacg ctccgtacca acgattcacg    88620
cgccacagtg gcggccatgg gcgccggcac gcctgcggtc ttcaagccct tgacatgcaa    88680
cgcaaattcg gcgggcgacg agaaccgcgg actagcacct aacacgtgag gaaactgcgc    88740
gtggttctgc gtcgttaagc gcgtcgtcaa cccgtgcagc gagccgatgt agtctttgaa    88800
gccataatag cagaggaatt tgttatggaa acggctttcc acgtaactca gcacacagtc    88860
tggcgccaca tccagcagat cgtgctcctg atagtcagcc gtcacagcca ccagaaattt    88920
gacgaaagca ttgaactcgc ccatgtcacc tatgggcaca ttcttgggca acgcgttgga    88980
acagaccttc tgccaaaact gtaagcaggg gagaccacat tcaggaaaga gtcgctcgtg    89040
atgtcgatac agcagaaatc ccaagcagcc cttagccgga ttacgacgcg gaacgtgatc    89100
gcggcgaaaa aacacgctac ccgcgttgcc cttgcccgcg cggtagatgg gtcggttttt    89160
cacccgcacc atgatcaacg tgggtaccga cagccgcgag agcttgatct ccatgggcac    89220
cacggcgtac gtgccctgcg cgtacagcct aaagtccagc aggcggtcgt gatccgaatt    89280 cttgacgac ttgatctgct tggtgaagag aaagcccttg cgcgacgacg tggtggagaa     89340
cgcgccgtga atggattgaa aatgctgcgt catccatttg gataccaagt tggtggtcaa    89400
cggattgtcc acaatgtatg aggtagcggt aataagcgcc acgttctgga tcacgtaaaa    89460
gacggatctg aaataggcgt aggctagcag cggctggaag gccacggcgt agggattcag    89520
atccaggttg aaggcctgcg tggcgcccgc cacctcgtcg cggctgctct tgaggcgcac    89580
ctccgaaacg aaacccaggg cctcgtcgtc cacaaacttg ttgagcgccg aaaagacggc    89640
cacaaagtcg cttttgccgt gcgcgctaaa ggtatcctcg cccgtcacgg ggtcgatgag    89700
```

```
ccgcatcttg cggcagtaat ccaagatgcg attgagccga taggtacggt ccacgctagc   89760
gcccaacatg cgaccgccgc gccccatcat tcccccggaa tccccaccac ccccaccacc   89820
acgaccgcca cccagaccgt cgctcgggcc cccgctcacg tctcgtccac cacccccgcc   89880
agcaccgccg cccggaaccc cgtcgtcacc tttgccgtcc aaaccccgt  ccttggcgtc    89940 gacgttgtaa cgccgaccga agctgcccaa aatatccacg tcgttgagaa aacgcgactg   90000
cacggtgatc acgcagggct ccttcttggg ctgcttgggc accacgggca agcgggtgcg   90060
cacccgcacg aaggccgtct gataacacgt gtggcaacaa gtaccccac  aggcctcgca    90120 cagccccgcg cgcagccca  ccaggtgatt cgtgagcgtc gacgaacccg acaagcccgt    90180
gttgtacacc gagacacgat tcagatacca gacgaagccc gaaactagct gcggacacgt   90240
gccacacacc aacgccaaat gctgcggccc atagcgttcg tccttgagcg gcgcgccctg   90300
aaacttgagc accttgcgcg cgtcgttgta gacgtcttcg caggccgccg acaacccgtt   90360
ggtgaactga atagccttga gcaacgtctc ctgactggcc gtaccgccgg cgctgggatg   90420
ccgcgccgac gactggagat acaccagcct gtgctggtag agcaccgaat tagcgctgaa   90480
gaccaaggcg gccacgtgcg tcgagagatg caacttgagc tcggtcagcg cgcggatcag   90540
atcgcggtga tcggttgcgt tggtcactaa aggccactcg gaaagagca  tagattcggc    90600 aggttggtaa gccgaatcga aaaataccga ggcaaaactg aaggccaact cgcaaaccac   90660
cgcgtcactc agcatcagat gatccttttc cagactgctg agtcgctggc tcatgtaccc   90720
caagtagcgc ttatgtggcg ccagcttcac cgactgctga ctgtcgtgca caaactgccg   90780
caacgccgcc tcgatcagca cacgcggctc cgagaagcgc agcgattgac accatgacgt   90840
gtacacgtag tagaaaagcg tctcgcttac ggccggcacg tagagccctc gcgcctccac   90900
aaaagcgctg cgcgcatcca gcgagacctc gtcggcttcg gcgtcaagct gcaacgaatt   90960
aaagagcgta ggcgggtaca acggcacgcg caccgcctcg ccgccgtgca gtcgcaccgt   91020
ggtcgcctcc tccacgcatg gaatcagctg accggcaaag agaaactcct tcaagccgtt   91080
gcccaccacc acgtgcacag tcgtctcgga cgcctgacag cccaccgccg cgcacaacgc   91140
cgccagatcg gtaggcacgc gatccgcctc gggcatgtaa gcctccaacg cgtacttctg   91200
gcgggcgtcc tcgcacagcc gatgcacgtc tccgtgatcc tcggtaaaag ccacgatgcc   91260
ttgcgtatga tgaaagtaga gcgcaaaagg acagaaggac gtgactttcg tgagcacccc   91320
gccgtcgtaa caaagcacag gcgtgcgcac agagacgccg aaatccgcct ccaccgtgag   91380
ccccgccaac aaaggagcga tcaccacgct cgaggaacgg tcgcatagcg agagagtggc   91440
cagaatctcc tgcgtttctg cgttcaacct gctgaagtag agaaaagccg cgggccccac   91500
cggcgctagc gcggttagtt cctcgtggct catggtggat gaacggaaga caatggctac   91560
gccgccactg agtgaatttt ataccaagga aaagttcagc acgtcatgtt tgacgcacga   91620
cgtctgagac accaccgtgg ccaccactgc ggtctggctg cggttgcgga ccaccaaagg   91680
cgacaaccgc aacgatccca gcaattcgta agaaaagcta accgctacgg tcaggtagcc   91740
tctcgcagcc agaccgctag ccgacgcacc cgcccgcgaa aatagcgtga tgttcgggac   91800
ggctttgcgt caccgccaac taacgtcggt agtcgagcac gtcgtttatc ctcagcacac   91860
cgtccgatca caatccgttt tcccactcag tcgcacaagc agcacataaa aaccccacac   91920
agggcacgtg aaaacaccgt ccctagaaaa cggcgttttc tgtcctaccg tcacccgtat   91980
acacaggcaa atcccaatcc cgatcccccga aaacaccgta cggtgtttgt gacctccaaa   92040
atcacatcag ctaacaaacc gtgaaaagtc acgtttcacg aacacggtgt ttttaaatca   92100
```

```
caaagaaccg cctgacggtt tacaagcaga acaccgcac cacgtggta caagcgcgat   92160
gaatctggtc tcgcaacctc aatcgccgct atcaccaccg attttcgctg cgctccgccg   92220
acaaaacgcc gtacaagcta cacacccaa aaacccgcgc gcctacgggc gccaaacctg   92280
tgtgttatct caacgtcaca acacgacaca aaccgcgtaa cgtggtttcc cgaacacgta   92340
cgcggcacag acccccgaca cgtactcgaa gaccttacag tttacgagtc aataaaacag   92400
gaaaagatcc gaactttaaa attgtgtgtt tttattttcc catccccctc ttttaccaa   92460
aaaacacatt tttcgtcttg taaaaagtaa ctttcgccca ttgccatgaa acaccgtgat   92520
ggggaacggt gttgtgtgtc gactgacgtc actacggcga tcagtatcga cgtcgtgtat   92580
acataacggt gcccggtgtt tttattcggg gcgttgtcgc gtcttgatgt aatgtaacct   92640
gaaaccgccg tgcccaagaa tgcggaagcc agcgtgtaat cataacgggg ttttgggtac   92700
aatctgacga catctggcgg cgagcgtaca ccatcgaatg tggcgatcgc cggctctacg   92760
tcacaatgac gcaaaaacac actgtaaaac ccgcgtagac agctttcctg gtcaacgagc   92820
gccatctggt gtcggcataa gaacaggcat caaccccgtg gccggcgagg cggtgagcac   92880
ttttgttggt cacgtgacca tcagcgcagg aagcgaggcc cgtagaaccg cccaagaggc   92940
ggtgccagat gccaacgtca taatcacaag gtgatttgtt acgtcacgcg cgcgcacgca   93000
cgcgcgcggt agaatacagc gatccctagt gaagccacac ccattacgtg tagccatatc   93060
cgcttacgta tacagccaca cccctaggta cgccacctta tctaccaatc acagaaacgg   93120
atatacaatg acccctccct agactccacc ccttgtacgg aaatttcaga taggtggaac   93180
ccgttagggt tccaccgtcc tcggtgtacg tacaggcttc tccgtctacc ggaaatatac   93240
acctgctgac gtagacgcta ctcccggata cgcgtcataa gctactggac cctaggggg   93300
agtgtctaca gggctacgtg cacgccccct tacctagggt atccgccccc ttcctctgtt   93360
ttggcctagt aaacttaacg ccgccgcttc tcacgtgacc cctgacaagc ctacgtcaca   93420
ctcgcgtgac cacacccact ccggatatac gtcatcctgt ggaattccgg acatacggtg   93480
acgtagcgag cgtagcgagc tacgtcacgt atgcgtgcgt catctccggc ggaaatcatc   93540
tctgatgacg tagcgagcga agcgagctac gtcatcagtc cgttttacgt ataccggatg   93600
ctaggcgacg ccccgtaggg gcggagccta gcttccaccc ctaggatgca taccctatat   93660
agcataattc ttctaacgaa acgttctacg aaaacggact ggcggaacgg gaaccaccgt   93720
aaccccccc cctcaccccc cccttctcc tccggaaccg gggggggcaa attttacca   93780
aatttgggca accatgattt ccaatgggac ggcgtttccg tgcgcatgcg cagtcgggc   93840
gagttttgg ttgtcagggc gttgccacgc ggattatggg atggtgactc gagtgcgcat   93900
gcgccgggga tgccgcatgg aaaacctata tataaggagg ggtgaaccag ggccccggg   93960
gcgcatgcgc gggccagggc ccgcgggagg gtcgccctgc gcatgcgccg gtaaaattcc   94020
actgtgtgtg tcgtgcgcat gcgccagtat ttttccacta gaggcggtca gtgcgcatgc   94080
gtcggtaaaa ttccactaga tgtgcgccgt gcgcatgcgc cggtatttt ccactgggcg   94140
gccgcaccta gggagcgcga gcccgtgcc gggcatgggc cgcggcggtg gaaaattacc   94200
gctccgccca cctaggcggg gcatctgaaa acctataaaa cccggcgtgc cgccgcccc   94260
ccggcgcagt ccgcggcagg gttccggccg tgctgcggtc cgcacgctgc gcccgctccc   94320
gcctgcctcc cgcccaccc cccacccctcc ccggccgagg cccggcgccg gtccgtccgc   94380
gggcccgtcc caccgcccctg gagcaccatc cggggccgtg ggccgggcac cgggcgcggc   94440
```

```
ccgctccgga cctcggccgg gggtccctcc cctcccccg ctcgaccccc ccatccgacg    94500
gcccggccgg gctgggaccc ccgcaccggg gtcccggttc ccgtccgtgg cccggggga    94560 cccgagcggg ggcttccac ccccaccccg ctcctccccg ggctccggcc cgggatccct    94620
cgctgctccc ggcgacctcc gccggcttcc cgtccaccc gccgcggaat ggacgggacc    94680
cggggtccgc gcccttcccc tcccccacg gggggctggg tcgcggaccc cggttcctag    94740
gctcgttccg cggtgggcga ccggggatcc cccacccagc tcccctcccc ggcccgcctt    94800
gctggctttt gggcccctgc gggctttttt tttccggctg ggggtcgcgg cggtcggccg    94860
acgacgacgg taggtgggcc gggtggacgg tggtggggac gggcgacgcc ccggctcgac    94920
ggcaatcggt cccggaaggt tggggctgg gggcccggtc aggagctccg ggagcggggt    94980
cgaccgcgac ggcttccggg tctcgcggcg gctccctctc ggcggctccg gttgggctcc    95040 cctccccct ctcgagggtc cggccgccag tcgtgaccgg gggtccctcg gcctagccgc    95100
cggctctcgg tccgccttat cctgggcgtt ggcctgtccc gtgacgctcc cctccccgc    95160 tgctccccaa aaaactccg cccgaaccgt cgcggcttgc tggccctggg cgtggtcccc    95220 cactccccctc cccccatcgg ccgcccagcc ggggtcggcg cctcggaccc caccaggctg    95280
tggcgtgtgt gctggccgat gcggcggcga ggttgggtgt ggccggaagc gctcgggtc    95340 gacggtgggc cgccatgaca cctcaattgt cgtcagtacg cccctccaca atcaccgtcc    95400
ccacacgatg ggcccggcag gtcacccaac gttggttcag gcccagtcgg gttttttccc    95460
cggcacgaac gcacgtcccc gtgggctcca cgcgttttcc acccttttcct ggaggggtcc    95520 ggaacaccgt gaatccacgg ggagggtccc ggcacgggcc gaggagacca cgaccgtccc    95580
acccggcgtg tcgactcgtc cgagacccgg gaagggaaca ggccccacct tttttttccct    95640 tctccgattt tgccgtggaa aaccgtgaa ccgatacggg tgcagacggc cgaaaaaaat    95700
cgagacgaca atatgacggc agggcgcgat cttctccccc atccgacaaa accgtgtccc    95760
ttaaaattcc ccacctttct ctgttcaaat ggccccgaaa ctgtaaaaca ccgtttgacc    95820
gcaccccaac cggcgccatc ttggtgacct tctcgacggt tctctcgctc gtcatgccgt    95880
tctgagctcc gacatggcgg acgagagaaa atggcgtcga gagcctagga gcgttttgc    95940 tccaggcggg taaaaaaata gcacgataac ttttctgtgc ttttttttga gacgttttag    96000
aagagctttt ttctgctcag agcgaaaaaa tgatagccct gaaaatctcg acgagtctgg    96060
ccgagcggcg ccatcttgga ggaggggcga gtcgcgggca ccgcctcggt acccctggc    96120 cgaggcgagt ccgcggtcgc cgcctgttcc gtgatgctac ctagagggcg ctgtcgaggc    96180
gactcttcct gttttcgccc tgagggctaa cggtcgctga cgtcaaacca tctcgtgctc    96240
gctgagtcac atccggttgt tgacaagcga tggaggaccg cacccaaagt gcgccctcta    96300
gtcatcgcgc ctgacccctt ttataaactg ctcgaagaaa agaacacctt atgtgaaaaa    96360
atacagaatg atgacaagtt catccaacac aaccgctcaa caacgccata tctatcagtg    96420
tccaaaaact atcttctatc ctttgaaact ataaatgctg cctatataca tatttagtat    96480
ccaagactct taccacgtag acgaaaagaa gtgatacaat gatcttgacg tgtatcgtct    96540
atatcgtgct agatatattc agataagacg cgcaaaccat agatttctca tcagtatcat    96600
gaaagaccta tagctctata tacgaaccta gtcatttttag gacagccgcc ggagaagccg    96660
acgagggatc gggcgggtgc agccagaacc tcacgcccga tccgcctcc ggtaggcgat    96720 ttgcatctgt ttggtaaaaa gctcataagt ctgtatgtga cctatatata ttatacgcta    96780
tgtacaccga actgtcgctg ttgtataaga agaaaaaact ctccatattt atatcgtctg    96840
```

```
aatttttgct tgatagacac gtgtttggaa ctctgtcccc ccacgttttc actgtgtata    96900
acaaaaatat gtgtttctca aaagatcttg aggtgtttga aaacggggga aacctgcgtt    96960
tgggtgctct aagccccgga ctgggacgta gccggcgtcc ggcacctata ttttttctatt  97020 ttttttaca aaatatatga tgaaccaaga ataaaactct agctctcgtc tatttttaat   97080
atgctctact tagaaccttt ttaatgacag aatgaactcc atgttatacg ctctttatat   97140
agtttctctg cactaacctt taaaaccgta tccttccctg ttgtacaaat catcttttga   97200
tacacaatga tgacctgata tccctccata tatatgatcg gatattattc cgttagactt   97260
gtcctccttt tttttcctca tctcctgtat ctggagatat atgttgacca ccaccgccat   97320
gaccaccaaa aagctagccg tcacgactag aaatgtgtag gattcggact ttccgttcga   97380
gaagaaaaag agaccgcgtc tctggacgct ctttttgtca gtctgaatcg acccgggata   97440
cgtaagagag cggccctaca tcgggggggcg ctcgagaccg acgacgttcc atctgaccag   97500
aaaaaaaaag gcacccctcg gtggcgacct ctcaccatcg tttgcccgtc cgcccgtcct   97560
tcgtagccat catcatctca ggctctatcg gtaccatcgt tgtcatctga aaaaaaaact   97620
gcctcaccca cctgcgtaaa aacaccatct ttccggaggt gcggtaagac gggcaaatac   97680
ggtcgtgccg aggcaaaaaa aacgcaccat cgacaccaca ccctcatgag caccacctgt   97740
cggtgttggt cgtcctccat cgttctctac gaacatctcg acgccgggt gacgacgac    97800 ggcaagacgt cccggagaag acggtgttct ctcgggcggt acgctctctg gatctataat   97860
atctatagta gctaaacgag actgtgagta cgacgaacca catcatcttt tttttatgtt   97920
gcttctttag aaaatgactt atgtcgacga cactcggcat cagccatctc gtgaaacacg   97980
ctcgcttttc gtctctccaa ggaacactgg gtccgctgaa agggaccgtg taccgaccaa   98040
agcaaaaaac acacgtag taacatgatc aaccacgtct gaatgacacg aaaacacaat    98100
cgtataacgc tctattcatg gaacgaactt ggaataaaaa aaccatcgca ggccagaggc   98160
taagccgaaa ccgtccgggg aagcgggcgc gagttttccg acttagcctt tggtgctcgt   98220
tgagcctctt tttttttttct gattctctga agaatcaccg tcacagccct atgacgcgaa   98280
atcaattgct agaacataaa cgttctcaac aggtatgaaa tgaacaaact agatgatgct   98340
ataaccttat attgtgtgta tatagatagg tgtgaaattt gtaggataaa aagtgtcgtt   98400
gtatgatgca caacgatcgt gaaactggag actgtagctc tctaccgaat gcaaatacac   98460
aaatgacatc gattcccgtc cccacataaa gaaatgtgct ttactgtgaa agaatgaaga   98520
agattcttgt tcctcgtacg acggggcct cgctcgtcgt gcctcttccc ccctccggga    98580
gaggggacgt cggggccctc cgtcgcaccg ggccgaagcc agtgaaatgt ttactacact   98640
gtcatcagaa tatatgatgt atattatttc ctccaaactc ctcaccatag ccaccaattc   98700
gcatcactta agaaagtagt agcaaccgcg gcggcggcga ccggccggtc gtcgtctcct   98760
cgtcctcaaa tgttgtacat gtgcagaaaa atgtgtaaat acgtgttatt tatcccatgc   98820
gtcttgtaca tagatatatg ttttatata cgctatttat actttatata tccttttgca   98880
taaccataga cagtcaagga ttttaatgat ttgctcatcc gcctttgagc catcgcttag   98940
gagttagttc ctctatgttc tcggcccacc ttttcgacta cagtagcaaa cccttgtact   99000
accaccccga taaaaaccac atcatcatcg tcaccacgac ctggaaacga cacacgttcc   99060
cccccaatct tgggcatgtg tatatataaa aagaatggga gggagaggac gtggggctcg   99120
agaagaaata aacgccaagc tcgattcgaa ccaaaaaacc acatgtgtat tgtgctttgt   99180
```

```
ttttttttttt acggtgggggg aaaaggaggg ggccgtcatt aacggaaacc gtgtatgggg    99240
tccggacacg aacagtacac agcttatggg gaaaaaagct cacagagaga aaaaacacca    99300
agctcaggca cgcgtacatc attattatca tcatcggata tctcaccacg ggtcatagta    99360
gtaccaagga gtgtgtaaca ccattttttc ttttctttgt aacgggataa gggacagcaa    99420
tcatcacgca caacacccct cactctcttt ttagtcatcc atatcatcgc tgtaacacag    99480
catgtcctcg taatcgggcg tctggcagcg cattaccacc gagtcgtctt cttgcggtac    99540
cggtggtggt ggtggtggcg gcggcggctg ctgctgctgg gttgccgtcg tactgtgatt    99600
accgttggcg gactgcaccg ggatgatggg ctgcttgtgg ggaacctggg gtggactgcc    99660
gccgtgagaa ggcgacggcg tcatcaagtt aagctcacca cggtgactcc ggacaccggc    99720
gaggggcgcc gggggactgg gagggaccgc ggtcgtcttg tagacgacgg tgtccccgtg    99780
tcgatccgtg gctcgtacca gatcttgact gctagcgtcg tcactgtctt cgtcctcttc    99840
cagctcgccc tcagagtagt gctgctgtgg ttgcgacggt ggctgggcgg gaggagcggc    99900
ggcgatcatt ggagagggat gtcgatgact cccttctctg tcctttttat cgtaggctgt    99960
cagcgttgct gggtccgtcc tgcttttccat atttgcgtat tgctcatcgg tgggatgaat  100020
ttggtctcct ccccgctgtt gtccgccggc agtggcgtgg ttgctggcgg ttgtcgttgt  100080
cgtaccggca aagacggtga gatccaatag cgactgctcg tcgaagggac agtacgctat  100140
catgaaacga tagggtgcca acgcgcgttg gatgcgcagt tcgcacatct cgttctgaca  100200
ctcgtggcac tgcagggcgc ctaggatcag gtccgagaca gcgccgcagc ggtaggtacc  100260
catggcgttg ttagtatcga actggtcaaa aaattggggc gtaccggtga cttgcaacgc  100320
gcgacggcgt agcgagacgg ccacgcgcga gaaagagcac acataggcca tggcgcggtg  100380
catgggttgc gagaaggtct cgggcggacg cttctgcaga tcgcagacgt cgtcgcgtag  100440
ccaggcgctc atttgaccgg gcttcttgac tagccgtttg agcgtgctgc aatggtcgcc  100500
ccagccgtcc tggtggtcca ggatgcagcc caggtccagg ttgttgagtt tgttgaagag  100560
tagctgacgc atgccgccca ccgtctccag atagggatcg tgcgggttga cgggtagccc  100620
gtgcaggtgg tggtacttca tgtagctgag cgtttcgtcg atgatggcca gcaacgtgtg  100680
caagttggga gcgttgtaca cggcgaagat cttttccacc accagcttgc gcagcaacgg  100740
ttcctccagc caatcgaact gttgacgaat gtgcaacagg tagtcggtgt gcatgagctc  100800
gtcgtgtgac agcaggatgc gaccgcgcgg ctgatgatct tgcgggaagg cggtggggac  100860
cttgagatcg gcggggtagg gtgccagacg tagactctcg gccgtgtagc gctgaaggtc  100920
gtaaacgggc gaggtagaac tcggtgaggt acccgacgag gcggcgccgc gctgcagacg  100980
cgctcttttt ttcttttcga tcaaacggct gagttgctgt agttcgtcct cgtccatggc  101040
gtccagttcg tcgtcaataa gcgccagcat ctgttgttgt tgcggtccgg cggacgatcc  101100
gtgatgatta ttggctgagg aggggtgaga agaaccgaaa gtcgtaggac aactgggaac  101160
tcggcgacga agatgcgtcg aatcgccgcc gtgatggtgc ggttcgccgt catcgttgtc  101220
gtaagactta ccgtagtggg ggttaagggg caccgaggcg gacgcggcca cgcgtcgctt  101280
gaaagaggag gacgccctat gtccgccacg gaagcccgcg gtgcccatga tgatgtgtcc  101340
gccggtgccc ccgagtgcgt ggcgggagga gggtggaagg ggaggaggat agtggtccgg  101400
atcgccttcg gtatcatcgt ctttgctgta gcggggtcgt cgtgcgggga cgcagggtcg  101460
gtgatgatgc gaggcggcgc cgacggtatc ttccgcgaga tggtgttcgc tggcggctgc  101520
tccgttccgt gtcgacggcg aggttggact tcgctcgcgt cggaacttcc gtggcacggg  101580
```

```
ttcgtaatcc agacagaagc gccgtgcgcg acgggcgcgg cgttcgcgct cgctcaggga   101640
agataacgac ggagcgtcgt gacggccgcg tgagtgcagc tccatggccg ccgtcgctag   101700
gaaggtcacg ttcgggcacg ctgatgtata tatagatgag accgctgccg gggggcgggt   101760
caccggcgcc gtggaaagtg aggctcagac ggcggtcgcc ggcggcacgg gcgcgtcggg   101820
cggtctgatt tgatggaaa tgtggacgtt tttggcgttg gagtgacact ttttggtgaa    101880
acagcggctc cagaggctgg cccagagcgc gtagctgtgc tcggtgcgca ggtcgatgaa   101940
cacctgcacg gtctcttgcg ggttgcggtg cgtgtagttg agacagcgaa aatcccgcgt   102000
gcgcgcgccg tcgcgccgct tgacggccac gcagcaggcg ccgtgggct gaaagaggag     102060 gacgtggggc gcggtaaact gctcgctgac gtgcggttcg tagtgttgcg tgaggtgctc   102120
gagcagcggc ggccacacgc gggtgacgac gagccgctgc aagtccgtgt cggaaatcgc   102180
agcggcagtg gcgccgtcgc caccgtacag gtgataggcg agcacctcgg tgagaccgcg   102240
gcgtcgataa cgcgtcacgt taagcgagcg cgtctcgata aagttggctt cggtcgaggg   102300
gcagattttg tcgcgtacgc tgagaatgac gcgtggcggc ggcgacaggg gcaacgcggg   102360
caggtcgtgc ggcgggtggt ggtgaagcag gttacgcaga tccagttggg cgcgcacaaa   102420
gcctagcggg tgttcgcggt aggcgtcggg cacgatgaac agcggcaaca gacggcgatg   102480
catgaaatag ccgtcgtctt ggtccatttt atacatgtag ggcagacgta cagagcgtcc   102540
atggtggtag atgcctgtgt ctaggctgct ctcgggatgc gagatggggt ccagcagcgt   102600
gtgcagttcg gcgtcgagac agacggcgtg attgagcacc tgcgccacgg cgcgtaaaac   102660
gctggggtgt acggcgacgg tgcaggcggg gaacggcgtg atgatgcgca gccccagttt   102720
gcccttgcag cggcagtaag ggggtgacgt gtcaacggag gacgttgttt tttggaaaac   102780
gccgttatcc gggacgttat ttttatcctc tttcccgtct tcgtcttcct ctgtgtcgcg   102840
ctcgtcccgg taatcgagat agtcgtcgtc atcgaaaggc gcgccggccg cgtccacggg   102900
cacgctgttg ggtgggcacg cgcttttgaa gaaatagacc gggtgccggt cggggtgcgt   102960
gtagccaaag aggctcgccc atacggtcat ccagacgcgt cgtagtccgc gacatagctc   103020
aaagacggtg tgtcgcgcca gaccggagac gccgtcgcgc agccgtaaat caaagtcggc   103080
cacaaaattg aagacgggca gacgttcgtt gaagacttcg tgtcgcgtgt agtagaactg   103140
tgtctcgggg ctggtgctgg ccacgtcgtc gtcgtgtagc cacacggtct cggtcagggc   103200
ctcgtccgag aaacggctgt cgggtacgtg acggagcagg tcacgcggaa agaggctgcg   103260
atgccaggtt tcgaggcca cggcgcagaa gacgtgctgg tcattgggca ggtgtacgcg    103320
gtagacgggc agcggtcgct ccagcagcgg tgccagcgcg ggctcgggta gcaggtagcg   103380
acgttgcgag taacgcgtta gcgtgccggt ggtgtaagtc tgggctgtgc gtagcgaggc   103440
gcatagacgt aacaagccgg acagggagcg ttccagcggg gagaagacag actcggaaag   103500
cgtgttgatg cgttcgagct ggcgcgccag ctgcgtggag gtgccgaaga gcccgccag    103560 gtgcgtgccg tcgatgcggc cgccgtagcc ggccagcccc aagccgtgcg ggctggtcgc   103620
cgagtggggg gattcgtcga dacgcagtag gtgcgtctcc acgtagtcgt gtagaaagtt   103680
gtcgagcgag aagtattttt gcatgacgtc cagcagctcg gtggaaagcc ggcggccag    103740 aaaacccggt tcgcgcgtgc actgcgcttc gggcgccgcg tcagcgtcgt aagccaccac   103800
gcgccggtac tcgagcaacc gcgcgcgtgc cagcgccgtg cggtaggcca ggtagacgta   103860
gtgcacgcag accgtgtcgg gcagacgcgc acgttcgcgg aacgcgttga tctgcgtgtc   103920
```

-continued

```
cacctgctct agctcggtgt agtcgcggcg gttgcgcgcg acggcgtacg ccacgaaagc   103980
ggacacgcgc tgacggaagg gcgagcccag tagcagacgc gcgaactcgc ccatggaggc   104040
gtgcgtgggg atgatggtgc ccaggtcgcg cgtgcagaag ctgcgcacgt actcctccac   104100
ggtggagatg gtgctgtact ggccctcgaa taggtagtag gccatggtca gcagcacctg   104160
gccctcggtg tgcccgaaga cgctgatgaa ccacgagggc gaggtggggc agaggaagac   104220
ctggttgaga tgacgtagca cggccgcgtg gtgaaagtac accaggtgct tgaattcgcg   104280
cacctcgccg ccgtgttcgg gcgagagcac gggcgtgcgg aaaagatgcc ggtagagcgg   104340
ttgcgtctcg gcctcgtcca gactggcgat gagcgccgag aggggatgg gctggcgcgc    104400 ggccaggtag cgcgagagct gcagcgtttc gttgttcacg gcgaagacgg gcgccacccg   104460
ccgcgagtcc gagcactttt gcgtctgtag gcagaagtaa acacgtcgcg agacctggtg   104520
tttgaccagc aggggaaga cgcagtggtc cgtcggtgtc tgcgagagta cgttggcgac     104580
tatatgagca gaatcatact ctgttgcgaa cagaacgagc gtcatcgtcg cgccggcacg   104640
atgcagctgg cccagcgcct gtgcgagctg ctgatgtgcc gtcgcaaagc cgcgcctgtg   104700
gccgattacg tgctgctgca cctagcgag gacgtggagc tgcgcgagct gcaggcgttt     104760
ctggacgaga actttaagca gctggagatc accccggccg acctgcgaac cttttctcgc   104820
gacacggacg tggtgaacca cctgctgaag ctgctgccgc tctataggca atgccagagc   104880
aagtgcgcgt tcctcaaggg ctatctctcg gagggctgtt tgcctcacac gcggccggcg   104940
gccgaggtgg agtgcaagaa atcgcagcgt atcctagagg ccctggacat tctcatcctc   105000
aaactggtgg tgggcgagtt tgccatgtcc gaggccgaca gcctggagat gttgctggac   105060
aagttctcca cggatcaggc ctcgctggtg gaggtgcagc gcgttatggg cctggtggac   105120
atggactgcg agaaaagcgc gtacatgctc gaggccggcg cggctgcgac ggttgcgcca   105180
ctgacgccac cggcggtcgt tcaggggaa agcggcgtcc gcgaggacgg ggaaacggtt    105240
gccgccgtgt cggcctttgc ctgtccctcg gtttcggact cgctgatccc cgaggaaacg   105300
ggggtcacgc gtcctatgat gagtttggct cacattaaca ccgtctcctg tcctaccgtt    105360
atgaggttcg accagcggct gctggaagag ggcgacgagg aggatgaagt gaccgtgatg   105420
tcgccgtcac ccgagcccgt gcaacagcag ccgccggtcg agcccgtgca gcagcagccc   105480
cagggacgcg ggtctcaccg tcggcgctac aaggagtcgg cgccgcaaga gacgctgcct   105540
acgaatcacg aacgcgagat tttggatctc atgcgacaca gccccgacgt gcctcgggag   105600
gcggtgatgt caccgaccat ggtcaccata cctcctcccc agatacccct tgtgggttcc     105660
gcgcgtgaac tcagggggcgt gaagaaaaag aaacccacgg cggcggcctt gctgtcctcc    105720
gcgtgaacag cctggcacgt tttggaaaac gtacgtgatc acggacacga cgagtacggg   105780
gtttctcata gacgtacttt attaggtcag ggatgacggg gaggtttcgg gccgacgtca   105840
aaaataacgt cattcgtgtt gacagggctt tctgcgtcgg agctctttc atcttcttct   105900 gtctcgtcga cgtcatcgtc taccggcgag ggtgtccgtt gcagcaacgc gtgctcggc    105960 gtgtgggtga aaccgatgtc gggggtgggc ggcacgatca tctgtcctag ggggtgactg   106020
cccaccggca gataggtaaa gcggtgggtg gtaaaaaccg cttttggctac ggtggtgtgt  106080 ggggagatgc agacggtggt gtgcgaagtg ttgaccaccg tcacgccggc cgcggtaccc  106140
gggagccaga tggtgggtcg gatgatgaga tccgattgac taaactggcg cacgcccact  106200
atgagggcgc agataccggg cgcgtgcacg taggccgcgt caaatagac ggtttgcgtg    106260 tgacccggac cgatcaccag cgtctgacgg gtacgtaacg aaaagaaacg gtgttcgttg  106320
```

```
ggcggcggca agttcatgag ctgccagggt tctggtacaa acaggggaa aacgccgata    106380
tcgccttcga tggtgcccgg aaagatggac tgaaaagtgt cgttgaggtt gacgacatcc    106440
aactgcggga cttgcagcct ggattccagc agctcgggca tgcaaacgaa ttgcgcgtcc    106500
aggcatttgt aaaaggtaat gccgaaaaaa ccttcgggga tatagaggct gacgcccagc    106560
gaggtgggca ctttgcgctc gcgtgatagc caaatgatgt gtttattgta aaaggccagc    106620
tgcgtgtggc attgtttgac gatgaaactg gaaggcatcc acttgtaagg aactttgagc    106680
ggtgacggta atggcgacga cgcttcatcc tctcccggat gctgctcttt gtcgtatttc    106740
tcctcggtcg attggggcag cgtaaatgtg gtttgaaaat cgctatcgct agcgaaacgc    106800
acgcagtaac gcatgttgac ggatttctcg gctaggatga tggagcctga tgacgatgcg    106860
gactcttcct tcattattaa cgtagggtc tcccagaatc gctgaaaacg ggagcgcggc      106920
agccgcgaca gtaccagttg agagtcgatt cggtcggtca acatcgtaag catcgtggcg    106980
gtggtgtgat ggagtggaac acactagtat taggtctttt agttttatcg gtagtggcag    107040
agagttctgg taacaattca tccacgtcaa cctctgcaac tacatcaaag tcttctgcta    107100
gcgtatcaac taccaaacta acaacagttg caacaacttc tgcaacaact acgacgacta    107160
cgaccttatc gacaactagc actaaactca gttctaccac ccacgatcct aatgtgatga    107220
gacgacatgc gaacgatgat ttttacaagg cgcattgcac atcgcatatg tatgagctct    107280
cactgtccag ctttgcggcc tggtggacta tgcttaatgc tctaattctc atgggagctt    107340
tttgtattgt actacgacat tgctgcttcc agaactttac tgcaaccacc accaaaggct    107400
attgagggtg gacagattta cagcccggcg gtgttccggc ggggtaaggt ttacatacgt    107460
gggtgaccgg aggctaaagt tacgaatctc atctagaaac agcagcgagt ctagatagtc    107520
ccacagggga tctataaatg ttctctgaaa ccccattgat ggtgacgtag gtgtagtttt    107580
gttactatcg gaagctgttt tgttttccac gaacatggtt tcgttgtaat ataaggagct    107640
catgtcgaga gtaccgtaaa tagtgtacgg cgtttcgtta cggattagta cgtgcgtgtt    107700
tttcataaat tctgacacgg cggttcggtt gcggcttggt tcacaaaaag gattttgccg    107760
gtaacgtaga gtggtataca cccacgttgc taggtcccct aactgtgtgg ccataatgga    107820
cttcataaag ctgctatcag gacgataagc aattgtagac gtggaaaccc gccttgcggc    107880
ggtagtaata ctataagtca cgttagtagt gacgttgaga gcggcagacg ttgtatagga    107940
aaagtatggc gtagtagtac tctgagtttt cttagctttt ttttcgaatt gttccttaac    108000
gggcgcttgt ttacgtttta gttttcgcat agtgtttttt aacttggtgc cgttaatata    108060
cttggggacg cgaaatagat tccggctcat ggcgttaacc aggtagaaac tgtgtgtaca    108120
gttgcgttgt gcgtaacgta aaagcagggc ggttaaacct agaaaataaa tcgtttgact    108180
atctacgtta accttagtcg gacccacgta caatttggtg ttccaacgcg gtacattgaa    108240
aaacatgggg ttgaacgtgg tgaaattacc gcaaccttgt tcgccagtat cattacgttt    108300
ggaaacgttt agcatttcgg aaagacaagt catggaaggc acagtaccac aaggtggggg    108360
tctgaatgtt atcgttttag ccgtatgatt gtactgtgag taaacgtatt ttgcgggttt    108420
tctaagctgg gtactataaa aatcaaacca cagataggtt atactataat tctgaatggg    108480
gcccgctaaa atgtagtatt gtggaaactc tgtcatgttc atagtgagat ttttaaccgg    108540
ttgtttactt acattgtatt ttgtagaaat agtcgtttct agttgtctca aaatttctaa    108600
cttaagctga tctaatttat atttgcctat cttagacagt accaagcccc tccaaggacg    108660
```

```
attataaagc gcttttgaca taactttaca gtttatgaaa gaaacaagca agaaagatat  108720
agatattaga aacaccatct tagggacgtc tctcaccatc atctcttttc tccccatgac  108780
agaggaggag accccgcacc gtccgtctgc cttgtggttt ggcttgcctg cgtgtactca  108840
ctgctgattc tggtcgtttt gctgctcatc taccgttgtt gcatcggctt ccaagacgac  108900
ctagtctccc gcaccttggc tgtgtaccaa gcttgtatcc agggcccgat atgtaaccag  108960
acccataaca gtacctcgta aataaagacg cacagacctc acgcatatag taccatcaca  109020
ccgtgtggcg tgtactttat tacaacgagc aagagtgccc ctaagtattg gggcccgtac  109080
cgttttagaa gatttgtgt gaatgtcttt aactttctg tccctttct cataaactgt  109140 caggttctac agtcagcatg tcttgagcat gcggtagagc agatagatgc cgatgatggc  109200
cgatagcgcg tagacggaca tcatgaggag acgactgtcg gtggcgtcca cgacgacgtc  109260
agttacttct aggaccgtac cgttttcaa aagcatgagg tagtgagttc gcggagatga  109320
gaccaccact tcgttgtagg gatccagggc gaaaaggacg tcgtccgagt cgtgcatgta  109380
catgatgttg atgacgcctt gcgtgtcgtc gtattctagc agggcgcttt ggcaaaaggc  109440
gcagttttct agtgaaatgt tgagcgccgc tgtgatgctg tgtgtggtgt gcatgttgcg  109500
cgttagttcg catttagttt gactgtccgt ttgggtgatg atgaggctct ggcctacgac  109560
ggtggtggag acagggtagg agatacctt gatcaggtac tggtttgtta cgacataact  109620
gacgtgttcg gagacggtta gcgcggagaa ggattcgccg agcggcagac aaaacggtc  109680 ggggaaggtt tccagcgtgc ttggttgcat ggtagatagg atggagaggg cggcgggaac  109740
ggtagcagga acgtggcat cggggaagag acgcgtgagg cgttcgagcg agtgatcgcg  109800
tcgcccgcta ctggaacagg gtgtgtacag gtcgctgagg tattcgtggt gcggatgagc  109860
tagcaactgc gtaaagtgtg atagctcggc caatgaacag aggcccgttt ctacgatgaa  109920
gatttcgcgt ctctccgtcg tatgtaccaa catggagtgg acgaggctgc ccatgaggta  109980
gagttcttgg cgcgcgaagg ctgaaagaaa agaggccagg tgcgttttgt gtaattgtag  110040
ggcaaagtcg gcgatctgtc gtagtgccca ctggggaatg agatgttgct gattctgttt  110100
agaaagtatg tagaccaggc gtacgaggct ggtgatgtcg gtgatctggt ccggcgtcca  110160
gagggctcgt ttggccaggt ccacggctgt gggatatagc agcaatgtgg tgcgtggtgg  110220 tgttgtgag aggcaggtga tcataaattc ttgtatttgt aagagtgcgg cctgcggtc  110280 tagggctcgt gggatggaga tttcggtgcc ggcctcttct tgtcgggctg ccgcgaacag  110340
tgctaatgcg taggcgaagg ccatttctac cgtgcggcgg tccaacattt gacatcgacc  110400
gcttttgagt acgtctacag cgtaacggtg aaagctgtta cgtaacagtg cgctgaggtc  110460
caggtagttg aagtcgagtg cggcgtcgag aaagtccgag tctttgagat aggagtgacg  110520
gtttagttga gctttcttaa ctagtaccag gagctcgtgt ttttcagttt gtcgtagtat  110580
aaagttgtcg cgttgatagg gcgctttgaa gagtacgcgt ggaagatgac cgaagataag  110640
cagcatgggt gtgtcgtcgt ctatagatac cgtaactacg aagaagtcct cggtcagtgt  110700
gattttaacg taacgtagtt cgtccatgag gtaaaagccc tggtgcagac agggcgtaac  110760
ggtgctgaaa agcagatcgt gtccatcaaa gaggatacag gtctggttaa agtgtggccg  110820
atgtagtccc gaggtggtgt gcgatccctt ccagtcgtgt ggagtggttt ggggtggcat  110880
ccaaacgtga ggtattgaca gatcaatggg cggtggcacg gtggtgggct gctgacccag  110940
gctgtcttgt gccttcagct gctgcgaaaa agatcggtag ctggccaggt ctttggatac  111000
caatgcgtag gtgttaagtc tctgttggta tcttctagg gtttcggtca gatctacctg  111060
```

```
gttcagaaac tgctccgcca gaggacccgc aaaaagacat cgaggcatat ggaatacata   111120
gtattgatta tagctttgga aaaagttgaa actgatggcg ttttccctga cgaccgtgct   111180 gttacgagg ctgctgttgt aggtgcactg ggtggtgttt tcacgcagga agcggatggg    111240
tctcccgtag gtgttgagta gtaggtgaaa tgcgtgaggg tccagcgctt cggatgcggc   111300
gtccgcgcca tatcgttgcg aaggtaggtg actgaggagg tagacggtga agacagtgag   111360
gtaggggggg aggccgggcc gcatagcgcg gctgcgccgc tgggttcagc ggcgtgatcc   111420
aggtggtggt tggcgttaca cccgagagaa ggagagaaag gatcccagga aggggcaccc   111480
gggtgtggcg ctacgggtta caaaagtcgc gtctctgtct atttaatacg atgtcattgg   111540
ccgctgcgaa ggaagaagag gggacacgcg ggtaagccat gccgtccggg cgtggggacg   111600
acgctgattc gacggggaac gctctgcgga gattgcctca cgtgcgtaag cggatcggta   111660
agcgtaagca cctggacatc taccgtcgcc tgttgcgggt cttccctcg tttgtggccc    111720 tcaaccgcct gttgggaggc cttttcccac ccgagctgca aaagtaccgt cgccgtcttt   111780
tcatcgaagt acgattaagt cggcggattc ccgactgcgt gttggtgttt ttaccgccgg   111840
actctgggtc gcgcggcatc gtgtattgct acgtgattga gttcaaaact acgtactcag   111900
acgccgacga tcagtccgtg cggtggcacg ccacccacag cctgcagtac gccgagggcc   111960
tgcgccagct caagggcgcc ttggtggact ttgattttct gcgtctgccg cgcggtggcg   112020
gtcaagtctg gagcgtagtg cccagtctgg ttttttttca gcaaaaggcc gatcgcccat   112080 cttttaccg gcttttcgt tcgggccgtt tcgacttgtg taccgattct gtcctggact    112140
atctgggacg gcgtcaggat gagtctgttg cacaccttt ggcggctacc cgtcgccgtc    112200
ttcttcgaac cgcacgagga aaacgtgctg cgctgccccg agcgcgtgct tcggcggttg   112260
ctggaggacg cggcggtgac aatgcgcggc ggggctggc gcgaggacgt gctcatggac    112320
cgggtgcgca acggtatct gcgtcaggag ctcagggatc tgggtcacag ggtgcagact    112380
tactgcgagg atctcgaagg gcgcgtgtcc gaggcggagg cgctgttgaa ccagcagtgc   112440
gagctcgacg aaggaccgtc gccgcggacg ctgctacaac caccgtgtcg tccgcgttct   112500
tcgtccccag ggaccggcgt ggcaggagct tctgccgtcc cacacggtct ttatagtcgg   112560
cacgatgcca tcacgggacc ccgccgccgcc ccgtctgacg tggtcgcccc gtctgacgcg   112620
gtcgccgcgt cagcggccgc cggtgcttct tctacctggc tggcgcagtg cgccgagcgg   112680
ccgttgcccg ggaacgtacc tagctacttt ggaatcacgc agaacgatcc ctttatccgc   112740
tttcacaccg attttcgcgg cgaggtggtc aacaccatgt tcgagaatgc ctctacttgg   112800
actttctcct ttggtatctg gtactatcgg ctcaagcggg ggttgtacac gcaaccacgg   112860
tggaaacgag tgtaccatct ggcgcagatg gacaactttt ccatttcgca ggagctgctg   112920
ctcggcgtgg tcaacgcttt ggaaaacgtg acggtgtatc cgacgtacga ctgtgtactc   112980
tccgatttgg aagccgccgc ctgtctgctg ccgcctacg gacatgcgct ttgggagggc    113040
cgcgatccgc cggactccgt ggcgacggtg ttgggtgagc tccctcagct gttgccgcgt   113100
ctggccgacg acgtgagtcg tgagattgcc gcttgggaag gccccgtcgc cgcgggtaac   113160
aactattacg cgtatcgcga ctcgcccgat ctacgctact acatgcccct aagcggtggt   113220
cgtcactatc acccgggcac ttttgatcgt cacgtgctgg tgcggctttt ccacaaacgc   113280
ggcgttattc agcatttgcc gggctacggg acgataacgg aggagctggt gcaagagcgt   113340
ctgtcgggcc aggtgcgcga cgacgtgctt tctctctgga gtcgacgtct gctggtcggc   113400
```

```
aagctgggtc gcgacgtgcc cgtctttgtg cacgaacagc aatatctgcg ttcgggcctg    113460
acctgcctgg ctggcctgct gttgttgtgg aaggtgacca acgcggatag cgtcttcgct    113520
ccgcgcacgg gcaaatttac gttggccgac ctgctgggtt cggatgccgt agccggcggc    113580
gggttgcccg gggggcgcgc gggcggcgaa gaggagggct acggggacg gcacgggcgg    113640 gtacgtaact ttgagtttct ggtacggtac tacatcgggc cgtggtacgc gcgcgacccc    113700
gcggtcacgc tgtcgcagct cttttcccggc ctggctctgt tggccgtgac cgagagcgtg    113760
cgcagcggct gggatccctc acgtcgcgag acagcgccg gaggtggcga cggcggcggc    113820
gccgtgctca tgcagctcag caagagcaac cccgtggccg actacatgtt cgcgcagagc    113880
tccaaacagt acggcgattt acgtcgctta gaggtacacg atgccctgct ctttcactac    113940
gaacacgggc tagggcggct gttgtcagtg accctgccgc gtcaccgtgt gtccactctg    114000
ggctcgtccc tctttaacgt caacgatatt tacgaactgt tgtacttttt agtgttgggg    114060
tttcttccga gcgtggcggt gttgtaattt ccaccacgtg tcgctcgctg cataaagggc    114120
gaacgtcctc ggagagggta tattcgttcg gcgagagcgg gcggcggtgg tgggtatgtc    114180
cccttctgtg gaggagacta cctcagtcac cgagtccatc atgttcgcta ttgtgagttt    114240
caaacacatg ggcccgttcg aaggctactc tatgtcggcc gatcgcgccg cctcggatct    114300
actcatcggc atgttcggct ccgttagcct ggtcaacctg ctgactatca tcggttgcct    114360
ctgggtgttg cgtgttacgc ggccgcccgt gtccgtgatg attttttactt ggaatctggt    114420 acttagtcag ttttttttcca tcctggccac catgttgtcc aagggtatca tgctgcgtgg    114480
cgctctaaat ctcagcctct gtcgcttagt gctctttgtc gacgacgtgg gcctatattc    114540
gacggcgttg tttttcctct ttctgatact ggatcgtctg tcggccatat cttacggccg    114600
tgatctctgg catcatgaga cgcgcgaaaa cgccggcgtg gcgctctacg cggtcgcctt    114660
tgcctgggtt ctttccatcg tagccgctgt gcccaccgcc gctacgggtt cactggacta    114720
ccgttggcta ggctgtcaga tccctataca gtatgccgcg gtggacctca ccatcaagat    114780
gtggtttttg ctgggggcgc ccatgatcgc cgtactggct aacgtggtag agttggccta    114840
cagcgatcgg cgcgaccacg tctggtccta cgtgggtcgt gtctgcacct tctacgtgac    114900
gtgtctcatg ctgtttgtgc cctactactg cttcagagtc ctacgcggtg tactgcagcc    114960
cgctagcgcg gccggcaccg gtttcggcat tatggattac gtggaattgg ctacgcgtac    115020
ccttctcacc atgcgtcttg gcattctgcc gctctttatc attgcgttct tctcccgcga    115080
gcccaccaag gatctggatg actcctttga ttatctggtc gagagatgtc agcaaagctg    115140
ccacggtcat ttcgtacgtc ggttggtgca ggcgttgaag cgggctatgt atagcgtgga    115200
gctggccgtg tgttactttt ctacgtccgt ccgagacgtc gccgaggcgg tgaaaaagtc    115260
ctccagccgt tgttacgccg acgcgacgtc ggcggccgtt gtggtaacga caaccacgtc    115320
ggagaaagcc acgttggtgg agcacgcgga aggcatggct tccgaaatgt gtcctgggac    115380
tacgatcgat gtttcggccg aaagttcctc cgtcctctgc accgacggcg aaaacaccgt    115440
cgcgtcggac gcgacggtga cggcattatg agcggcggcg ctgtacggca gcggggagaa    115500
aagtggcaga taaatcacgt caggttcaca cgtcgttagc cagcgtcggc atatgaaggg    115560
cgcgggcggc cagtacggcc tctgggctga gacaggacga ggcagggtga gaaagaggag    115620
gatggggggg accggggtgg tggtgctgct gctgttgtgg gtgcggacgg tgcgggtgcc    115680
gggacagcgt gccggcgaac gttctgtaat cttccataat aaaagtaaaa atgcccgtct    115740
cgtgtcgact ccgctggatc tcgaaggcgt cgggggtaat gcgcatcttg ccggtgccga    115800
```

```
tgagataaaa gtaccacatt ttttgacaga tgatgcgaat caagggttcg tacgcttcgg    115860
caccccagtg gcgcgtgaag aaggccgcca gacgaaacaa gcggtgtccg tagagcgtgc    115920
ctagggagaa gaggatgttg ccgttgcgcg ccaggtcttc ggggaaaacg accggcaggc    115980
cggtgtggcg ctgcacaaag cgcgtcagca gtccgccgct caagcgcggg tgacacaggc    116040
gctggctgag acgggcggcg cgcgtttcat cgaacacggc cgcctcaaag tccagccccg    116100
ggaaggcctg gcgcagttcg cggtacagat gaggccagta gggttgcggc gtcttgcgac    116160
taagcacggc gtggtccgag acacccaggt tgttcatggt ttcgcgcagt agcagcgttt    116220
cgagaccgcg gtgaaagagg aggacgcaga tgaggcgtac gatcttgagt tcttccaaac    116280
gcagcgagct cagcggctgt ccgcgcgaca tcttctcgct aatctgtaat attagatgat    116340
tggcgcaagt aaaggagaat ttgcccgtgc ggacccgcgg gacggcgggg ttctcttcgt    116400
cgcgggccat catcgttcgc tcggtgagcg ggtagcgacg gtgacgacaa tgacgatgga    116460
cgagcagcag tcgcaggctg tggcgccggt ctacgtgggc ggctttctcg cccgctacga    116520
ccagtctccg gacgaggccg aattgctgtt gccgcgggac gtagtggagc actggttgca    116580
cgcgcagggc cagggacagc cttcgttgtc ggtcgcgctc ccgctcaaca tcaaccacga    116640
cgacacggcc gttgtaggac acgttgcggc gatgcagagc gtccgcgacg gtcttttttg    116700
cctgggctgc gtcacttcgc ccaggtttct ggagattgta cgccgcgctt cggaaaagtc    116760
cgagctggtt tcgcgcgggc ccgtcagtcc gctgcagcca gacaaggtgg tggagtttct    116820
cagcggcagc tacgccggcc tctcgctctc cagccggcgc tgcgacgacg tggaggccgc    116880
gacgtcgctt tcgggctcgg aaaccacgcc gttcaaacac gtggctttgt gcagcgtggg    116940
tcggcgtcgc ggtacgttgg ccgtgtacgg gcgcgatccc gagtgggtca cacagcggtt    117000
tccagacctc acggcggccg accgtgacgg gctacgtgca cagtggcagc gctgcggcag    117060
cactgctgtc gacgcgtcgg gcgatcccct tcgctcagac agctacgcc tgttgggcaa    117120 cagcgtggac gcgctctaca tccgtgagcg actgcccaag ctgcgctacg acaagcaact    117180
agtcggcgtg acggagcgcg agtcatacgt caaggcgagc gtttcgcctg aggcggcgtg    117240
cgatattaaa gcggcgtccg ccgagcgttc gggcgacagc cgcagtcagg ccgccacgcc    117300
ggcggctggg gcgcgcgttc cctcttcgtc cccgtcgcct ccagtcgaac cgccatctcc    117360
tgtacagccg cctgcgcttc cagcgtcgcc gtccgttctt cccgcggaat caccgccgtc    117420
gctttctccc tcggagccgg cagaggcggc gtccatgtcg caccctctga gtgctgcggt    117480
tcccgccgct acggctcctc caggtgctac cgtggcaggt gcgtcgccgg ctgtgtcgtc    117540
tctagcgtgg cctcacgacg gagtttattt acccaaagac gcttttttct cgctacttgg    117600
ggccagtcgc tcggcagtgc ccgtcatgta tccggcgcc gtagcggccc ctccttctgc    117660
ttcgccagca ccgctgcctt tgccgtctta tcccgcgtcc tacggcgccc ccgtcgtggg    117720
ttacgaccag ttggcggcac gtcactttgc ggactacgtg atccccatt atcccggtg    117780 gggtcggcgt tacgagcccg cgccgtcttt gcatccgtct tatcccgtgc cgccgccacc    117840
atcaccggcc tattaccgtc ggcgcgactc tccgggcggt atggatgaac caccgtccgg    117900
atgggagcgt tacgacggtg gtcaccgtgg tcagtcgcag aagcagcacc gtcacgggg    117960 cagcggcgga cacaacaaac gccgtaagga aaccgcggcg gcgtcgtcgt cgtcctcgga    118020
cgaagacttg agtttcccag gcgaggccga gcacggccgg gcacgaaagc gtctaaaaag    118080
tcacgtcaat agcgacggtg gaagtggcgg gcacgcgggt tccaatcagc agcagcaaca    118140
```

```
acgttacgat gaactgcggg atgccattca cgagctgaaa cgcgatctgt tgctgcgcg   118200 gcagagttct acgttacttt cggcggctct tccctctgcg gcctcttcct ccccaactac   118260
tactaccgtg tgtactccca ccggcgagct gacgagtggc ggaggagaaa cacccacggc   118320
acttctatcc ggaggtgcca aggtagctga gcgcgctcag gccggcgtgg tgaacgccag   118380
ttgccgcctc gctaccgcgt cgggttctga ggcggcaacg gccgggccct cgacggcagg   118440
ttcttcttcc tgcccggcta gtgtcgtgtt agccgccgct gctgcccaag ccgccgcagc   118500
ttcccagagc ccgcccaaag acatggtaga tctgaatcgg cggattttg tggctgcgct    118560 caataagctc gagtaagaga gacgctatat ttagggcttc cctctctttt ttttctacac   118620
cgtgataccc taataaagca caccgcggtt attatcaacg tctctgtgtt tttattattt   118680
agaaataaat acaggaatg ggaaaaacac gcggggaaa aacaaagaag tctctctcta      118740 gatgcgggt cgactgcgtg gggtgctgga agtggaagcg gtgctgatgg gtgagggtcg     118800
tggcgcgggc acggaccgca acgtgctgct gatgtctgcc gcggtacgca cgtcgccgtc   118860
catgtcgctg cgcagataag aggtaggtcg tagtgcggcg tgctgcacgc tcaccgttaa   118920
tggtaccaag tcgtcaaggc tcgcaaagac gtgccacgag gggatgacga gcgtgagagc   118980
cccgttgtta ccgcttcgac gtctttgtcc ggtcaggatc agtgccgggg acagtccggc   119040
ttgggtgtcc gagtcctcgt cgccgctggc ttcctcgaag ccggcaaaca tggcttcgga   119100
caggggggtc ggcgtcggtg tggaggagag gtcatcttcg tcgtcctctt cctcttcttc   119160
ctcctcttcc tcggtgggtg gtaatccggg ggactgcggg agaaactcgg agacggcgcc   119220
gcgcatgacg ttgctccgtg gaaagagacc ggcgcgcagc tgcacctggg gacgcttgat   119280
tttgtccggt ttaccgggtg tgagagtcca aaacccacgg cggaaaaagt ggatgcggcc   119340
tagcggctgt cggtgttcca aatgaacggc ctgatcgccg gtcagcgtga cgcggagggt   119400
gattcgcaca cgatcgggta gcgggccggc ttctatggag acgcccggga tgttttccgg   119460
gaaaaagatg gtgtcgtgag tctgattggt ctcgaaagca ttctggatct gcacgatgta   119520
ctcgggatgt atgcgcgtca gcgtaaaact tttgggaatc aacagctgga agccgttgtc   119580
cggcaagcgt cgtaggtgcg ggtacggatt gtgtcgcgcc accacctcgg cgcgatgcgt   119640
gtaaaccgaa aagtgcagaa acacgctggt cggcgggtgc ggtgagtcgt gatgcagaaa   119700
cagcatgatc cattggcctc gttcgtccgt ctccgttttg tggatgtacg tgttagggtc   119760
cgaacaggcc agctgctcca gggcgtctac cagcgtcagc gggatggcgc cggcgcgaaa   119820
ggcgaactgg ctgacaaaga tctgccctgc ctccaaactg ctgtcggttc tgcggcgcca   119880
gttcggcgtt acggtcagtc gcacggccca gtggtgagcc gtgcggcgga tgatggcgcg   119940
cgcttccatt cgcggccgat tttcttcgcc gccgcgccgc tggctctgaa agaggtgcag   120000
tccgctaacg ggcacgcgt ccagcggcag cgcaaaggcc agtaccgaga ccgtgttgtt     120060
ttctgagcct ggcgtcaggc gtcgtgggcc aaagttgttg aggtccacca gcagtcggtc   120120
ctgttcgccc accacgcagc ggcccttgat gtttaagtcg gtcaggtcta cggtgtcgtg   120180
cggagatttg ttctcctgaa aacagcagag aaccgagggc cggctcacct ctatgttggt   120240
acgcaggtcc aggagtcgca gacgaccggc ttccagcgag ccgccttcca cgttggtgat   120300
gagccgaagc acctggcagt gcaggcgacc aaagcttccg ctggcggctt cggcctcgct   120360
gatcgcggcc gcttccgacg agggtccctc accgggcgag gacgatgcct gagacattgc   120420
gaaggcggga tggggggagg gtcagggat gcgcaaaggt gaacgggtct tcgtgggagg     120480
tcgggaaggg ttccggcaac tgtcgcaaat atagcagcgg tgacaggtgt ggcggccaaa   120540
```

```
agttgcgtgt ctgagtggac gtgggttttt atagagtcgt cctaagcgcg tgcgcggcgg   120600
gtggctcaac ctcggtgctt tttgggcgtc gaggcgatgc atggcccggg caaggcgtct   120660
tgccggtggc ggcgacgttt gggttgcgca gcgggctgcc atacgccttc caattcggcg   120720
aagatgcggt agatgtcgtt ggcgtcccag aagaattcct ggtacttcag attctgaccc   120780
tgaaccgtag ccaccatggg caccaggttg cgggccagga tgccggcctg ccagggcggc   120840
caggtgaaca cggccggatt gtggatttcg ttgtcggaat cctcgtcggt gtcctcttcg   120900
ggcgcgacgg tggactcggc cttaaggcgg ccgcgtgtca taacgcccga cgtgcacgcc   120960
gtcgccgagg atgctgattt gcgtttgcgg cccgcggaag tggaggcgcc cgccatggcc   121020
ccgccgccgg tgacgcgggg cgtcttgcgc tcggtggtta cgagttcttc gtcggagtcc   121080
gatccgctgg tccagacgtc gtcgtcgccc tgggcggcac cctcgtcgtg ccggtcccag   121140
gtgtgtcggt actcaagctt gccctggatg cgatactggc tggtgaaggt ggggtgctcg   121200
ctgtactgag gcccgcgctg cagcagcaag tcgatatcga aaagaagag cgcagccacg   121260 ggatcgtact gacgcagttc cacggtctcg cgtatggctt gtacctccag gaagatctgc   121320
tgcccgttca tcaacaggtt acctgagatg ctcaggcccg ggatgctctt gggacacagc   121380
agcccaaaat gctcgtgtga ggtaaaagcc acatccagca tgatgtgcga gatcttgccc   121440
ggtttgatta tcatattttt gggacacaac accgtaaagc cgttgcgctc gtgggggcgc   121500
atgaagggtt gcgggttgcg ggtcatcgtc aggtcctctt ccacgtcaga gcccagcgtg   121560
acgtgcataa agagcttgcc ggagggcacg tcctcgcaga aggactccag gtacaccttg   121620
acgtactggt cacctatcac ctgcatcttg gttgcgcgcg tgttctccat ggagcaaacc   121680
agctcgtgcg cgcacaccac gtgccgcagt gccacgtcct tggtgggaaa cacgaacgct   121740
gacgtgtagt agacgtcggg ctcttccac tggttctgct gacgcgtcca ggccagtccc   121800
gagaccgtga gacgcgcctg ccacatctgc ttgcccgacg cgtgaatcac agcgtcagct   121860
acgggcaggt gtcggtgttt gcgctcggcc gccgacgggt agtggtgcac gttgatgctg   121920
gggatgttca gcatcttgag cggcagcgcg tacacataga tcgacatggg ctcctggctg   121980
gggcagatgc ttcggcccgt ggggttgtgc acgttgaccg acacgttctc cacctcgctg   122040
cccgtaaagt acgtgtgctg cacctgcagc tgattgtcgc cgcggtggca tggcgtcgag   122100
tcgggcgtgt actgcgatac caagatcagc gagggctggc tcacgcgtac gtggataccc   122160
gtctgcagga gtcgcgtctc gtgcggcagc accggcgtat cgccgcgact aaacacggct   122220
ttcagcacgt gccccgaaat gggacccagt acggatatca tttcgggaca acggcgaccg   122280
cgcgactcca tgctgcctgc gcgtacgggt gtaggcgact gagcggcgcg ccctctgcgg   122340
ccgccgcctt acataggcag gcgaccaaac gcggaacccg aaataaaaac gttctacaca   122400
gagacaaccg cggattattg agtgtctttt tttattacaa aaaaagagg cgaagcccca   122460 ccgtcaccac accccatcac acaccaccac cgattttttt ttgttttaat cccgtatggc   122520
gcggacgcct agtgtccgtt tcccattatc agggtcctct gtttagagat cgccgcagac   122580
catggctaaa gtgacaggac tcgtcttctc tgtcgtattt ccgtaagct acagtcttg    122640 cggttccgtc tccggggacg ccagtcgcat ggcagcagg tcctccagcg cgatggaagc   122700
gcccagcacc gagagctgct gttgcgacgg cgaatgggat gtggaccgcg agtgtagcgt   122760
ggatttgact tggtgcgtca ttgctgacag gcaaccccga ttcagcgtat gctttgacga   122820
gataaaatag aggcgcccca ggagcgcgtc ccgtgggaac gtggcgccgt tctcgtcgct   122880
```

```
caccagtacg gttaattcca accaggagcg cggtagccag accgtaacgg gcattttgag    122940
tccctgacgt tgtgtggta caaaaacacc cagataaggc ccgtaaaagc ggcggtagat    123000
acgtaacgtg tgcgagttct tcagcgtcaa ttcgtaaggg acgcgcacct ccagtccctc   123060
gtccgccgcg ccggagcgtg gcggtacaaa gtaaggcagt ggcgcgtccg aaaagaaggg   123120
tcgtcgcacc gtttcgcgtc gcagccgcag gcgaaacgcc actgggtcgg ctggcgcctc   123180
ggtgcggtcg caggtcacgt tgaaacgtaa tatgccgtct tggtatagcg tgagtgacga   123240
cagcgtcagg tccggcggtg attcgttcgg gtctagctcc aatcgtccaa agacggaggg   123300
tcccaatgtc ttggccgtgg tttccgagag gcgcgccgag atacggctgg tgagtccacg   123360
cggccccgag atgccgcctt ccactcgatg ccagcacagc gcgtgtcgta cgcgcaccgt   123420
cagcgtgggc gtcagatccg cgtccgttga ttccgcggta tcagcgacgg aagccgcgtt   123480
ctccgttacg ttgtttatat ccagcgtcgg ctcgaacgtg agttctggca gatgcagcgc   123540
cagacagtcg tgtaacgccg tgtgatgcgc ggctttacgt cgtagcggta gccgtttcaa   123600
cagcggcgtg atgatacgga gcgcgaagag attgagtgat aggcgcacga tggccatgcg   123660
cgtcagttgt tggtcaatta ccgagcgcag gatatggcag cctgggcgtg cgggaaagag   123720
agagaaggcc gggcgcacgt cagaatcctc gttagagacc acgcatagaa tgccgcgttc   123780
acgatcgtcg ttgcggtcat cctcgtcctc ttctttcttc tcttgttttt ccttttttt   123840
ctcgggctcg tgggaagccg ccgtttcttc ttcttgcaac gtcgcggggg cggtttgaga   123900
ctcgtcgttc gcttccccca attgcagcgg cgtagagagc agaatctgga agggatcccg   123960
caattcttcg ggtcggaggt cgaggtgcaa ctggatcaga tggtaggtgc cgcggtgcac   124020
ccgaggctga cggatgtcgt gtttatccgt cagtgtgagg atggtctgcg gcgagccgct   124080
gtacttgtcc agctcgtccg gcgttttcag gaggagactg tcgtcgtcgg tactggcgac   124140
gcccatcatg gtcgtggtgg tagtggtggc gaggaaagtg agcggcggcg ccgacagagc   124200
tcggcgttgg cggcggcatt ttccgctgtg tcggctgcta ttgctgccaa cgccaccgcc   124260
gccgcctcgt ctggctcgtg gccggcgggc ccgattccga aggttggggt cgacgcgtgg   124320
catgcttggt gtctgcgggc gcgagagggc cggctcagcc tttaaatatg caggtcgcgg   124380
atttgttatc gggtgaaacg tcacacaccg tgaagacgac ctgttcgcgg atgaggtcat   124440
ccagctgtcg cagcatgacg aaaagcgccg acagccgcgc gatctcgtcg tcgggcgaca   124500
cgtgctgcgg ccgcgcgggc gtgcgcggct cgccgacgct gcgctcgcgg tccagccgca   124560
tcagcagctc ctggcacttg acgagcagca tggagctgtc ctctagcgcc aacttgcgca   124620
cgtaggtcat ggtcagctcc gaggctaggt tggccaccat ggacatggag aggcaggcgg   124680
tcttcatgtc gatcagcagg tgctggtcga tgaccggatc ggggatggtg aaggtggcgt   124740
cgcgaaaagt aatggtctgc agctgctgca cggcagcctt tacctcctcg tacgaacggt   124800
cgagcgagaa gaggcccatg atgagtagtc gctggttgat ttccagcgcc agtggcatgg   124860
gtacgatcca gggcagcacc agctcccact ggcccagcgt cagcaggttc tcgcgcgcca   124920
gcggtccgtg gaagagcggc ggcagcacgc atagcgcgtc gcccttctcc caagtcacgg   124980
gtcccgtgtt gaggacggtg tagagcagtc cgtgcgtggg tacgtgtagg aggatctggt   125040
tgccttctac gcgccgcatc aacgtcagcg tcatattgcg cagcaggccg cgcagtcgta   125100
cgtagccgcg ggtgtgatct acgaactggt gtaggcccag ctggtagtgc ttgatgagat   125160
gtagacgttg cggaatgggc acaacggccg ctactagctt ggtcagtttg cctacgtcgg   125220
cgatgctgag cttgtggtcg aaagtgcaga agatgttggc ctccatggcc gccatagcgg   125280
```

```
cggtgaaatc ctggccgcga cggaggagag gcagagacga acaacgtctg caccgggcgc    125340
ggcgtcagag cgagcgtggc gcgtccgggc ccgcgtttgc gtctaggtga ctcgccgcta    125400
acctgcggtc gtcgccgtcc tcctcaccgg acggcctcac gagttaaata acatggattg    125460
ctgcagcggg atgatttcgc ctacgacgta gttaccaaag tgcgtttcgg acgtagcaaa    125520
agccccggcg ccacccttga gtttggtctc catcagcgcc agcgtggtgg tgctgaggat    125580
cggtagcgct tcctgcgtca gacggcacgg gttttcgatg agttgttccg tgccttcgac    125640
gcagacgtac tgcgtgtccg tgtcgccgcg gatgcagtcc ttggcgcgta gcaggtactc    125700
gtcgatggtt ttgaagagcg ttttgttggc cgcgataatc tcttctgtgt aaagtactg     125760 cgcgcaaggg ctgtagaatt tggagttgta gcctagacgt tcgcgatgtc gggtgttgta    125820
gagtacgtcg ctcagacagc cggcttgcga ggcccagggg ttgtgtgtgg ccgcgaaagt    125880
ctgtgcgtcc gcttcgcgat ggtcgtagat ggccttggtg gcggcctccg tgtcgtacgg    125940
atcgacggcc agcatgcagg aggcacgccc gcgcgggttg ttggggatct aaagtaatt    126000 aacgtccatc gtcaccggcg taaggattag ttcgcacgcg gccttttgtc cgtgcaccgt    126060
ggcggcggca ttgcgctcgg acatgctgcc gaacgtcagc atagagatgg tctccgtgtc    126120
taacagttgc ggccgttcta cgccggccgc gtgccggatc cagcggtcca cctcgtcgtg    126180
ccggtacacg ttcataggga agacgcgaaa gaggtcctgc acgcggacgc ccatgtcggt    126240
tcgcacgcgg tttacgtagg ctacgcaggt atttgacgtg taacccagac ccatgtctac    126300
ggtgttaatg ttctgcgtga cgtggtacgt agtgctgatg tcgcgttcct ccttggtcac    126360
gatagggttg ttgatgataa ctgacgtgca tgatttgccg ctgtagagca gcatgtccac    126420
ctcgaaggtg tcggtgcgta cggccgtgag tgcgaatccc gggtggatgt gcgccttggt    126480
ctgcagcacc agtgaaactg gtgagatttt gtataacatg gcggccagcg tcatgactga    126540
gtgcaacacg ttgggacagg tggccgagta acgcgaaaag ggcgagcgca gccagttgtg    126600
gtactcgtgc gcgaaggctg tgggtagcgg gaaaccaccg tcgtgacggt gatagtgcgg    126660
gaactcggtc acgtagcgtt taatgtcgtc gctcaacgcc gcgcagatgg tggggtttga    126720
gtagaaacgg tggaaaggta cgggtaggct gtactcgatc aacgtcttag gcgccgtcac    126780
gacgcagcag ccgttgtaaa gcacgtgctg acgtgagata aagtccggca ggccctgacg    126840
ctgcgcgtgt tccagaggcg cgcgcacttc gagcaccttg acgtgctcgc ccacgaattg    126900
cacggccaaa aacagttcac gacaggcctg cagcagcggc gtatgtgcgt cggtggcgac    126960
gtcctccacc agctcggtca gcatctcgcc tacggcttga cgttgcgccg ctatcgagtc    127020 ttcggggtg acaccgcttg tgctctcttt cgacgtcgta cctgacgtgg agaccgcggt     127080
ggcggccggc atcaggagaa acgccggtcg gtaaaagagg tctactagca gcgtcttgag    127140
gttgagtccc aggccgcagg cccggttgtt ggtcatggcg ggcatgaggc agagataaaa    127200
gaccttttgt aacgtccatt cgtcgtcggt ggcacggtaa tcgtccacaa acagcggctc    127260
gtcggcatcc atggcgccca aacgcggtac gtccgaaacg ccgtggtgtc gcgcctcgat    127320
gttggccggg ttcaacggtt gccggtcggc cactacctgt acgccttcca tgttacgcgg    127380
caggtgcgta acgaagggg gccacagccg gtggtcgtgc agcgcgttca cgtaagccga    127440
tagcggttcc tcagccagtt gaccgttgtt aagtcccggc agcgctgaga tgcgcgttac    127500
cagacgcagc acgcgaccaa gattgcggta gtgaaagagc aactgcggtg gtagggcgcc    127560
atcagccagg tgttcggcga tcaacgtcac cagcgcgtag ctgtgcgcaa aaaccagcag    127620
```

```
ctgacgtgtg tgaaacatgt tgacgataca acgtgctacg aaagtgcgga ttagcaaaaa    127680
agcgtcgacg ttgccgtgta ccagcacgtc gaccaggtag caaagctcgg ggtaattggg    127740
gcttgtcacg gtggttttga aaagtcgcaa cgtctcttcg tagtcgggtg gtggccgcag    127800
tcgcatgtgt tccatgatct cccaggtgcg cagttcgtgg aaggggcccg gtgccagtcc    127860
atctggcaaa ttaccgatga cgatacgcgg tgtacacagc gccaccgttt cgctgttttc    127920
ctggcagtgc gtaaagtcga agaaggggtg cagctcggtg tagagcgtga tgttgcccac    127980
cttgtagaag tcggtgacca caaagtcctg cttcatttcg ttcaccgtgc gcgggacctc    128040
gcgtcgtacg cggtaaaaat gcggtatgcg gcgcgccgca ccgcccatgg gttcctgctg    128100
aaaacgacac tcgagcagtc gttgcatggc gggttccgag ggcggtccgc gttccgtgaa    128160
ggtctgtaga cagggcgcgg gctcgtgcag caccgggtgg cacagcgtct tgagcgcgtc    128220
cacaaagtct attttttgta cggcacggtc ccggtttagc aggtaggccg tggtgggcaa    128280
cgcgttgcga acgtgtcgt taagcttaac tttgctttcc accgtggtgt aaccgcgatc    128340
ctcgggcaga tacagcccta cggggaagaa aaacgtcagg tccacgttac gttctagcgg    128400
atctttggta tcggtgtttt tgtagacgcg ccgcaagttt tccataatca ccgttttttc    128460
gcccagtcgg atcacgtcca tgctcagcgg cgttaagctg tgcgcccgg cctgcgaaag    128520 cgagtcgttg ggcaaatgcg gttggcccga agtcagatga gccttgtacg agttgaaatc    128580
ggccaggatc gagtgatagg atatggcagt gacggcattt cgggactga gtacaaaatt    128640 gccgtaggtg gccggcgccg agaccgtttc tttggtgatg tggcttgaga gcagcgacat    128700
gatgatctgc ataacgttgg ccgtgcttac catcacgccg ctgatcttgg cccccgagct    128760
cgtggtgtac gtggtggggt tgtctaggat gctatcggtg gccgcttcgg ccagacgcgt    128820
gaggaacttg agcacatagt cgcgatcgcg cgtgcgattc agcaaaaaga gcgtggccag    128880
cattttggcc ttgaagctct gcaagatgtt gcttcgctgg atgcggttca gtgcctgtcg    128940
cgccagtgtg gcgttttcta ccagcgtctg caccacaaag tacggcggcg ccttgcgtag    129000
cagtgtctgt aaaaagctgt gaatcaagcc gcgctccatg gcgtcggccg tgtttttaag    129060
cgcgcgcagc accgtgtgca tggcttccac gttgaggatc ttgtccaaga tggtgccctc    129120
gaatgtctcg cgcagatacg tgaggcaggc tgcgctgagc tcgaagggga tggtgatggg    129180 ggattttttca ctgtatttgg tgaccataat ggtggtctga cgactagtgg gcaaaccggc    129240
gccgctggcc acacgcggca cctgcacgtg gaacagcatt ttgcccgtag tcagtttatt    129300
gaggtcgtgg aacttgatgg cgtgcgccgc gcggccaag ccgctggtca aaaaataaac    129360
ccattccagg cgattgcaga aggtgccgaa gatggcttcg aagtgaatat tgtaacgctc    129420
ggggtcatcg ccgtagtaga tgcgtaaggc ctcaaacatc tcctcgccgg cgctggtctt    129480
gacgtgcgtc agaaagtcag tgggaatgcc tactttaggc aggagctcga gcgccgacca    129540
gttctccatc gcggcggcgg cgtgagcgcg aggcgtcgga gctcggggaa agcagcgcga    129600
cccggagaat ggccggcgct gcgccgcgcc gcctcggctg tgacgctcta atagtcgttg    129660
gcggctccgc tatgccgcgc cgggttttac acgtccccgt gcacgttcgc gcctgcaacc    129720
tcacccaaga gctatcgacg ggcgaggacg cccgcttttg tcgtccgcga cccgttaacg    129780
tcgaacgggt gcgcgctgtt tttgcggctc tctaccgtgc ctgtccgata cacgtgagga    129840
ccgagcccga gcgtgtcaag ctggtactgg gtcgtctgtt actgggaccc gtggccgtac    129900
cctgtttttg cgacggtgaa gtggagggcc acggtgaaca tctggtacct acgacgcagt    129960
tttgtcgcgg gccgctgctc tacgtgcacc gacgttgttg ttgcggatcc gtgaccgccg    130020
```

```
ggcgcgcgct gtcctaccac gttctcgaaa accacgtggc cacgcatgtg ctacgcggat    130080
tgctctcgct gacggaatgg aatcgagaat tgccgagcct cttttgcgac tgtcctggcg    130140
gcggtggcgc ctcgggaacc gaggaacgct acgctatggc ctgcctgccg cgcgacctca    130200
gcctgcacct ggacgactat ccttacctga tggtggaaat cggacgcgta ctcagtgtca    130260
gcgaggtaga cgactacgta accgccgtct ccggctacct gggcgaggcc gcggcgccgc    130320
gcatccaggt tcactacaag ctgctctttg gactcaacgt cgtccgcaa cgccgtgcg     130380
cgttggacgc tacacgcgac ttttttctgc tggagctgca aaagctttgg ctgggcgttg    130440
aatatcacca cgaagtcacg tcggagtttt tcggtcgcgt actggctcag ctgcatcgcg    130500
accgcgcccg cgtcatgatg gcgcttcgct gcccgagca gacggtgtgc cacctgagca    130560
ccttcgttct cagtcgcttc aagcgacagg tactgtactt caagctacag gtgagctacg    130620
gcaagtgccg gactggtcac gctgacagaa gtggggagg ggggaacggt ggaaatcagg     130680
gacaccacaa cctactgtgt tatcgacgcc ttagcgtcac atttgccgac acagacacgg    130740
tgtggagaaa ccttttctac gtttattacg aactagctcg ggatctgggg tccatgggga    130800
cggaggacca acccgtaagc cgcggttacg gtgtttcttg cgcttcgagg acgtcgcgac    130860
tgtcaccgtc agaatcgacg gtggtttcgg cgaacggaca cgcgctgtct tccaccgcgc    130920
tcccgacgac gagcgcgggt cacaagctgt cactgccgcg cgacccggcc gcagatcgcg    130980
ttcgacgtta cgtatgcatt atctcgcgtc tcatgtacgc tcggtacggg gagagatggc    131040
gtaaacactg tcaacggcgg tcggagacgg gagaagagga ggaggaagag acgctggaat    131100
cgggggagac tgacgccacg ccgccatttg actttacggg gcagcagctg cgccgggcct    131160
atcaggaaca ccgacgtcgt aaacatctag ccgtgcagcg ttacgcgccg tgccgtcgta    131220
agctcatcgg cgggatggag tttgccgagg tgacgggcgt gagtctagac cgcatcgccg    131280
tcaacgcttt caacaccaac cgcgttatca atatgaaggc tgcgctctcg tccatcgccg    131340
cgtcgggtct cggcgtacgc gcgccgcggc ttcccaagaa catgacccac agttttgtga    131400
tgtacaagca cacctttaag gagcccgctt gcaccgtcag cacttttgtt tccaacgacg    131460
ccgtctacat caactcgctc aacgtcaata ttcgcggttc ctaccccgag tttctgtact    131520
cgctgggcgt gtaccggctg cacgttaata tcgatcactt ttttctgccg gccgtggtgt    131580
gcaacagcaa ctcctcgctg gacgtgcatg ggctggagga ccaggcggtg attcgctcgg    131640
agcgcagcaa ggtgtactgg accaccaact ttccgtgcat gatctcgcat actaacaacg    131700
tcaacgtggg ctggttcaaa gcggctacgg ccattgtgcc gcgcgtctcg ggcgccgacc    131760
tggaagccat tctgctcaaa gaactctcgt gcatcaagaa catgcgcgac gtgtgcatcg    131820
attacggtct gcaccgtgtt ttcacgcaac tagagctgcg caattcgtac cagatcccct    131880
tcctggccaa gcagttagtg ctgtttctgc gtgcttgcct gctcaagctg cacggtcgag    131940
agaagcggct gcagttggac cgcctagtat ttgaggcggc acagcggggt ctctttgact    132000
acagcaagaa cctcacggcg cacaccaaga tcaagcacac ttgtgcgctc atcggcagtc    132060
gtctagccaa caacgtgccc aagatcctgg cccggaacaa aaaagtcaaa ttggatcacc    132120
tgggccggaa cgccaacgtg ctgacggtgt gtcggcacgg ggaagcccac aagatccctc    132180
gcacgcgcct caaagtgtta gtcgaggtgc tgggcgcgtt gcagagtatc agcggtacgc    132240
cgcacacgcg cgaagtgatc caccagacgt tgtttcgatt gtgctcggcg gccgcagcca    132300
catcgggcct gtgttcatcc cctccccat tgtgtgtgtc ctcatcttcc tccgtccctt     132360
```

-continued

```
ctgtcccaac ctccgtcagc gttgacggca gttctgaacc cacgtcgccg cgagcgcggt 132420
ttgcatcacg atgatggaag ccgcggccgc tgccgccgcg gcgtttcgtc cggaggagcg 132480
tccgacgccg ggttggcacg acgcggcgtt gttaatggac gacggtacgg tgcgcgagca 132540
cgcgtttcgc aacggaccgc tgtcgcaact gattcgccgt gtgttaccgc cgccgcccga 132600
cgccgaagac gacgtggttt tgcttccga gctgtgtttt tattgcagcg gtcgttttaa 132660
ccgcaggtcg tccgtcttct ccatctattg gcagaagcat agcgatctgg tgtacgcgct 132720
tacgggcatt acccattgcg ccaagttggt ggtggaatgc ggtcagttgg ggagtagtag 132780
gctacggtgg cgcgacggtg atgcgagtgg tgaggagcgc cggggagacg acgacagcag 132840
ggacgagctg tacgacgtgc cgggcattta tatgattcgc gtcaacgacg gcggcagcac 132900
cggccccaga cacgttattt ggccgggtac cagcgtgctt tgggcgccgg acgttgtgat 132960
cactacggtg cagcgacgaa tctcggcggc gcgcgccctg gtgaacacgt tccgccaata 133020
tttttttttg ctggaacggc gctcgcacga ggagctggtt cttgtccgc ccagatggaa 133080 ggagcgtcta gcgccgctgt tgcagagtgc cacgcgcggt gattcggaca tgtttgacgg 133140
tgtggtggcc agcgcttatc accgtttgcg aatgagtaat attccgcgtt catccgcccg 133200
tctgctggaa cactgcgtgg ggctggcggg tgctaagaag ctgctcttgc tcgacgtgcc 133260
gcgtctggag aactattttc tttgtcaagt ctgtctttac gagctggacg aggacgagat 133320
gggcgaggag atgctgggca tgttggccgg aaagcccgag gatgccgccg tctcgggcgc 133380
aagcggcggt tttctgctac atcgcaagac gatgaagctg ccgcctgtc tgtgtttgtt 133440 gctcaattcg ctgcatttgc accaggaggc gctggaggcc ttggatcctc cgccgccgcg 133500
cgtcgaggag aacgaccttg tcaacgtggt gctgcgccgt tattatcgca gtcacggcgg 133560
cgtgcaggcg cggacgctgg cggcggcccg ggctttgtta ccgactacg ccgaaacgtt 133620 ttcgcccttg gggagtttta cgcgcctggg ttacgatcgt ctcgtttctg ccgatgccgg 133680
cgtcagtcgc cggcacctgg tggctctgct gcgtgcctag ctgaccctga acgatggc 133740 gtgtatatcg tcacacaggt aggtggccat gatgacggcg atgataagat cgtccgagat 133800
acgattctgg cgcttggccg agtaacgcgc cgtcgtgcct tcggccagcg tgacgcgtg 133860 caggttctga atctgctcca gaagatactc gatggggtcg tggctcagct tgatggtgta 133920
ggagacgagc tcttgcgagg cttttgatgta gcccgagttg aaacgcgaga tgaactgttc 133980
cacggccagc gccttgtcgc ggcccatgag gtagaagggc tgttcgatgt ggttctggtc 134040
gggcgtgtgg tagaagagca cgcggatgag cgtgctgctc tgcacgctct gtcggatgag 134100
gcaggcgatg cgcacggccg ccgcctggtt ggtgttgccc tccacggcga tgcgcagttc 134160
gtccaggtaa gggtgcaggc tcagcaccga gatgatcatg tgcgccgcgc actcggcgat 134220
ggctacctca gaactctcgg agaggtcgcg caaaaagaaa tgctctaggc cgtaaatgag 134280
aaactggtgt cggtaggcgc ctacggccgc cacgcccgtg cccgaggcct tgcggttggt 134340
ggtgaaggcc gggtccagat acacgtaaag cgtcttgccg aaataatcgt aggcgttggt 134400
gttgagcgtg ctgtaacgca aaatatcgaa ctcttcgcgg ctctggtccg tgatgagcac 134460
ggtgttctgc gagattttat tggtaccgcc gatgatctcg tccatgaaag cgcccggcat 134520
aaacatgttg gccgtcttgc gcacttgcga gttgaggctg atgaaggtgg gcttgtgcag 134580
tcggtagcaa ggacacgccg tggcgtcgcc cttctccgtg aagctgtgca ggtgctcttc 134640
gcacacgtaa gagaccacgt tgagcatgtc aaagggcgca ttgttaaggc gcgtcaagaa 134700
acacgtggag tcactggtag tgttggtgga cgatatgaag atgatcttgg tggtattctg 134760
```

```
ggccaggaac cccagaatgg tgttgaaggc ctctttcttg atgaagtgcg cctcgtccac 134820
cagcagcaag tggaagtttt gtcctcggat gctctgtgta gagaggagac agaaaaggga 134880
ctcttatgat tacgcacgct cgactggaag cctacagagt cggggtgggg ccggacaggt 134940
gagccaggtg agccgccagg tgaggcggga tcgccgtgtg ccaaccgggc tgcgacctga 135000
aaaccggaac caatccgccg acaccggcgc cgcgtgacgc gcgcccataa aaacgaaagt 135060
gtcgtcgtcg cgaccgcca cagccgccat gaactcgttg ctggcggaac tcaaccgact 135120
aggggtcgcg cacgccacta cggaggatgt ttttatcttt gtcgaccgcc tctttcaaca 135180
cttttccttc cttttccagg ccgaggagtc aggcccgcgc cgcttggaac tggtcgcgtc 135240
cgtgttcgag cacctgacgg tggagtgcgt taacgacatc ctggacgcct gcagtcaccc 135300
ggacgtgaac gtcgcggaga caagcaacac ctgtcgtccc tgcccttctc ctgttccctc 135360 cgccccaaa actgtcagcg gcgctcagac gtcatgtgcg acgcctcggg cgcctgtgac 135420
atgaggcacg tccagaacgc gtttaccgag gagatccagt tacactcgct ctacgcgtgc 135480
acgcgctgct ttcgcacgca cctgtgtgat ctgggcagcg gctgcgcgct cgtctccacg 135540
ctcgagggct ccgtctgcgt caagacgggc ctggtatacg aggctctcta tccggtggcg 135600
cgtagccacc tgttggaacc catcgaggag gccgcactgg acgacgtcaa catcatcagc 135660
gccgtgctca gcggcgtgta cagctacctc atgacgcacg ccggccgtta cgccgacgtg 135720
atccaggagg tggtcgagcg cgaccgcctc aaaaagcagg tggaggacag tatttacttc 135780
acctttaata aggttttccg ttctatgcat aacgtcaacc gtatttcggt gcccgtcatc 135840
agccaacttt ttattcagct tatcatcggt atctactcaa agcagaccaa gtacgacgcg 135900
tgtgtcatca aggttagtcg taagaagcgc gaggacgcgc ttctgaaaca gatgcgttcc 135960
gaatatggaa acgcacctgt attcggatct ggcgtttgaa gcgcggttcg ctgacgatga 136020
gcaattgcct ctacacttgg tgctcgacca ggaggtgttg agtaacgagg aggccgagac 136080
gctgcgctac gtctactatc gtaatgtaga cagcgctggc cgatccacgg gccgcgctcc 136140
aggcggagat gaggacgacg caccggcctc cgacgacgcc gaggacgccg tgggcggcga 136200
tcgcgctttt gaccgcgagc ggcggacttg gcagcgggcc tgttttcgtg tactaccgcg 136260
cccactggag ttgctcgatt acctacgtca aagcggtctc actgtgacgt tagagaaaga 136320
gcagcgcgtg cgcatgttct atgccgtctt cactacgttg ggtctgcgct gccccgataa 136380
tcggctctca ggcgcgcaga cgctacacct gagactggtc tggcccgacg gcagctatcg 136440
tgactgggag tttttagcgc gtgacctgtt acgagaagaa atggaagcga ataagcgcga 136500
ccggcagcac cagttggcca cgaccacgaa tcaccgtcgg cggggcggac tgcgtaataa 136560
cttagacaat gggtcggatc gccgtttgcc cgaagcggct gtggcttctc tggagacggc 136620
cgtcagtact ccatttttg aaattccgaa cggagcagga acctcctccg cgaacggcga 136680
cggcagattc agtaacctgg agcagcgggt agcgcgtttt ttgcgcggcg acgaggaatt 136740
catctatcac gcgggtccat tggagccgcc ttccaagata cgcggtcatg agttggtgca 136800
gctgcgcctg gacgtaaatc cagacctcat gtacgccacc gatccgcacg accgcgacga 136860
ggtcgcgcgt acgacgagt ggaagggtgc cggtgtctcg cgtcttcgcg aggtctggga 136920
tgtgcagcat cgcgtgcgcc tccgtgtgct gtggtacgtc aattccttt ggcgcagtcg 136980 cgagctgagc tacgatgacc acgaagtcga actataccgg gcgttggacg cttatcgggc 137040
gcgcatcgcc gtcgagtacg tgctgattcg cgccgtgcgc gacgagatct acgctgtact 137100
```

```
acgacgggac ggcggcgcgt tgccacagcg tttcgcctgc cacgtgtcac ggaacatgtc    137160
ctggcgcgtt gtttgggaac tttgccgtca tgccttggcg ctctggatgg attgggcgga    137220
cgtgcgtagc tgtattatta aggcgctaac gcctcgtctg agccggggtg ccgccgctgc    137280
cgctcagcga gctcgtcgcc agcgcgagcg ctcggcgccc aaaccgcagg agctgctttt    137340
cgggccgcgg aacgagagcg gtccgcccgc cgaacagact tggtacgctg acgtggtgcg    137400
ctgcgttcgc gcgcaagtgg atttgggcgt ggaagtgcgc gcggcgcgtt gtcctcgcac    137460
cgggctttgg atcgtccgtg atcgccgcgg acgcctgcga cgttggctct cgcagcccga    137520
ggtgtgcgtg ctgtacgtca cgccagactt ggacttttac tgggtgctgc cgggcggctt    137580
tgccgtctct tcgcgcgtca ctcttcatgg cttggcgcag cgggctttgc gagaccgatt    137640
ccagaacttt gaagcagttc ttgcaagagg aatgcatgtg gaagctggtc ggcaagagcc    137700
ggaaacaccg cgagtatcgg gccgtcgctt gccgttcgac gatctttagt ccggaggacg    137760
acagctcgtg tatcttatgc cagttgctgt tgctctaccg cgacggcgaa tggatcatct    137820 gttttttgctg caacggccgt tatcaaggcc actatgcgt gaaccacgta catcggcgtc    137880
gtcgacgcat ctgtcatcta cctaccttgt accaactgag cttcggaggt cctttgggtc    137940
cagccagcat cgatttcttg ccaagcttta gccaggtgac cagcagtatg acgtgcgatg    138000
gtattacgcc cgacgtgatt tacgaggtct gcatgttggt gccccaggat gaagccaagc    138060
gtatcctggt caagggtcac ggtgccatgg acctgacctg tcagaaggca gtgacgctag    138120
gcggcgccgg cgcctggttg ctgccgcgtc ccgaaggcta cacgcttttc ttttacattc    138180
tgtgttacga cctgtttacc tcatgcggca atcggtgcga tatcccttcc atgacgcgcc    138240
tcatggcggc ggccacggcc tgcgggcagg cgggttgcag cttttgcacg gatcacgagg    138300
gacacgtaga tcccactggc aattacgtgg gttgcacccc cgatatgggc cgctgtcttt    138360
gttacgtgcc ctgtgggccc atgacgcagt cgctcatcca caacgaggaa cccgcgactt    138420 tttctgtga gacgatgac gccaagtacc tatgcgccgt aggttctaag accgcggcgc    138480
aggtcacact gggagacggc ctggattatc acatcggtgt taaggattct gagggccgat    138540
ggctgcccgt caagaccgat gtgtgggacc tggtcaaggt agaggaacct gtgtcacgta    138600
tgatagtgtg ttcctgtccg gtgcttaaga acctagtgca ctaacggggt ctgacagttc    138660
acggggagaa gaaacaagaa acaacaaaaa aaaggaggac atggactcgc acgtttgt    138720 ggcaaggcgt atgttatcat catggagcta ctcacgttgg tgttgtagca actggcaaaa    138780
agcgccgtgc tcttggcgcc gcggtggtcg atgctgatca cgttgtcctt gttctcgacc    138840
acgtagtcgc gcgcgaaggt gtggcggcag cggaactcga cctctttgag cacaaactgc    138900
gacacgtgct tttggtgcgc cacgtagccg atgctgatgc cgatcatgtg cttaagcaga    138960
aacgagataa tggggatgat gaaccaagtc ttgccgtgac gtcgcggcac caggaacacg    139020
gtggctttct gcttaaagat gtcgatggag gtctgcgaga ggaagtcgat ctggaaggcg    139080
tggatgaggt actgcagcac gcgattggcc agcacgggga tcttggtcac ggctataaaa    139140
aagatgacgt gtatcaataa attcttttga aacggttcga gtcggatggc ttttgcgtcg    139200
ccctcgacgg cggtactgaa gccgccgtcg agccactttt taaagtcggt catgaagttg    139260
ttgatctgct gaaactgcgg atcgcggtag agctcggtca acgcgtccag cttctggtag    139320
gaggcgcgct gctcctcgga gcacgggcga aacgtcagtt tatcgagcgc gctcttgagg    139380
cgctcgtgaa acagcagctc gcgctggctt tcctcgggcg agttgtagtc gcggtggcgg    139440
ccgcagaagg ccatgagcgg caggaaggcc tcgttgcacg agtgggccag cccgagttcg    139500
```

```
gggtgcatca tctggtagcg cttgcggcac agcgtcgcca cattggtgaa ggccgtggag   139560
atgcaggagg tggggtggct cttgcgcttc tgcagctccg cgtagcgctc ctggatcttg   139620
gcggccgagt ctccgcgcaa catgatggcg gcggcggtgg tgcgagcgga ggttaggcgg   139680
cagcggcgag aggagaggaa aaagatggcg gccgcgagga cgacggagga tccacccgaa   139740
aaccacgttg ttgcggacgt ggctcgtggg acgggcgccg tcactcgttc gtcttcgtcg   139800
tccctagtgg tgtcgtcttc ctcggcgtca ggctcggacg aatcttcctc cgcctctcct   139860
ctcagtttcc ccgtctcctc cccctcaact gccgtcaggt ctccggggtc cgccggggtt   139920
tcaacgtccc tgtgctcggt ggaacggatg gtcgagctgt cggcgcagtc tccggccgcc   139980
gatttctcgg tctccgaggc ttggcgcttc gaggaggccg taaatatggc gctggtggcc   140040
tgcgaggccg tgtcacctta cgatcgcttt cgcctaattg aaacgcccga cgagaatttc   140100
ttgttggtca ccaacgtaat tccgcgcgaa tcggccgagg tgccggtgtt ggatagcagt   140160
agcagcggtg gcgatagcgg gccggaggac aaaaagaaaa acgtcgggaa taaaaccgcg   140220
ggggaaaaga acggcggtgg gtctcgggcc aaacgccgtc gtagacgacg cgctccgaaa   140280
aacgacgccg ccacgccgtc ttttctacgt cgacacgacg tgctggagcg tttcgcggcc   140340
gcggctaagc ctttgccgtc gctttgtgtg cgtgattatg cgttacgcaa tgctgaccgt   140400
gttacctacg acggcgaatt aatctacggc agttacctgt tgtatcgcaa ggctcacgtg   140460
gagctgtcac tctccagcaa caaggtgcaa cacgtggaag ccgtgctgcg acaggtgtac   140520
acgccgggct tgttagatca tcacaacgtg tgcgacgtgg aggccctgct gtggctgctg   140580
tactgtggac cgcgcagctt ttgcgcgcgt gacacttgtt tcggtcgcga aaagaacggt   140640 tgtccttttcc ccgcgttgtt gcccaaactc ttttacgaac ccgtgcggga ctatatgacc   140700
tacatgaatc tggctgagct gtacgtcttt gtttggtatc gcggctacga attccctgcg   140760
ccgacgccgc aggcgacgac ggcgggtggt ggtggtggta gtggtggcgg cggcggggcc   140820
ggcgcttgtg cggtcgagac gagcgcgtca gcaggccggg tcgatgacgc cggcgacgag   140880
gtgcatttgc ctttaaagcc cgtctcgctg gaccgtctca gagaggtgtt gcaggcggtg   140940
cgcggccgct tctcggggcg cgaggtgccc gcctggccgg cctcgtcgcg cacctgtttg   141000
ttgtgcgcgc tctacagtca gaaccgtctc tgtttagatc tcgcgcgtga cgaggcgcgg   141060
accgtgagtt atagccccat cgttatccaa gactgcgccg cggctgtcac cgacgtcact   141120
ttgagccaca tcttgcccgg ccagagcacc gtctcgcttt ccccgtctca ccacgtcggc   141180
aagttgctga cgctctctc gctgaacgac gcgggtctca tcacgttgaa tctatgcgt   141240 cggtcaacaa acagctctta aaggacgtga tgcgcgtcga ccttgagcga cagcagcatc   141300
agtttctgcg gcgtacctac ggaccgcagc accggctcac cacgcagcag ctttgacgg   141360 tgatgcgtgt ggccgctcgg gaacagaccc gatacagtca gcgaacgacg cagtgcgtgg   141420
ccgcacacct gttggagcaa cgggcggccg tgcagcaaga gttgcaacgc gcccgacagc   141480
tgcaatccgg taacgtggac gacgcgctgg actctttaac cgagctgaag gacacggtag   141540
acgatgtgag agccaccttg gtggactcgg tttcggcgac gtgcgatttg gacctggagg   141600
tcgacgacgc cgtctaacag gtatagcaat ctccgtcacg cctctgttca gatttatta   141660 aaaaaaaaac acaacataac gacagtgtcg gtgtggtagc tagtgcagcc ttaggaacag   141720
ggaagactgt cgccactatg tcctccgcac ttcggtctcg ggctcgctcg gcctcgctcg   141780
gaacgacgac tcagggctgg gatccgccgc cattgcgtcg tcccagcagg gcgcgccggc   141840
```

```
gccagtggat gcgcgaagct gcgcaggccg ccgctcaagc cgcggtgcag gccgcgcagg   141900
ccgccgccgc tcaggtcgcc caggctcacg ttgatgaaaa cgaggtcgtg gatctgatgg   141960
ccgacgaggc cggcggcggc gtcaccactt tgaccaccct gagttccgtc agcacaacca   142020
ccgtgcttgg acacgcgact ttttccgcat gcgttcgaag tgacgtgatg cgtgacggag   142080 aaaagagga cgcggcttcg gacaaggaga acctgcgtcg gcccgtagtg ccgtccacgt   142140
cgtctcgcgg cagcgccgcc agcggcgacg gttaccacgg cttgcgctgc cgcgaaactt   142200
cggccatgtg gtcgttcgag tacgatcgcg acggcgacgt gaccagcgta cgccgcgctc   142260
tcttcaccgg cggcagcgac ccctcggaca cgtgagcgg cgtccgcggt ggacgcaaac   142320
gcccgttgcg tccgccgttg gtgtcgctgg cccgcacccc gctgtgccga cgtcgtgtgg   142380
gcggtgtgga cgcggtgctc gaagaaaacg acgtggagct gcgcgcggaa agtcaggaca   142440
gcgccgtggc atcgggcccg ggccgcattc cgcagccgct cagcggtagt tccggggagg   142500
aatccgccac ggcggtggag gccgactcca cgtcacacga cgacgtgcat tgcacctgtt   142560
ccaacgacca gatcatcacc acgtccatcc gcggccttac gtgcgacccg cgtatgttct   142620
tgcgccttac gcatcccgag ctctgcgagc tctctatctc ctacctgctg gtctacgtgc   142680
ccaaagagga cgattttgc cacaagattt gttatgccgt ggacatgagc gacgagagct   142740
accgcctggg ccagggctcc ttcggcgagg tctggccgct cgatcgctat cgcgtggtca   142800
aggtggcgcg taagcacagc gagacggtgc tcacggtctg gatgtcgggc ctgatccgca   142860
cgcgcgccgc tggcgagcaa cagcagccgc cgtcgctggt gggcacgggc gtgcaccgcg   142920
gtctgctcac ggccacgggc tgctgtctgc tgcacaacgt cacggtacat cgacgtttcc   142980
acacagacat gtttcatcac gaccagtgga agctggcgtg catcgacagc taccgacgtg   143040 cctttttgcac gttggccgac gctatcaaat ttctcaatca ccagtgtcgt gtatgccact   143100
ttgacattac acccatgaac gtgctcatcg acgtgaaccc gcacaacccc agcgagatcg   143160
tgcgcgccgc gctgtgcgat tacagcctca gcgagcccta tccggattac aacgagcgct   143220
gtgtggccgt ctttcaggag acgggtacgg cgcgccgcat ccccaactgc tcgcaccgtc   143280
tgcgcgaatg ttaccaccct gctttccgac ccatgccgct gcagaagctg ctcatctgcg   143340
acccgcacgc gcgtttcccc gtagccggcc tacggcgtta ttgcatgtcg gagctgtcgg   143400
cgctgggtaa cgtgctgggc ttttgcctca tgcggctgtt ggaccggcgc ggtctggacg   143460
aggtgcgcat gggcacggag gcgttgctct ttaagcacgc cggcgcggcc tgccgcgcgt   143520
tggagaacgg taagctcacg cactgctccg acgcctgtct gctcattctg gcggcgcaaa   143580
tgagctacgg cgcctgtctc ctgggcgagc atggcgccgc gctggtgtcg cacacgctgc   143640
gctttgtgga ggccaagatg tcctcgtgtc gcgtacgcgc cttcgccgc ttctaccacg   143700 aatgctcgca gaccatgctg cacgaatacg tcagaaagaa cgtggagcgt ctgttggcca   143760
cgagcgacgg gctgtattta tataacgcct ttcggcgcac caccagcata atctgcgagg   143820
aggaccttga cggtgactgc cgccaactgt tccccgagta accgggacgc ggaacgtgac   143880
ggttgctgag gggaaaggca acagagaagg tacaaaccca ccggcgggga aaataccgag   143940
gcgccgccat catcatgtgg ggcgtctcga gtttggacta cgacgacgat gaggagctca   144000
cccggctgct ggcggtttgg gacgatgagc ccctcagtct gtttctcatg aacacctttt   144060
tgctgcacca ggagggcttc cgtaatctgc cctttacggt gctgcgtctg tcttacgcct   144120
accgcatctt cgccaagatg ctgcgggccc acgtacgcc agtagccgag gactttatga   144180
cgcgcgtggc cgcgctggct cgcgacgagg gtctgcgcga cattttgggt cagcggcacg   144240
```

```
ccgccgaagc ttcgcgcgcc gagatcgccg aggccctgga gcgcgtggcc gagcggtgcg   144300
acgaccggca cggcggctcg gacgactacg tgtggctcag ccggttgctg gatttagcgc   144360
ccaactatcg gcaggtcgag ctcttccagt tgctggaaaa ggaatcgcgc ggacagtcgc   144420
gcaactcggt gtggcatctg ttgcgtatgg acacggtctc ggccaccaag ttctacgagg   144480
ccttcgtcag cggctgtctg ccgggcgccg cggcggcgga cggttcgggt ggcggcggct   144540
cgcactacac gggttcgcgc gccggcgtct cgccgggcat ccagttcggt atcaaacacg   144600
agggcttagt caaaacgctg gtggaatgtt acgtgatgca cggacgcgag ccggtgcgcg   144660
acggcctcgg tctgctcatc gaccccacgt cggggctgct gggcgcttcc atggacctgt   144720
gcttcggcgt gctcaagcag ggtagcggtc gcaccttgct ggtggaaccg tgtgcgcgcg   144780
tctacgagat caagtgccgc tacaaatatt tgcgcaaaaa ggaggacccc tttgtgcaga   144840
acgtgctgcg gaggcacgac gcggcggccg tggcctcgct gttgcagtca cacccggtgc   144900
cgggcgtgga gtttcgcggt gaacgcgaga ccccgtcggc acgcgagttt ctgctttcgc   144960
acgacgcggc gctcttcagg gccacgctca agcgcgcgcg cccgctcaag ccgcccgaac   145020
cgctgcgcga gtacctggcc gatctgctgt atctcaataa ggccgagtgt tcggaagtga   145080
tcgtgtttga cgccaagcac ctgagtgacg acaacagcga cggggacgcc acgatcacta   145140
ttaacgcgag tctcggccta gccgcgggcg acggcgctgg cggcggcgct gatcaccacc   145200
tgcggggcag cccgggcgat tcgccgccgc cgatacccttt cgaggacgaa aacacgcccg   145260
agctgctggg ccggctcaac gtgtacgagg tagcgcgctt ttcactgccg gcttttgtca   145320
atccgcgtca ccagtattac tttcagatgc tcattcagca gtacgtgctc agccaatact   145380
atataaagaa gcatccggac ccggagcgga tcgatttccg cgacctgcct accgtctacc   145440
tggtctcggc catcttccgc gagcgcgagg aaagcgaact gggctgcgag ttgctggccg   145500
gcggtcgcgt tttccactgc gaccacatcc cgctcctgct catcgtcacg cccgtggtct   145560
ttgaccctca gtttacgcgc catgccgtct ctaccgtgct agaccgttgg agtcgcgacc   145620
tgtcccgcaa gacgaaccta ccgatatggg tgccgaactc tgcaaacgaa tatgttgtga   145680
gttcggtacc acgcccggtg agcccctgaa agatgctctg ggtcgccagg tgtctctacg   145740
ctcctacgac aacatccctc cgacttcctc ctcggacgaa ggggaggacg atgacgacgg   145800
ggaggatgac gataacgagg agcggcaaca gaagctgcgg ctctgcggta gtggctgcgg   145860
gggaaacgac agtagtagcg gcagccaccg cgaggccacc cacgacggct ccaagaaaaa   145920
cgcggtgcgc tcgacgtttc gcgaggacaa ggctccgaaa ccgagcaagc agtcaaaaaa   145980
gaaaaagaaa ccctcaaaac atcaccacca tcagcaaagc tccattatgc aggagacgga   146040
cgacctagac gaagaggaca cctcaattta cctgtccccg cccccggtcc ccccgtcca    146100
ggtggtggct aagcgactgc cgcggcccga cacacccagg actccgcgcc aaaagaagat   146160
ttcacaacgt ccacccaccc ccgggacaaa aagcccgcc gcctccttgc ccttttaact    146220
cataaacttt caggtctcgc gtacgattcg cgagtcggga atgggacacc cgtgggtgtt   146280
tctccgtgtg tatattattt ttttttttg tgtgtgtttg cgccccgtg tgtctaatgt     146340
gctgtttgaa acacgtaaag tagctggtgg aagaacagat aaacctttaa taaaaaaaaa   146400
agtatgtgct cccgacccac ggtctgcgtg tctcttttt atgtccatgt ctccaagtct    146460
ggtgcgggtg gcggcgggt taagcgtcct cgaagtcttc atcatcgtcg tcgtcctctt    146520
cttcgcggag gcgacggctt tccaagctgt cgtggtgact gagcacagcg acttcttcgc   146580
```

```
cggaggctgt ggccagcgcc tggtacttga cactgccgct accgcgtccg cgaaagtagc   146640
ggacggcgcg acacgtcgta acatggccc atatgaaaaa gagcatgccg aacgaccagc    146700
tgatgccggt gcggtattcg ttgctgagga aggtatcgta ctgcacgatg gggtagatga   146760
ggccgcagag tccaaagaag gcgcccaggt ggtagccgaa ttgcaccttg acgtattgaa   146820
aaaagacggc ctcgatcagt aaaaagtaga tgatggagat gatagcgtag accacgaaga   146880
cggctaacac catgtggcct gtacgcacga aaaagttgtt tccgaagccg tagcacaggg   146940
ccatggctac cacggtggtg ttgaaaccaa gcgctacctc taccaggttg acgatgagcg   147000
tgcggaactg caccgtacct ttgagcttgg ggtgcagacg cgagaagaaa aagagtgagc   147060
gtttgtagct gcggtactgc gtgaccatgc tcacgttgaa aatggtcagg cagaaaaagt   147120
gcacggcggc catgaaggcg atcatgctgg gcagccgaaa tgacatggtc agtgtgaata   147180
gttggaacgt gtccatgctg agaatgaaga ggaaggctgt gaggctgtcg cccatgtacg   147240
aaatgtcgcg tgtcgactgg tttaggctca tgcctttgtc cttgcgcatg ctgatcttga   147300
tccagcatac caggtagtag atggtcacgg ctaaaaagac gagctgcatg aacacggcgt   147360
agcacaccaa ctgcaccgag tctaagaaaa gcataggcgt gtgcaggtgc attacgttgt   147420
aggccgacat gttgagcctt tcaaagtcca cgacgtgata gtagacgcag gggtagccca   147480
ggtgcggaaa attgctcagc actagatgca cgctgacgtt gacaaaagtc agcaccatga   147540
aaacgataga agcgctccat gtccgtgtat tcaccttatc cacgtgcgag ggggccatgg   147600
cgatagcggc ggcccgctcg ctcgggaggc gatgggggcg cgccgatgac gacaggctcg   147660
cgggtcgtta aatactacga tgggagccgc cgcggctcac gacgcggttt gagcacgtcc   147720
gggcggtcgg tgaaaaaaga ccccgcgggc cttcgcgact ctcttctgtc cgaggatgac   147780
cgctcagccg ccgctgcacc accgccacca cccgtacacc ctgttcggga ccagctgtca   147840
tctcagctgg tacggccttc tagaggcctc ggtgcctatc gtacaatgtc tgttttgga    147900 tctgggtggc ggccgtgccg agccgcggct tcacacgttc gtggtgcgcg gtgaccgtct   147960
accgccggct gaggtgcgtg ctgtgcatcg cgccagctac gctgcgctgg cctcggccgt   148020
gactacggac gccgatgagc gtcggcgcgg cctagagcag cgtagcgccg tgttggcgcg   148080
cgtgttgcta gaaggcagcg cgttaatccg cgtgttggcg cgcaccttca cgccggtgca   148140
gattcagacg gacgctagtg gcgtggagat tttggaggcc gcaccggcac tgggcgtgga   148200
aaccgcagcg ctgtcgaacg cgcttagtct tttccacgta gccaagctag tggtcatcgg   148260
ctcgtatccc gaagtgcacg agccgcgtgt ggtcacgcat accgcggaac gcgtctccga   148320
agagtatggc acccacgcgc acaaaaaatt gcgtcgcggt tactacgcct acgatttggc   148380
catgtcgttt cgcgtcggca ctcacaagta tgtgctggag cgcgacgacg aggccgtcct   148440
ggcacgcctc tttgaggtgc gcgaggtgtg ttttttgcgc acctgtctgc gtctggtcac   148500
gcctgtcggt ttcgtggccg tggcagtgac cgacgagcag tgttgtttat tgctgcagtc   148560
ggcctggact cacctttacg acgtgctttt ccgtggtttc gctgggcagc cgccgctacg   148620
cgactacctg gggccggacc tctttgagac gggcgccgcc cgttctttct ttttttccgg   148680
tttcccgccc gtgccgtct acgcggtcca cggtctgcac acgttaatgc gcgagacggc   148740
gttggacgcg gcggctgagg tgctctcgtg gtgcggcctg cccgacatcg tgggctcggc   148800
cggcaagctg gaggtggaac cctgcgcgct ctcgctcggc gtgcccgagg atgagtggca   148860
ggtcttcggt accgaggccg gcggcggcgc cgtgcgtctc aatgccacgg cttttcgcga   148920
gcgaccggcc ggcggcgatc gtcgctggct gttgccgccg ctgccacgtg acgacggcga   148980
```

```
cggtgaaaac aacgtcgtgg aagtcagcag cagcaccggc ggtgcgcacc cgccgagcga 149040
cgacgccact ttcaccgtgc acgttcgcga cgccacgcta catcgagtgc tcatcgtgga 149100
tttggtcgag cgcgtgctgg ccaagtgtgt acgcgcgcgc gacttcaatc cctacgtgcg 149160
ttatagtcat cgactccaca cttatgcggt ttgtgaaaag tttattgaga atctgcgttt 149220
tcgctcgcga cgcgctttct ggcagatcca gagtctgctg ggctacatct ccgagcacgt 149280
tacgtcagcc tgcgcttcgg ccggccttt gtgggttctg tcgcgcggcc accgcgagtt 149340
ttatgtctac gacggctatt cgggtcacgg acccgtctcg gccgaagtgt gcgtgcggac 149400
tgtggtcgac tgttattggc gcaaactttt tggcggcgac gatccgggtc ccacctgtcg 149460
tgttcaagag agcgcgcccg gcgtgctgtt ggtctgggc gacgagcggt tggtgggtcc 149520
cttcaacttc ttctacggca acggcggcgc cggtggtagt ccgctccacg gggtggtggg 149580
tggtttcgcg gcgggacatt gcggtggcgc ttgttgcgcg ggctgcgtcg tcactcaccg 149640
ccattctagc ggcggcggtg gtagtggcgt gggcgacgcg gaccacgcga gtggcggcgg 149700
tctagatgcc gctgccggga gtggtcataa cggcggtagt gatcgggttt ctccctccac 149760
gccgcccgcg gcgttaggtg gctgttgctg cgcagccggt ggcgactggc tctcggccgt 149820
gggtcatgtc ctgggccggc tgccggcgct gttacgggag cgcgtgagcg tgtccgagct 149880
ggaagccgtg taccgcgaga tcctctttcg tttcgtggct cgccgcaacg acgtggactt 149940
ttggttactg cgcttccagc ccggtgaaaa cgaagtaagg ccgcacgctg gggtgattga 150000
ctgcgcgccc ttccacggcg tgtgggccga gcagggccag atcatcgtac agtcacgcga 150060 tacgcgttg gcggccgata tcggctacgg cgtctatgtg gacaaggcct ttgccatgct 150120
cacggcttgc gtggaggtct gggcgcgaga gttattgtcg tcctccaccg cttccaccac 150180
cgcttgttct tcttcttccg ttctctcctc cgccttgccg tccgtcactt cgtcctcttc 150240
gggcacggcg acggtgtctc ctccgtcttg ttcttcttcg tcggcgactt ggctcgagga 150300
gcgcgacgag tgggtgcgct cgctggcggt tgacgcgcaa cacgctgcta agcgggtggc 150360
ttccgagggc ctgcggtttt tccggctcaa cgcttaacga gtcacgtagg gaactacgt 150420 gggtaagtga cgtggatact agtaaaaaaa gtgcgtcaaa gctcttagcg tgtgacgtgg 150480
atactagtaa aagggacgtc aaagctcact acgtgttgcg tgtttttttt ttttctatga 150540
tatgcgtgtc tagttcgctt ctcactcttc ctctcctcgt tcccagcgcg gcggcagctt 150600 gggggtgag ggcaaattgg ggtagttggc gttgagcacg tctagcaggc ccaggcccac 150660
gggccaaccg tccacggtct tgcgctcggt cagcttgagg ctgaacgagt gtgcctcgtc 150720
ctgaccggta aggcggaaaa agaagcgtgc taccagctgc aggcaggtat gccgcgtctg 150780
ctggaagagc acgaaggtag cgggcacgta ctgcacaatg tgcggctctt tttcctcaaa 150840
gagcaggtag agcgcgctgc agatcagccg cctggcgctg tggtgcagca gccggccgaa 150900
gctttcgcgc acgttcaccg cgtccaggta ctggagcagg tcgtgcaggc acttgcgcgt 150960
taagttgcaa ttttccacgc acgaaataac ggtacagagc gcgaagtgca gcaggttgtc 151020
ggctttgacg atgccgcagc ggtgtttgag ccgcagatcc gagagcctca cctgcgtgac 151080
ggcgtcttcg gtctcgagca aaacacggc ggagtagcct agaaaggccg aggtgcacag 151140
caactcgctg cggtactcgg ccatggagac cagcagcccg tgctccgtgt gcagccacag 151200
cttgtcgccg cgcaccgtaa agtcgagcac ttgcggctcc atgatcatca cattctgtct 151260
agtgaaatcc gtatggacct ccagcacgcc gcggatcatc agggcctcca tttcgaaatc 151320
```

```
ggccgacacg ctctgggccg cgccgctcct cgtctgccgt gatcaagcgg cgcggcgcgg    151380
acctttcaag tgttcctggg ccgccgctcg aggcagttcc cctttctggc actccgcccg    151440
ccgcttcgcg gctcatttgg cgccgacgcg ccttctcgcg gctgcaaatc agctccacgt    151500
atcggcaaaa cttgctgtcg tcgtaggcgg cggccacgat ctcgccgaag gagagctgca    151560
ggtaggcctc gggtacgggg tccagcgtgc ccagcgccag gatgtgacac agatagggca    151620
gggtcacgcg ctctaccgtg taattggagt agacgatggc ctcttcggcc ccttgatgcg    151680
tgaccagacg ccgtaggcga aaggtacgga aatactcgtt ttcccacaac tgcgtgagga    151740
agcgttccag cgactcggtg ccgggcacga actgcgagaa gaagctgttg gccaccaggc    151800
ggttgtcttc caccgccagc ggacggaagg gcgccgcgtc gcgcgccttg cgcacggcct    151860
ccaacacggg caggtggtag agttcggcgt cgcgcgcgcc caggctcatg gagtcctcgc    151920
gccgcgaggc gtagcgcgtg agcaggtcgc gcagttcgcg cacgcgattc tcccaggtct    151980
ggttaagcgt gcgcaggtcc tggatctcgt ccacctgcga ctggatctgc tcctccaggc    152040
acttgataac ctgcttctta aacaggtcgc ggatgtcccg ctcgggcgcc gccgggccgg    152100
gtggcggcgg cagcagcccg acgtggcccg cgggtcctcc caccacgcg ccgccgggtc    152160 ccaccacgcc gggtccgccc ggaccacgcg cgggtagtag acggttttgg tccaccagcg    152220
agggggtcag gtcctgcaga aaggactcga cgctgtcctc gatgccgatg cgcgatttgc    152280
tgtccgagac gttaagcaaa aacttcataa tggacttttt ggcgtcgctg ccccggtcgt    152340
gctgctccat catctccacc agcttcttgc agttgagctc gtggcggctg gcggtcacca    152400 cttttcacagg aaaggtattg agcaactggc agatcttttg gtggcggcag agcccgtcgt    152460
agcgcagaat ctcctcgtgc aggtgtgcca ccggcgtggt gaacagcagc ttgtcgcgct    152520
cataagccag cggttcggcc gccacgtaca agcggatgtg cttgccgcgc agctgcgcct    152580
ccagccgctc cgagcgcacc ttcttgaaga cgcgtacctc gggcgcgttg gctacgcgca    152640
cggcgcccag gcgctcggcc acctgcagca gcagcgccag gttagcctgc agcaggtcct    152700
gcgccagcgg gtgtgtctcg gtggcccgct gcacggccgc gcgtacaaat tgcgcccgct    152760
cggccgcctc gctcggcttg gtcttcacgt ccagcagcgg taccagtccc accgttacgc    152820
accaatccac gtagagacca tagtcgtcgt tatcggcgta ctgatataaa atgtcgcgga    152880
gcgcgcccag cacgcccgtt tgcacgctct ggcgcaacga ggcgctccac accaacagat    152940
actgctccag gtcctcttcg tccagcgcgc ggtagggaaa tagcgccgcg tgcaacttcc    153000
actcctcggc cacgcgccgc accgtgatgg tgtcaaagag cgttttgcac actccgtaga    153060
gcagctgctt gcgcagcacg cacgggtcgc gcagcacctg gtgcatgctt tggccgcgac    153120
acgtccccag aaagccgtgc agcaaccgca ggaagctcat cgtctgcccc gtggggaaaa    153180
tgtcgatgac ggcctcgtca tccacgccgc ggcccacgcc caagtacgac gacgccttga    153240
tcctcaacct ctcgtcggcc gccaagatcg aacggatcgt cgacaaggtc aagtccctct    153300
cgcgcgagcg ctttgcgccc gaggattttt cgttccagtg gtttcgctcc atcagtcgcg    153360
ttgaacgaac gacagataac aacccctctg ccgcaactac cgccgcggca acgacgaccg    153420
ttcactcctc cgcctcctct tctgccgccg ctgccgcttc gtccgaggcc ggcggcacgc    153480
gcgtgccctg cgtcgaccgt tggcccttct ttcccttccg cgcgctgctc gtcaccggca    153540
cggcgggcgc cggcaagact tccagcatcc aggtgctggc ggccaatcta gattgcgtga    153600
tcaccggtac cacggtgatc gccgcgcaga acctcagcgc gatcctcaac cgcactcgct    153660
cggcgcaggt caagaccatc taccgcgtct tcggcttcgt cagcaagcac gtgccgctgg    153720
```

```
ctgacagcgc cgttagccac gagacgctgg aacgctaccg cgtgtgcgag ccgcacgagg    153780
agaccaccat ccagcgcctg cagatcaacg atctgctcgc ctactggccg gtcatcgccg    153840
acatcgtgga caaatgctta aatatgtggg agcgcaaggc cgcttcggcc tccgccgcgg    153900
ccgcagccgc cgcctgcgag gacctctcgg agctgtgcga gagcaatatc atcgtcatcg    153960
acgagtgcgg ccttatgctg cgctacatgc tgcaggtggt ggtgttttt tactactttt    154020 acaacgccct gggcgacacg cgactttacc gcgaacgccg cgtgccctgc atcatctgcg    154080
tcggttcgcc cacgcagacc gaggcgctgg agagccgcta cgaccactac acgcaaaaca    154140
agagcgtgcg caagggcgtt gacgtgctct cggcgctgat tcagaacgag gtgctcatca    154200
actactgcga catcgccgac aactgggtca tgtttattca caacaagcgt tgcaccgacc    154260
tggactttgg cgacctgctc aagtacatgg agttcggtat cccgctcaag gaggagcacg    154320
tggcctacgt ggatcgcttc gtgcggccgc ccagctccat ccgcaacccc tcgtacgccg    154380 ccagatgac gcggcttttt ctctcacacg tcgaggtgca ggcttacttc aagcggctgc    154440
acgagcagat ccgcctgagc gagcgccacc gtctctttga tctgcccgtc tactgcgtgg    154500
tcaacaaccg cgcgtaccag gagctctgcg agctggccga cccgctgggc gactcgccgc    154560
agcccgtcga gctctggttc cgccagaact tggcgcgcat cattaactac tcgcagtttg    154620
tcgaccacaa cctctccagc gagatcacca aggaggcgct gcgccccgcg ccgacgtcg    154680 ttgccaccaa caactcctcc gtccaggctc acggaggggg aggatctgta atcgggagca    154740
ccggcggcaa cgacgagacg gcgttttttcc aggacgatga taccaccact gcgcccgata    154800
gccgtgagac gctgctcacc ttgcgcatta cctacatcaa gggcagttcg gtgggagtca    154860
actctaaggt gcgggcctgt gttatcggat accagggcac ggtcgaacgt tcgtggaca    154920 tcttgcaaaa ggacacgttt atcgaacgca cgccctgcga gcaggcggcc tacgcctact    154980
cgttagtttc gggcctgctc ttctcggcca tgtactactt ctacgtgtcg ccctacacga    155040
ccgaggagat gttgcgtgag ctggcgcgcg ttgagctgcc cgacgtgagt tcgctctgcg    155100
ccgctgccgc cgccacggcc gccgctcccg cttggagcgg gggagagaat ccgataaata    155160
atcacgtcga cgcggattct tctcagggcg gccagagcgt gccggtatct caacggatgg    155220
aacatggcca agaggagacc cacgacatcc cctgcctgtc caaccaccat gacgactcgg    155280
acgccatcac ggacgccgaa ctcatggatc acaccagtct gtacgcggat cccttttttc    155340
tcaaatacgt caagccacct agcctggcgc tgctttcttt cgaggacacg gtgcacatgt    155400
acactacctt ccgcgacatt tttctcaagc gctaccagct catgcagcgt ctcacgggcg    155460
gtcgcttcgc cacgttgccg ctcgttacct acaatcgccg taacgtggtg ttcaaggcca    155520
actgtcagat cagctcgcag accggctcct tcgtgggcat gctttcgcat gtgtcgccgg    155580
cgcagacgta cacgctcgag ggctacacca gcgacaacgt gctcagtctg cccagtgacc    155640
gccaccgcat ccaccccgag gtggtgcagc gcggccttc gcggctggtg ctacgcgatg    155700
cgcttgggtt cctctttgtg ctcgacgtta acgtttcgcg cttcgtcgag tcggcgcagg    155760
gcaagagtct gcacgtgtgc accaccgtgg actacggcct cacttcgcgc acggccatga    155820
ccatcgccaa gagtcagggc ctgtcgctcg agaaggtggc cgtggacttt ggggaccatc    155880
ccaagaacct caagatgagc cacatctacg tggccatgtc gcgagtcacg gaccccgaac    155940
acctcatgat gaacgttaac ccgttgcgac tgccctatga aagaacacc gctatcccc    156000 cctatatctg tcgcgcgctc aaagacaaac gcaccacgct tatttttga cacaacaccg    156060
```

```
tgtaaggaaa acgtgacttt attgagcagg gtaaaaacca cgtacaagaa ccacgttgtc   156120
tatccccaaa aaaacacaca ccgtcaggga acacatcgcc tatagatagc ggcactttac   156180
ataaaaccac cgtacctgca tcacggtggc tcgatacact ggaaattcaa taaaaaccac   156240
cgtgtctccg tgacggtact tatcgggtca gcgtcttttg agatttctgt tcgtaaactt   156300
atccgtttcc ccggtccgcg gtgtctcctc gcgaggctga cagtcgacgg gtggtacctg   156360
caagagaaga aacccgggtg ggagcgacgc cgtcgctggg tatcaacccc gcggctgacc   156420
gtcgtccggt aaaggaacaa cccgtcgtcg caagccgggt tcgaccaaga gaaaaaaccc   156480
gggtgcgggg ggagacgggt cgtcctttgg ttgttcgcgg acggcgtaca tgccgcgtgg   156540
gtcagtcgac ggcgtcgctc cgtgcggtcg gtcatcattc tgcttcacat atatgggttg   156600 tttgtgttt tttttataat gaatacgcac tgatcctatc cgtgactgcg cgtgtggcag   156660
agaggatgcc ttataacatg tattttgaaa aattgccaac agctataatt tctctcatgt   156720
agcagaatag agaccttttg tcgtcttttt gtttgtcatt acttgttttc cagggaatta   156780
gagagaggga accgcgcctc cggcggcggt gcccgcggac cccggcccct tctgcgcgtgc   156840 gcggtgtgac tggttgagcg aatgagcagc taggcttggt ggtgctccgc gtgcggggga   156900
gaagacgatt aacaacaaaa aataagtgga agtggccggt gggtctttgt ccgcgtgcgc   156960
gcccatccgt cgccgggacc gagcagaaag tgatgtggtg gtacattgat tttttccttg   157020
acaggaaaga aaaaaagag ttttgttttc ctatgtgaga ggagaaaggt atgtgaggag   157080
atgttcgatg atcgtatgtt acagttatgc tgtaaggaag cttttatcgt gcgtcctgtt   157140
tttcatttga tgtatatgac acaattgaaa cctatcgata ggcgtatatc gaggattcat   157200
caattcttag aatcgtcgtc tttttggcta attggacttt gcccatgttg ttgtcattc   157260 gtggcctgag gtcatcgtcg tccacgacga cgtgtctata gcgtgcggtg tgatcattgt   157320
gtcgagccag agaaagcgcg cctcgcacga cgtttgcgga tcggctcgcg ggtgtgtgga   157380
attcctaaga acataatcag ctggtcgtct ttctttgatg tgttgttgtc gtcgaggtct   157440
tgcttcgttt tctttttttct tttagtcga tggaactttt cttcggtacg ggttcttgtt   157500
atggaagctt gtgttttcga acatgaattc gaaaaaataa aaaggcctat cttcgtttca   157560
aaaaaaggac agatatcaat cttcttaact tatatcatgg taaattcaga atcctatggt   157620
gtcttattat ctctaaagta gtcaacatta tggtctaact tgtatttccc tgacgagata   157680
tatatgatcc ttataacctg gctactatca tgaacaacaa tatccttact tacagtcatc   157740
ttcgtgagtt aatgaagtat aatatcggtc atctatcaac ttatctgcta tgtaacgtac   157800
ccttttaggt atttttgcgtt tcttaacgag tgtacccgcc tgtgtgaggc gaaactctga   157860
gaagtctacc gagtcgagtt acaagtcact aaaacactta cacgagttat ctatactaaa   157920
atcactatct atgttgtttg cttacctaat tattatccta catgacgaag ctacctccca   157980
acgtaaggta gggggagagg agacagaaca ataaaaagta actaatgttt cttagaactt   158040
acccgctaag gacttaccaa actatattca ccaaaaaaca acagctacgt gtttcatttg   158100
ttttaatcta ccgaagtaaa aaaaaaaga tgattagcta tccagaacct acttacttct   158160
taatgtttta actaaggatg cctatgggat tggaaaaaaa atcacagcaa cttgctacta   158220
atcagttgac agcgaagaga ctcataacaa agatttctgg gtaatacggt tataataatg   158280
cttatggact aaaggatact tggaaaaaaa gaacgggcta tgactataga gattcgtcga   158340
gatatcaaac ttcaaatagg cggctatcat tcatggttgt ggtgactata tcgtggaaa   158400 aaaatgtgat cgttagttag ctaggtgaga cttacagcta tccatccgtc tagttttcg    158460
```

```
ttgtaatgat gatagtacgt ctatggtggt gatcgatttt ggttaacaat ttgttcgttt 158520
aaaggcttaa tgtacttatg ctacatgatg tattattctt tgattcatcg ttcctcctaa 158580
gggggtgtat gtatgtatgt actagtcgta tagtgttcct aacatcatga ctattcagac 158640
tatggcttca tctatcgtgt ctaaagttca cttattctac tattactata tatatgcact 158700
actatgtaac taggatatgg tcctataagg tgtcttctat cacggtggct tgtttatcgc 158760
ttggcggtta cgagcaagag ttcatcacgg accagccgtg aggcagggca cacgcgggtc 158820
ggcggcgatg atgtcccccg cgaaggggac aacgaaaaca agaggccgcc ggccgcggcc 158880
acggatgcgt agcggttaca caatgtttgg ttgagcgttt tgtttcatcg tcgtggtggt 158940
tttgttgttc tctgtatata tcgtgtggtg gctttatcgt catcattatt atcatcattc 159000
ttgtttccat catcacgatg agttttctcc gttttcctct cctccagtgg tagtcgtgta 159060
tcatcatcaa tcatcgtagt gacgtcgttg ctgctgctgc tcttgccttc atggcggtat 159120
ttctcttcct cccccctaac cccatattaa ctcgtgagtg tgatggttag agtggctgct 159180
tgtttttttt ttcttttctc tttggaacaa caaaagagga taaagatggt cggtgaatgt 159240
attattatta tcatcattat gatacggtcg cggtcttctt ctccgatgac gaaacctgcg 159300
cacatcgaag aaaagacgag cgcgcgaacc gatagccgtc cgtctgggac gaaggagaag 159360
atgatgggga gaggaggaga gccccagaag ccagagcgag aagggagacg acagacatac 159420
gtcgtcaccg tcctctggag gaggcacggc ggcgctgttt gttgtttgga tgcttgatta 159480
tatcctgttc tatggggtag attattatca ataggcttgg ttttcaaagg tcagcctgtg 159540
tattgtcgtg tctttttttt tcgttctcat gatcgcggag accacacaga cgtgcgcgtc 159600
tcccaatggc taggcgttct ttttaggtag taatttttg atcttttttt tttcttaaca 159660
agtctggctt gatttctttt atctatgatc gattcttctt tttctcgggg gttgcatctt 159720
ccgtgaaagt aaagtgacac tactctaaat ggtaaccata ttatctgttg attaggagaa 159780
aaaataattt tttcgcacga aatcgatcct aagtgaggtg atttacttgc tatcacacga 159840
aatgattatc ttttgctgct aacgtactga attttttaac agaattgctt ctccgtaact 159900
atttccgcag attcagacag attgtcaaaa aagaatacgg cacagaaata gtgggtctgt 159960
ggcttttggt tcgtgtacat tcgcgtttgc gtgtcgagat ttctacggta tgtttattct 160020
tcctgcgatg atgtagggtc cttggtgtaa gtaggatttc gagtatctct cttagagcga 160080
acaaaataat caaaaaacaa cagctaggaa atcgagggtt actctacgat aaagtgtctc 160140
tacaaagtga agaatgttac gttgtggtgg aataataaga ctcgcgtgat cgatgagtga 160200
tcgagagcgg ctcgaacctt ctttaagagc tttgtttagt gcaactttaa attacaagga 160260
gtagaaagct gaaatgaatc tatgaaggtg ctattctttg aatatcttac tttgtacgct 160320
tcacattcgt tatttggata gagagttgtc tagagaaaat ctgtgattct ctatgagtgt 160380
tatttttatt atccttttgg ggactacgat ttttcttctt gttctacata ccactactac 160440
tcgtaatcac atacatggac gaaaaaaaaa ttcgtcaggc agtagatacc agattctccg 160500
acgttacggc gtcttttttt tcttttgaga gagtatctgc tgagattgtc cgtggtgtat 160560
ctagtcgcta ttttgttgt tactagtagt tttgcacaca gttattcag tatagttttt 160620 cttcttgcca tgatcaatta agcccaccac cttttttttt agagaggagg aatttcgtct 160680
tgatctccag ccggagacaa cggcggtggt ggtggtggcg ggagagactt caaggcaatg 160740
aaaaaaaaaa tttcgttttg ccatcaagtg gtgacgataa cccgtcagat tgataattgg 160800
```

```
ttcctacaga aactattcta accgcggaag aaagaaattg aaaaaaaaaa ttgacaaaaa  160860
catcataaca taaaggacca cctacctggg acgcgcagtt gggcggcgga ctgggacggc  160920
atgctgcggc gatgctgtcg gtgatggtct cttcctctct ggtcctgatc gtcttttttc  160980
taggcgcttc cgaggaggcg aagccggcga cgacgacgat aaagaataca aagccgcagt  161040
gtcgtccaga ggattacgcg accagattgc aagatctccg cgtcaccttt catcgagtaa  161100
aacctacgtt ggtaggtcac gtaggtacgg tttattgcga cggtctttct tttccgcgtg  161160
tcgggtgacg tagttttcct cttgtagcaa cgtgaggacg actactccgt gtggctcgac  161220
ggtacggtgg tcaaaggctg ttggggatgc agcgtcatgg actggttgtt gaggcggtat  161280
ctggagatcg tgtttcccgc aggcgaccac gtctatcccg gactcaagac ggaattgcat  161340
agtatgcgct cgacgctaga atccatctac aaagacatgc ggcaatgtgt aagtgtctct  161400
gtggcggcgc tgtccgcaca gaggtaacaa cgtgttcata gcacgctgtt ttacttttgt  161460
cgggctccca gcctctgtta ggttgcggag ataagtccgt gattagtcgg ctgtctcagg  161520
aggcggaaag gaaatcggat aacggcacgc ggaaaggtct cagcgagttg acacgttgt   161580
ttagccgtct cgaagagtat ctgcactcga gaaagtagcg ttgcgatttg cagtccgctc  161640
cggtgtcgtt cacccagtta ctttaataaa cgtactgttt aaccacgttg cgtcgtgacg  161700
ttgtttgtgg gtgttgctag gcgggctgga aagatgatgt ataaatagag tctgcgacgg  161760
ggttcggcgc tctgccggct gcggcggcac tcgctccacg gcctccgacg agcgttgcgc  161820
tcgcgctttg cgccgccgcg tcatggatct ccctactacc gtcgtgcgaa aatactggac  161880
ttttgcgaat cctaatcgca tcctgcatca aagcgtcaat cagactttcg acgtgcgcca  161940
gttcgtcttc gataccgcgc gtctggtcaa ctgcgtggac ggcgatggca aggtgctgca  162000
cctcaacaag ggctggctct gcgctaccat tatgcagcac ggcgaggctt cggccggcgc  162060
caagacgcag cagggcttca tgtctattga cattacgggc gacggggagc tgcaggagca  162120
cctctttgta cgcggcggta tcgtcttcaa caaatccgtc tcctcggtgg tgggctccag  162180
cggacccaat gagagcgcgc tgctcaccat gatttccgag aacggtaatt tgcaagtgac  162240
ttacgtgcgg cattacctga aaaaccacg cgaatcctcc agcggaggcg gtggttgcgg   162300
cgccgcgtct accgcttccg ccgtctgcgt gtcctcgctg ggtggcagcg gcgggactcg  162360
cgacggccct tctgcggagg aacagcaacg gcgaaggcag gaacagcgtc acgaagaacg  162420
gcgcaaaaag tcgtcctcgt ctgccggtgg tggtggaggc ggcggcgctg gtggtggcgg  162480
tggcggcggc gggagcggcg gtcagcactc ctcggactcc gccaacggac tgctgcggga  162540
tccccggttg atgaaccggc agaaggagcg gcggccgcct ccctcctccg agaacgacgg  162600
tgagtcccgg ccctcctcgc gtcacggtgc tttccgagtg gactcgtgag cctcccgtag  162660
cgcacgagcg agcaggcgag cggtgttggt gcgctggtgg ttgtgtggat gataaccatg  162720
tgcttttcg tgcgctatgt gtcgtcccgt ctgtaggctc cctcccctc cgggaggcga   162780
agagacaaaa gaccaccgca cagcacgaag gccatggcgg cggcggcaag aacgagacgg  162840
agcagcagtc cggtggtgct ggcggtggtg gtggcggcgg cagcggccgc atgtcgctgc  162900
cgctggacac gtctgaagcg gtggcctttc tcaattactc gtcctcatcc tccgcggtct  162960
cttcttcctc caacaaccac caccaccatc atcaccacca taacgccgtg acggacgtgg  163020
ccgccggcac cgacggtgcg ttacttctac ccattgagcg cggagcggtg gtttcgtcgc  163080
cgtcgtcgac gtcgccgtcg tcacttcttt cgctccctcg acccagcagc gcccacagcg  163140
cgggcgagac ggtgcaggag tccgaggcgg cggcgacggc ggcggctgcg gggttaatga  163200
```

```
tgatgaggag gatgaggagg gctccggctg aggcggcgga ggcaccaccg cagtcggagg   163260
aggagaatga ttccaccact ccagtctcta actgccgtgt tcctccgaat tcgcaggaat   163320
ccgcggcgcc tcagcctcct cgcagtccgc gttttgatga cattatacag tcattgacca   163380
aaatgctcaa tgattgtaag gagaaaagat tgtgcgatct cccctggtt tccagcagac    163440 tcttgccaga gacgtcgggc gggactgtcg tcgtcaacca cagcagcgtc gcgaggaccg   163500
ccgcagctgt ctccgcagcc ggcgttggcc ccccagcagc cgcatgtccg ccactcgtca   163560
ccaccggtgt tgtaccctca ggttccgtcg ccggtgtcgc gcccgttgcc gccgcaatcg   163620
aaacaccagc tgctcctccc cggcccgtgt gtgaaatcaa gccctacgtg gtaaaccccg   163680
ttgtcgccac cgccgcggct gccagtaact cttcctcgtc ttcttcggct ccactgccgc   163740
cgccgccacc accgtcgggc ggacgtcggg gtcgggcccg gaacaatact cgaggaggcg   163800
gcggtggtgg cggtggtaga aacagccggc ggcaggctgc atcgtcgtcg tcctcctcct   163860
ctcggagatc gcgacggaga aacaaccgcc acgaggacga ggaggacaac gaccctctgc   163920
tccggttgtc gcaagttgcc ggcaacggcc gccggcgagg gccctcgttc ctcgaggacg   163980
gactcgaaat tatcgatccc agcgaggagg ctgcgatcgc cgccgcctcg atcgcggcgt   164040
ttttcgacga ttaaaaaacc gagccgagac cggaaaaaat atgaaacagg acgcgcttgg   164100
acatttgggt ttccacccct tttggtgtgt gtctatatat attggtcact gatttttttt   164160
acaataaaga gatagacatc acagttcacc accttgtctc cccggtgtgt ctattatcat   164220
caatcaccca cagagtcgcc agtccatggt ctctcggtaa tgcgtgtcca gatacgcgtt   164280
ggccagtata aaatggtcgt tgcccacgaa ggcgcgggtg gtgttgcgcg cgacgggtg    164340 gcaggacttg agtaccaagt gccgccgtcg gtcgatcagg tactcgcagg tgtgcgcgtc   164400 ggcgcccac agcatgaaca ccagatgctc ccggcgctct gacagcctcc ggatcacatg    164460
gttactcagc gtctgccagc ctaagtgacg gtgagatcca ggctgtccgt gcaccacggt   164520
gaacacggtg ttgagcagca gcacgccgcg tcgcgcccag gcgtccaggc aacccgaggc   164580
cggacgctga aacccgtcca ccgtacgcgc cagttcgcga aacacgttgt tgagggaggg   164640
cggcggcggt cggcccgcca gcgtgccgaa ggccaggcc ctggcgctgc cgtcgcagta    164700
cgggtcctgg cccacgatca ccacgcgcac ctgctcgggc ggacacagat agctccagcg   164760
gtgtacgtgc tcgggtgccg ggtacaccat ctcgagttgc cgcgcgccct ccaccgccgc   164820
caccgtgtcg cgcagcagca ccgtgtcgtg gtcgggcaag ctgaggaagc ggatccagtc   164880
ggcgctcaga caaaacacgc gagcctgctc gtcgggggtt aacagagagc ctttattatc   164940
agcaatgtta gcgagcatcc actgcttgag ggccatagcg cgagtgagcc ggcaggttga   165000
cgcgcgtctg cttcagctcg ggcggcagtc cggcgtagta tttatctagg tggcgtagta   165060
gcggcgggtc cagctggtga cgcaggcaga attccttcac tgcgttgtac aggccgtaaa   165120
agagtgtgat gccctcgggc gcggcagcgg tgctcacggg cagacgcacg gcgcggttgg   165180
tacgcgtggc ttcgttgcgt atggccacca ccacgttaaa gagagacggt ggcaccagct   165240
cgaagcctaa cacgtgttcc gtgaagatgc tgcgcccgta tgacagtcgc gtgaggtcgt   165300
agccgcggca caggtcgtcc acgcacgtgt acacggccgg cgagccatcg ccgcactcgc   165360
tgtagccgcg catcaccgtc atccagcgcg gcgctgtgtc cgagctcaac agcgtcagca   165420
gggcccgcaa ttgatccgga ttgttgtaca gcagggccag agtgtccagg aaagcatcgt   165480
ccaacagcac ggagttggcg gcctccggcg taacgggacg gtaacgaata agttgcgata   165540
```

-continued

```
gcgggccatc gcgtctggta acattcacca acgggcgcag ccaactttca tacttgtcac   165600
cctgaaacac ctcacccaac aggcatcgac gcgttagttc ggggcactcc gcggggactt   165660
tctcggcggc ggtaggagcg acgctgacgg cgactgagga acaatgggc agcagaaggc    165720 aacaccacag cagtaccacc ggtccaggtg agaaagagaa gccgcaatcc gggcggcggc   165780
acatcaagtc tgcggcacga tgagagtgtg acggtaagga gccagttggc gccgaaagtt   165840
ggcgctcagg tcttcgatcc ctaaaacgtt atatattgca tccagcaggt gagccaggct   165900
aaacggattc acgtaccagg tttggttacc cgcgacgatg acggccagac cgtgggcgct   165960
acagttggag aggttcctgg gtacgaaggt aactgagtcg atgtcgcgcc acggggggaa   166020
tgagacagac gactggcgca cgctgtaatc acaactgtga ttgacgtgta gcgtgtaatt   166080
tcggttgcac tcagcctcga agtagagggg gaaccacagt tcgtcgtact cgtcgtcgtc   166140
ctccagttct ggctcttctt catccaccgc aatgtctacg ctgctctgag attcctcttc   166200
gtacaggatg attgacaggt tatggctaca caggtcctgg gcgggaggac gcgtgggagc   166260
gcgggtggtg gtaatgtttt ccagatcgtc aaaagtcgga gtgtagtctg acgccgtgac   166320
gacaccgtcg acggagatgg tagaagttgc ggccggtgtc acggtggtaa gtatggatac   166380 agaagggag ggggaagtag cgttcgtacc gatggttgtg gtattattat tccctgtgtt    166440
tcttgttcca gaaaccgttg acgttgagat gggaatcgac gtggtgctgg acgtcagatt   166500
gctgaccgag gaaaccgtgg tgggagtggt gacggtgtta ctcgtggttg aagtgacgtt   166560
aggggaggta gtagtggtac cggtggtggc gacggtagtg tttgtcgtgg cggcggcagc   166620
ggtggtactg gtaacggtgg tcgcgttggt ttccaccgct tcacacagta agcaaaagca   166680
cagggccggg aaaagcaacc agccccgcca tcgccgccgc cgcttcatga ggtgggcagg   166740
cgaaagctgt tgaattcgtt gtacagcggc aagtggggcg ccgcgatcga agggtacgtc   166800
aacaagctga cgttgatatt aaatacgtct ggctgctttt ctacgatgga agcgcacagg   166860
gttacggcgt caaacaggtc tttcttggtg gcgcccgaga cccacatctg gtatacaccc   166920
gtctcgtggt acgaagtaga gcgcggcacc accggacgga tgcagtccag aacgcggttg   166980
ggatcctggt gaaagaattt gaacgtggct acggcctgtg gcgtgtgcgg catcgtctgc   167040
gtgatgagct gctggcccgc taacacggtg acgttgtgca acttgagcag ggcactcttg   167100
agggcctgga aagcgttgcc gcacgaggcg ctgatctgca gctgcacggc cgtggagtcg   167160
tgcagccgca tgagacgtga tacctcttcg aagacgtact tgtatttgct ggcaaaaagt   167220
ggcgcgtacc gacagtcggc cggcaaaatg taggtggcgt taccgccgtt ggtggccacg   167280
gcgggcgcag cggccgcgga ggccggcgta aacagcgtca gcggccggtg gtggctggta   167340
aggtcgatca tgggcggcgt ggtgaccgtg cggtggcgg gcatgacggg gtttgcggcg    167400
acgggcactc cggccacagc ggcggccgcg gcggccacgg cggcacttgc cgagcccaca   167460
cccgccggca gtcctccgcc acccatgacg ccgccgggca gagcgtcgcc cagacagact   167520
tccgcagtgg cgggcgcgct ctcagcgtc agtacggttt gccgatcgac ctcgcgacga    167580
aagctggtga ggaactcact gtgatccatg gccgcagggc ccgagatccc gggattctgc   167640
gggtgctgac cgagtcgggg gcgagttata tggaagacga ttagcttgga gcggagtttt   167700
gcgtccctag ctgacctgcg gatcagcgac gtgccatagg gatagactgt gagcggcggc   167760
cgcaacggcg gggtcggccg ccgctcgtcg tcacggggcg gcgcgaggga ggaggaggtg   167820
gtgggtacga tcttgacgtg gttgacgtcc tgccgtccg gggaatacg caaaaaaccc     167880 cgtcgcggcg ctaccacgat ggtgcgatgg gtctttctct tgttggccgg ggccagggac   167940
```

```
ttgcagatgc gtgtggagcc gtagacgatc tggacgtggt cctgggagaa catgaccatc  168000
gccgccaacg ctcagcgggg ggacgtgttg ggaacacaga ggctgaggga aaactccgta  168060
gaagtcagcg aaataaagac aacacagcag ccactcctct cgtctcgggc cctaccactg  168120
cttgaagtag ggcaccgggt gtttcttttc ctcaacgggc tcctccagtc tcttatagga  168180
ccagtcccgc cggcgcgcca gcatgtaggt cacgtacaaa agaataatca ccatgaacac  168240
caggaaagcc agcacgccgt aggccagcag ccggtcctcg aacagcgggt cgctcttgat  168300
aaacacgtag gtggtggtaa aacttcggcc cgcaatctga acgtggagac gcacgacagt  168360
atacgtgccg ttgaggtaga agacaaactc gcgtaaccgt tgtccgttat acgtcacgtt  168420
actaatattc cacggcggaa tgagctggtt gccctgatgc agatgcacgg tgctgttggg  168480
gtgatagagg ctgctaccgt tgagcaagca gtgttcgtgt tcctgaagca gcacgcggac  168540
ccgcatcgtg gtggcgttca ggcgagtccc gtacacggcg tagatgggat aggtgaaaag  168600
gtcccaagtg gcgttgtgat ggcggcccca gctgaagaaa gagcacgtgt actcagtggt  168660
ctcctgcggc ctgagtcccg agataagcag ctcttgagca gtagcgttgt aggagagatg  168720
tagttttcct gtggataaaa ttcataagtt gtttattttg ttggcaggtt ggcggggag  168780 gaaagggt tgaacagaaa ggtaggtgct acttaccttc attatcgggg gggaaggcgc  168840
taagataccc cacctgagtg aagggaccct tgcagtctgt ccgtgcataa caagtaactg  168900
ataaaatgtc tggattttg gtgttattca acaggataac tttgcaggtg gcgtttagag  168960
acacttggtc gtggctgtag ctggcttcgc aattcacagt atacaggtgc ccctcttct  169020 gcgtcgtggc tatcacggaa gtggaggcgg acgaggtaga ggtttgtacc gtggtggtga  169080
cagcagaagt gacgttgtta gaggtactta ttgacgtagt agacgtgacg gtggtattac  169140
taggggaagt gacggcgctt gtggtgctac ttttcacccc cgggtgcatg tcgcccaaga  169200
gcgcaactac gagcgcgatc gccagtacgg aacacatgtt gccgtgtgac gagacggcgt  169260
gtggacgagc tatatgtggc aggaggtcgc gtcacctctt gtgacgccta aacgtccagc  169320
tccagataaa agaggcgtta ataatgaaga ccacaaaaac cacttgcgtc agtatgacaa  169380
tcataaaggc tcggtgattg ctacgcctaa agtacgcggg attatccacc agttcatcct  169440
gctgaacaaa gtggatgatt gacgtattgg tgttactatc cgtgttgttg accatggatt  169500
tgactaagaa agtcttggcg ccaaaagtcc cgttagagcc ccagcaggtg acgctgctat  169560
tcacataagt tcccggtgcc cccgctagca tgtatttcag ttggtgggta aattttttc  169620 tgtcgttatc catgtcattg ctgtagttga ccttgctggt gagaaagcgt gttttcaacg  169680
gggcacttat catcatccct gaggccaaaa agggcgaatt gcaagctgta gtgttacaaa  169740
aaatagtcaa gttagtgtca ttgtattgat aaatgtaagc catgcttact tcaggctcat  169800
accacccgat tccaatcgcg gccgccatcg ttaccacgtc ccatcttccc agacttacca  169860
ccgccaccac taacagcgtc acccccgcac ggtacatagt taccctctcg acgtcgccgg  169920
ctgtcaatga cgtgcctgcg tcagtggcta tgatttatag cttttgggcc caaccgcaac  169980
ggatctgtcg taatctacct tccacagggc cgccgcgacg atgctgaacg acaggatcag  170040
acagacggcg tacaaaagtc ctaggtcggc gtcgacgcgg caggtgcgga tgtctcgcag  170100
ggtgggtaga tgggcgatgc acaactcttt ctccccccgc ccgtacatcc catcttgtat  170160
cagcagccgt agcgtggcat tgatggtcag cggggtaacc aaagaaatca catagggatg  170220
tgtacaggaa gtgcagtgac gggtatccgt gagatgtaag tcaccaccct cctcaccgtc  170280
```

-continued

```
atcatgaaag accaggactc gggtgagacg acccgatgaa tactggatct cccaccacag   170340
tctttggtcc aacaccgaga gggcgcaaga gattctaagt ctccctgggt tgggggagca   170400
gatgtaagtc ccgtatgtgc ctctcgccat cagggccata cacatgaggg ggagaaggac   170460
aattatccgg gaccacccgc accccacat cacgagacca gagacggaga tgtataaaaa    170520
aagctacttt tattaaacag cattctcacc acacgttaat actgtcacgg ggaatcacta   170580
tgtacaagag tccatgtctc tctttccagt ttttcactta ctgagacttg ttcctcaggt   170640
cctggatggc tgcctcgatg gccaggctca gggtgtccag gtcttcggga ggggtctcgg   170700
tgggctgctc aaactgcccc acggcgtagg ccttcgcggc cgtctcgtag ataggcagca   170760
tgaacccacc ctggttggtg gagaagatgc gcaccatgac ctgtttggga aacttttgca   170820
tcaggggcag gcacaggttg agagcgccca acaggtccac gggggtggca gcgtggatga   170880
tcatgttgcg gtaatcggag gaacgggggc ataattggtg ggtgtgcaat tctttgaggc   170940
tccacgcggc cttgacgcct tcgttacaag catcggctgt gcgctgcgcc acttcgggtg   171000
gatgtgtcac gggcatggtg tgctccatga ggaagggagt ggagagggcc aggttgcaca   171060
tggtgcccag gcgacaccgc accgcatcca cctcactctt cacctcatga ttgcgggtgt   171120
agataatctg gatgcccttg ttgttcacct gcatggtttt gcaggctttg atggcctcat   171180
ctaacacctg gtgcatactg ggaatcgtga agggcaggtt cttgtactca agagagcgat   171240
tggtgttgcg gaacatgcgg ctcacctcgt caatcttgac gcgaccccgc cgagtctgca   171300
cgttgggtgt gcagaagggg gtgttcttat ctttcatgat attgcgcacc ttctcgttgt   171360
ccaactcgga gatgcgtttg ctcttcttct tgcggggtcc ggtgctcgcc ccgccgctgc   171420
tctgatggcc gcagctcagc agagaggagg aggccgcgcc accaaaaccg ccgcgcccat   171480
ggtggctcga ggtcacggat gctcctccgc cactgctgca tttcatctcc tcggactcac   171540
tctccgagtc cgaagccgaa ctgcaggagg aggaagacga agaggaacta tcttcatcgg   171600
gccggcccaa gggatcggga agaggagggt ggttcatctg ggagagcggg tgcgtgggag   171660
aggtcactcg cggcgtgccg ctgccggtgg aaggggaaga cgcggtagca ccgcgggttt   171720
cgacttcttc accctgttct tcctcgctat cagagatcac gatacagccg gcggtatcga   171780
taatcttgtt gcggtactgg atggtaaagt cgggctcggg cttgatgtct tcctgtttga   171840
tgagggcag catgataggc gcgggaggca cgggcggttt aataatcacc ttgaaaggac     171900
gcgtggtttt gcgcggtttc ttacgcgggc tgagctcggg agtagcggat gccccgggga   171960
gaggagtgtt agtaaccgcg acgctggtgg gggtcggctt gttaagaggg gcgctgctaa   172020
cgctgcaaga gtgggttgtc agcgtggggc cggtgctact ggaatcgata ccggcatgat   172080
tgacagcctg ggcgaggatg tcacctgatg gtgataagaa gacacgggag acttagtacg   172140
gtttcacagg cgtgacacgt ttattgagta ggattacaga gtataacata gagtataata   172200
tagagtatac aatagtgacg tgggatccat aacagtaact gatatatata tacaatagtt   172260
tactggtcag ccttgcttct agtcaccata gggtgggtgc tcttgcctcc agaggcggtg   172320
ggttcctcag caccatcctc ctcttcctct ggggcaactt cctctatctc agacactggc   172380
tcagacttga cagacacagt gtcctcccgc tcctcctgag caccctcctc ctcttcctca   172440
tcactctgct cactttcttc ctgatcactg ttctcagcca caattactga ggacagaggg   172500
atagtcgcgg gtacagggga ctctgggggt gacaccagag aatcagagga gctgacacca   172560
gcggtggcca aagtgtaggc tacaatagcc tcttcctcat ctgactcctc ggcgatggcc   172620
cgtaggtcat ccacactagg agagcagact ctcagaggat cggcccccag aatgtactgg   172680
```

```
gcaaagacct tcatgcagat ctcctcaatg cggcgcttca ttacactgat aacctcaggc   172740
ttggttatca gaggccgctt ggccagcatc acactagtct cctctaagac atagcagcac   172800
agcacccgac agaactcact taagagagag atgcccccgt acatggtcat catacaagcg   172860
tcactagtga ccttgtactc attacacatt gtttccacac atgtagtgag gatatccata   172920
aatatgtgat caatgtgcgt gagcaccttg tctctctcct catccaaaat cttaaatatt   172980
ttctgggcat aagccataat ctcatcaggg gagcactgag gcaagttctg cagtgccgcc   173040
atggcctgac tgcagccatt ggtggtctta gggaaggctg agttcttggt aaagaactct   173100
atattcctgt agcacatata catcatcttt ctcctaagtt catccttttt agcacgggcc   173160
ttagcctgca gtgcaccccc caacttgtta gcggcgccct tgctcacatc atgcagctcc   173220
ttaatacaag ccatccacat ctcccgctta tcctcaggta caatgtagtt ctcatacatg   173280
ctctgcatag ttagcccaat acacttcatc tcctcgaaag gctcatgaac cttatctaag   173340
atatctaagg cattctgcaa acatcctccc atcatattaa aggcgccagt gaatttctct   173400
tccgtctggg tatatttttt cagcatgtgc tccttgattc tatgccgcac catgtccact   173460
cgaaccttaa tctgttttgac tgtagaggag gataacaaca catataagta tccgtcctcc   173520
tgactcattt atcgctatct cgatgccccg ctcacatgca agagttaatc tttactctat   173580
ctgacataca caagtaaatc cacgtcccat gcaggttagt atacatcaca tacatgtcaa   173640
cagacttacc gagttctgcc aggacatctt tctcggggtt ctcgttgcaa tcctcggtca   173700
cttgttcaaa agttttgagg gattcttcgg ccaactctgg aaacagcggg tctcccagac   173760
tcagctgact gttaacctcc ttcctcaaca tagtctgcag gaacgtcgtg gccttggtca   173820
cgggtgtctc gggcctaaac acatgagaaa tagagtcata agcacatggg tcacatacag   173880
gagatatgta tataacatta atacaatttt attaaaaaaa aagggggggc acaaacccg    173940 acacgtaccg tggcaccttg gaggaagggc cctcgtcagg attatcaggg tccatctttc   174000
tcttggcaga ggactcttcc ggttttagaa gctccacatc gaagacgaga gtggcatgtg   174060
gtgggatgat gcctgggtgc ccagtggcac cataggcata atctggagat atagtcagtt   174120
tggctctctg acccacactc atctgggcaa ccccttcttc ccagcctcgg atcacctcct   174180
gcttgcctag cataaactta aagggcttgt ttctgtcccg ggaggaatcg actttctttc   174240
catcttcaag catcccggtg tagtgcacca cacaggtctg gccgcgcttg gggaaggtgc   174300
gcccgtctcc tggggagatg gtttccacct gcactcccat cgtgtcaagg acggtgactg   174360
cagaaaagac ccatggaaag gaacagtctg ttagtctgtc agctattatg tctggtggcg   174420
cgcgcggcag caacgagtac tgctcagact acactgccct ccaccgttaa cagcaccgca   174480 acggagtta cctctgactc ttatcagaac acaacaactc agctgcctgc atcttcttct   174540
gccgctgcct taagtcttcc aaatgcgtca gcggtgcaag cccgctcccc gagctcattt   174600
tcagacacat accctaccgc cacggccttg tgcggcacac tggtggtggt gggcatcgtg   174660
ctgtgcctaa gtctggcctc cactgttagg agcaaggagc tgccgagcga ccatgagtcg   174720
ctggaggcat gggagcaggg ctcggatgta gaagctccgc cgctaccgga gaagagccca   174780
tgtccggaac acgtacccga gattcgcgtg gagatcccac gttatgttta ataaaaactg   174840
cgggcactgg ggacggtggt gttgtatatg tgaatttgta aataataaat gagacccat    174900 cctgtaaaaa tacagagtcc gtgtcagtct ctgaaggaca gtgtattggc atatagccaa   174960
taaagagagt tgtggcaaag agccatgtta tggattagta atggaaagta tcgtcaccaa   175020
```

```
tagggggagtg gtcaataatg gtcaataacc cacacctata ggctaagcta taccatcacc    175080
tataacatga ggaagcgggg gtgtatagac cccaagccaa aaacagtata gcatgcataa    175140
gaagccaagg gggtgggcct atagactcta taggcggtac ttacgtcact cttggcacgg    175200
ggaatccgcg ttccaatgca ccgttcccgg ccgcggaggc tggatcggtc ccggtgtctt    175260
ctatggaggt caaaacagcg tggatggcgt ctccaggcga tctgacggtt cactaaacga    175320
gctctgctta tatagacctc ccaccgtaca cgcctaccgc ccatttgcgt caatggggcg    175380
gagttgttac gacattttgg aaagtcccgt tgattttggt gccaaaacaa actcccattg    175440
acgtcaatgg ggtggagact tggaaatccc cgtgagtcaa accgctatcc acgcccattg    175500
atgtactgcc aaaaccgcat caccatggta atagcgatga ctaatacgta gatgtactgc    175560
caagtaggaa agtcccataa ggtcatgtac tgggcataat gccaggcggg ccatttaccg    175620
tcattgacgt caatagggggg cgtacttggc atatgataca cttgatgtac tgccaagtgg    175680
gcagtttacc gtaaatactc cacccattga cgtcaatgga aagtccctat ggcgttact    175740 atgggaacat acgtcattat tgacgtcaat gggcgggggg cgttgggcgg tcagccaggc    175800
gggccattta ccgtaagtta tgtaacgcgg aactccatat atgggctatg aactaatgac    175860
cccgtaattg attactatta ataactagtc aataatcaat gtcaacatgg cggtaatgtt    175920
ggacatgagc caatataaat gtacatatta tgatatggat acaacgtatg caatggccaa    175980
tagccaatat tgatttatgc tatataacca atgaataata tggctaatgg ccaatattga    176040
ttcaatgtat agatcgatat gcattggcca tgtgccagct tgatgtcgcc tctatcggcg    176100
atatagcctc atatcgtctg tcacctatat cgaaactgcg atatttgcga cacacagaat    176160
cgcccaagtc accaaagtcg tctatcgcca tccccgtaa acgatataag cgctatcgcc    176220
agatatcgcg tatgcccaaa aatcactttt ggaaaaatgg cgatatcagt tacacagaaa    176280
ctcacatcgg cgacattttc aatatgccat attttcaaat atcgattttt ccaatatcgc    176340
catctctatc ggcgataaac accactatcg cgcgacatga atttagtcgg cgacagaaat    176400
ctcaaaacgc gtatttcgga caaacacaca ttttattatt cactgcagca tatagcccat    176460
tttagcgcgg cacacatcca gccgtttgtg ttttttaacg ctctccaggt actgatccag    176520
gcccacgatc cgggttatct tgtcgtattc caggttgatc catcgatagg gaacgctgcc    176580
agcggcgccc agcaggtact gcgccttgtc gttcactttg ccgcagcgta ttcgcccgtc    176640
agcttcgagg tataacctac aacacggagg ggaagggggg gtacaaaacg tgaaattaga    176700
cttttttttt aatgatgttt tgtccctctg tcttactttc ccataggctg taaggccctc    176760
gaggaagaga cttacggatt gtagttgcag ctcgtcagtt tgttgtgtac gacctggcgt    176820
gtcaatgaat gggtcatggt ggtgacgatc ccgcgaatct cagccgtttt ctcgggactg    176880
tagcagactt cgccgtccgg acaccgcagc ctgtggattc atgaaaatct actctggcat    176940
tcccgaggat cgtcgatgga acatggctat cagaaacgtc gagagacaaa tccgagcgca    177000
ccacagaacg cagacaatca taaaaatacg tacgcgacgg tgaagcgatt gcacattttg    177060
aaatcgtaac agcgttccgg cgggtggttg acgtttatga attcgcaaca ttcttctgcg    177120
cgcacccgcg gcacgcggct gtgacccaat agcagccaca acgtcgtcaa gaacggcgtc    177180
aggtctttgg gactcatgac gcgcggtttt caaaattccc tgcgcgcgcg acgggctcaa    177240
acgatgagat tgggatgggt acagaaggtg taagtctggt tattggcctc ggtgaacgtc    177300
aatcgcacct gaaaagacac gctgtagtcc cggaagacgt gggcccagct ctccagcttc    177360
atcacacaca tctgataacg cgtgccatcg ttgacgacga agcgtagcag cttggtctgc    177420
```

```
ttgggcacca tgtgcgctcc aaaaatcttg gcgtcttcca cgctgatctg cacgtttccg   177480
tcgctcggtt tcgaagccgt ttggggcatc cgttggagga tggtctggtt gcgaccgctc   177540
agataccaga tcaccttttt cacccaggtg gagcttctct ccaccaaggt ctggccttcc   177600
cggttgtaca gcagatacag ggtctcgttg cgacactcgg gacccgttga tacctgctgg   177660
aaccccgaga attgcaaggg ggaccgtggg ggcgagggat agagaaaagg acagtaaaac   177720
gtcgccgcgt catgcggttt ggaatacgtc agtttagacc atggcgggga cggattctgg   177780
tttgccgtta gcgtcgacca cggagacgcc agacagggcg ttgcccaaac cgcgcacaga   177840
agcaggcagt gaaagtggtg acgaagcaga agccgcagca tattatttcc cgtgacgcag   177900
gctagttggc aaagagccgc acgctgaact cgaggctccg ggcgtgtggc gccagcgaac   177960
cggcggcgtt gaacgtggtc cttttgttgg tgccgccgcg acggttctga cgtctaaagt   178020
cgctgatgag caacgacacc tcggtcacgt tgattctgca agcacaggtt ccaaacgtca   178080
tttcataccc catgcggtta cttagccgtt acccgttcgc ccttaccttc ccgttgtcat   178140
gcacctttag cgcgtacccc cacctcttga gcacgtcaaa gttgtccaag ccgtggctcg   178200
catcgtagtg gtagttcaac gtgaggtcca cgagctgttc cacatacttg taacgggttt   178260
ggtcgggcag cgcgcgagag cacgcgtccc agtaatgcgg tactcggtaa taatcgtttt   178320
tttccgcggt ttcccgctgg cactgaccca gcaccacggc gcacagacaa acagacagcc   178380
acacccgaca cagccgcatg ttgcagactg agaaagaaag ctttattatg agacatcata   178440
cacatagtat aggcgaggtg atggggcggg gaaagagttg gaaccgaaag acaaaaaaaa   178500
aagcctagtc gtactcggga tctctgagcg agacgggttg catggcaact ttcattagtt   178560
tgggaatctg ccagctggtg ctgttcgaag gttcttccat ttccgaggcg gtcagttcat   178620
cgtacaccga aacgtagtac ctgatggggt cctcctcatt gtccgagagg tgagattcga   178680
tggtcaaagg cgagcctctc ccataattgg gattcacgaa cgacgtgtcc aagttgccat   178740
cctttctgaa atagatgacg ttctcaggat catgtttcat gcgctcgcgg gccgcggacg   178800
cctcctcctc ctcgtcccag tcccgagttt ccaaccgctg ataagggctc gaggaacaaa   178860
atccggcggg gatctgagaa cctcgtcggg aaccgctgcc aaacgggctg ctgccgccac   178920
tgtcgtccgt gtcgtccaac aggttgacgg cctcttcgtc ggcgaaacga aagcggcccg   178980
ggtgcttgca acacgaggag taaactaccg cgatcagtac cgctatgaag ctgaaaatgg   179040
aggtgcctgt cacgatgtag aagaggatag ccagcacttt catgatttcg tcattgcgcg   179100
cgtcgtgaac ggaagattcg cgggcagtgg tcatgttggt ttcggttgta ggttcgctac   179160
tcgtggtgct ctcgacggta tttctgctgc tggtgctagt agggacgttt gtgctgctgg   179220
tcatatttgt agcgtcgctg aagtcgatgt gaagcagcaa cccgaacgcg accaggacca   179280
ggaatgttgc gcgaaggaga ccccgcgggg ccggcattct tgagacgtgg cgacgtggat   179340
ttcttgttat gtccgcgaac gacgtgtaac gaggacgtgg tttccgcaag cctctaccga   179400
cgccgcgaca ccaggtaggt tatcaaaacg cgagcccata tcgccgccat cattgtaatc   179460
agcaatgtgt tgaggtactg cacgatgaat ctgtctagtg acaccagcca accctctgct   179520
tttgcgggca agcgcgcttt cggtgacagg gtgtatcgta cgtagccgcg ggtcaggcgc   179580
gcgttgtagc ggtacacgca gaaatctatc cacaggccaa cgcccggctg tagcttcgga   179640
tggtggataa tagcgcggtg acgtacgccg cgtggcttta gaatctccac ctgtaaggcc   179700
atctcctcca ggtagtgggt ctgactgcga cgcagcgtcc agttcatgta aaagtcggtc   179760
```

```
tcgccgtgtc cggccacgaa gaggctgctt actaatccag tctacattgt gccatttctc   179820
agtctgattg cattttttag agttatgttg ccaccaacgt atcctgttac gttgattacc   179880
tcgtaactgc ggtcgcatct tttatggact gtataattga aaccatcaca agtaacggtc   179940
gtggtggtgt tggtacatgt ggtagtctca acgtttgtat ttgtcgttgt ggatatctgt   180000
gtggttgttt tcgacggttt tgtagaaacg gtggttgctg gtgcagttgc agtagagcaa   180060
tttatagatt ctgaagtgct tttattgctg ataactgttg tactgtatgt tgatgtggct   180120
gtctcagtac tagtggaata gttaacggta gtactacagg gacattgaca ggaacaggtt   180180
tgattgcagc tttctgataa cgcggatatt agtatcgtcc acataaccgt aaatcgccag   180240
tccattgcaa tattagttct cgctcaatgg gcattaatat tcctttgaac gctgagcctt   180300
acagaatgtt ttagtttatt gttcagcttc ataagatgtc tgcccggaaa cgtagctcaa   180360
tcttcatgtt ctgtgtgata tcgaacaatg aattctgatt cactgacggt gtcttgcaac   180420
atatggtact ttttgttaaa ggctcgtcgt gcaaaaaaca gaactatgca ggccataccaa  180480
accaacacga tggtccatac ggtgcggctt ctttgcgagc tatgatagag attacgtttg   180540
tggtgatgtg tattgttagt atgttgactt cctttctctc tatcttcatt ttcgatatcg   180600
gtgttgtatc tagggcaaac gaaagtagca ttaatagctt cagtatgatt ttttggtgtt   180660
actaataggt agaaattttc atcttcgtga tgtcctgtga agtaattttc tttaaaacaa   180720
cgtctgctgt acctgccgga attggtgata tttagatcgt acagatgtag ttctgtgttg   180780
ttgcacgaac gacataagtc atggtacagt gaaggtcttt catgttgaga atgacataca   180840
gtatgagagg taaggatgcg taaccaatac caagattggg tatgtgcgtt cttacgatga   180900
cctagatgat gtccgtgtgt ggatcgattg taatgtcgta tccaggcgac tgaaagacaa   180960
tcccacgtag aattacccttt tatggtgaca ttactcccctt ctattcctgt tgtattagtt   181020
tctttgaaac gtatgattgt tgtctctgtg tgacaagcgt tggaagagtt agtacggttg   181080
tacgtggtgt acgttgtggc gctgcaattt gtaagccatg gcgtgcttat aagtgcagta   181140
ttagtggata cgttgtgcga agtttcatct gacgtgatag ttacggtgat tgttgtgtta   181200
taagatgatg tagcgtttgc tgttacgttg gtaaaagata atatagtgtt ggtatttgtt   181260
gaaatcaatt ctgtagtggc agccgtattg gatatattag catatgatgt attgaatgta   181320
gaatatacgg ttgtgaaagt actcaagtcg gaggtaacgt tggtgatgtt gccaatggtt   181380
gacgcttgtg aggtgacaga tgtgtgtggc gtcgttgatg tgttgttatt cggagtagaa   181440
aatacgctgg tcacaaaggt ggtagaagca gtgttgggtg atgtgatgga tgcagtattg   181500
gtagtagtac tgttgcatgt aactctatgc agaatataga atattatgat tgtatacgcc   181560
gtatgcctgt acgtgagatg gtgaggtctt cggcaggcga cacgcatctt ttactgtaaa   181620
tcccccgtcca ccgtcaacaa caaaggttcc gtatctaggt ccgtccgcag atgttcagcg   181680
tcctgttccc cgattcgttg cgatcgcagg aagcagatga ccagcgcgcc aacaaagatc   181740
atcattcccg aaacccaggc gcaatggagt gagaggccgg accactggcg tttttaaatcc  181800
gagataattg cccggtctgc ctcttgggaa tccgtaacca caactctccc tggtcccgga   181860
taaaagcatc gacgcgtttc caaggctcgg cagaagctac gtgggtggat gatgaggtag   181920
aaagcctcga catcgccggt atactgatcc tgcaggaggt agactcccgt atctttaacc   181980
gtgagattgt acagcgtcag atttttggcgc gtgcacgcga acgccgcacc gccctgacgc   182040
gtggtttctt tataggcgtc tgtaatgata caaagtggcg gcatacgacg catgtatctg   182100
ctgtagatat cataacgctg ccagactacg ctgtgatggc tagtgttaag cctggtaacc   182160
```

```
agcgtgcgtg tacggtcctc gcaggtggca cggtagttgg cgagctttag gggttttttg   182220
gttggttcga cggcgttcga tgaacttccc tgagttgtga acaaaaacag cgacgtgact   182280
atgacaagcg tgagggggt gctgtaggtc tgcatggtgc aaaacacgtt ctcgccttcc   182340
ttatcagacg ttgtcgtcct cgtcctcttc gtcgtctgtg cccgtcggtt cgatcaacgg   182400
ggagttatct ttctgtctgg agggtcggta tggaatccgt tcgtagatgt tctgcttttt   182460
agccgcgtgt tgttccagct ttttgcgtgt caggctccga taggccagac attgatctac   182520
ctcggtgccc gtgttgtttt tctcctcctc gcgcgcgtaa attacaaaga agaccaccag   182580
caggactatc agcgtagcca cgaacgagcc cgcgccccag gccgagtatg cgcctagcat   182640
ggtaatgggt tctgtgatcc ggcatttgca catcgcgtgg cacttgctgc cattgccggt   182700
attagatgat gtgttattcg gactgcactt gcacgtcaaa tgggtatttt ctgatttcac   182760
gagacagttg gtggcgactt tggtttcggc gcagacggcc acatagctta ccaagctgag   182820
tgccagaaag cacaccgcgt gcattacacg cggatacata ttaaaacacc gtgttccaca   182880
agcaccgcac acgtcaatcc tccccgcacg gtcttcagcc cgcccatgac atgatctccc   182940
tcacgttacc cttcaacacc ctgtagtact ctgtctcggc ttccggtccc catgtcctaa   183000
ttataacaaa acaccgtgac actgtccatc tccctgtctt tttgcgccgc cggtcccccc   183060
caaatcatgt tctagatgc cgccggccac caaccggagg cacggcggct attggattcg   183120
gcattggtgc gccgcgtctt ggcctgcatg atcatcgtca tcatgattgc cattagcatc   183180
tggatcctga cctacgtgct gtttctctaa taagaacccc ggcccctgac ggtaattttc   183240 cttttcttctc cgtttctcct cagctgccgt acgtgatgcc tcacggccat ctccgacagg   183300
ccctctcccc gacctcctgg acatgtgagg gcttgttgct cctcctggga ttgctggtgc   183360
tcttctttca ccaccacaac cagtcggccg tggagaggcg tcgccgcgtc tcgttcgtcg   183420
aggccgatcg actgccgcat gagagcgggt ggtattcttc cgatgacgac ggagaccggg   183480
acggtgatga ggaaactgga gagagccaca acagaaacag cgtgggactg tccgctgttt   183540
ttagctgact ggcgtgcgac ctgtaaaccg ttactcgggt ctcaagatgg tttggaagtt   183600
gtgactcatc ttcctgtggg tgatacccaa ccggacgcga gtgttccata aaagccgggc   183660
gctccggcga gaccatgcca tcctcgcctt cggacgcccc gctcctcttc tctctcctct   183720 cctcccgct gccgcggcca ttgccgccgc cgcccatacc atcggcatgt cggccgacaa   183780
atcgcagctg tcttcgccgc cgcagctgta gcagttaacg tcgccggcct ccaggaggag   183840
atggcgctgt cgtcgtctc ttcgtcccgt ctccctctgt ggtcgtgggt ggtgcgagag   183900
tacacgatgg gtggctctcg tctcggggga ccacagggg aggggggtaa tttattattc   183960
gtattactgt aattttgtat cgcttaattt gtttagagcc gcacgcttga caacgccttg   184020
tatagcctta tttatcccga tgactttttt ctccgtacaa gaaatggacg tcacttgagc   184080
agacacagtt tcatcgacca cgacagtctc atgatctgac tacctctgac ccgccaacga   184140
gaaaaccgaa aagtaaaaga tgaccgcgcc ctcggagtcc tttttcctt ttcaatcatg   184200 aaagcaagag gcagccgaga gaatgccagt aagagacgac catcgcagac acagtacgat   184260
actcatctta gaacgaacca gcgaataacc atcacacgta cagcagaatc tcatgaacta   184320
gtcaaccaac gtcataaaat cttcacacaa tcgttttgc gaacttttag gaaccagcaa   184380
gtcaacaaaa gactaacaaa gaaaaaccat cttggaatta aaaaagtag catcgttacc   184440 ttatgaacca gcagcattca gtatatacac cagatataat atatttatta atgtatcctc   184500
```

```
tctttctcct gatgtaattt tgtttttgta aattcaattg ttgaaagtct ctccctgggg    184560
gaattgcata tcttattgat gaagaagaaa tccctgccat atgtgttgtc aaactatcat    184620
tatttctcta tatgggtatt ttttttctaa gaagcaaaag actagcagca gccaaaataa    184680
acctgatgaa atctttaact gaactcccag tggtctgtgt gtatatttct gttggtggtc    184740
ggttgtctga acccgggtgg gttgttcgga aacggcggga cggggaaacg gatggaaaca    184800
gcgtcgctat atacgtgact tttgatctaa acggacgtcg ctaggctgac agtttacgaa    184860
ttgctaaaca agataggaac aaaacaagcg gggctttgcc tggtaggatt tcctgtggaa    184920
acaataaccg gatgtgattg tggctggtac ataagctggt tctggctgca agcgcttttc    184980
actgcattag gtttggcgtt tgcttttgcc tgggaacgct atggctataa cgggaaagaa    185040
ccggtttggc aacattccat tgtggggggg gggtacttat agcgtgccta gctatgacgt    185100
tgatatatgt ggatgcggat aatactcgta atgagctaaa agcgacgact ggtagtaatt    185160
ttaccattac gcataggaaa gatccgttga caactaagtg gaaaaccgtt tttggtaaca    185220
atggtgatca gtggttgtgc aacgttacgg gtataggtaa tgctactgtg aatagtaacg    185280
caactatttg tgtgtcgagc tgtggtcata atacgttgga tttatgtaat ttaaagtcgg    185340
gagattctgg cttcttcgat ctgtctcgtt ggttcggtga aaacatggat gaatacagtg    185400
gtgatgtgtg gcacttggaa gtcagctaaa tgttgtatcg cttagtgaat tggtgttctt    185460
acagttttca tgtaataaac tacgtgtaat tcgttaaatt tgtgtgtttt tttgttagta    185520
ttctgcgtaa cggtggaata aaattgcgtt gacctagtta gatttcctgt gtagaacaat    185580
gaccggacgt gcttggactg gtacatacgc aggggctgga cgtggttacc ggtcactgga    185640
ctcggtttcg ctgtagctgt ggttcaacct gaacatggct cccagagctg ctaggaaccg    185700
gtccagtcac atttttttggt gggtgggggg tactaaaaaa gtgtttaata tttgggttta    185760
atgataaaat ccaggttatg gatatgagga aactgaatac ctcgcagggt cgaaatctta    185820
ccacagttga tgatagaaga cggttttcca tcgggtggga aacatgggat aacggtggtg    185880
actaataatg gtacaacggt cgtcaataca acagcctgtg tttcaagttg ttcgcatacg    185940
tcgcttgtgc tttgcaatat gacgcagcag actgattcgt tgtacggagt gggtcatcgg    186000
ttgaatgacg aagaagatgg tgaactgtgg agagtttcgg tttcttaata atcccatacg    186060
acatgtgttc atttatatct gaattttagg atgatgacta tagtataact ctggggaaca    186120
aatatcatac gttaatcact ttaagttacg ccgttaggaa aagaaaatca gtccgaatga    186180
agcatagtca gccgaatgat acagcaatag cttgtttaca acgtgttctt ttttacatta    186240
tgaacgtgcc ttgcttttta tacacacatg gagacagagg tccctcagcc cttgtcacga    186300
caactccctt tttctaaacc gtatgtgctc caaaccgtat ctcctcatcg tcacgtgaaa    186360
taccatggga cccctttttcg tcacacacgt ctttccgctt acccaacgcg tcagcccgcg    186420
ctcggcagag ctaccatata aaaacgcagg ggtttagcag cttccccaga tcgctgctgc    186480
cccggcgttc tccagaagcc ccggcgggcg aatcggccgg ctggtcggtc ggcgctcgga    186540
cggatgggga gaacggcggt gacttagccg cccgtggccg ggagaagacg gaggagccga    186600
gatgacaaca gcagtcgtgg aagggtcgcc aagcccggt ccttctcttc tgtctggtcg    186660
aatcttgttt tcttttttca accgctcttt ttgtcacctt tttatgtgag tttctcttcc    186720
gcgtctcccg gccgtaccat ccacccatgc agcatgcacg cgtgtatgta tgcatcgcct    186780
ctcctccgtc ccgactacca tcagcagtac cactgccgcc accccagcg ccaccaccgc    186840 tgccgtcgcc accgcgttat ccgttcctcg taggctggtc ctggggaacg ggtcggcggc    186900
```

```
cggtcggctt ctgttttatt attttttttt attttttatc ttctcctttc cttaatctcg 186960
gattatcatt tccctctcct acctaccacg aatcgcagat gataaacaag agggtaaaaa 187020
gaaaaaagct acagacattt gggtacctca gctttccgat aactcgaaga attcaaagtc 187080
gacgattccc aacaagagaa aacagaacaa aaacaaggtc attttttattt atcctcatcg 187140
tcaacaacaa ctaccgacaa caacgaaaca ccaccaagaa tgtcaatccg caagggtgtt 187200
cctgccccct cgacgcgcct gtcgcgatcc tcatggcgag gaccgcgatc tccgtatagg 187260
tagatgaaat tatcccgtgt ccggtcctga ttccccgcat gccctgcaca tcctgacgcg 187320
tcggtcagca gccaaacaat cataggaaat gaaccagaag aacaaaaaga tcatctctct 187380
cggtgtatag caacaccaac aacaaccgca tcgcaacatc ttcatccgca agacggaaag 187440
aaaacaacaa taatgagaat gaaatcacca caaccaagcc agatttcacg tccatggagtt 187500
tttattatat tattatcaaa acgaaaaaca gaaaaactgt catagataaa tataaaaaaa 187560
aatagaaacc acaaacgact actagtactc caatcttaga tgtatatgct cctagataag 187620
atttagtatt accataatca tcgaagaatg aaagacgacg atgattcctt accgctcctg 187680
ccacccggtc tgtatgtaga gagagaagag agaaaacggt gaatccaaga tccccgggtc 187740
ggcgtcggca tgccgctgat cgcagtggcc ccacctcggc atgccggcgc cgggcgagga 187800
attgctcatg aaaaaaagta tctttctgta aaaaagaaa acaatacatg attaaccgaa 187860
aagaaaccaa caaaaagaac ccgagatcag tcgatttcga tcactacgat aaacacatgg 187920
aagatttctt gaaaaagaa aagagaaaga gaccaccttc ccggcggcgg acacgctcct 187980
ctccgtcgcc gttctgcacc atgattcgat caataacaac atcatcatcg gagaccatct 188040
tttaatcaat cagcgttgca gtagtcgact ccctggacac gaaggagtca tccatttta 188100
tcctcgcact tcttcgctct caaagccgcc tttaaagttg aaatgaaagg atggaaacat 188160
ggaatacagt tttaattgca cgtatcacca ttttactaca aaagaaaaa aaacaactt 188220
acacatagta ttaccttagg tttacggata agtagagtgt aggcgttttt gaaacagttc 188280
agccaatgca atcttgtctc ggcataatca ctctttctgc atataatagt agtagtagat 188340
ttattcacat caacacagcg aaaaactcca gcatcaaagt acacctagag acagccctta 188400
aaatatagtt tgcagctttt agatgtactt acaccaaaga agattaccgt ccttacgaga 188460
aaacagatac tcggatatag gaatcaagac agctctgcac tgaaaacaca ctctcctgtc 188520
acgacaccgc gccacaccag aggcgtacgc gtgacttcat cgcaacgatc catcgtgatg 188580
tccctcgcag aacctaaaaa gaccaaaaaa aaatcttgga ccacagttgt cgatacttga 188640
agacaatatt ctcgtgagaa ctttgagatt cgcacttgaa acctcttagg atccacaaaa 188700
acaacaacct ctgtatggaa aatgcgctat tttatctcag cttttctccc aaacctcggt 188760
ttcttcctat tcttatgttt tccctagtat atttgcctcc ttataagaaa agaagcacaa 188820
gctcggtcgc acggattatt ccttctgcta atctattatt ttgttccttt ttttttttctt 188880
tgccttcacc ctcttcactc cctgtagcaa cacagagtag tagacacaat aaatgagaag 188940
tttgcatgca tttgtcgtgt ccgtggtttg ttatggcgtg tggagtgctc gggatgggtg 189000
gacgtgggga cggattcttg aggctacaaa gatacgcgga gacgtcgtgg cgaggggatg 189060
ggtttattgg atatcggtga agcagcgtgg cggcgaaaga cgcgatccct gggctggtag 189120
atccccctac cccgtctacc agggacgttt atcctttgga cacgtaaatg tctcggccgg 189180
catccacgcg ccacgttcac cgcgttgtgc ccagcgccat gtgcgggtcg tttcggcgtg 189240
```

```
aagttggacg gcgtagtttc ggggattgtg aaccgtggct gagggtgtag atgggacagg   189300
aaaaagcgtg tgatctgacc gaggcgaagc atgtgggtgg tgcgatgcgg tggatgtggc   189360
ggggtgcggc ggtttccgac gtggagatgt ggagatgggg gtgatccgga tgcgtggcaa   189420
gaggcctcga gcttgggctt ctcccgcgga tggacgttct aactgtacac ggcggccgtg   189480
gcctccgagt aaaaaaacca ggtgctgacg ccagacagag acgccgtcct cggaatcgtg   189540
tgcgcgaaag cctgtgccgc ggcagcgtac gacgttccag tcagcgaggc cgtcgcgttg   189600
gcgcgccaac agtaaggtga cgacaggttg gcggcccatg gttccgaagc gtccccacat   189660
gcaccagcag tcggcgtcaa agtcgcttgc gctgtcggcc cagtcgccac cgccgcggcg   189720
gatttccgcg cgggggacgg ggtagccgag tgctgcgccc tcgccaatgt tgtgaagtgg   189780
atgcgtgagt tgatgttgat tctctgtggg aaaatgagcg ctgtcctgtg ggttggtgtt   189840
ggggtatgcg agtagtaggg gttgtgtttg atcgtagagg tgttggcggg cctgtgcgca   189900
agcagcgtag tctgcggcgt cgagctccat ctgtgtgcgg tgttcttcgt cggcgtgttt   189960
gtccgaggtt tggacatgcg gttgtgtgtt gctgtggtgt aagggtaacg tgtgttgggc   190020
gtctgggtga agcggcgtgg tgtgggtgct gtttgtgtct gtggctggca tgattgtgcg   190080
gcatgtgtgt gttgtagtgg gtggaggtta aataggtgag gtgggttccc tggtccgcgc   190140
cgcaaactgt ccccgtcccc aacgtaacct cccctacgcg gcgcgaacag ccccggcccc   190200
agcgcaaccc ccgtccccgg ccccaacacc gtcccgcaca ccccccgtct ccgcaacacc   190260
ccggcatcgc cggcggccag aacgctcgaa aaccccgac aagcgcagcg ccgaaacgac    190320
acaggcaagg accgtggaac gcaccggcag gcgccgaaa caccgtcccg aagcccggtg    190380
ccgacaacaa ataccgtggg acgacacgca ccggcagtgc gcaggcagcg tcggacacaa   190440
cacgcttacg gccctcaaca ctccctcgag gacccaccac gcggcccgc accggcggtg    190500 ttttgggtgt gtcggggcgc ggccgggtgg gtgtgtgccg ggtgtgtcgc gggcgtgtgt   190560
tgggtgtgtc gggggtgtgt tggcagggtg tgtcagggtg tgtcgcgggc gtgtgccggg   190620
tgtgtcgtgc cgggtgtgtc gcgggcgtgt ggcgggtgtg ccggcggggt gtggtggcgg   190680
ggtgtgtcgg cggtgtgcgc ggcctcgggg tgtgcggctt cgcaggaacg agtgtgtggc   190740
ctcgcggccg ttatttcccc cgcggtcccc agggccgtcg tccctcgccc ccgggcgttg   190800
cttttcgtgt gtccccaggg acccatgctg ccgtccccg ggaacttcct cttttccccg     190860
gggaatcaca cagacacaga cacgcgtctt cttttcgccg tgcgcgccgc acgtcgcttt   190920
tattcgccgt cgccgtcctc cgcaccacac gcaactagtc gccgtccaca cacgcaactc   190980
caagtttcac ccccccgcta aaaacacccc cccgcccctc gaggacccac cacgcggccc   191040
ggaatggatg tcgggcgtcc acctagatgg gtgcgcgccc gggaggcggc tgtgcgctcc   191100
agtggtacgc gcctgccgcg cgtcttcctt cgggtagctg cctttcccag tccacggcct   191160
tccagactgc gtggcgccaa ggcggcgcca gcacgcgccg tgcacgtcgc tgcctataaa   191220
agccagctgc gtgtcgcccg cggcacacgg gcgacgaagg cgtccgcgtg tctaaaccgc   191280
gtgctcgctg acgcgggttt gcttcctata tagtggacgt cggaggtgtc cggcgcccat   191340
ggcccagcgc aacggcatgt cgccgcgccc ccgccccctt ggtcgcggcc gcggggccgg   191400
agggccttcg ggggttggtt cctctcctcc ttcttcttgt gtgccgatgg gagcgccgtc   191460
aacagcgggc actggtgcga gtgctgcggc tacgacgacg ccgggccacg gcgtccaccg   191520
ggtagaaccc cgcggggccgc cgggcgcccc tccgagtagc ggcaacaata gcaacttttg   191580
gcacggcccg gagcgcctgt tgctgtctca gattccggtg gagcgccagg cgctgacgga   191640
```

```
gctggaatac caggccatgg gcgccgtgtg gcgcgcggcg tttttggcca acagcacggg  191700
ccgcgccatg cgcaagtggt cgcagcgcga cgcgggcacg ctgctgccgc tcggacggcc  191760
gtacggattc tacgcgcggg tgacgccgcg cagccagatg aacggcgtgg gcgcgacgga  191820
cctgcgtcaa ctgtcgccgc gggacgcgtg gatcgtactg gtggctaccg tggtgcacga  191880
ggtggacccc gcagccgacc cgacggtggg cgacaaggcc ggccatcccg agggtctgtg  191940
cgcgcaggac ggactgtacc tggcgctggg cgccgggttc cgcgtgttcg tgtacgacct  192000
ggcaaacaac acgctgatcc tagcggcgcg cgacgcggac gagtggtttc ggcacggcgc  192060
gggcgaggtg gtgcggctgt accgctgcaa ccggctgggc gtgggcaccc cgcgcgcgac  192120
gctgctgcct cagccggcgc tccgacagac gttgctgcgc gccgaggagg cgacggcgct  192180
cggacgggag ctgcgccggc ggtgggccgg cacgacggtg cgcgctgcaga cgccgggcag  192240 gcgactgcag ccgatggtac tgctgggcgc gtggcaggag ctggcgcagt acgagccgtt  192300
cgcgtcggcg ccgcacccccg cgtcgctgct gacggccgtg cgtcggcacc tgaaccagcg  192360
tctgtgctgc ggctggctgg cgctgggcgc ggtgctgccc gcgcggtggc tgggctgcgc  192420
ggcggggccg cgcgacgggga cggcggcggg gacgacgtcg ccgccagcgg cgagcggcac  192480
ggagacggag gccgccggcg gggacgcgcc gtgcgcgata gcgggagccg tggggtccgc  192540
tgtacctgtg cctccgcagc cgtacggcgc cgccggcggg ggcgcgattt gcgtgcctaa  192600
cgcggacgcg cacgcggtgg tcggggcgga cgcggcagca gcagcggcgc cgacggtgat  192660
ggtgggttcg acagcgatgg cgggtccggc ggcgtcgggg accgtgccgc gcgccatgct  192720
ggtggtgctg ctggacgagc tgggcgccgt gttcgggtac tgcccgctgg acgggcacgt  192780
gtacccgctg gcggcggagc tgtcgcactt tctgcgcgcg ggcgtgctgg gcgcgctggc  192840
gctgggacgc gagtcggcgc ccgccgccga ggccgcgcgg cggctgctgc ccgagctgga  192900
ccgcgagcag tgggagcggc cgcgctggga cgcgctgcac ctgcacccgc gcgccgcgct  192960
gtgggcgcgc gagccgcacg ggcagtggga gttcatgttt cgcgaacaac gcggtgaccc  193020
cataaatgat cccctcgcat ttcgtctttc ggacgctcga actctcggtc tcgaccctcac  193080 caccgtcatg acagagcgtc aaagtcaatt gcccgaaaag tatatcggtt tctatcagat  193140
taggaaacct ccttggctca tggaacaacc tccacccccca tctcgccaaa ccaaaccgga  193200
cgctgcaacg atgcccccac cgctcagtgc tcaggcaagc gtcagctacg cgctccgata  193260
cgatgacgag tcctggcgcc cgctcagcac agttgacgac cacaaagcct ggttggatct  193320
cgacgaatca cattgggtcc tcggggacag ccgacccgac gatataaaac aacgcagact  193380
gctgaaggcc actcaacgac gaggcgccga aatcgacaga cccatgcctg tcgtgcctga  193440
agaatgttac gaccaacgct tcactaccga aggccaccag gtcatcccgt tgtgcgcgtc  193500
cgaacccgag gatgacgacg aagatcctac ctacgacgaa ttgccgtcgc gcccaccccca  193560 gaaacataag ccgccagaca aacctccgcg cttatgcaaa acgggccccg gcccacctcc  193620
gctgccgcca aagcaacggc acggttccac cgacggaaaa gtttctgcgc cccgacagtc  193680
ggagcatcat aaaagacaga cccgaccgcc aaggccgcca ccgccaaat tcggggatag  193740 aaccgcggcc catctctcgc aaaatatgcg ggacatgtac ctcgatatgt gtacatcttc  193800
gggccacagg ccacggccgc cagcacctcc gcggccgaaa aaatgtcaaa cacacgcccc  193860
tcaccacgtt catcattgaa agtctctcca gtccatatgt tgtcaggacg tgctgtcgtt  193920
ctccgcttgc tgcgaagccc gttcttccga gtcgtgtcgc tgcgtccagc gtcgcgccca  193980
```

```
agatgggaat ttgggtctttt tcacgcgtag cctcctccac cacggctgct gatcgccgtc  194040
actaaggacc gacacggagg atgacgagga gcttctcccc gactccgcgg tccgcgaccg  194100
gctacgtagc gcgtgtccct gccagtctcc gcagttacac cacacgtcgt gagcagcgtg  194160
cacctgctgc cgccactggg cctcggcgtg ctcaggccac ccgccggagc ccggtctgag  194220
ctccgacgca ggatgcgcgt actcaacgtg cgccttccag tccatacagc aacaccatag  194280
gtcgtgcgag tcgtcggcta cccgccgcca ggccagttcc cgcatgggaa ggctggacac  194340
gccgaccgag aggtcaccga gcccggacgc catctcttct tcctctccgt cgctgtcatt  194400
aagcagccag gtcacctcct ccgctccgcg gtccgccggt ctcgacggac cgcgccgccg  194460
tcggcaacac ggaaaacagc acgccagccc gagccgctaa ggccgcatgc ccctgccgcc  194520
caactgaaca cgcataccccc gctcaactgc gttttgccac ccctgtcagt gctctcgctc  194580
gagcaccacc ccgcatctcc caacctttt ccaataaacg aaaccgacat gacacacgta  194640
atgggtactc gtggctagat ttattgaaat aaaccgcgat cccgggcgtc tcagcacacg  194700
aaaaaccgca tccacatcat agacaagtta cagtccacag tcatatacac gataaacaat  194760
accaacaggg taatgtttat ggagtaaaac actattgtcc aggccacatg cgtgtatgac  194820
ttccgcacca tcccgtactg catgttccac atgtacgcgc tagacgtgta atccactcgc  194880
agttcgggga cgcaacgcag ccagatcaca tccccttgca gtaccagacg cagggctagc  194940
gtctcgaaga tcggcatcac atctaagttc cgcacgttcc actttaacga ctccccggga  195000
acgaactcca cgtcgtcggc gtgtacgtac aggttctctc ccacgccgcc ataatcggcc  195060
ttcggatcga agacgaaccg actcatgttg cccacgatgc tcccccgagc aaacaacttg  195120
ccgttgtcaa tgtagcaccg gttgtcctcg atttgaaacc agggatgctt ggccgtggac  195180
ttccagggcc ggagcgcgtc ttccccggct ttagtgattc catcgggcag gcggatcaag  195240
ggacccatgg aggtccaaag acccacccag gctttccaga gattgttcat ggtgaaacag  195300
cgtgtggact gtacgctctt tcccaattta tatcccagag tagtgacgtg agcccagcca  195360
cctcccagat tcctgacgtt ttggttgtct ttcctgccaa ttcctcccgt aaacttatga  195420
ttatcctagc ccattcccga taaaaataca cggagacagt agatagagtt acgaataaac  195480
cggtttattt attcaagtgt ctcaggagat tattgaacga gcgtggatac cacgccgtcg  195540
tcagttcatg gtggcattga gcagccatag caccagagtc ccggcgcccg gtatcagaca  195600
cgctgaccta ccgggcgcct tcgagtccgt accccgcggc ctgggtgtta gagtccgtac  195660
cttgcagccc aggtaggttt caggtaccag ctggttcgta cctgttaaat aaatcgcaga  195720
cgggcgctca cccctacggt caggagcaca agaacaacca gagagaacag atatacgagc  195780
agggttctga acagcagacc ccaattgtcg tctctcatgc ttcgctgaag gtaccagttg  195840
atggtctgag agctatagtc catcctcacc tgaggaacac acgcggcata tttcttgggg  195900
tctccccacc tcgtagacaa cgtgatgtcc accatatcca cggtgtgcgt caccgggtgc  195960
ccaccgatgt tccactcgaa ataggctccg cgctcatcat ggtggtactg ctcaccggac  196020
acctgcagtc tgtccatgta agattgagag acgatacccca cgttcacaaa gtgtttctcg  196080
gtgaagttgc ccgacatcct ccccttgaag tacagcatgc ccatatggaa ccagcattgg  196140
ttctcctcca ctcgaaagtg ggccgatctg atctccgata ccaccacatc caggggccgg  196200
ggcaccgagt ccgcgagtct caggaacaag acggccagga tcgcgagcac caacaccggc  196260
ttcatggctc cgaaggtccg ctgctcggct ccgctcaccg ctccggtctg gctgcagcag  196320
tgcttcgctg agaagtagcg tgtggactga acggtgtttt tgaatatata gcgtttcttg  196380
```

```
gtgacgttgt ttcccctacg tagtaggcaa ctacgtgcca aaagaggcgt tacggtactt   196440
tccgtactgg gatttccaaa ccgggacttt ccacacggcg gtttcaacac cgggactttt   196500
cacacggtga tttcggcacc gggactttcc gcacggcggt ttcgccaccg ctgacgttct   196560
catgccgcc cacgtcaacg gtggcgacac cgtactttcc catgcggttt ataaacgtca    196620
agagtcacgt cagtcgccca cccccattac acggcgatat cccgataggg catgagggga   196680
cccgggtgtc gcgacatgtc gacgacaggt gcggattagt ggtcgtgtcg cgacatggac   196740
gtgcagggg atgtctgtcg cgatagagtt gatgtgacag cccgctacac ctctctgtcg    196800
cgacatgcat acacaacggg ccggcttgtc ggcgattgtc gcgacatatc gttatcagtt   196860
agcgaccgga gttgtctatc gcgacatatc gtcgactatc gcgacagaaa aaataccgtt   196920
cgtagagaat gccgtgttga aggaacgcgc ttttattgag acgataaaac agcatcagga   196980
gccacaacgt cgaatcccac gtccagtcga ttcgtatgtt atgctgcaca gcaatgctag   197040
aataacaacc agcagggtaa tcccgcaaca taaatacaaa gtcacagcga gaatccgtg    197100
tcgttctatc aagcgaaacg cgttccaaac ggccccgtca cagacgcagt tattcataag   197160
cgttaacaac cggtggctag gatgaatatc caaatcacag ggcagtagcc gacggactcg   197220
ttgacaggtc agcctaccct caaggttcct atcgttcgga cgggatttgt gcgttttagg   197280
cctcttttc gccgcctgca agcattggtg cgcaaagtcc tcacccagct gtttccagct    197340
atcatctgca tctgtgcagt cccctgtatc gttgtaacaa acgggtctgt gcgacttcgt   197400
tctcggaaca caagcttgtt gtcgcggaga cagagagaga agggttttcg ggtcacgcga   197460
agaccgctca ccgggggtcg gcaacgcaca catcaacaga aaaccgagac gaatcaagag   197520
atccatagtg aaggagtgat atcgacgtgc ttacgaaacg gcgattatat atgttctcaa   197580
caataccgcc ctacgttgta tgatgtaacg tgtgacgtga gtctgatcca acactgaacg   197640
ctttcgtcgt gttttttcatg cagcttttac agaccatgac aagcctgacg agagcgttca   197700
tcggggcatg aagtacgcat tacacaaact ccatatattt gttacgatag aatacggaac   197760
ggaggaggct ttcgccacac ctatcctgaa agcgttgcat tctttatgat aggtgtgacg   197820
atgtctttac cattcccacg gctgctttgc gtgatgatga cattcatcat gtatttccat   197880
tcacacatac cttttgtgca tacggtttat atatgaccat ccacgcttat aacgaaccta   197940
acagtttatt agcccttgac aggataggtc aaaagattat atgtaggttt tccggtaaac   198000
cgaattgtga tatttctctg caggaaatag aacagcctgg tacctataaa acggacaatg   198060
cagtactgta gcagcgtaac caagtaggtc cacatgaaca cgtacaaaat tatggtaagc   198120
catcgttttt cataccacag cctgtagctg tcgtacatga atgaggacgg tcgaggaacc   198180
cagggtagtt gtaattgggg gcgacattcg tactgtccag aagacaattg cacggggttc   198240
agtgagatga gtactttagc gatgtcggcg ggggcgctac gtttcaccgt gacggtgaga   198300
acttgaccgt cgttttgtat ttcatgaggc acgttataca agccactggt atcatgaagg   198360
atgacctctg atgcgatgtg aggattaaat tgtccctcaa accgccaaac gctggtcatg   198420
tttccaccgt caattacgca gctgacggtg tgagatacca cgatgttgga cttaggtttg   198480
ggggctaatt gccttttac aaattccctt ctgtattgca ggtcctgctg ccactgcttt    198540
tccgtgcgga aagtcgccat gtcttccaca cgtgtggcga cgatagacgc caccaaggta   198600
gctaccagaa gcagctggat ccgcatggca ttaccgtatg tcaattagaa agttgagcgg   198660
acacggttat cgttcctggc ggatataagt atataaacgc gagttagcct ttcccgtccg   198720
```

-continued

```
ttttgtacac ccgttcccca cacaaatgac gaatacgacc ttttttttta taaaaataaa 198780
ccacgtgtat tatataaaaa catttacata gaaaagagac acacggatca acataaggac 198840
ttttcacact tttggggtac acaggcgtgc caccgcagat agtaagcgct ggatacacgg 198900
tacacagtcc tggccagcac gtatcccaac agcagcacca tcgccataca gatggcgatc 198960 acgacccga gctctaagtg tctgtattca tagtgtagtc gccgcaggtt atccactgaa 199020
ttcccgtaac tgaaataacg tatatggtac cgaggctggc accacatggg tttgcatttg 199080
gtgcacggca ccaaatgcag agtgagatgg tccaagtccg tgggcaccca ctggcgcaaa 199140
cggaatacgg cttcggtggt ctccacgagg cactccgggg cgtgcagacg gccccacttt 199200
cgtccgcgac ggcccgacca gccgacccga gccactatcc ctttctcggg atagaacgta 199260
ccctgtacac gccacacagc gtccaacacg ccgtccttga cgacgcagct ggcctgatag 199320
ctggacacgt tgttaagcgg cggaaagcga aactgacgtg ccggcggagc cacatagttc 199380
ggttcaccgt gttgtcgcgg ttcgtcctcc ctatagtaat agtagtcgtc gtcctcatag 199440
gggttgccgg cgtgagccag cgttacccaa cagcagccca ggccgacgag gaggcgcagc 199500
caccgcctca tggcggcttc gccagtcaat cgtctttagc ctcttcttcc cgtgaggtcc 199560
ttccggtggc gcggtgccga cctcggaccc agggacgtat ccacctcagg tacacacagc 199620
aggctacctg gacaccgaag ctgaacaagg ctacgtgttt cacaaactgc accagtacca 199680
catagaggaa tgtcaggtag cgtctctccg caaacagccg ttccaagtct gagggcgtta 199740
cccgcagcgg caaccagggc agcctggacg ccggccggca atggagcacg ctccggttac 199800
aggcactgca ggggtaaacg gttaacatca cgtaagagag tcgtgcgtcc acctgtggga 199860
gctcagtttc gtaacgtaga gccccgtcat tttccagctg gggtgcgccg accttgaaat 199920
gggtcgcgct ccgctcgtta ccccaggtgc cgtaggctct cggggccgta tcggagaagt 199980
tgccacgcac aagccaggcg gccacgagta ccccgtgctg gacgtaacat tcggacacgg 200040
aactggagac acgtagccg gacacgtccc caaacccgcg agggtactgg ggcagacgga 200100
cggacttgct atttgacaac ggacagatac gagacgacga ggacgcagac gactcgtcgc 200160
tggaccacga caaccggagc gactccttgg agcggctcga gagtacactt actgcgatca 200220
gacaccagtg ccagaagaag gaacaggtgg acggggacca caggatcata gccgccggca 200280
ccgcggccgg ccgcaggaag ccgcccggcc gtcgtctgt gtgcgggagc cgaaacaccg 200340 tgcctctta tatcgtcccg acgtgacgcg agtattacgt gtcagggaa accccgtca 200400 cgacgaacgt gatttgtaag tgacgcgggg tgctgacggg gttcggcccg agaggtgacg 200460
gagcgcctca cgtcagtatg atgtccgatc cgcgtcagcc ccgacgtggt tgtggtcacc 200520
gaaacccacg tttatatgga cgttgagagc agcgcctgac cacatgattc atcataccat 200580
ttctcggaat cgggcccatg ccgggaaagc acattccttt tcagtaaaca acaatgacat 200640
cataacaaat cattttattc gcgaggtgga taataaccgc atatcaggag gagggatcgg 200700
gtgatgacgc aggcccccgca gaacagtccg aaataaattt ttagtattgc cccatagtcg 200760
cctagatacc agaggtacgt taagttcatc aaaacgccca tcggcgtccc ggaatcgtat 200820
accgggcaca cgaagcgttc ataacaatcc cgggaggcga gtgttagggt agcagagtag 200880
tttcggggtc ggtttccttc cggcgacgac agttccgtgg gcagcagaat gtacagcgcc 200940
tcggtagctg tcgcggtgcc ttccacgagg atgggctgcc ggtgcctttc gtgatttttcc 201000 ccgtcgtgta gccaagccga ggcccgcaaa gtcttaggcg aggggaattg tccatagagt 201060
ttcaccgcac ccttcagtac atggttctga ataacacagc cgcacgtgaa gtaggtaggt 201120
```

```
tctctcgtct cctccgtggc tgccgccacc actcccagcc accacaacag gcagatcgcc   201180
agagggttcc ggaggcttcc ccggcgtagc atggttttgg gttaaagcaa aaagtctggt   201240
gagtcgtttc cgagcgactc gagatgcact ccgcttcagt ctatatatca ccactggtcc   201300
gaaaacatcc agggaaaatg tcggtgcagc caacctttca catacagccc ccaaaacact   201360
tgaatcactg ccaccatcat cagcgtatac tgcgccgact taatcgtgag cgcgtagtac   201420
gccattagac ggcgatcttc gaacaatagt cgttcgatgt cctctaacga gctccacagg   201480
ggaacccaag gcacgaggca ccggggttcg cactctacat aataagtttg gcattggtgg   201540
caggggaaa agtagaacaa cacgagtttt gtgcgttggg gaacacgata gtcccggagc    201600
cagtagcgtt ttgcgacgag gctttcggag acgtcctcca ccggcgtcgg cactcgatcc   201660
gcgtagccct ccagcgtctg gtagtacacc cggggtgtcg gcgtgggcac ggacaggttc   201720
ccgcgcaggg tccacagagc ctccagtcga ccgcccgatc ggagcacgca gcgcgcctcg   201780
gaatactcta ctcggtactc cgaaacatcg gacagaggcg gtaacggctc cgtctccacc   201840
aagggcggag gttcatcgaa aagagtcaag gataattcag gcatactacc cgcgaccggg   201900
gcccagaggc ctagaataag cattacaagg ttcattctgt cttacaaggg aaggctgtta   201960
ccctgtctag actcaaaagc tgtaaggctg tcttatagca tgtagtcttg cacgtcacgg   202020
ggaacagggt ggtgatctag tgacgtcggg agaacacggt gttttagggt gcggggaca    202080
aaggacagta cgacagatta ggtgatagaa acgttttttt ttatttatga aaaagccagt   202140
gtgccgtgcg gcctagggcc ccggcgtagt ttggatacca gatgggggcc gtcagggta    202200
ctaccacgag cagaaacata atgacttggt ccatgtatag cagcatagcg gtgcgcagca   202260
ggtcgccgtc cgtgtagcaa tttgacggtg agcgataaag caccgttaat gtgtcgcgga   202320
taagcacgat cttgaggccg tagatgaagc tcacagtcag tgctaaaatg atgcgttggt   202380
atggttccca ggactgcacg gcgatgaaga gccagagtat gggaagcatg aagcttagca   202440
aacagaggat ggctaaccgt cgttgcatgt tccaggccat gagccaggct aggcccgtac   202500
accagacgca gagcatggat gacaggacat aggcctggat taccacggtg cgatcgaaac   202560
acagcccgat ggtggacacg gatatcgtag tgagggtggt ataccatg accagcatca    202620
gggtcccggg tcggcgccga cgttccagcc agtacgcgtg gcaacgcaga gcgcaggta    202680
gcagtgtgct ccagaagggc aatgtatcgc gcaggtaggg ggccgtcacg cgccacggta   202740
tgagcatgaa aaggatggta gtggctatgg tggcgctggt ctggaacacg acagtgccgt   202800
agagacgtac catccagaga aagtgttgaa cgctccgcag ggtgtcttca tctttggtga   202860
ttacggtgac tcgacggatc ggcggtggtg acggcggcga cacgggtggg ggtttctctt   202920
tcttatggcc gagtggctcg ccttggtgaa actggatctg taccatgacg ggtgctcgac   202980
gaacagtcgt gggggcttta ggtacccggc aagttttata gagaaagggg gacgatgggt   203040
ggtggctacg agccaccgcc accttcgcaa tacgaggatc tgaaggcggc aaagacggtc   203100
gtccagggca ggcgccagag gttgggactg agcacgatca gcgtgatttt aaacatggtc   203160
accagtccta cgtagatcag cagcgagccg cgtaacgtct gagcagccgg cagttcgtcg   203220
cggatgtaac gcgtgccgta gaaagtcacg gtcatcataa ggaagacgat ggcgccgtag   203280
ccgtagagta gaatacgctg atgatggaac acggtctggt cgccgataac ccagagcgtg   203340
atgaaaaaaa cgctggtgag tacccgtgag catatgagct cccaacgctt agcgcgaaag   203400
ctgtccccaa ccatgacagc gccggtgcaa gctatccaca gcgtgaggac cagtgtgtag   203460
```

```
tcgatgagga tggcgggcag gtcggagcac caggtgtaga aaaccgtggt aacggagagg    203520
aggcctacgt agcccatggt caataccacg tcgtcggggt gcctttcgcc ctgtatcaag    203580
accaaacacc agagaaggga gggggcaaaa accagcagca gaggggaaga ttcatgttga    203640
catatgttgt gggaatcggg gatacccagc caaatcattc cgcagaaagc cgtactgatg    203700
gcgatgtgaa agaccactag ggcgtagacc cggacgagga cagcaaaacg gcgcagccac    203760
ataaggccgt ggtgcagctg caggagggaa gcccattgcg gcgaatgtag cgacggtagc    203820
ggcgggtcca tgaggcgggt gatgcgcccg agtgaacggg tgagcgtctc ggtggagtct    203880
tcttataaac cagcggagct caggcagcct tgctctggaa cgtcgcagtg gtggtgttga    203940
ggatgacgct gagcgtgccg ttgtcaatca ggtaatgatg ataggtgccg agcttggcca    204000
ggtagctgaa catttggtcc cagcgtgccg accacaccac gggcgtgagc atcaggagtg    204060
tggtgtgata gattagtgtt tcggtggcgt aaagtatcag cgagctgcgg atgacgtggc    204120
tcacgggcat tttggtggcg atgtagcgca cgtcttggaa aaggacggcc aggatgcagc    204180
ccacgaacac ggtgtagaga cacagcaaag tcttatgtaa ccaggtgtaa gtagaagcca    204240
ggacgctgac catcaccgtc aaaagtgtgg aggtaaaaag cgcgtcacgc cacacggagc    204300
tgagacggtg ctcccaagcc acgccgttgc aggccacgaa caacgtccac gttaggatga    204360
ggctagaaat gccgatgggc gctgtggcgc acaggttgag cccggcggtg gtgaacgaga    204420
gaagcgccac atacagcgca aacaccaggc cgttgctggg gtgtctgtga tcggtgagct    204480
ccagcgcgcc cagaaccaat actggtgtgc agctaagcaa tagcggcgag ggatcgtcgc    204540
tgcacttgta gcccagcgag gggtaaccca gccaaaccag cgcgctaatg agtacgctga    204600
aagcggtttc cagcgtcagc aatccgtaga cacgcatgac aatcgcggtc cgccgtagcc    204660
aacacacggc atcttcggaa actgtggacg ctgtttccga ataccgggag gagatcgtgc    204720
ttccctcttc caaggatcgg aaagtagcgt ccgtcgtttc cgcggacgcg gcttccctgg    204780
tacgctccgt ttccgacgac gcggtttccc gctgcgtgga aactgtctcc atgtcgggac    204840
cgcagcgccc ggcggcgtat ccgcaaggtc tcgaagctac agcttgtcag aggaaaagta    204900
ggtttgcaaa aaggtgcgca gggtcatgat tctcagcacc atcagcagag tgaaaaccag    204960
actgagaaac accttgacgg ccgccaaaag cgcgcgttcc agcggcgtct cgtagcgtac    205020
agccagggcc gcttcgtgga aatgcgagac ggctagacag gtaatgagca cgctgaagga    205080
caagacgatc ttaaagcacc aggaccaacc acgcctcaag atgaccacca cgattgccgt    205140
gaaggtcaac gtgatcaaag catggacgac cacgatctga cggcggacgg tacgttcggg    205200
agccaacaac gctacgccgg tgcagctgag aaaggccagt aaggtgaaca acgcggccga    205260
gatgaccaac gtaccgtcca ggcagagaca tatcacgatc aacggcggca cgtgaagcag    205320
cgtgtaaaag agcagaacgc cgatattgct gggatgcgat gtttcgtaac agtgaatgaa    205380
gatcactgac gtgacgggta tgacaaagac gaggctgggc gaggactccg tgagacacag    205440
acgagaatgg tgaaaccacg tcgcgggcgc cgcgtagcag aaggcgctca acaacgcggt    205500
caagccggcc agctgccaac ccacggcgcc ataggtgtgc agcgccacgc ggcaacagtc    205560
gacccaagcc agactgcggg tcgccagccg ggtctcttgg atcccggggg gcacgtagat    205620
gaccgtgcca tcggtgggta cttgaaaccc ttttctctt tcatggtgc gctgcgttct    205680 ctggaaacgg ctgctctgtc cgaaaaccag ttccgaacga aaatctaggg cgagagggtg    205740
gacaacggcg tcgacgacga agcatgggac aggtcgttcg gcgttaacgt catcgcgtcg    205800
gacgacggta gttctaagag acgtagatcg ctcagcaggt cctgacagtt gcggattcgc    205860
```

```
aagatcagaa aaaaaaggga aatgaacgta ataaagagct gtagcgacgt atgcgccaca 205920
tcgcgtggca taagaacgtg acggacgaaa aggacctgct gcgaaaagtg accggcgaag 205980
ataaggccca ccgtgctgta gaagcccaaa agcagccgca ggggccaagt ccagggccgc 206040
gtgaagacga tgagaacgtt gaccagaaag accacgaccc agacgccgtt gatgagggta 206100
aattgatcgg acagggtgca gttgtcgcga cagatgaaga ctacttccgc gcagagcaag 206160
gtgatgacca acgtgagcac aaacgacgtc aacacctcgc ggggctcctg gcaggcacac 206220
gtgacaccta gcgccgggat gtgcgccagg aggccggcga gtaatagcac cagctgtcgg 206280 aacgacgac ggcagcgcgg gtgccggttt cgctgagcga gaaccggtcg ctcatagcgg 206340
aaatacacga agagcgcgga ggccacaggc accaggagga gcacctcggg cgcccagaca 206400
acgtgacaag gaaagcccgg acgcgacttg agagtcgctg tagggaagac cagagagaag 206460
ctacccaaga cggccaccgc cgcggagatt tggaagagga gcaagccggc gattcggacg 206520
acaacctcga agcgatgcac ccagcccagc acggccacca cggccgcttc atcatagtcg 206580
tcgttgttgc cgctgtcgaa cagccgccga acacgatct gtcgctgggt cgcggtggga 206640
aagcgcagac ccatgacagc cggaggctat atgaccgcgc gtctaagacg cgagatccgt 206700 gggggactt ttagatgttt gggcggcccg cggttctaac aggcttgatt ggtggagacg 206760
gccggcgcgg cgggtggggg aaacgacgag ttttccgtt acgccatggt tcgcgtgagg 206820
tttctctgta cctcccgcaa aaggtcacag cccgaaatgg aggccgcgtt ggtggccccg 206880
gtggcgcgtg acgataacca ggtcatccaa gcgatgagtt tgtctaatga gtcctcggtg 206940
gtgaagagga tgagaatgag caggtacagg tacaccaggt tctcatagag acacaaggtg 207000
agcaggtcag cctcggacca cgcgatctca acaggcgcg tggtgtcaaa gaccgtgacg 207060
accagcatga agctgagcgc catggcgtaa tagcccaaaa aaagtttgtg ccccaacggt 207120
acgggctgca ggtaaagtgc gatcaagaac gcgataacgc cgatcacaaa cagcgtgacg 207180
atgacctgcc atcgacggtg attatggccg gctagacccg tgacgcagct gcagaggcta 207240
aaaagcacgc aagccaagag gcccgagaag gtcactagcg tagaggagga gcaggcgctg 207300
gccacgatca ccgaaagcgt cgtgagcacg ctataaatgg tgagcaggcc agggctcggt 207360
ggcgacgtga acgatccttc atcgcgtttg ccgtgcagca gggccaaaca gatggtgggc 207420
accatcaaac ttaagggcgg cataaagccg gtgcaacaga gaaagacggt gcctttaaga 207480
tgcggaaaag ccagcaccag gcccagacag agcaagaagg tgcaggtgcc ctgcacggcc 207540
acggtgctgt agacccgcat acaaagtaaa agcgacgta cgtcgttcgt cgacacggag 207600
gaaatcataa tgactccgcg cgagggtcgc ggggtgggg gcgcccaggc cgtcccggtg 207660
gcctctgagt tcggagacat gacggcgtg gcgatcaaaa ggcgcgtatg agaaaccgtt 207720
tatagagtgt aatagaatca ccgtcattcc cacacggcgt tcccccataa agtcacgtaa 207780
cactcgagta agcgtgaaaa agctttattg ttgaataaaa aacacgagta caacaccgag 207840
ttgcggtgtc ctgtctgtct actgggtggg gaaggttcat cgtctgtctc tagagggaag 207900
gtggggaatg tctaagcgag cgggagcgtg tcatctcccc catcttttta caacaagctg 207960
aggagactca cgccgtcgat gcgtccgccg tgtttctcgg cgtactgctg cacccagacg 208020
tggccgctaa atatggcgac gctcatgttt aggagactca tgacgatggt gtacaacacg 208080
acgctgacac agacgctgtt tttagacaac gttccacgct ggtagatgag atccagggtc 208140
tcgtaaataa gcacggccga agcggcggtc accaccagga cgtagagtcc gctgtagatc 208200
```

-continued

```
ttgctgaccc acagcacggg cgaaaagtaa agcaataggt aaaagacgat gacggaccag 208260
ccgtagccaa tcccgatgac tttccagcgc gtgggattgt tgccggccag gtaggtgaga 208320
ccgctgcaga gaacgaaaaa gaccatcacc agggcaaacg acagaccgat gacgcgcctt 208380
tctccgcaaa agcccgtgca cacggtgatg ccggtgttga tcagcaagca cgccaccgtg 208440
agatgagcaa aattggtggt gtgtgggcga aactcggcga aaccgcgtag catagccagc 208500
gtggacacgg gtacgatgga ggatagggct ggcactatgc cgttggcgca ctgtccctgc 208560
acatcgggga aggcgagcca agccagcaag cagaccgtga gggtacaagc cagctgccac 208620
acgagcccgt gatagacctc catgagcagc ttaaagcgtt tcaaccattg gaagagctgc 208680
tgttcggcca ccagcgcgtg gctgcgatgg agcggcacga tggtgaccgt cggcgactca 208740
tggtgttcgg aaaccgaggc ggtgtcgccc atgctgccgc ttacgaccgc tgtcggtcta 208800
aggtaggcgt cgatgaaaca gtccgtctta tcagcacccg gttaccgcgg atttgattga 208860
cgtcacgagt gtggtcaaac cgtggcggca ccctgtatcc gacccgtcgt catgggctcc 208920
acaaccagag cctcagaaga tggtacatgc cgatgaataa agccacattt tcgacataga 208980
ggcgtagcga gggctgaaaa ctctccggga aagaactctg acaggtgatc agggacagat 209040
cgtgaattag catcagcgtc accgtcaaca gcgtcgtcgc gtgtaaaccg agaaagaacg 209100
gggccgcggc ccgcagcagc caaagtccca gcgccgtagc gcagagcaga gacaggaccg 209160
acggtagcca cagccgccgg agagacgcgc caggatcgca acccaaaagc gaggccccca 209220
ggcagctgag atctaccgcc agggcgagaa gagccgcgcc gacaaaggcc tgcggcgacg 209280
gctggcacat cagcaaggtc agaaaggcta gcgcgtgcgg caggcagtaa gccaacagga 209340
gtgggagttt gcggggacaa cggtcgatcg acggaccgcg tagcagcagg aacaggcagc 209400
cgacgggcac gacgaggctg agatgagaaa gcggcggtgg gtcgtcgtcc cgtcccgct 209460 cgcatagctc ggccaccggt ggcggcatga gccaccagct gagcacgctg agggcgacgg 209520
tggcggtaag ctggaaggcg acgaggacgg aggcgcgcag ccataccgcc agcctctcta 209580
ggtaggggac tacctcctcg acggtccatt ctagcgggac gacatgaagc atggcgacaa 209640
gcgcggctgc tgtgaaaacg ggcacggttt tataggcatt aggacttccc cgtcgtactg 209700
gcggctgtca aagtcccgtt gtccaaaggc gcgccgtccg aaagactaat ccaacgggga 209760
cccgagagca tgagcaacaa cgtgagaaag atggccatgc tgtccaggta gagacagacg 209820
gcgtgacgga tgcattggtt aggtgggcag aaaaagatga ccataagact gtcgtaggcc 209880 agaatacccca aaaagaagct gatagagaag gcgcacaacg tcaccactat cttctgcagc 209940
caatcggcgt cgcttagcag agcgagcgtg aggaacgaaa gcagcattac cacgtagacg 210000
cagctgatgc atttccagcg acgtcggtca cggccaccta gaaacgccag ccccgtaaag 210060
gagataaaca acgccagggt catcacgtag gaacctacta gtacgcggct ttcagagcac 210120
atttggaaga tggccgccgt caggctgttg gccaacagat agatgaaaag caccgtggcg 210180
ttactagggt gttcgttgcc caacgtgtac gtgatgaaca tgcagacgat gggcacgagc 210240
acggtgagaa agaagctgta gttctcgacg caaaagttgc ggttttgtgg gaaccccaac 210300
caaaaaacgc ttcccaagcc gaagctgaaa gccagctgaa agatgaagat ggcgtacacg 210360
cgcagccata cggtgaactt tttgaaccac tcgagagcct ccatgcggga gagcagcagc 210420 ggcgttagcct cctgcgcctg catggtggcg acggtctcgg cacaaagccg ctgcggcgca 210480
cctacccttc tcttatacac aagcgagcga gtggggcacg gtgacgtggt cacgccgcgg 210540
acacgtcgat taggagacga actggggcga cgccgctgct gtggcagcga ccgtcgtctg 210600
```

```
agcagtgtgg gcgctgccgg gctcggaggg catgaagtag agcacggaga caaagaggta   210660
catgaggtcc atgtacaagc agagcgcgcc cgggatataa ctctcatact cgatgtcgtg   210720
caggatgtcc tgcgtatcgc acaccaccga ggtcacgatg acggccaaac cggctatcat   210780
caccaggatc tcacttaccg cctcgggaaa aagagaaaat acggcgaaca gtaagagaat   210840
cagcgtggat gcgcccgtca atagggaacg ctgtaattcc acgtcgcggg caaacagata   210900
cgtagcgagc gtgaggaaac aaaatagcgt cactgtggcc accatggcat aaatgactga   210960
acgatgacta aagtggaagc ctgacgccgt gacagccacg ctggtaagca acgtgtacgt   211020
cagtaagatc catacgtttt tgggaaagtt gggctcggcc caacgcaaca gacctaggca   211080
cacgatggag atcattaagc aagacagcgt cagacgcacg ctggaaaaga gctgctccaa   211140
ccggtgcgga acaccagcc agcaaaaggc gcagacgctc ataaggatga ggcattgcac   211200
ccagataagg atgtagatgc gcagcaggaa gaccgaccgg gctatctgga cctgaccgcg   211260
gagcgacatg gcggcaacgc cggcggttat cgccgagatt cgtctaaata cacgaagcga   211320
actagaaaac gcacacacgt gatttgcaaa aagaaagcag ctgccggctt attatttat    211380 taaaaattta tctgtgcaga atcataagtt tatgatgaat aaaaacgggg aaagggaatc   211440
tgcttttagg gacccgggtc tggtccgtcg tctcccatct ggtcgggttc ggggatgggg   211500
acctgtttca gcgtgtgtcc gcgggcgtgc atggcttttg ctcgccggcc gcgctgtaac   211560
caggcctctt tctctgtggt cggcgagtct tccgacgggg agggagcctg ggagtccatc   211620
gcttcaggcc caccgctcgt tccctcgacc gtcgtgtcgt cctcgttttc gctattacac   211680
ggggtttctg gagtatcgcc tatacggttg gcgattctcc gggggcggcc gctctcgtcc   211740
tcgtcgctgc tatcgccgcc cggtaattcg acgccgcatt cgttgtacgg aacgcggcac   211800
atgggcggcg gaaagaactt gggcatgcga aagcagcgtt gtccatccac ggtctgcgtg   211860
gtttcatcgt tatcctccca taatccccc tgtagcgccg gcagcgtttc gacgctgtga   211920
gaggggaagg cccagttctg gttgtcttgc agcgcgcccg tgggcagtag gtccgtgcgg   211980
ccccatgcgc tgctgttgtt gggtaccttg tcagtgccgc gagtaggtcg cagaaaccag   212040
tccagagcgc tctctagctg cgagcgtgtg atggtgccca gtgcgccgtg ccagcgcagc   212100
acgtctcttt tcagcgtgtg gtgacagacg ggcagctcct ccaaccgaca ctcgccgcgc   212160
aatccgcggt cgaagcggca gagaccacgc agtttaagca gaccgcactt gagaaacatg   212220
tgaaaattat cggcaatgcg atataggtcc gagtcctcga tcttgtgtag gtagaccacg   212280
ccaaacttgt cgagcagcac caggccgctg ggcacaaaag gcccgtaggc caggtaatag   212340
cccacgaggc cgacgacgta ccactcgcag cacaagcgtt gacgaataaa gttcagaaga   212400
tcgcgaaagt ccgcggccgg catgtggtca aaaggccggc aggcgcgcag gccctcgatg   212460
gagcccagca tgagcaacgg ctccacctcg gtgcgacccg gcgtgcggat gaccaggttg   212520
agaccgctca tttcgcgggc cgtcttggcc acggccgcag cgtcagtggg gtcggtgcag   212580
aggaattttt gcacatgata gcgcggttcg gtggtggcga acggcgtttg tgggtgccga   212640
tacacatatt cgcaccagag taggccgttc ttggaaaagg ctttgatatc actggccacc   212700
tcgtagagcc cgtcggtctc ccagtcgtag acgtagacgg tgccgtaatg acttagcatg   212760
agcacgcagg gcagttcctg cgcctgcttg gtgtttcgtg ttagatcgct gtcgggtgga   212820
cgcacggcta gtacaccgac ggcttccagg gtgtcatcgc agcagagata gtcggcggcc   212880
agagaacgtg cgtaaatctg cgggatggcg gcctgttcgc gcatcactag gaaccagttg   212940
```

```
gcggggttgc gcagtgctac ggtggttcct tggtggcgtt gcacgtaggt tctcagcgcc    213000
ggaggatcgt actggcgcag atagaggcct tgcagcatcg ataacgtctt ttgaaagacg    213060
gtgtttctaa attgaaaaac gccgtagtcg cagcggatag catcttcgca gcgctcgtcg    213120
cgctgtcgga gataggtgcc ccaggcttcg gcggcggctt tggtgagtag ggacatgccg    213180
gcggagccgt ctcgacagcg agtcggataa agcgcgctgc gcgaaagctt aatataggag    213240
cagcgtcaga cgaatcgcgg ctggtggccc gggggtggg acgcgccgcc tacacaaagt    213300
gctcccgaaa atcgaaactc ttgacccact ccggagacaa atccgtattc agattgatgc    213360
gtcgagcttc cacttcggct tccgaaacct cggcctccgt ccggtaggcg ttaacaatac    213420
gctgacccag gtgccaacgc tctttctctg ccaaacgccg ttgctcaaac cattcgtcta    213480
cgtccttgag gtcaaagaca gtgtcctcct caaggtcaaa gcctaggtct tcccactcgt    213540
cgtcatcgct ctcgtggccg gcggccatac gcgcggcaac cgcgtcttcc cctcctcttc    213600
tttcaacgtt gggtaccacg ttgttttctt cgggttccat aggttctgcg ccgctgtcgt    213660
catcatcctc tccctgctcc tcatcgtccg ccaaggcgtc gtggattacc tccaggttct    213720
gattgtcggg tacgacgtgg ttatcttcgt cgtcgtcgcg tggcatgggc ggcggccgac    213780
ggcggacgac cggcatggcg cggccgtcgt ttccttcgtc ttcctcttca ccgtctccca    213840
aggaacgcgg tcgacgacgt tccgcgaagt cgccgcggac cacgcgcgcc tgccaaatgg    213900
taaacgcgtc ccaaccgtcc cagttattga gcatttcggc gcgaaaacgg tcgcctcgac    213960
agagccagcg aaactgccgc cgtagtcgc ggtctacgcc gctgtcgaac atggtaaagt    214020
gcagacgcgc cgcctcgccc atgtgtacgc agcctccgtt gcgttccagc ctggccgcgc    214080
gccgtagacc gtgttcgtag cggcgacgca cgtacaccct catgaggccg gcgcgaaaaa    214140
gttcctctag gctgtcggcc agccggtaga tttcaccggc tagacgctgc aggggcggcg    214200
agcggtccag atgcgacttg acaatcacca cgtaaaaacg acagaaacgg tcgaagatga    214260
tgaggaagga cgtgtcaaaa aaaccaccgg cgcggtaaga gcccacggca cccagcaggt    214320
accagcggca acgcagttgc agcgtgacgt acatttcgca ctcggccaag cgggcggctg    214380
gcgctacctc gaagggccag cagtccgtca agcagccgaa actggtcagg agtttcaacg    214440
ttttggcatg gcgtccaggt gtatgaaagt tcacgtcgcg tccgtggtgt tcgccaacgc    214500
aggcggccaa cgcgtcggcg tcatgaccgt gacgcagcag catcgctacc acgtcgtgcg    214560
gtacccgcgt agcaaatggc gtctgtggct gacggtatac ggcttcggtg tacatcatac    214620
cgtaacgcgc cagctcgtcc agatgacgcg cgcacagcag cagaatctct tgcgagggtt    214680
cgtagatgta gaggcgcgta ccgccaccca tgcagagcac cagctccgtc tcttcgtagt    214740
gatcttccac catgatcacg cacttgccta gcacgataag gcgttcgggg caacaaatca    214800
cgtcgtccag cagctggtcg cgtagctccg gcatggtgct gccgggccgt acctgcagga    214860
accagttgtg cggaatgccg agcgacagca cctggtcgac gtggttacgg acccagtcgc    214920
gaagcacgtc ggcgctgtac tggcactcga agatgccctg aaagtcgccc atgacccgca    214980
gaaaagtttc gtagcgcgtg tggcaataga ggaattcatc gtttcgcgta acgtgggag    215040 ctccgtcttc ccaacgtgta cgccacatgt caaaagaggc cgccagctag acacccccaga  215100 aaagaagcag agaaagagac ttctttgtgc gacacgtttt attctgcgtc ctccgctcga    215160
cgttcaaatc tggatgtact cgcgcacacc cgtcaggctc tttaagggaa aagggtccga    215220
gtacgtcact aaccgcgact gatgcaccag ggcggtaatc acccgctccg cgccctcgcg    215280
cgtcgacgaa cgcgtcgtca ccaggcaatg cagccgcggg cccgtatcgt cctgatgacc    215340
```

```
agcggcctcg cgctcggctg cttccacacc gacaatgtcg ggatccaaca cgtagctctg   215400
cgagttggtg tcgtagcggt gtagcaccaa cgtgttgggg tccagacgct cccacgcgcc   215460
ctcgtgcggg tcaaaacgct ccgttaaaca gagccagtca tactgctgct gcagaatacg   215520
ccgctcgcgc tcgcgtcgct catcgggcaa cgcggcgtct tcgttgaaga gaatgtcccg   215580
cttgtggtct acggcacgct cgtggtggtg cgggcacagg tgacggtgtt ccatacgcgt   215640
ctgacgttga cgctcgcgct caaaacgccg gtgtcgaaag accattttca gcaacccat    215700 gcggaaaaac tccgtgatgg tgttggcaac gcgccgcaca tagtggttgg ggtcgtccat   215760
ctggatggcg tacacggcac cgaaccagtc cagcagtacc agcacttcgg ccacaaaact   215820
gcgtcccggt cgcggacgtc ccgtcacgcc tagcacatac cacggcgtgg ccagattagc   215880
acggacagcc caccaccaac gacggctctc cacctcggtg agcgcacaaa agggccaaat   215940
gcggtgtaac tgctgtaccg ttttcatcaa ccgcataatc accgtaccgt aacccggtgt   216000
atgcaacttt acgtcgcaac ccaggattcg ttcggccgtg gcgtacgagc cctcgggcgt   216060
ggtgtcattg agaaacaaaa catgcatggt acgcgcgccc ttaggatatc gtcgcggaac   216120
gggtaccgtc attctccgca gagtggtgtg aatcacgtcg cgatacgcaa tctccgaacg   216180
tgacacaccg taacgtgcca gttcgtccag gttgtgcgat accaacacca tgtactttc    216240 acgagtgtcg taggcgtaga cgcgagaaaa gcgacccata aaaaccacgt acggagtagc   216300
caccatgcca tcatggtgat cgcgacgtgg ctcgggcaac aaaataacag cgtatcccaa   216360
cggcgtcaac ggctcgcggc aacagatgag ctttgacgcc gcctgtttgg cggcggtaat   216420
gatcccgtcc tccgtacgta acatcacatg ccagcccttg gggggaccca aggacagaca   216480
gcgtccctcg ttacgatgaa cgtaacgcgt gatttccatt ggctccaggc aaaagaacag   216540
ttccttaaaa tcccgcaaca cttgtcggta taacgccatg ggatcctcgg ccgccacagg   216600
cagcgcgggg agctccggcg gcataactgc agcgccgtca gggccagaac ccgcagccgg   216660
atccatcatt gagcgacact ctcagccgga caaccggcgt cactgacaga agccgagcca   216720
aatacagaga aagcaacgct acaccgtcac cccgctccca agcgccgcgg aaagtgctcc   216780 gattttcac cgtcgttcgc gacgttgatt tgcctcggtc tgagaaccga cctagcgttc    216840
ggaccggtgc gcagaaacag ccggcggtcc gagccactga gcggttcaca gccccggccg   216900
ccgatagtta ccggagagac gttcgagctg caggtacatc agcgcttccc gcttcgccac   216960
cccgcgcccg ccccagttta tactctccga cgccccgtcc aacgcgcctg tggagggcca   217020
atcggaccgc gggagctctc caagtggatg acaggcacag ccgagtgccc gaccgtgaag   217080
agccctcatc cacctgaaca gaccgctaac cgaaggaccc cgagtcgcgt ccgtcggtcc   217140
cgacgtccgt cgccatctgg ctccctgctg ttggctacct ctcggatttc aaaaagagc    217200 acgtgccgat gacggtgcac aggaaagagc caaagtgtca cggcgtcttt ttttatttgt   217260 attcctttc tgttttgtac tcgtaaactg ttgatgttgt ttttacatcc aaagggcaa     217320 gtaagaaaca ggatgaggca tggtaggttt gggcgtgggg cggccctcca gcacggcggc   217380
ccgggccgcc cggcgggtga gcacccggcg ttgcgccgtg tctatcttgt gtttcttctg   217440
tgtctttttc ctatcttgtt ccgcgacggc ctctttcatc acgttcagca tgcgttcctc   217500
gacgccctcc agggatcctg ggaggaggg agtcctagtg aggcttccaa tgttgttttg    217560
tggattttcg gttccttttt cttggtcgtc atcgtcggac gtgtcgtctt cctcttgatc   217620
ctcttcttcg tccgagtagt agacgcatag tccttggttc atcaggctgg gattcatcag   217680
```

-continued

```
gttctgacgg ggaatccgct gttgtagacg tttaaccgcc cgttccaggc gagagctcat 217740
gccgcaccag acgctgtaac gccgcacggg cccgtagcgg gctgtttgtt cgcgtacatg 217800
atcgttgagc tcttgccaat attgtttggc acactccaga tcggaggttt gtggatagtc 217860
gggtcggatc cgcggatccc aactgacatc ggcggtgccg gagacttcgt ccagactgtt 217920
acgcatagag caccagtcgg gtcggacgat aaacctgtcc ttgcggatta accatttata 217980
acgtagttcg tgatggcgtg tagaggcccg tacacgctcc acggtcccaa agcggtccca 218040
gaagggaaag ttttcgtggg ggcagcgacc cggcacttcc agacgttcgg cgtcgtccac 218100
ggcgtagtga aaacgccggc cggcctggta aattttgagc agaccactg ttaacaacat 218160 atccacgctg tcagccaacc gccagatctc gcggcgagac acgtcaaaat agaaaaattc 218220
gcaggctcgg tcgaccagga tcacgaaatc ggcgtgaaag acgccggagg gtagcgattc 218280
gcccaccaca cccattatca tggtttcaca gcataagcgg tccacaaaga acttcaacag 218340
gtcgttgaat tgctccgtct ccatacagat gaagggccag acgcctttga ggttctcggc 218400
ctggccgcag agcagtagcg gacgtgtcat ctcgcccgga gtgcgcagag gcacgcattc 218460
gccgcgataa cgacaggtca cacgctgtag ttcgctgatg ctgttgtcgt gcaggcgaag 218520
gtcgcagata atatgatccg gttgcgtggt tagcagcggc gtgcgcattt gctcgccgta 218580
gatggcctcg cagtgcaaca gcccgtgtcg cgcaaaatcg tccaaactgt gcgccaggta 218640
gtaaagcacc ccgcgatcgc ggtctagaca ccacacggtt tcgtaacgtc ctaacaggag 218700
caccagacgg gcctggctag gtggctcaat ttcctctaca tacacgaaaa agtcgtcatc 218760
gtccgagtcc tcgtcctcag aagaggaccg cggcccgtgt actctgggca acacggtggt 218820
agagaactgc aggacgccca gagactcgag cgattcttcg cagcagatga gctgaccca 218880 gggcgtttcg ggcccgtcgg tgacagccgc gctgccaaag atgtcctcaa actctacaaa 218940
atctagacgc catccgggtg gcgctgaaat gggaaggcta atgttcatat cagcatagct 219000
acgaactaag tggcggatgt cctgccgcaa gtcttggcag agaatgagct ttcgtaaacc 219060
cttgagggtc ctccgaacaa cggccccaga cgcgtagcga taggactggc gcatggtgcc 219120
gcggcgtgga gcggcacttg gcagcctatt ttatggagtt tcttcagtga cgtggcttgt 219180
tcacgtcgtt cgtgggctgc ggttggcagc tccggtctgt aaaccacccg aaaagactga 219240
catcgacgtc aaagactcac gtaatttgga acatgtgcga ccgcaaagtg cgtcagaata 219300
gcacgtggct ttaggacata aaaagtaccg tgaggtctag acgtgggttt tgtgattgac 219360
acttacacca ggtaagccaa gggacggtga aactgtatgt gaggaatctg ggtgcttaga 219420
cgactaacgt gtaatgcttt ttacaggact gttcgacagg tgatagtacc tgtaaggtga 219480
tgaccacctc tacaaataat caaaccttaa cgcaggtgag caacatgaca aaccacacct 219540
taaacagcac cgaaatttat cagttgttcg agtacactcg gttggggta tggttgatgt 219600 gcatcgtggg cacgttctg aacgtgctgg tgattaccac catcctgtac taccgtcgta 219660
agaaaaaatc tccgagcgat acctacatct gcaacctggc tgtagccgat ctgttgattg 219720
tcgtcggcct gccgtttttt ctagaatatg ccaagcatca ccctaaactc agccgagagg 219780
tggtttgttc gggactcaac gcttgtttct acatctgtct ttttgccggc gtttgttttc 219840
tcatcaacct gtcgatggat cgctactgcg tcatcgtttg gggtgtagaa ttgaaccgcg 219900
tgcgaaataa caagcgggcc acctgttggg tggtgatttt ttggatacta gccgtgctca 219960
tggggatgcc acattacctg atgtacagcc ataccaacaa cgagtgtgtt ggtgaattcg 220020
ctaacgagac gtcgggttgg ttccccgtgt ttttgaacac caaagttaac atttgcggct 220080
```

```
acctggcgcc catcgcgctg atggcgtaca cgtacaaccg tatggtgcgg tttatcatta 220140
actacgttgg taaatggcac atgcagacgc tccacgttct tttggttgtg gttgtgtctt 220200
ttgccagctt ttggtttcct ttcaacctgg cgctatttt agaatccatc cgtcttctgg 220260
cgggagtgta caatgacaca cttcaaaacg ttattatctt ctgtctatac gtcggtcagt 220320
ttttggccta cgttcgcgct tgtctgaatc ctgggatcta catcctagta ggcactcaaa 220380
tgaggaagga catgtggaca accctaaggg tattcgcctg ttgctgcgtg aagcaggaga 220440
taccttacca ggacattgat attgagctac aaaaggacat acaagaagg gccaaacaca 220500
ccaaacgtac ccattatgac agaaaaaatg cacctatgga gtccggggag gaggaatttc 220560
tgttgtaatt cgatcctctc tcacgcgtcc gccgcacatc tattttgct aattgcacgt 220620
ttcttcgtgg tcacgtcggc tcgaagaggt tggtgtgaaa acgtcatctc gccgacgtgg 220680
tgaaccgctc atatagacca aaccggacgc tgcctcagtc tctcggtgcg tggaccagac 220740
ggcgtccatg caccgagggc agaactggtg ctatcatgac accgacgacg acgaccgcgg 220800
aactcacgac ggagtttgac tacgatgaag acgcgactcc ttgtgttttc accgacgtgc 220860
ttaatcagtc aaagccagtt acgttgtttc tgtacggcgt tgtctttctc ttcggttcca 220920
tcggcaactt cttggtgatc ttcaccatca cctggcgacg tcggattcaa tgctccggcg 220980
atgtttactt tatcaacctc gcggccgccg atttgctttt cgtttgtaca ctacctctgt 221040
ggatgcaata cctcctagat cacaactccc tagccagcgt gccgtgtacg ttactcactg 221100
cctgttccta cgtggctatg tttgccagtt tgtgttttat cacggagatt gcactcgatc 221160
gctactacgc tattgtttac atgagatatc ggcctgtaaa acaggcctgc cttttcagta 221220
ttttttggtg gatcttttgcc gtgatcatcg ccattccaca ctttatggtg gtgaccaaaa 221280
aagacaatca atgtatgacc gactacgact acttagaggt cagttacccg atcatcctca 221340
acgtagaact catgcttggt gctttcgtga tcccgctcag tgttatcagc tactgctact 221400
accgcatttc cagaatcgtt gcggtgtctc agtcgcgcca caaggtcgc attgtacggg 221460
tacttatagc ggtcgtgctt gtctttatca tctttggct gccgtaccac ctaacgctgt 221520
ttgtggacac gttaaaactc ctcaaatgga tctccagcag ctgcgagttc gaaagatcgc 221580
tcaaacgtgc gctcatcttg accgagtcgc tcgccttttg tcactgttgt ctcaatccgc 221640
tgctgtacgt cttcgtgggc accaagtttc ggcaagaact acactgtctg ctggccgagt 221700
ttcgccagcg actctttcc cgcgatgtat cctggtacca cagcatgagc ttttcgcgtc 221760
ggagctcgcc gagtcgaaga gagacatctt ccgacacgct gtccgacgag gtgtgtcgcg 221820
tctcacaaat tataccgtaa tataacttcg tatagcatac attatacgaa gttattaaaa 221880
aagcgctacc tcggccttt catacaaacc ccgtgtccgc ccctctttc cccgtgcccg 221940
atatacacga tattaaaccc acgaccattt ccgtgcgatt agcgaaccgg aaaagtttat 222000
ggggaaaaag acgtaggaaa ggatcatgta gaaaaacatg cggtgtttcc gatggtggct 222060
ctacagtggg tggtggtggc tcacgtttgg atgtgctcgg accgtgacgg tgggtttcgt 222120
cgcgcccacg gtccgggcac aatcaaccgt ggtccgctct gagccggctc cgccgtcgga 222180
aacccgacga gacaacaatg acacgtctta cttcagcagc acctctttcc attcttccgt 222240
gtcccctgcc acctcagtgg accgtcaatt tcgacggacc acgtacgacc gttgggacgg 222300
tcgacgttgg ctgcgcaccc gctacgggaa cgccagcgcc tgcgtgacgg gcacccaatg 222360
gagcaccaac ttttttttct ctcagtgtga gcactaccct agtttcgtga aactcaacgg 222420
```

```
ggtgcagcgc tggacacctg ttcggagacc tatgggcgag gttgcctact acggggttg  222480 ttgtatggtg ggcggggta atcgtgcgta cgtgatactc gtgagcggtt acgggaccgc  222540
cagctacggc aacgctttac gcgtgaattt tgggcgcggc aactgcacgg cgccgaaacg  222600
cacctaccct cggcgcttgg aactgcacga tggccgcaca gacccctagcc gttgcgatcc  222660 ctaccaagtg tatttctacg gtctgcagtg tcctgagcaa ctggttatca ccgcccacgg  222720
cggcgtgggt atgcgccgct gtcctaccgg ctctcgtccc accccgtccc ggccccaccg  222780
gcatgacttg gagaacgagc tacatggtct gtgtgtggat cttctggtgt gcgtccttt  222840 attagctctg ctgctgttgg agctcgttcc catggaagcc gtgcgtcacc cgctgctttt  222900
ctggcgacgc gtggcgttat cgccgtccac ttccaaggtg gatcgcgccg tcaagctgtg  222960
tcttcggcgc atgtttggtc tgccgccgcc accgtcagtc gcaccacctg gggaaaagaa  223020
ggagctaccg gctcaggcgg ccttgtcgcc gccactgacc acctggtcac taccgccgtt  223080
tccgtccacg cggatacctg acagtccgcc gccaccgtac cagcttcgtc acgccacgtc  223140
actagtgacg gtacccacgc tgctgttata tacgtcatcc gacatcggtg acacagcttc  223200
agaaacaacg tgtgtggcgc acgctactta tggggaaccc ccggagcccg ctcgatcgac  223260
ggctacggtt caggaatgta ccgttcttac cgccccgaat tgcggcatcg tcaacaacga  223320
cggcgcggtc tctgaaggcc aagaccatgg agatgcggtt caccatagcc tggatgtggt  223380
ttcccagtgt gctgctgata ctggggttgt tgacacctcc gagtaacggg tgcaccgtcg  223440
atgttggacg aaacgtatcc attggagaac agtgccgcct tcgaaacggt gcgacgttct  223500
ccaagggaga catcgaaggt aacttcagtg ggcccgtcgt cgtggagttg gactacgaag  223560
atatcgatat tactggcgaa cggcagcgac ttcggttcca tctcagcgga ctcgggtgtc  223620
ctacaaagga aaatataaga aaagacaatg aaagcgacgt caacggtgga attcgctggg  223680
ctctatatat acaaaccggc gacgccaagt acggtattcg taaccagcat ttgagtatac  223740
ggttaatgta tcctggggaa aaaaatacac aacagctgtt ggattctgat ttcagttgcg  223800
aacgtcaccg gagaccgtcc acgccgttgg gaaagaacgc cgaagtgcct cccgcgaccc  223860
gcacgtcttc tacatacagc gtcctcagcg cttttgtagt gtggatcgga tccggcctca  223920
atatcatctg gtgaccggc atcgtgcttc tggcggtgga cgctctcgga cttggcgagc  223980
gttggctgag gttagcactg tctcaccggg acaaacatca cgcatcgcga accgcggcgc  224040
tccagtgtca acgcgacatg ttacttcggc aacgtcgacg ggctcggcgg ctgcacgccg  224100
tttctgaagg caaactgcag gaagagaaga aacgacagtc tgctctggtc tggaacgttg  224160
aggcgcgacc ctttccgtcc acacatcagc tgattgtgct gcccctcct gtagcgtcag  224220 ctcctcctgc ggttccctcg cagcccccg agtattcgtc tgtgtttccg cctgtataaa  224280
aataaagaga cgggaggctg atcgcggcct tcagcgtctc atttgtcttt actctcgagt  224340
gcggtcggtt tctcgtcggt gagacgaggc gccgcccga caagttcgat ctcatgtcgc  224400
tcttggagcg cgaagagagt tggcgtcgcg tagtcgacta ctcgcacaac ctgtggtgta  224460
cgtgcggtaa ctggcagagc cacgttgaga ttcaggacga ggagccaaac tgcgagcagc  224520
cggagcccgc acactggctg gaatacgtgg cggtccagtg gcaggccgg gttcgcgatt  224580 ctcacgatcg ctggtgtctc tgcaacgcct ggcgtgatca cgccttgcgc ggccgttggg  224640
gtacggcgta ttcctcgggt tcctcggcct cttcctccgg tttcgtcgcg gagagcaagt  224700
tcacctggtg gaaacgactg cgccacagta cccggcgctg gttgtttcgc cgccggcgag  224760
ctcgatacac tccgtctaac tgtggggaaa gtagcactag cagcggccag agtagcggtg  224820
```

```
acgagagtaa ctgcagtcta cgcacccacg gcgtgtacac acggggtgaa caacactaat 224880
cgataagtcg cgtgtaggcg actggctaca tcaaccggat atctgcgggg atttaaaaag 224940
acgacccgtt gtcatccggc ttagaccaaa ccgtccttt atcatcttcc gtcgccatgg 225000
ctatgtacac atccgaatcc gaacgcgact ggcgtcgtgt aatccacgac tcgcacggcc 225060
tgtggtgcga ctgcggcgac tggcgagagc acctctattg tgtgtacgac agccattttc 225120
agcgacgacc cacgacccga gccgaacgga gggccgccaa ttggcggcga cagatgcggc 225180
ggttacaccg tttgtggtgt tttgtcagg actggaagtg tcacgcgtta tacgccgagt 225240
gggacggcaa agaatccgac gacgagtcgt cggcgtcttc ctcgggcgaa gcgccagagc 225300
aacaggtccc cgcttggaag accgtgcggg ccttctcgcg ggcctaccac caccgcatta 225360
accgggtct gcggggcacg cccccaccgc gcaacttgcc gggatacgag cacgcctccg 225420
agggctggcg gttttgcagt cgacgggaac ggcgagagga cgatcttcgc acgcgggctg 225480
agccggaccg cgtggtgttc cagttagggg gagtacccc tcgccgtcac cgggaaactt 225540
acgtgtaaga acacggcgtg acaataaaca acatagcgta aatcccgtg tgatgtgtgt 225600
gattgacgtt cgggaaacat gtccccatca tcagcgtcac aattgacgtg ggttggtcac 225660
tgacgtgcag gatgttacgc gagtcagaga atcgcataag aacggagtgg tgagcgggtt 225720
cccacaggag tctctggcgc aaaagcacca tgagcctcag gttccccgag agggtgggtt 225780
acgagaaact gggataccgc cgcatgcca aacgcgtgcg ggtgcatgac tcgttgggat 225840
tgacgcggtt tatcatgagg caactcatga tgtacccgct ggtgttgccg ttcactttc 225900
cgttttacgt gccgcggtcc tagcacgtca gtggtgacgc tgataattgc aacatggccc 225960
atgacgaacc cgcttgggac gaacgtcaat accacgtcaa accaccgtga cttggctgaa 226020
cgttgaaaca taaagccaaa gcgccgtcgg cacttggctt cagagcagcg cctcggggcg 226080
atgcgacggc gatgaactta gagcaactca tcaacgtcct tggtctgctc gtctggattg 226140
ccgctcgtgc tgtcagccgc gttggtccgc atggctccgg actcgtttat cgtgagcttc 226200
atgatttcta cgggtatctg cagctggacc ttctgggacc agtggtggcg gggaatcgct 226260
cagtccggac ctggagagag caggcggacc gagccagagg gaccttcgct tggcgttcag 226320
gccttaatac tagccgcatc ttacctgtcg gcagcatgta tcggggctcc gacgccttac 226380
ccgccggcct gtatcgtccc gaagaagagg tgttcctcct cttgaatcgc tgccatggcc 226440
cactgtcaac gccgaaaaat gcttgtctgg ctgaggttgg tgtcgctaat gccacttttt 226500
tgtctcgctt caatgtcggt gattttcacg gagcgtcatg ggaaaacggt accgctcccg 226560
atggagagcc cggggtatgc tgaaattcct cttaaaattt cgtaaacgac gtcgtccagt 226620
cgttgtgccg cgattcgtac ggttcatcgt ctacgtcgtt ttgttcaccg tcgctgtgca 226680
acgcgtgaaa caagagcgtg atgcgcacct tcggcggtat gaagaacgat tacggaaaaa 226740
ccgcgcacgg cgtcggcagt cttttccgtg acttggggcg atgggtccga gctgcgtat 226800
gggtcacggc ggcgtgtgtt ttattgacga agatgccgat gtgtgactaa aaacgtccca 226860
gccccagagc gatatgtttc aataaaaaaa atatgtagta tcatattatg cgtgtcctgg 226920
tttttcattt ttggatgtat gtatcgcata aagggtggcg aggtgtgagg atgaaacata 226980
tgcagatacg cagtgttgtt atccgaacga aacccgtgta atgcgtacaa cggtacttca 227040
gtatgaaagt cccgtgtgtg gggggggggg gcaaatagtt gcgtttgccg ttgggcgtac 227100
gctacgtttg tatttctggc tataatatgt gcggtcatgt gtcgatgttc ctattgggaa 227160
```

```
gggtgtgact gtagggtgta taaagtacgg tgggacgcag agggacattg atagaaacag   227220
gttgagcgct gtacgagttt cacacgctga atcggcgcca agaataaaac agtggttatt   227280
cgtaaaagta tgggggggggg gggatgttg tcgacggttg ttagatgcat tgcgtatctg   227340
tattagtagt tttgcaagcc gtggtgcgtg ttattgtgac gtagcaatta tcgtattgtg   227400
catgtgtcgt tcatcacaga gtttagtata ctaatatgaa gcgtcgcgag tattaaagca   227460
attggtgtct ctgtgctagt ctaacaacac ctgtgtaatg cgtacaacga gaaaaaagac   227520
gcgaaagcaa cgtgtatggg gggggggggg aataatattg ctaatcatgc gtcttgcagt   227580
acagatagcc gctgtatctt acgcgtattg tcgcaacagt tccacatcgg tgtaattgga   227640
tgtctggtac ttatcactgg cgtcgttata acattgtaaa acaagttttc gaaacataac   227700
gacagctgca aaagaaaacc agtttattga gcattgtaat ggtagtgtgt ggctatatta   227760
gaaaacgtga cgcgtcgcat gtcgcggcac aatctggcag cggggtcggg gtagggtacg   227820
gtgggaggca tgtacacaga tggaacaaaa gcagaagtaa cgtgagaagg agcatacagt   227880
ccagtatcca gcggttcctg agtagcacca cccatcaact gaatgccctc atgagtaaaa   227940
gtctgcgggc gacagccctt ggggaccgtt ggcatgggac gatcaatctc caaaccacag   228000
cgtaacaccg ttttcttcca acgtcgttga tagacgtcgt ttttacggtt actcccaaga   228060
acccagaaag tctcgtccaa gtcgtaccag gaatcttctc cggggagacg cgacggtttc   228120
caatcctcgt cgtctcgtct caaagcacgt cccaaactgg cttgaggagt caacggtggt   228180
tctgtgggtc gggtgtagcg cgagtgtttt cccttcatga gcgattcatc ctccttgcct   228240
ttaggctttt tggtcttttt gtgtatcatc tggccgccgg cctccataac caccgtggcc   228300
aagtccagtc ccagagcttg agcgtcggcg cggcgtcggg cgtcttgcag gtagtcttcc   228360
acatttgcac agatggccgg gtgtttggtg gctagggtga ggacctcagc ctcgccgcga   228420
cccggacgta gcaaaaaagc caactgcccg tgcggctcgc gcgcccacag cgcggcgcgc   228480
gggtgcaggt gcagcgcgtc ccagcgcggc cgctcccact gctcgcggtc cagctcgggc   228540
agcagccgcc gcgcggcctc ggcggcgggc gccgactcgc gtcccagcgc cagcgcgccc   228600
agcacgcccg cgcgcagaaa gtgcgacagc tccgccgcca gcgggtacac gtgcccgtcc   228660
agcgggcagt acccgaacac ggcgcccagc tcgtccagca gcaccaccag catggcgcgc   228720
ggcacggtcc ccgacgccgc cggacccgcc atcgctgtcg aacccaccat caccgtcggc   228780
gccgctgctg ctgccgcgtc cgccccgacc accgcgtgcg cgtccgcgtt aggcacgcaa   228840
atcgcgcccc cgccggcggc gccgtacggc tgccgaggca caggtacagc ggaccccacg   228900
gctcccgcta tcgcgcacgg cgcgtccccg ccggcggcct ccgtctccgt gccgctcgcc   228960
gctggcggcg acgtcgtccc cgccgccgtc ccgtcgccg gccccgccgc gcagcccagc   229020
caccgcgcgg gcagcaccgc gcccagcgcc agccagccgc agcacagacg ctggttcagg   229080
tgccgacgca cggccgtcag cagcgacgcg gggtgcggcg ccgacgcgaa cggctcgtac   229140
tgcgccagct cctgccacgc gcccagcagt accatcggct gcagtcgcct gcccggcgtc   229200
tgcagcgcca ccgtcgtgcc ggccaccgc cggcgcagct cccgtccgag cgccgtcgcc   229260
tcctcggcgc gcagcaacgt ctgtcggagc gccggctgag gcagcagcgt cgcgcgcggg   229320
gtgcccacgc ccagccggtt gcagcggtac agccgcacca cctcgcccgc gccgtgccga   229380
aaccactcgt ccgcgtcgcg cgccgctagg atcagcgtgt tgtttgccag gtcgtacacg   229440
aacacgcgga acccggcgcc cagcgccagg tacagtccgt cctgcgcgca cagaccctcg   229500
ggatggccgg ccttgtcgcc caacgtcggg tcggctgcgg ggtccacctc gtgcaccacg   229560
```

```
gtagccacca gtacgatcca cgcgtcccgc ggcgacagtt gacgcaggtc cgtcgcgccc 229620
acgccgttca tctggctgcg cggcgtcacc cgcgcgtaga atccgtacgg ccgtccgagc 229680
ggcagcagcg tgcccgcgtc gcgctgcgac cacttgcgca tggcgcggcc cgtgctgttg 229740
gccaaaaacg ccgcgcgcca cacggcgccc atggcctggt attccagctc cgtcagcgcc 229800
tggcgctcca ccggaatctg agacagcaac aggcgctccg ggccgtgcca aaagttgcta 229860
ttgttgccgc tactcggagg ggcgcccggc ggcccgcggg gttctacccg gtggacgccg 229920
tggcccggcg tcgtcgtagc cgcagcactc gcaccagtgc ccgctgtgga cggcgctccc 229980
atcggcacac aagaagaagg aggagaggaa ccaaccccg aaggccctcc ggccccgcgg 230040
ccgcgaccaa ggggcggggg gcgcggcgac atgccgttgc gctgggccat gggcgccgga 230100
cacctccgac gtccactata taggaagcaa acccgcgtca gcgagcacgc ggtttagaca 230160
cgcggacgcc ttcgtcgccc gtgtgccgcg ggcgacacgc agctggcttt tataggcagc 230220
gacgtgcacg gcgcgtgctg gcgccgcctt ggcgccacgc agtctggaag gccgtggact 230280
gggaaaggca gctacccgaa ggaagacgcg cggcaggcgc gtaccactgg agcgcacagc 230340
cgcctcccgg gcgcgcaccc atctaggtgg acgcccgaca tccattccgg gccgcgtggt 230400
gggtcctcga ggggcggggg ggtgttttta gcggggggt gaaacttgga gttgcgtgtg 230460
tggacggcga ctagttgcgt gtggtgcgga ggacggcgac ggcgaataaa agcgacgtgc 230520
ggcgcgcacg gcgaaaagaa gacgcgtgtc tgtgtctgtg tgattccccg gggaaaagag 230580
gaagttcccg ggggacggca gcatgggtcc ctggggacac acgaaaagca acgcccgggg 230640
gcgagggacg acggccctgg ggaccgcggg ggaaataacg gccgcgaggc cacacactcg 230700
ttcctgcgaa gccgcacacc ccgaggccgc gcacaccgcc gacacacccc gccaccacac 230760
cccgccggca cacccgccac acgccgcga cacaccggc acgacacacc cggcacacgc 230820
ccgcgacaca ccctgacaca ccctgccaac acaccccga cacacccaac acacgcccgc 230880
gacacacccg gcacacaccc acccggccgc gccccgacac acccaaaaca ccgccggtgc 230940
ggggccgcgt ggtgggtcct cgaggg                                  230966
```

SCALABLE CHROMATOGRAPHY PROCESS FOR PURIFICATION OF HUMAN CYTOMEGALOVIRUS

CROSS REFERENCE TO RELATED APPLICATIONS

This application is a U.S. National Phase application under 371 National Stage of International Application No. PCT/US2019/028216, filed on Apr. 19, 2019, which claims priority to U.S. provisional Application No. 62/661,928, filed on Apr. 24, 2018.

FIELD OF INVENTION

The present invention relates to a scalable chromatography process for the purification of human cytomegalovirus (HCMV) particles from cell culture medium. In particular, the process can be scaled for the production of commercial quantities of HCMV particles for use in vaccines.

REFERENCE TO SEQUENCE LISTING SUBMITTED ELECTRONICALLY

The sequence listing of the present application is submitted electronically via EFS-Web as an ASCII formatted sequence listing with a file name "24557-SEQTXT-2APR2019.TXT", creation date of Apr. 2, 2019, and a size of 294 kb. This sequence listing submitted via EFS-Web is part of the specification and is herein incorporated by reference in its entirety.

BACKGROUND OF THE INVENTION

Human cytomegalovirus (HCMV), also known as human herpesvirus 5 (HHV-5), is a herpes virus classified as being a member of the beta subfamily of herpesviridae. HCMV is an enveloped virus, having an outer lipid bilayer envelope containing a variety of glycoproteins including glycoprotein B (gB), gH, gL, gM, gN, and gO, with a double stranded linear DNA core in an icosahedral nucleocapsid. See Crough et al., 2009, Clinical Microbiology Reviews 22:76-98.

According to the Centers for Disease Control and Prevention, HCMV infection is found fairly ubiquitously in the human population, with an estimated 40-80% of the United States adult population having been infected. The virus is spread primarily through bodily fluids and is frequently passed from pregnant mothers to the fetus or newborn. In most individuals, HCMV infection is latent, although virus activation can result in high fever, chills, fatigue, headaches, nausea, and splenomegaly. HCMV infections in immunocompromised individuals (such as HIV-positive patients, allogeneic transplant patients and cancer patients) or persons whose immune system has yet to be fully developed (such as newborns) can be particularly problematic. See Mocarski et al., 2007, Cytomegalovirus, In Knipes and Howley (Eds.), Field Virology pp. 2701-2772. HCMV infection in such individuals can cause severe morbidity, including pneumonia, hepatitis, encephalitis, colitis, uveitis, retinitis, blindness, and neuropathy, among other deleterious conditions. In addition, HCMV infection during pregnancy is a leading cause of birth defects. See, e.g., Adler, 2008, J. Clin Virol 41:231; Arvin et al., 2004, Clin Infect Dis 39:233; and Revello et al., 2008, J Med Virol, 80:1415.

To date, there is no available HCMV vaccine. However, a promising candidate based on a live attenuated HCMV is currently in clinical trials. See U.S. Pat. No. 9,546,355 and Wang et al., 2016, Sci Transl Med 8:362ra145. This vaccine is produced using human retinal pigment epithelial cells (ARPE-19) infected with a genetically modified HCMV.

For commercial vaccine production based on a live virus, process impurities resulting from the upstream production process, including host cell contaminants and cell culture components, such as serum, endonucleases and supplements, need to be removed. Purification of HCMV has typically involved centrifugation- and filtration-based methods. See, e.g., Chambers et al., 1971, Appl Microbiol 22:914-8; Huang et al., 1973, J. Virol., 12:1473-81; Talbot et al., 1977, J. Gen. Virol. 36:345-9; Vicente et al., 2014, Eng. Life Sci. 14:318-2; and Schneider-Ohrum et al., 2016, J. Virol. 90:10133-44.

While effective at laboratory scale, centrifugation-based methods such as density gradient sedimentation are not easily applied at a manufacturing scale. In contrast, while filtration methods are amenable to manufacturing scale, their effectiveness and/or efficiency decreases with cruder feed streams having higher levels of impurities, causing fouling of the filter. Other options for the scalable purification of an enveloped virus such as HCMV are often constrained by a narrow stability range (e.g., pH, ionic strength, compatible detergents/solvents, shear stress, and temperature) and large particle size, which challenges chromatography efficiency (capacity and yield) and decreases sterile filtration yields.

Various purification methods for live viruses employing chromatography and/or filtration have been described. See U.S. Pat. No. 8,124,106 (anion exchange chromatography and size exclusion chromatography) and U.S. Pat. No. 9,663,766 (mixed mode chromatography and anion exchange chromatography for adenoviruses); International Patent Application Publication Nos. WO2003/097797 (ion exchange chromatography for adenovirus), WO2013/106398 (ion exchange chromatography and tangential flow filtration for herpes virus) and WO2016/156613 (aseptic solid-phase matrix chromatography for viruses); Puig et al., 2014, Methods Mol Biol 1089:197-210 (hydrophobic interaction chromatography and anion exchange chromatography for canine adenovirus); Langfield et al., 2011, Methods Mol Biol 737:345-66 (tangential flow filtration for measles virus); Mundle et al., 2016, Vaccine 34:3690-6 (core bead chromatography and TFF for respiratory syncytial virus); Tseng et al., 2017, Vaccine S0264-410X(17):30322-5 (anion exchange chromatography and ligand core chromatography for influenza virus); Lee et al., 2016, J. Chromatography 1445:1-9 (negative chromatography for hepatitis B virus like particle); James et al., 2016, Sci Rep 6:36826 (Capto™ Core for reovirus); and GE Healthcare Life Sciences Application Note 29-0003-34 AA, 2012 (Capto™ Core 700 for influenza virus).

SUMMARY OF THE INVENTION

The present invention is directed to a two-step chromatography process suitable for large-scale purification of HCMV particles. Specifically, the present invention is directed to a method of purifying human cytomegalovirus particles (HCMV) from a cell culture medium, the method comprising: a) contacting the cell culture medium comprising HCMV with an anion exchange chromatography medium under conditions that allow the HCMV to bind to the anion exchange chromatography medium; b) eluting the HCMV from the anion exchange chromatography medium to obtain an eluate; c) contacting the eluate with a polishing chromatography medium; and d) collecting the HCMV from the polishing chromatography medium to obtain purified HCMV. In one embodiment, the polishing chromatography medium is selected from a mixed mode chromatography medium and a cationic exchange chromatography medium. In one aspect of the embodiment, the polishing chromatography medium is a mixed mode chromatography resin and the HCMV flows through the mixed mode chromatography resin. In another aspect of this embodiment, the mixed mode chromatography resin has size exclusion properties and the HCMV is excluded from the mixed mode chromatography resin. In one aspect, the mixed mode chromatography resin is a hydrophobic anion exchange chromatography ligand having a molecular weight exclusion of about 700 kDa. In another embodiment, the polishing chromatography resin is a cationic exchange chromatography medium, wherein the HCMV binds the cation exchange chromatography medium, and the HCMV is eluted from the cationic exchange chromatography medium.

The methods of the invention can be used where the cell culture medium comprises one or more contaminants selected from proteins and nucleic acids. In certain embodiments, the cell culture medium comprises serum proteins, host cell proteins, Shield-1, exogenous endonuclease and host cell DNA.

The methods of the invention also contemplate additional steps either before or after the two-step chromatography. In certain embodiments, the method further comprises performing tangential flow filtration on the eluate from step b), the purified HCMV from step d), or both. In certain embodiments, the method further comprises e) a sterilizing filtration step using a 0.2 μm membrane made of PVDF or cellulose acetate. In certain embodiments, the method involves a step prior to step a) wherein the cell culture medium comprising the HCMV is subject to nuclease treatment. In certain embodiments, the method involves a step prior to step a) wherein the cell culture medium is subject to clarification.

In certain embodiments, the methods of the invention provide for eluting in step b) using a salt selected from sodium chloride, potassium chloride, ammonium chloride, and sodium sulfate each at a concentration of about 0.5-2 M. In certain embodiments, the methods of the invention provide for eluting in step b) using an amino acid selected from arginine and histidine each at a concentration of about 0.25-1 M.

In one embodiment, the two-step chromatography process is performed aseptically. In one aspect of this embodiment, the two-step chromatography process is performed aseptically using an anion exchange membrane and a sterilized slurry of a mixed mode chromatography resin.

The methods of the invention can be used to purify any HCMV and can be used to obtain purified HCMV having at least 80% HCMV protein purity and/or a process yield of at least 40%.

The present invention also directed to a method for the purification of HCMV from a cell culture medium comprising the steps of: a) harvesting cell culture medium from a culture of ARPE-19 cells infected with HCMV; b) subjecting the cell culture medium to nuclease treatment using an endonuclease at a concentration of 10-160 U/mL; c) clarifying the nuclease-treated cell culture medium using a 1.2 μm glass fiber filter to obtain a clarified cell culture medium; d) contacting the clarified cell culture medium comprising HCMV with an anion exchange chromatography membrane under conditions that allow the HCMV to bind to the anion exchange chromatography membrane and then eluting the HCMV from the anion exchange chromatography membrane to obtain an eluate; e) contacting the eluate with a mixed mode chromatography resin which is a hydrophobic anion exchange chromatography resin having a molecular weight exclusion of about 700 kDa and then collecting the HCMV from the mixed mode chromatography resin to obtain purified HCMV; and f) performing tangential flow filtration on the purified HCMV collected from step e) to adjust to the desired concentration and buffer. In one embodiment, step b) is run prior to step a) by addition of nuclease to the cell culture medium prior to harvesting, i.e., during cell growth. In another embodiment, step b) is run following step a). In one embodiment, the cells are grown on microcarriers. In one embodiment, the purified HCMV has at least 80% HCMV protein purity. In one embodiment, the purified HCMV has a yield of at least 40%. In one embodiment, the purified HCMV contains 10 ng or less hcDNA per dose.

In certain embodiments, the HCMV is a recombinant genetically modified HCMV. In one aspect of this embodiment, the HCMV is a recombinant genetically modified HCMV having a genomic sequence of SEQ ID NO: 1.

The present invention also is directed to a process for sterilizing a large virus comprising: a) applying cell culture medium comprising said virus onto a 0.2 μm membrane made of PVDF or cellulose acetate; and b) collecting purified virus.

DETAILED DESCRIPTION OF THE INVENTION

The present invention is directed to purification of HCMV using a two-step chromatography purification process (anion exchange chromatography followed by polishing chromatography) in combination with additional processing steps to yield an active, concentrated virus product, having high purity and low host cell protein and DNA levels, suitable for use in a vaccine. Vaccine preparations must be sterile (i.e., free from independently replicating organisms) and should contain no more than 10 ng of host cell DNA (hcDNA) per human dose, per World Health Organization guidance.

The purification processes described herein are readily scalable, use procedures and reagents that are compatible with current good manufacturing processes, and are sufficiently simple, rapid, and efficient to be used for the production of purified HCMV for vaccine use. With the proper choice of chromatography materials, the process can be performed aseptically. The HCMV purification process described by the current invention is capable of achieving an overall process yield >40% and a resulting protein purity of >80%.

The present invention is based, in part, on the discovery that HCMV purification using a tangential flow filtration-based scheme was not a robust purification strategy for large scale processing as host cell impurities may increase under these conditions. Applicants discovered that a chromatographic product capture step was necessary to reduce filter fouling for large scale purification of HCMV.

In one embodiment, the two-step chromatography process is performed aseptically. Due to the large size of the HCMV particles (~100 to 400 nM), it may be desirable to perform the chromatography process aseptically and avoid a sterile filtration step (which potentially would decrease overall yield). In another embodiment, the two-step chromatography process is followed by sterilizing filtration using a 0.2 μm membrane made of PVDF (polyvinylidene difluoride). In another embodiment, the two-step chromatography process is followed by sterilizing filtration using a Pall Supor-Life® 0.2 μm membrane made of PES (polyethersulfone). In another embodiment, the two-step chromatography process is followed by sterilizing filtration using a 0.2 μm membrane made of cellulose acetate.

The present invention is also directed to a method for sterile filtration of a large virus such (such as HCMV; size range of ~100-400 nm) comprising applying a cell culture medium containing a virus preparation onto a 0.2 μm membrane made of PVDF or cellulose acetate. This invention is based on the unexpected observation that virus particles which are larger than the nominal 0.2-micron pore size of most sterilizing filters can pass through membranes made of cellulose acetate or PVDF, and in some cases, PES.

The present invention is also directed to a purification process comprising the following steps: (1) harvest of cell culture medium, (2) nuclease treatment, (3) clarification, (4) anion exchange chromatography (bind and elute), (5) polishing chromatography, and (6) tangential flow filtration (TFF). The process is scalable from laboratory scale (<3 L) to manufacturing scales (e.g., 50-2000 L) and capable of purifying a range of feed streams, including medium from static cell culture (e.g., from cell stacks) and culture in bioreactors. In the purification sequence, nuclease treatment may be performed before (added to cell culture medium) or after harvest of the cell culture medium, and the TFF may be performed before and/or after the polishing chromatography (i.e., before, after, or both).

The following purification attributes have been achieved by the processes described herein.

TABLE 1

Purity Results Demonstrated by HCMV Vaccine Purification Process

| Attribute | Analytical method | Result Demonstrated |
|---|---|---|
| Protein Purity | Mass Spectrometry | ≥80% HCMV protein |
| Residual BSA | BSA western or ELISA method | ≤50 ng/dose |
| Host Cell DNA | qPCR | ≤10 ng/dose |
| Process Yield - Total Viral Particles | Flow Cytometry (Particle Counts) or Viral antigen (western blot) | ≥40% |
| Process Yield - Infectious Viral Particles | Relative Infectivity assay | ≥30% |

As used herein, purification of "Human cytomegalovirus" or "HCMV" generally refers to purification of HCMV particles.

As used herein, in connection with chromatography, a "support" refers to the base matrix without a ligand. A support can be in the form of a membrane or resin.

As used herein, in connection with chromatography, a "medium" refers to the support with a ligand.

As used herein, in connection with chromatography, a "resin" refers to a bead-based chromatography medium that can be packed into a column or used in a slurry mode.

As used herein, in connection with chromatography, a "ligand" refers to a chemical species affixed to the chromatography support media that is used to effect separation between the desired product and other species.

As used herein, "mixed-mode chromatography" or "multimodal chromatography" refers to the use of a solid phase chromatographic support that employs a combination of two or more chemical mechanisms in order to achieve separation of components such as protein, DNA, and virus in a mixture. Examples include, but are not limited to, chromatographic supports that exploit combinations of cation exchange (i.e., in which the support is anionic), anion exchange (i.e., in which the support is cationic), hydrophobic interaction, hydrophilic interaction, hydrogen bonding, pi-pi bonding, and metal affinity. Mixed-mode chromatography may also employ a size exclusion component. The solid phase can be a porous particle, nonporous particle, membrane, or monolith.

As used herein, "anion exchange chromatography" refers to the use of a solid phase chromatographic support that uses a positively charged ion exchange support that has an affinity for molecules having net negative surface charges in order to achieve separation of components. The solid phase can be a porous particle, nonporous particle, membrane, or monolith.

As used herein, "cation exchange chromatography" refers to the use of a solid phase chromatographic support that uses a negatively charged ion exchange support that has an affinity for molecules having net positive surface charges in order to achieve separation of components. The solid phase can be a porous particle, nonporous particle, membrane, or monolith.

As used herein, "cell culture medium" refers to the liquid portion of a cell culture having one or more components other than HCMV particles, such as, but not limited to, proteins, nucleic acids, lipids, various cell culture medium components and additives. HCMV particles are released by the cells into the cell culture medium without any intervention or the cells may be lysed or rendered permeable to virus through chemical agents or mechanical means. The cell culture medium can be partially purified using centrifugation, clarification or other methods. In certain embodiments, the cell culture medium contains HCMV through its release into the cell culture.

As used herein, "polishing chromatography" refers to additional chromatography operations after a capture step to remove residual impurities such as host cell protein and DNA. For purposes of the invention, polishing chromatography includes cation exchange chromatography and mixed mode chromatography.

As used herein, "process yield" refers to the fraction of product (viral particles) that is recovered after executing the purification operations. The yield of total viral particles is measured using particle counting techniques or by quantifying viral antigen. The yield of infectious particles is also measured using infectivity assays, to verify that the infectivity of the viral particles is sufficiently maintained during purification.

As used herein, "protein purity" refers to the proportion of product related proteins in the purified product, expressed as a fraction relative to total protein content.

Cytomegalovirus

The purification processes of the present invention can be used to purify any cytomegalovirus, including wild-type cytomegalovirus, a recombinant cytomegalovirus, and a genetically modified cytomegalovirus (for example, cytomegalovirus containing a transgene). In some embodiments, the cytomegalovirus is a human cytomegalovirus (HHV-5). In some embodiments, the HCMV is AD169 strain, Toledo strain or Towne strain. In some embodiments, the cytomegalovirus is a recombinant HCMV, particularly, a conditional replication defective HCMV. In some embodiments, the cytomegalovirus is a recombinant HCMV delivering one or more transgenes. The processes of the invention can also be used to purify both infectious and noninfectious HCMV particles. See Schneider-Ohrum et al., 2016, J Virol. 90:10133-10144.

Methods of propagating cytomegalovirus are known in the art. See, e.g., Britt, 2010, Human Cytomegalovirus: Propagation, Quantification, and Storage; in Current Protocols in Microbiology, 18:E:14E.3:14E.3.1-14E.3.17; Chambers et al., 1971, Appl Microbiol 22:914-8; and Schneider-Ohrum et al., 2016, J Virol 90:10133-10144. In some embodiments, cell cultures are inoculated with cytomegalovirus and cultured for a period of time (e.g., 24 hours to 3 weeks) before harvesting the virus. Various methods of harvesting virus from cell culture are known in the art. In some embodiments, the cytomegalovirus is harvested from the cell culture by collecting the medium. In some embodiments, the cytomegalovirus is harvested from the cell culture by lysing the cells (e.g., by mechanical or non-mechanical lysis methods). In some embodiments, the cytomegalovirus is harvested from the cell culture by adding a cell permeation agent to release virus from host cells.

Any cytomegalovirus preparation can be used in the present invention, including unpurified or partially purified cytomegalovirus preparations from natural, synthetic, or recombinant sources. Unpurified cytomegalovirus preparations can come from various sources including, but not limited to, bacterial cell culture supernatants or lysates, yeast cell culture supernatants or lysates, mammalian cell culture supernatants or lysates, including cell culture supernatants obtained by cell harvests (e.g., by adding a cell permeation agent to release virus from host cells). Partially purified preparations can come from unpurified preparations that have been processed by at least one filtration, chromatography, clarification, precipitation, or fractionation step or any combination thereof. As used herein, "cell culture medium" is meant to encompass both unpurified and purified cytomegalovirus preparations. In some embodiments, the cytomegalovirus preparation comprises a mammalian cell lysate. In some embodiments, the cytomegalovirus preparation comprises a culture harvest of cytomegalovirus released from mammalian host cells. In some embodiments, the cytomegalovirus preparation contains one or more contaminants selected from proteins (e.g., host cell proteins, cell culture serum proteins or exogenously added proteins), and nucleic acids (e.g., host cell DNA).

Suitable host cells include, but are not limited to, epithelial cells (e.g. ARPE-19 human retinal pigment epithelial cells), endothelial cells (e.g. TIME, HUVEC), and fibroblast cells (e.g. MRC-5 human fetal lung fibroblast cells, WI-38 human fetal lung fibroblasts, HFF, etc.). In one embodiment, the cell culture medium is obtained from a cell culture of ARPE-19 cells. Suitable culture media for these cell lines is well known to those skilled in the art and includes, but is not limited to, DMEM (Dulbecco's Modified Eagle Media)/F12 medium supplemented with 10% fetal bovine serum (FBS), DMEM supplemented with 10% FBS, and EMEM (Eagle's Minimum Essential Medium) supplemented with 1% to 15% FBS.

Culturing a cell is performed to enable it to metabolize, grow, divide and/or produce virus of interest. This can be accomplished by methods well known to persons skilled in the art and includes, but is not limited to, providing nutrients for the cell, for instance, in the appropriate culture media and providing an appropriate substrate. The methods may comprise growth adhering to surfaces, growth in suspension, or combinations thereof. Culturing can be done, for instance, in dishes, roller bottles or in bioreactors, using batch, fed-batch, continuous systems, hollow fiber, and the like. High density cell culture systems, such as Corning HyperFlask® and HyperStack® systems can also be used.

In order to achieve large-scale production of virus through cell culture, it is preferred in the art to have cells capable of growing in suspension or microcarriers, and it is preferred to have cells capable of being cultured in the absence of animal- or human-derived serum or animal- or human-derived serum components. Suitable conditions for culturing cells are known. See, e.g., Tissue Culture, (1973), Kruse and Paterson (Eds.), Academic Press, and Freshney, 2000, Culture of animal cells: A manual of basic technique, fourth edition (Wiley-Liss Inc.).

In some embodiments, the cells used to propagate the HCMV are grown on microcarriers. A microcarrier is a support matrix allowing for the growth of adherent cells in spinner flasks or bioreactors (such as stirred bioreactors, rotating wall microgravity bioreactors and fluidized bed bioreactors). Microcarriers are typically 125-250 µM spheres with a density that allows them to be maintained in suspension with gentle stirring. Microcarriers can be made from a number of different materials including, but not limited to, DEAE-dextran, glass, polystyrene plastic, acrylamide, and collagen. The microcarriers can have different surface chemistries including, but not limited to, extracellular matrix proteins, recombinant proteins, peptides and charged molecules. In one embodiment, the microcarriers are Cytodex™ microcarriers (GE Healthcare Life Sciences) which are based on cross-linked dextran matrices.

In some embodiments, the processes described herein employ a nuclease to remove contaminating nucleic acids, which are mostly from the host cell. Exemplary nucleases suitable for use in the invention include BENZONASE®, PULMOZYME®, or any other DNase and/or RNase commonly used within the art. In preferred embodiments of the invention, the nuclease is BENZONASE®, which rapidly hydrolyzes nucleic acids by hydrolyzing internal phosphodiester bonds between specific nucleotides. BENZONASE® is a genetically engineered variant of an endonuclease normally expressed in *Serratia marcescens*, and can be commercially obtained from Millipore Sigma (Burlington, MA). The concentration at which the nuclease is employed is preferably within the range of 1-100 units/ml.

In certain embodiments, the nuclease is added to the post-harvest cell culture medium. The batch can then be incubated at temperatures ranging from the culturing temperature (e.g., about 37° C.), or at room temperature (around 20° C.) or lower (e.g., around 0° C.), wherein, in general, longer incubation times are required at lower temperatures to achieve the same result.

In certain embodiments, the nuclease can be employed before the cell culture medium is harvested. It may be added just seconds prior to (or virtually concomitant with) the harvesting step, but preferably, the nuclease is added to the culture at least one minute before the harvesting step and up to several days before the harvesting step. The cell culture with the added nuclease can then be incubated above process temperature, e.g., around 40° C., or at the culturing temperature (e.g., about 37° C.), or at room temperature (around 20° C.) or lower (e.g., around 0° C.), wherein, in general, longer incubation times are required at lower temperatures to achieve the same result.

In certain embodiments, the HCMV is a recombinant HCMV vaccine. See, e.g., Lilja et al., 2012, Vaccine 30:6980. In certain embodiments, the HCMV is a recombinant vaccine vector expressing a heterologous antigen. The antigen can be from another pathogen or be a tumor antigen. See, e.g., U.S. Pat. No. 9,249427 (pathogen antigen or tumor antigen), U.S. Patent Application Publication No. 20160354461 (HIV, SIV or TB antigens) and International Patent Application Publication No. WO1998/010311A1 (HIV or malarial antigens); Marzi et al., 2016, Sci Rep 6:21674 (Ebola virus); and Tierney et al., 2012, Vaccine 30:3047 (tetanus toxin).

In one embodiment, the HCMV is a conditional replication defective HCMV (rdHCMV). As used herein, the term "conditional replication defective virus" refers to virus particles that can replicate in certain environments but not others. In certain embodiments, a virus is made a conditional replication defective virus by destabilization of one or more proteins essential for viral replication such as 1E1/2, UL51, UL52, UL79 and UL84, or a combination thereof, for example, by fusion with a destabilizing polypeptide such as a sequence of FKBP or a derivative thereof. Preferred FKBP derivatives have one or more of the following substitutions at the denoted amino acid positions F15S, V24A, H25R, F36V, E60G, M66T, R71G, D100G, D100N, E102G, K105I and L106P. The FKBP derivative having the F36V and L106P substitutions is particularly preferred. The nucleic acids encoding the wild type, non-destabilized essential proteins are modified in the conditional replication defective virus. In more preferred embodiments, one or more essential proteins are destabilized. Such fusion proteins can be stabilized by the presence of a stabilizing agent such as Shield-1, commercially available from Cheminpharma LLC (Farmington, CT) or Clontech Laboratories, Inc. (Mountain View, CA). See, e.g., U.S. Patent Application Publication No. 2009/0215169; and Clackson et al., 1998, Proc Natl Acad Sci USA 95:10437-42).

In one embodiment, the conditional replication defective HCMV is derived from AD169 strain that has a restored gH complex expression due to a repair of a mutation in the UL131 gene. As used herein, the terms "pentameric gH complex" or "gH complex" refer to a complex of five viral proteins on the surface of the HCMV virion. The complex is made up of proteins encoded by UL128, UL130, and UL131 assembled onto a gH/gL scaffold. See Wang and Shenk, 2005, Proc Natl Acad Sci USA 102:1815; and Ryckman et al., 2008, J. Virol. 82:60.

In one embodiment, the genome of the rdHCMV has a destabilized 1E1/2 and UL51 and has a sequence as shown in SEQ ID NO:1. See U.S. Pat. No. 9,546,355.

Manufacture of Conditional Replication Defective HCMV rdHCMV can be propagated in the presence of a stabilizing agent such as Shield-1 (Shld-1) on permissive cell types, preferably human epithelial cells, and more preferably human retinal pigmented epithelial cells. In additional embodiments, the human retinal pigmented epithelial cells are ARPE-19 cells deposited with the American Type Culture Collection (ATCC) as Accession No. CRL-2302. In some embodiments, Shield-1 is present at a concentration of at least 0.5 µM in the tissue culture media. In preferred embodiments, Shield-1 is present at a concentration of at least 2.0 µM in the tissue culture media. Shield-1 can be used to control replication of the rdHCMV in conjunction with FKBP (FK506 binding protein). See, e.g., U.S. Pat. No. 9,546,355.

In certain embodiments, Shield-1 is one of the components to be removed during the purification steps described herein. After purification of rdHCMV from cell culture media containing Shield-1, there may be a small amount of residual Shield-1 remaining in the rdHCMV preparation. In one embodiment, the level of Shield-1 in the HCMV composition after purification is at least 10-fold below the level used to sustain replication in tissue culture. In another embodiment, the level of Shield-1 in the rdHCMV preparation after purification is 0.05 µM or less. In another embodiment, the level of Shield-1 in the rdHCMV preparation after purification is undetectable.

Determination of Shield-1 levels in a composition can be detected using a LC/MS (liquid chromatography-mass spectroscopy) or HPLC/MS (high performance liquid chromatography-mass spectroscopy) assays. These techniques combine the physical separation capabilities of LC or HPLC with mass analysis capabilities and can detect chemicals of interest in complex mixtures.

Chromatography Media

The methods of the invention employ a combination of different chromatography technologies, including anion exchange chromatography medium and a polishing chromatography medium selected from a mixed-mode chromagraphy resin and a cation exchange chromatography medium.

Anion exchange chromatography exploits positively charged functional groups on the support to bind to negatively charged molecules. The anion exchange chromatography medium can be any weak or strong anion exchange chromatography medium. In some embodiments, the anion exchange chromatography ligand comprises a strong ionic group. Structural groups that are useful as strong anionic exchange functionalities include, for example, secondary, tertiary, and quaternary amines (e.g., diethyl aminoethyl, dimethyl aminoethyl, trimethyl aminoethyl, and quaternary aminoethyl). In certain embodiments, the anion exchange chromatography support is in the form of a column. In certain embodiments, the anion exchange chromatography support is in the form of a membrane.

Commercial examples of anion exchange chromatography media include, but are not limited to, Nuvia™ Q, UNOsphere™ Q, UNO® Q (available from Bio-Rad Laboratories, Inc., Hercules, CA), Capto™ Q (available from GE Healthcare) and POROS™ HQ (available from Applied Biosystems). Anion exchange chromatography media are also described, for example, in U.S. Pat. No. 8,138,291. Example of anion exchange chromatography membranes include, but are not limited to, those produced by Pall (e.g., Mustang™ series including Mustang™ Q) and Sartorius (e.g., Sartobind® series including Sartobind® Q) and Natrix Separations (e.g., NatriFlo® HD-Q membrane).

The cation exchange chromatography medium can be any weak or strong cation exchange chromatography medium. In some embodiments, the cation exchange chromatography ligand comprises a strong ionic group. Structural groups that are useful as strong cationic exchange functionalities include, for example, sulfonic acid ligands. In certain embodiments, the cation exchange chromatography support is in the form of a column. In certain embodiments, the cation exchange chromatography support is in the form of a membrane. Examples of cation exchange chromatography resins include POROS™ XS resin (Thermo Fisher Scientific), Capto™ S (GE Healthcare) and POROS™ HS (Applied Biosystems). Examples of cation exchange chromatography membranes include Sartorius Sartobind® S and Pall Mustang® S.

Mixed-mode chromatography resins exploit a combination of ion exchange (i.e., negatively-charged or positively charged moieties on the mixed-mode support) and hydrophobic interaction, optionally with hydrogen bonding or pi-pi bonding interactions. In some embodiments, the mixed mode ligand comprises at least one acidic moiety such as a carboxyl group, and also comprises at least one hydrophobic moiety such as, but not limited to, a phenyl ring or an aliphatic hydrocarbon chain. In some embodiments, the support is hydrophobic and weakly cationic. For example, in some embodiments, the mixed-mode ligand comprises a carboxylic acid end group in combination with at least one hydrophobic moiety, such as an aromatic hydrophobic ring. Those skilled in the art will understand the definition of "strong" and "weak" ionic groups as those groups which are, or are not, respectively, capable of maintaining their charge across a wide pH range, such as pH 2 to pH 12. In some embodiments, the mixed-mode ligand further comprises an amide bond serving as a hydrogen bond donor/acceptor. Mixed-mode chromatography supports are described in, for example, U.S. Pat. No. 7,999,085.

In certain embodiments, the mixed-mode chromatography also employs core bead chromatography. In core bead chromatography, molecules may be separated based on size. Larger molecules or complexes flow through the chromatography column, while smaller molecules or complexes flow into pores on the surface of the bead. The pore size on the surface of the bead will determine the size of the molecule that may pass through to the inner core of the bead. Accordingly, one skilled in the art may select a mixed-mode resin with an appropriate pore size smaller than the molecule or complexes (such as, for example, the HCMV virus) that is the subject of purification, such that the molecule or complexes to be purified passes through the column, while smaller molecules or complexes enter the pores of the mixed-mode resin. In certain exemplary embodiments, the mixed-mode resin comprises pores having an approximate size exclusion of 500, 600, 700, 800, 900 or 1000 nm whereby virus particles having a diameter greater than the size exclusion size are excluded from the pores in the mixed-mode resin and do not come into contact with the ligand which is in the interior of the resin.

Examples of mixed-mode resins include, but are not limited to, Capto™ Core 700 (multimodal anion exchange octaylamine resin; GE Healthcare), Capto™ Adhere (multimodal strong anion exchange N-benzyl-n-methyl ethanolamine resin; GE Healthcare), Capto™ MMC (multimodal weak cation exchange cross-linked resin; GE Healthcare), hydroxyapatite Type 1 (Bio-Rad), and Nuvia™ cPrime™ (Bio-Rad Laboratories, Hercules, CA).

Capto™ Core 700 is a layered, bead-based matrix having a particle size of about 90 µm. The surface of the bead consists of an unliganded, inactive shell with pores that have an approximate MWCO (molecular weight cutoff) of about 700 kDa. The interior of the bead comprises an active functionalized core with multimodal octylamine ligands designed to capture impurities that are small enough to enter the bead through the pores on the surface. Smaller molecules, such as impurities and/or host cell proteins having a size smaller than about 700 kDa, pass through to the inner core octylamine ligands, where they are adsorbed, while the larger virion particles flow through. Large molecules or complexes can thereby be purified from smaller contaminants in the negative (flowthrough) purification mode.

Any solid support can be used for mixed-mode chromatography and ion exchange chromatography. The solid support can be, for example, porous or non-porous and can be in the form, for example, of a matrix, bead, particle, chip, or other conformation, e.g., a membrane or a monolith, i.e., a single block, pellet, or slab of material. Particles when used as matrices can be spheres or beads, either smooth-surfaced or with a rough or textured surface. Many, and in some cases all, of the pores are flow through-pores, extending through the particles to serve as channels large enough to permit hydrodynamic flow or fast diffusion through the pores.

The solid support can be utilized in any conventional configuration, including packed columns and fluidized or expanded-bed columns, monoliths or porous membranes, and by any conventional method, including batchwise modes for loading, washes, and elution, as well as continuous or flow-through modes. In some embodiments, the mixed-mode chromatography support and the anion exchange chromatography support are each packed in a column. In some embodiments, the mixed-mode chromatography support is packed in a column and the ion exchange chromatography supports are each in the form of a membrane. In other embodiments, the mixed mode chromatography support is a resin which is used in slurry mode, which is more amenable to batch sterilization than a packed chromatography column.

In some embodiments, the mixed-mode and/or anion exchange support is packed in a column of any dimension required to support preparative applications. Column diameter may range from less than 1 cm to more than 1 meter, and column height may range from less than 1 cm to more than 30 cm depending on the requirements of a particular application. Other column dimensions may also be used.

Chromatography Methods

The methods of the present invention utilize a combination of forms of chromatography to purify cytomegalovirus particles from a cell culture medium, typically containing host cell proteins, host cell DNA, serum proteins, and additives. In some embodiments, the methods involve an initial mass capture of cytomegalovirus particles from the cell culture medium using an anion exchange chromatography medium under suitable conditions as known in the art to allow the cytomegalovirus particles to bind to the anion exchange chromatography medium. The cytomegalovirus particles are then eluted from the anion exchange chromatography medium and subjected to a further purification process on a polishing chromatography medium.

The ion exchange chromatography (both anionic and cationic) media that are used in the methods of the present invention are operated in a bind-elute mode. "Bind-elute mode" refers to an operational approach to chromatography in which the buffer conditions are established so that target molecules to be purified (e.g., cytomegalovirus), and optionally undesired contaminants or impurities, bind to the chromatography medium when a preparation is applied to the chromatography medium. Separation of the target molecule (e.g., cytomegalovirus) can be achieved subsequently by changing the conditions such that the target molecule is eluted from the medium. In some embodiments, contaminants or impurities remain bound following elution of the target molecule. In some embodiments, contaminants or impurities either flow through when the preparation is applied to the chromatography medium, or are bound and eluted before elution of the target molecule.

The mixed-mode chromatography resins that are used in the methods of the present invention are operated in a flow-through mode. "Flow-through mode" refers to an operational approach to chromatography in which the buffer conditions are established so that target molecules to be purified (e.g., cytomegalovirus) flow through the chromatography medium when a preparation is applied to the chromatography medium. In certain embodiments, when using mixed mode chromatography resins with a size exclusion component, the target molecules to be purified do not come into contact with ligand because the pore size prevents contact. In both cases, the target molecule does not bind to ligand. Contaminants or impurities remain bound to the chromatography medium following flow through of the target molecule.

Anion Exchange Chromatography Step

In the methods of the invention, a cell culture medium containing HCMV (e.g., pH 6.6-7.0, conductivity ~15 mS/cm) is first subject to anion exchange chromatography medium to bind HCMV to the anion exchange chromatography medium. The bound HCMV is optionally washed with one or more solutions under conditions in which the HCMV remains substantially bound to the medium, wherein the presence and amount of the solution displaces and/or removes one or more contaminants (e.g., serum proteins, host cell protein, and host cell DNA). A variety of washing agents can be used. In some embodiments, the agent is histidine and/or sodium chloride or another neutral salt (e.g., potassium chloride, ammonium chloride, or sodium sulfate) at a pH between 6 and 7. In some embodiments, the washing agent may include other amino acids such as arginine to affect separation.

Following the optional washing step or steps, the HCMV is eluted from the anion exchange chromatography medium. In some embodiments, the HCMV particles are eluted with a salt gradient (e.g., from 0 M up to 2 M salt or higher). Other elution conditions can also be applied as desired, including, e.g., elution by inclusion of mobile phase modifiers such as amino acids. In some embodiments, the HCMV particles are eluted using an elution buffer comprising sodium chloride or another neutral salt (e.g., potassium chloride, ammonium chloride, or sodium sulfate) at a concentration of about 0.5-2 M (e.g., about 0.5, 0.6, 0.7, 0.8, 0.9, 1, 1.1, 1.2, 1.3, 1.4, 1.5, 1.6, 1.7, 1.8, 1.9, or 2 M). In one embodiment, the HCMV particles are eluted using ~1M NaCl in a buffer of approximately pH 7. In certain embodiments, the HCMV is eluted with an amino acid with a basic side chain, e.g., arginine or histidine, at a concentration of about 0.25-1 M.

Some exemplary bind-wash-elute conditions for the anion exchange chromatography step are:
  binding condition: cell culture media, conductivity between 0-30 mS/cm, pH 6-8
  wash condition: 50-300 mM sodium chloride, pH 6-7, in a histidine buffer containing 25-100 mM histidine
  elution condition: 1 M sodium chloride, pH 7, in a buffer (e.g., histidine)

In some embodiments, prior to contacting the cell culture medium comprising HCMV with the anion exchange chromatography medium (e.g., an anion exchange membrane), the chemical environment of the support is equilibrated. In some embodiments, the anion exchange medium is equilibrated to establish an appropriate pH, conductivity, and/or concentration of salts. Equilibration of the medium is accomplished, for example, by flowing an equilibration buffer containing appropriate reagents through the column. Buffering compounds may include, but are not limited to, histidine, phosphate, Tris, MES, HEPES, BICINE, and imidazole. In one embodiment, the equilibration buffer comprises histidine in an amount between 1 mM to about 50 mM, and NaCl in an amount between 50 mM and about 200 mM. The cell culture medium containing the HCMV particles can also be equilibrated to conditions compatible with the anion exchange chromatography medium equilibration buffer before applying to the anion exchange chromatography medium. In some embodiments, the cell culture medium is equilibrated by adjusting the pH, the concentration of salts, or other compound as desired. In some embodiments, the cell culture medium is equilibrated to a pH of about 6.0 to about 9.5. In some embodiments, the cell culture medium is equilibrated to a pH of about 6.0 to about 8.0 (e.g., about 6.0, about 6.5, about 7.0, about 7.5, or about 8.0). In some embodiments, the cell culture medium is equilibrated to a pH of about 7.

In some embodiments, the cell culture medium is diluted in a buffer prior to applying to the chromatography medium. In some embodiments, the cell culture medium is diluted in a buffer that is the same as or that is compatible with the anion exchange chromatography equilibration buffer. In some embodiments, the cell culture medium is diluted in an equilibration buffer that contains Tris. In some embodiments, the cell culture medium is diluted in an equilibration buffer that comprises Tris and sodium chloride or another neutral salt. In some embodiments, the eluate is diluted in buffer (e.g., equilibration buffer) at a ratio of about 1:1, about 1:2, about 1:3, about 1:4, or about 1:5 of cell culture medium to buffer.

After the chromatography medium and cell culture medium have been equilibrated, the cell culture medium can be contacted to the anion exchange chromatography medium (e.g., membrane) under conditions that allow for the cytomegalovirus particles to bind to the anion exchange column. In some embodiments, the cell culture medium can be contacted to the anion exchange medium at a flow range of, but not limited to, 0.1-5.0 chromatography bed volumes per minute.

Polishing Chromatography Step

For polishing chromatography, a number of different options are available for removal of trace contaminants and impurities in this step. In certain embodiments, a mixed-mode chromatography step is used. In certain aspects of these embodiments, the mixed-mode chromatography is performed by flow-though (i.e., impurities bind to the mixed-mode chromatography resin while the cytomegalovirus particles do not). In certain embodiments, a cation exchange chromatography step is used using bind-elute.

In certain embodiments, the eluate from the anion exchange chromatography is processed through a suitable bioburden reduction filter prior to application to the polishing chromatography resin. The bioburden reduction filter can be, for example, a 0.2 to 0.45 micron filter.

Mixed-Mode Chromatography Step

In some embodiments, the eluate from the anion exchange chromatography step comprising cytomegalovirus is contacted with a mixed-mode chromatography resin (e.g., a mixed-mode column, e.g., a hydrophobic cation exchange chromatography column). In some embodiments, the mixed-mode resin is equilibrated to establish an appropriate pH, conductivity, and/or concentration of salts. Equilibration of the resin is accomplished, for example, by flowing an equilibration buffer containing appropriate reagents through the column. Buffering compounds may include, but are not limited to, histidine, phosphate, Tris, MES, HEPES, BICINE, and imidazole. In some embodiments, the equilibration buffer comprises histidine. In some embodiments, the equilibration buffer comprises histidine in an amount from about 1 mM to about 50 mM (for example about 25 mM).

In some embodiments, the mixed-mode chromatography resin is equilibrated to a pH of about 5 to about 7. In some embodiments, the mixed-mode chromatography resin is equilibrated to a pH of about 5.5 to about 7.5 (e.g., about 5.5 about 6, about 6.5, about 7, or about 7.5). In some embodiments, the mixed-mode chromatography resin is equilibrated to a pH of about 6.

The eluate (from the anion exchange chromatography) comprising the HCMV can also be equilibrated to conditions compatible with the mixed-mode chromatography equilibration buffer before applying the eluate to the mixed-mode chromatography resin. In some embodiments, the eluate is equilibrated by adjusting the pH, the concentration of salts, or other compound as desired. In some embodiments, the eluate is equilibrated to a pH of about 5.5 to about 7.5. In some embodiments, the eluate is equilibrated to a pH of about 5.5 to about 7.5 (e.g., about 5.5 about 6, about 6.5, about 7, or about 7.5). In some embodiments, the impure preparation is equilibrated to a pH of about 6.

In some embodiments, the eluate is diluted in a buffer prior to applying to the chromatography medium. In some embodiments, the eluate is diluted in a buffer that is the same as or that is compatible with the chromatography equilibration buffer. In some embodiments, the eluate is diluted in an equilibration buffer that comprises histidine. In some embodiments, the eluate is diluted in buffer (e.g., equilibration buffer) at a ratio of about 1:1, about 1:2, about 1:3, about 1:4, or about 1:5 of eluate to buffer.

In one embodiment, the mixed-mode chromatography support is in the form of a packed column, with the eluate (from the anion exchange chromatography step) flowed-through the column. In another embodiment, the mixed-mode chromatography support is in the form of a resin slurry, with the eluate contacted with the resin in a mixing vessel. The resin can be removed from the eluate using a sized based separation which removes the resin beads without removing the HCMV particles. For instance, the eluate may be passed through a straining mesh followed by a clarifying filter with a pore size between approximately 0.45 µm and approximately 10 µm. In one embodiment, a 50 µm mesh followed by a 1.2 µm filter is used.

Following flow-through of the HCMV through the mixed-mode chromatography resin, the resin is optionally washed with one or more solutions under conditions in which any residual HCMV flows away from the resin. In certain embodiments, the composition of the wash buffer would match the equilibration buffer. In some embodiments, the solution contains histidine or another salt. Other wash agents can also be used.

In some embodiments, the HCMV that is recovered from the mixed-mode chromatography resin (as the second step in the process) is substantially free of impurities. As used herein, "substantially free" means that the impurities are 30% or less of the purified HCMV, e.g., less than 30%, 20%, 10%, 5%, or 1%. Various methods of assessing the purity of HCMV are known in the art. In some embodiments, the purity of the cytomegalovirus that is eluted can be analyzed by gel electrophoresis (e.g., SDS-PAGE) and bands corresponding to viral structural proteins may be visualized by staining (e.g., Coomassie staining or SYPRO Ruby staining). The purity of the HCMV that is purified can also be assessed by measuring the amount of host cell protein and/or host cell DNA contaminants or serum proteins such as BSA, if any, that are present in the final purified product. The amount of host cell protein can be measured, for example, by immunoassay (e.g., ELISA) and the amount of host cell DNA can be measured, for example, by PCR (e.g., quantitative PCR against a housekeeping gene or ribosomal RNA gene). The purity of the HCMV can also be assessed by a mass spectrometry method, by quantifying the relative contributions of HCMV proteins to the total protein content of the product.

In some embodiments, the final purified product (after the two chromatography steps) comprising HCMV has a process yield of at least 40%, or at least 50% or more of the HCMV particles of the starting cell culture medium (e.g., cell lysate or cell harvest). Methods of measuring HCMV particles are known in the art (e.g., quantitation of viral particles by a flow cytometry (e.g. Apogee Flow Systems), quantitation of viral antigen by ELISA or western blot techniques, or quantitation of infectious particles by infectivity assays (e.g., plaque)). In some embodiments, the activity of the final purified product comprising HCMV can be determined by comparing the infectivity before and after the two chromatography steps (e.g., comparing the infectivity of the original cell culture medium to the infectivity of the purified product). In some embodiments, HCMV activity is measured using plaque or relative infectivity assays.

Cation Exchange Chromatography Step

In alternative embodiments for the polishing chromatography step, the eluate from the anion exchange chromatography step is subject to a cation exchange chromatography medium to bind HCMV to the cation exchange chromatography support. In these embodiments, the cationic exchange chromatography is operated in bind and elute mode.

The bound HCMV is optionally washed with one or more agents under conditions in which the HCMV particles remain substantially bound to the chromatography medium, wherein the presence and amount of the agent or agents displaces and/or removes one or more remaining contaminants (e.g., host cell protein, host cell DNA, etc.). A variety of washing agents can be used. In some embodiments, the agent is sodium chloride or another neutral salt (e.g., potassium chloride, ammonium chloride, or sodium sulfate), in a buffered solution. Following the optional washing step or steps, the HCMV is eluted from the cation exchange chromatography medium. In some embodiments, the cation is eluted with a salt gradient (e.g., from 0 M up to 2 M salt or higher). Other elution conditions can also be applied as desired, including, e.g., elution by inclusion of secondary modifiers, e.g., an amino acid. In some embodiments, the HCMV particles are eluted using an elution buffer comprising sodium chloride or another neutral salt (e.g., potassium chloride, ammonium chloride, or sodium sulfate) at a concentration of about 0.3-1 M (e.g., about 0.3, 0.4, 0.5, 0.6, 0.7, 0.8, 0.9, or 1.0 M).

Some exemplary bind-wash-elute conditions for the cation exchange chromatography step are:
  binding condition: 1-50 mM histidine, 1-100 mM NaCl, pH 5.5
  washing condition: 1-50 mM histidine, 50-300 mM NaCl, pH 5.5
  elution condition: 1-50 mM histidine, 0.3-0.6 M sodium chloride, pH 5.5

In some embodiments, prior to contacting the eluate comprising HCMV with the cation exchange chromatography medium (e.g., a cation exchange membrane), the chemical environment of the chromatography medium is equilibrated. In some embodiments, the cation exchange medium is equilibrated to establish an appropriate pH, conductivity, and/or concentration of salts. Equilibration of the chromatography medium is accomplished, for example, by flowing an equilibration buffer containing appropriate reagents through the chromatographic support. Buffering compounds may include, but are not limited to, histidine, acetate, phosphate, Tris, MES, HEPES, BICINE, and imidazole. In some embodiments, the equilibration buffer comprises histidine or a combination of histidine and sodium chloride or another neutral salt. In some embodiments, the cation exchange chromatography medium is equilibrated to a pH of about 5.0 to about 7.0 (e.g., about 5.0, about 5.5, about 6.0, about 6.5, or about 7.0). In some embodiments, the cation chromatography medium is equilibrated to a pH of about 5.5.

The eluate (from the anion exchange chromatography step) comprising the HCMV can also be equilibrated to conditions compatible with the cation exchange chromatography equilibration buffer before applying to the cation exchange chromatography medium. In some embodiments, the eluate is equilibrated by adjusting the pH, the concentration of salts, or other compound as desired. In some embodiments, the eluate is equilibrated to a pH of about 5.0 to about 7.0, e.g., about 5.0, about 5.5, about 6.0, about 6.5, or about 7.0. In some embodiments, the eluate is equilibrated to a pH of about 5.5.

In some embodiments, the eluate from the anion exchange chromatography step is diluted in a buffer prior to applying to the cation exchange chromatography medium. In some embodiments, the eluate is diluted in a buffer that is the same as or that is compatible with the cation exchange chromatography support equilibration buffer. In some embodiments, the eluate is diluted in an equilibration buffer that comprises histidine. In some embodiments, the eluate is diluted in an equilibration buffer that comprises histidine and sodium chloride or another neutral salt. In some embodiments, the eluate is diluted in buffer (e.g., equilibration buffer) at a ratio of about 1:1, about 1:2, about 1:3, about 1:4, or about 1:5 of cell culture medium to buffer.

After the chromatography support and eluate have been equilibrated, the eluate can be contacted to the cation exchange chromatography medium (e.g., membrane) under conditions that allow for the HCMV to bind to the cation exchange medium. In some embodiments, the eluate can be contacted to the cationic exchange medium at a flow rate of, for example, 0.1-5.0 chromatography bed volumes per minute.

Tangential Flow Filtration

Following the anion exchange chromatography step and/or the polishing chromatography step, the eluate (in the case of ion exchange chromatography) or flow-though (in the case of a mixed-mode chromatography) is optionally subject to tangential flow filtration. In some embodiments, a combination of anion exchange chromatography, optionally followed by tangential flow filtration, and mixed mode chromatography, optionally followed by tangential flow filtration, is used to purify the HCMV. In some embodiments, a combination of anion exchange chromatography, optionally followed by tangential flow filtration, and cation exchange chromatography, optionally followed by tangential flow filtration, is used to purify the HCMV.

Tangential Flow Filtration (TFF) (also referred to as Cross Flow Filtration or CFF) is well known to those of skill in the art and equipment and protocols for its implementation in a wide range of situations are commercially available from a variety of manufacturers including but not limited to the Pall Corporation (Port Washington, NY), Spectrum Labs (Rancho Dominguez, CA), and GE Healthcare Life Sciences (Malborough, MA). Generally, TFF involves the recirculation of the retentate across the surface of a membrane. This gentle cross flow feed minimizes membrane fouling, maintains a high filtration rate and provides high product recovery. In one embodiment, the TFF step may be implemented with a hollow fiber system. Hollow fiber systems are amenable to aseptic processing, if desired, with sterilization performed by gamma irradiation or steam sterilization. In one embodiment, presterilized hollow fiber units (ReadyTo-Process hollow fibers from GE) are used. In another embodiment, flat sheet TFF systems can be used. In one embodiment, the Molecular Weight Cut Off (MWCO) of the TFF system is between 500-1000 kDa, preferably about 500 kDa or 750 kDa.

A method for clarification and concentration of HCMV employing TFF is described in Vicente et al., 2014, Eng. Life Sci. 14:318-326.

Pre-Processing

In some embodiments, the cell culture medium comprising the HCMV particles is subjected to a treatment step or purification step prior to contacting the cell culture medium to the anion exchange chromatography medium. As a non-limiting example, in some embodiments, the cell culture medium is subjected to a filtration or clarification step prior to contacting the medium to the anion exchange chromatography medium. Filtration methods and reagents are known in the art; see, e.g., International Patent Application Publication No. WO2011/045381 and U.S. Patent Application Publication No. US2011/0207202. As another non-limiting example, in some embodiments, the cell culture medium is treated with a nuclease prior to contacting the preparation to the anion exchange chromatography medium. This nuclease treatment can take place through addition of nuclease during virus propagation or through a post-harvest nuclease addition. Suitable nucleases for treating the impure preparation are commercially available and methods for treating the preparation with a nuclease are known in the art. In some embodiments, the nuclease is added to the cell culture prior to or during viral propagation. For example, Benzonase® (EMD Millipore) or TurboNuclease™ (Accelagen) can be added to the cell culture (during virus propagation) for up to 8 days prior to harvest or added to the cell culture supernant (post-harvest) for at least one hour prior to the anion exchange chromatography purification step.

In some embodiments, prior to contacting the cytomegalovirus preparation to the anion exchange chromatography medium, the preparation can be subjected to a combination or two or more treatment or purification steps (e.g., a combination of a filtration or clarification step and a nuclease treatment step).

In some embodiments, the cytomegalovirus preparation comprising the cytomegalovirus particles is not subjected to a treatment or purification (e.g., filtration) step prior to contacting the cytomegalovirus preparation to the anion exchange chromatography resin.

Aseptic Processing vs. Sterile Filtration

Preparation of sterile compositions is typically achieved by subjecting a final composition to sterile filtration, i.e., though a 0.2 µm filter membrane, prior to administration. For compositions, such as viral vaccine compositions, comprising relatively large viruses (i.e., approximately 100 nm or larger), sterile filtration may result in a substantial loss of virus due to it being retained in the membrane, reducing the viral yield from the purification process. The present invention provides two alternative methods for providing sterile compositions.

Aseptic Process

In one embodiment, the two-step chromatography process is performed aseptically. In this embodiment, the anion exchange chromatography is an anion exchange membrane since sterilizing a packed chromatography column can be very challenging. The AEX membrane can be autoclaved, and the use of mixed mode polishing resin in "impurity binding" mode means no elution is necessary and a packed column is not required. In an impurity binding mode, the eluate is contacted with the resin whereby impurities bind to the resin and the HCMV does not bind to the resin. Because no elution step is required, this operation can occur in a mixed slurry mode rather than a packed column. The mixed-mode polishing resin resin can be autoclaved to achieve an aseptic resin preparation. The chromatography beads are then removed from the batch using an aseptic filtration train—for example, a 50 μm mesh followed by a filter with a nominal pore size between 0.45-10 μm.

Sterile Filtration

In another embodiment, the two-step chromatography process is followed by a sterilizing filtration using a 0.2 μm (nominal) membrane made of cellulose acetate, PES, or PVDF (polyvinylidene difluoride). In the case where TFF is employed following the polishing chromatography step, the sterile filtration would follow TFF.

The present invention is also directed to a method for sterile filtration of a large virus such as HCMV (size range of ~100-400 nm) comprising applying a cell culture medium containing virus or a virus preparation onto a 0.2 μm (nominal) membrane made of cellulose acetate or PVDF, and in some cases, PES. This invention is based on the surprising discovery that viruses which are larger than the nominal 0.2-micron pore size of most sterilizing filters can pass through membranes made of cellulose acetate or PVDF, and in some cases, PES.

Exemplary Process

In one embodiment, a complete purification process involves: (1) Nuclease digestion (with Benzonase®) prior to harvest in a bioreactor containing cell culture medium and microcarrier beads having cells infected with HCMV; (2) harvest of cell culture medium from microcarrier beads; (3) clarification of harvested cell culture medium by a 1.2-micron glass-fiber filter (e.g. Sartorius Sartopore® GF Plus); (4) capture of viral particles by anion exchange (AEX) membrane chromatography (e.g., Sartorius Sartobind® Q); (5) polishing purification by Capto™ Core 700 chromatography (GE Healthcare) operated in a flow through mode; (6) concentration and buffer exchange by 750-kDa hollow fiber TFF (e.g., GE Healthcare or Spectrum). In one aspect, a sterile filtration using a 0.2-micron filter selected from Sartorius Sartobran® P, Millipore Durapore™ PVDF filter, or Pall SuporLife® is performed before or after the TFF step in (6). In an alternative aspect, no sterile filtration is performed and the process is run completely aseptically.

In one embodiment, a 750-kDa hollow fiber TFF (GE Healthcare or Spectrum) step may also be included between the AEX and polishing chromatography.

This purification can generate vaccine having ≥80% HCMV purity (as assessed by HCMV protein) and ≤10 ng DNA/dose, with a process yield ≥40%.

Examples are provided below to further illustrate different features of the present invention. The examples also illustrate useful methodology for practicing the invention. These examples do not limit the claimed invention.

EXAMPLES

Analytical Methods
Protein Purity by Mass Spectrometry

Fractions of HCMV, host cell protein (HCP), and bovine proteins were assessed using a proteomic approach that uses LC-MS/MS (liquid chromatography-tandem mass spectrometry) to determine the approximate percentage of these proteins in HCMV process samples. The HCMV sample was trypsin-digested and then the peptides were analyzed using LC-MS/MS. Relative quantitation at the protein level was determined by summing the MS scan intensity of all the identified peptides that met an acceptance threshold. This summed intensity of each protein is the result of the total signal arising from all the peptides (with acceptable MS/MS results) matching that protein. The reported relative abundance of each protein type (HCMV, HCP, or residual bovine protein) is reported.

Viral Particle Concentration

A relative size distribution and total concentration of viral particles in the HCMV sample can be obtained by flow cytometry (e.g. Apogee Flow Systems). As the individual particles pass through the instrument's flow cell, they are illuminated by a 405 nm laser and the scattered light is detected. The obtained distribution is a relative size distribution of light scattering signal on a logarithmic scale. Counts in total particles per milliliter were also determined.

Relative Infectivity Assay

This analytical procedure is a cell-based relative infectivity assay based on expression of a HCMV protein following infection. ARPE-19 cells were plated and incubated in 96-well micro-titer plates followed by infection with serial dilutions of HCMV samples, controls, and standards. The infected cells were incubated for approximately 1 to 5 days then fixed with a fixative (e.g. formaldehyde). After washing, the plate is incubated with a monoclonal antibody (MAb) reactive with a HCMV protein. After incubation with the anti-HCMV MAb, the plate is washed and incubated with a detection antibody. After this final incubation, the plate is washed and read on a plate reader instrument. The relative infectivity assigned to the test article is based on signal generated with an assay reference standard tested on the same plate.

BSA Content by ELISA

This analytical procedure is a sandwich ELISA method which measures bovine serum albumin (BSA) in vaccine samples. This method is used to measure the amount of residual BSA in the purified HCMV sample. Dilutions of the purified HCMV sample are incubated on plates pre-coated with an anti-BSA capture antibody. Captured BSA is subsequently detected with an enzyme-conjugated, BSA-specific antibody. The residual BSA in HCMV sample is quantified using an optical density standard curve generated with a BSA reference standard.

BSA Content by Simple Western

For some samples, a Capillary Electrophoresis based Simple Western™ is used to monitor BSA mass. The sample is reduced and denatured, then loaded to a capillary and separated by size, bound to the capillary using a photo-linking technology and probed with an anti-BSA monoclonal antibody. A secondary antibody, luminol, and peroxide were utilized for chemiluminescence detection of BSA. Virus concentration of test samples was determined relative to a BSA reference standard of known concentration.

Host Cell DNA Content by qPCR

Total nucleic acids were isolated from the sample by proteinase K treatment, phenol-chloroform extraction, and alcohol precipitation. Host cell DNA concentration is measured by a real-time quantitative PCR (qPCR) standard curve assay (standard curve range: 200 ng/mL-20 pg/mL).

Measuring Virus Mass Content by Simple Western™ HCMV Glycoprotein Assay:

A Capillary Electrophoresis based Simple Western™ can be used to monitor virus mass. The HCMV sample was reduced and denatured, then loaded to a capillary and separated by size, bound to the capillary using a photo-linking technology and probed with a rabbit HCMV glycoprotein monoclonal antibody. A goat anti-rabbit HRP conjugate secondary antibody, luminol, and peroxide were utilized for chemiluminescence detection of the HCMV glycoprotein. Virus concentration of test samples was determined relative to a purified HCMV reference standard of known virus concentration.

Quantitation of Total Protein Using the Pierce® 660 nm Assay

The Pierce™ 660 nm Assay (Thermo Fisher Scientific) is a colorimetric method used to quantify total protein concentration. The assay is based on the binding of a propietary dye-metal complex to protein in acidic conditions that causes a shift in the dye's absorption maximum. A standard curve was prepared at seven concentration levels (15, 25, 50, 75, 100, 150, and 200 µg/mL) from Bovine Serum Albumin (BSA). Samples were diluted and then incubated in the presence of Benzonase® to reduce nucleic acid interference. The Pierce® 660 nm Assay Reagent was added, the plate was incubated at room temperature and the absorbance was read at 670 nm. Unknown sample concentrations were determined by interpolation from the standard curve using a linear fit.

Protein Analysis by SDS PAGE

To measure relative purity of HCMV proteins versus impurities, SDS PAGE was used to quantify HCMV Tegument protein. The sample was reduced and denatured, then loaded to a Bis-Tris SDS PAGE gel. Staining was executed using SYPRO® RUBY gel stain (Thermo Fisher Scientific) following the manufacturer's protocol. Densitometry was used to quantify the percentage of HCMV Tegument protein present relative to other protein bands.

Chromatography Methods

Anion Exchange Chromatography

Cell culture medium, optionally clarified, was loaded to the Sartobind® Q AEX membrane at between 1-3 bed volumes per minute. A wash step was conducted. In some examples, the wash was conducted using 225 mM NaCl in histidine buffer at pH 7. In other examples, the wash step was conducted by increasing histidine concentration to ~80-100 mM Histidine at pH 6. The HCMV particles were then eluted by increasing NaCl concentration to approximately 1 M NaCl, in a pH 7 histidine buffer.

Mixed Mode Chromatography (Capto™ Core, Capto™ Adhere, CHT™ Hydroxyapatite)

AEX eluate was purified by contacting the eluate with a mixed-mode chromatography resin (Capto™ Core, Capto™ Adhere, or CHT™ Ceramic Hydroxyapatite) in either a packed column or in a mixing vessel. As described in the examples below, the AEX elutate was sometimes contacted directly with the mixed-mode chromatography resin, at a pH of 7 and a salt concentration of approximately 1 M NaCl. In other examples, a TFF step was used following the AEX step to adjust the NaCl concentration to approximately 150 mM NaCl, at a pH between 6 and 7.

Cation Exchange Chromatography

AEX eluate was processed through a TFF step to adjust the NaCl concentration to approximately 75 mM NaCl at a pH between 5 and 6. The batch was then loaded to the Sartobind® S membrane adsorbers cation exchange (CEX) membrane at between 1-3 bed volumes per minute. A wash step was conducted at 225 mM NaCl at pH 5.5. The HCMV particles were then eluted by increasing NaCl concentration to approximately 500 mM NaCl at pH 5.5.

Example 1

Demonstration of a Need for AEX Capture Step, Comparing to TFF-Only Purification Purification of HCMV virions or dense bodies using Tangential Flow Filtration (TFF) has been reported. See, e.g., Vicente et al., 2014, Eng. Life Sci. 14:318-326; and Schneider-Ohrum et al., 2016, J. Virol. 90:10133-10144. During development of a commercial process for HCMV vaccine purification, it was found that TFF purification alone may be capable of achieving the desired purification results for harvests with minimal host cell impurities (e.g. harvest from static cultures). However, for harvests containing more impurities, as was seen with microcarriers, TFF was found to be insufficient to achieve the desired protein purity of ≥80% HCMV protein when using similar TFF conditions as those used for static culture. Improving TFF purification by increasing membrane area or crossflow was not feasible as the TFF process developed for static culture already required feed flowrates in excess of 100 liters per minute at the desired manufacturing scale. Implementation of an anion exchange capture chromatography step was explored to reduce the amount of protein being loaded onto TFF.

ARPE-19 cells (ATCC No. CRL-2302, American Type Culture Collection, Manassas, VA) were initially cultured in static vessels (i.e., T-225 Flask). Through cell expansion, cells were eventually cultured on microcarriers in a 3 L stirred tank bioreactor. Upon appropriate cell growth in the 3 L reactor, the cell culture was infected with a recombinant HCMV as described in U.S. Pat. No. 9,546,355.

On harvest day, the contents of the bioreactors were harvested, clarified using filtration across a 1.2 mm clarification filter capsule, and treated with nuclease (Benzonase® endonuclease, EMD Millipore, 80 U/mL for 2 hours).

The cultures were then purified using either (A) tangential flow filtration (750 kDa cutoff) or (B) AEX capture chromatography followed by tangential flow filtration. In each process scenario, the tangential flow filtration step was conducted by concentrating the batch to approximately 20 percent of the original harvest volume, then diafiltering against eight diavolumes of buffer. In the arm including AEX, the AEX step was conducted using a Sartobind® Q membrane adsorber. The feed material (nuclease-treated cell culture medium) was loaded on the Sartobind® Q membrane adsorber. The HCMV particles were eluted by increasing the NaCl concentration to approximately 1 M NaCl at pH 7. Protein purity was measured by mass spectometry as described in the analytical methods section. Results are shown in Table 2 alongside previous results obtained using the TFF purification process and virus harvested from static cell culture.

For the microcarrier harvest, the TFF only arm experienced membrane fouling and the purity of the resulting product, 9%, was significantly below the target value of 80% HCMV protein. Incorporation of an AEX capture step resulted in a reduced protein load to the TFF and and a significantly higher purity than the TFF-only arm. The data indicates that the AEX capture step is required to approach the goal of ≥80% HCMV protein, but also that additional polishing is required.

TABLE 2

Purifications of HCMV vaccine harvest using either TFF or AEX capture followed by TFF. For each arm, the volumetric loading to TFF was similar (~70 liters/m² membrane). The feed material was nuclease treated prior to the membrane steps in all cases. The same feed material was used for both arms of microcarrier culture purification.

|  | Static culture | Microcarrier culture | |
|---|---|---|---|
| Process | TFF | TFF | AEX/TFF |
| % HCMV | 88% | 9% | 71% |
| % Human | 9% | 18% | 24% |
| % Bovine | 3% | 74% | 6% |

Example 2

Identification of Polishing Chromatography Resins Capable of Achieving ~80% HCMV Process Yield To increase purity following an AEX capture/TFF sequence, various polishing chromatography steps were evaluated. In a high throughput screening experiment, product previously purified by AEX/TFF was incubated with various chromatography resins in a plate format. A filter plate was then used to remove the resin and the products were analyzed by mass spectrometry.

Table 3 shows the protein purity results. For this purification, feed material was measured at 47.2% HCMV.

TABLE 3

Purity results for evaluation of polishing resins in a microscale study. Resins were evaluated in a negative purification mode (product does not bind to resin)

| Sample Name | % HCMV |
|---|---|
| Feed Material (AEX/TFF Purified) | 47.2 |
| Capto ™ Adhere | 82.3 |
| CHT ™ Hydroxyapatite Type 1 | 87.7 |
| Capto ™ Core | 77.3 |

The experiment identified three polishing chromatography resins (Capto™ Adhere, CHT™ Hydroxyapatite, and Capto™ Core) all with the ability to increase purity to near the 80% HCMV target.

Following this initial evaluation, although all three resins appeared suitable for use as a polishing chromatography, Capto™ Core was selected for the polishing step. During subsequent development experiments, HCMV polishing step yields seen with Capto™ Adhere and Capto™ Core were more consistent than with CHT™ Hydroxyapatite (data not shown).

As part of comparing Capto™ Adhere and Capto™ Core as polishing resins, the two resins were evaluated for their ability to remove BSA under different salt conditions. The results are shown in Table 4.

TABLE 4

Comparison of BSA Clearance for Capto ™ Adhere and Capto ™ Core at varying salt conditions. Batches first purified by AEX/TFF were contacted with these polishing resins under the conditions shown.

| Resin and conditions | BSA per dose (ng/dose) |
|---|---|
| Capto ™ Adhere, 150 mM NaCl | 63 |
| Capto ™ Adhere, 1M NaCl | 356 |
| Capto ™ Core, 150 mM NaCl | 80 |
| Capto ™ Core, 1M NaCl | 86 |

Removal of BSA was shown to be more consistent across a broad range of salt backgrounds for Capto™ Core than for Capto™ Adhere. The ability to use Capto™ Core in high salt conditions following AEX elution allows for greater process flexibility and means that there is no conductivity adjustment required following AEX elution. Reducing the conductivity of the AEX elutate requires either a significant dilution or a tangential flow filtration (TFF) step.

Example 3

Identification of CEX Chromatography as a Polishing Step Capable of Achieving >80% HCMV Process Yield A membrane CEX step (Sartorius Sartobind® S) was also identified as a polishing technology with the ability to achieve >80% HCMV.

In this experiment, cell culture harvest prepared as described in Example 1 was purified using a nuclease treatment, clarification, AEX capture, and TFF. The batch was then treated via either (a) incubation with Capto™ Core resin in batch mode or (b) pH reduction by titration, followed by bind-elute CEX chromatography (Sartorius Sartobind® S).

Table 5 shows mass spectrometry purity results following TFF and following each capture step. The purity results show that either option was capable of increasing purity to ≥80% HCMV. The data also again demonstrates that two chromatography steps (AEX followed by a polishing step) were required to achieve >80% HCMV.

TABLE 5

Mass Spectometry Purity results: Head to head polishing comparison using Capto ™ Core or CEX Membrane to increase purity following the AEX and TFF Steps

| Sample Name | % HCMV |
|---|---|
| TFF product (following AEX/TFF) | 50.4 |
| Final product using Capto ™ Core | 90.2 |
| Final product using CEX Membrane | 84.3 |

Example 4

Efficiency of AEX/Capto™ Core Sequence Compared to Capto™ Core Alone

Purification of viral particles from cell culture using Capto™ Core chromatography as the primary chromatography step has been reported. See, e.g., Mundle et al., 2016, Vaccine 34:3690-6. Mundle describes using approximately 10 L of Capto™ Core media for every 100 L of cell culture harvest.

The use of an AEX capture step prior to Capto™ Core results in a more efficient use of chromatography media than that described by Mundle et al. Table 6 shows data characterizing protein content before and after the AEX capture step. In this example, viral protein makes up a small fraction (<5%) of the protein present at harvest.

As shown in Table 6, the AEX step removes >95% of the total protein load entering the process. Because most impurities flow through in the AEX step, less chromatography media is required than for a chromatography step such as Capto™ Core which binds impurities. As shown in Table 7, the AEX-Capto™ Core sequence uses less total chromatography media than the previously published process which uses Capto™ Core alone.

TABLE 6

Characterization of total protein removal by AEX capture step.

| Clarified Bulk (AEX Feed) | Volume of Batch | 500.3 L |
| --- | --- | --- |
| | [Protein], µg/mL | 1061 |
| | Mass Protein | 530.8 g |
| AEX Product | Volume of Batch | 100.5 L |
| | [Protein], µg/mL | 214 |
| | Mass Protein | 21.5 g |
| | Percent of Protein Removed by AEX | 95.9% |

TABLE 7

Amount of chromatography media used per 100 L batch, for previously published Capto ™ Core process and process described herein.

| | Previously published process (Mundle et al.) | AEX - Capto ™ Core process |
| --- | --- | --- |
| AEX Chromatography Media | N/A | 2 L per 100 L batch |
| Capto ™ Core Chromatography Media | 10 L per 100 L batch | 1 L per 100 L batch |

Example 5

Demonstration of Purification Containing Two-Step Chromatography Sequence (AEX→Capto™ Core), Using Aseptic Purification Following identification of the preferred chromatography sequence (AEX membrane capture followed by Capto™ Core polishing), a series of bioreactor harvests were purified using aseptic processing unit operations. The batches below were purified as follows:

1. Benzonase® digestion by addition to bioreactor;
2. Removal of microcarriers using a 50 µm mesh;
3. Batch clarification by 1.2 µm filtration (Sartorius Sartopure® GF Plus capsules)
4. AEX membrane capture using autoclaved membrane capsules (Sartorius Sartobind® Q);
5. TFF concentration and diafiltration;
6. Capto™ Core chromatography using autoclaved resin in a batch binding mode;
7. Concentration and Buffer Exchange by hollow fiber TFF.

Table 8 summarizes the results for the purification.

TABLE 8

Aseptic purification process

| | Target/ Claimed Value | Batch | | |
| --- | --- | --- | --- | --- |
| | | Batch #1 | Batch #2 | Batch #3 |
| Purification Scale (Harvested Bioreactor Volume) | N/A | 50 L | 200 L | 500 L |
| Protein Purity (Mass Spec) | >80% HCMV | 94% | 94% | 90% |
| Residual DNA (ng/dose) (qPCR/ELISA) | <10 ng/dose | 0.82 | 0.3 | 0.24 |
| Residual BSA (ng/dose) (ELISA BSA/ELISA dose) | <50 ng/dose | 16 | 30 | 35.9 |
| Product Yield (Viral Particles or HCMV glycoprotein Western) | >40% | 42% (HCMV Western) | 48% (HCMV Western) | 59% (viral particles) |
| Product Yield (Infectious Particles) | >30% | 45% | 33% | 37% |

The results show that at 50, 200 and 500 L scale, the process was able to achieve >80% HCMV (protein purity), <50 ng per dose BSA, <10 ng per dose residual DNA, >40% viral particle yield, and >30% infectious particle yield.

Example 6

Ability to Sterile Filter HCMV Particles

The current regulatory expectation is that a vaccine should be sterilized by a 0.2 µm sterilizing grade filter—if the product cannot be filtered with this membrane, a fully aseptic process is typically required. The size of the HCMV particles ranges from 100-400 nm. Therefore, it is not obvious that the HCMV particles can pass through a filter with a nominal pore size of 0.2 µm, or 200 nm.

Two experiments are shown below in which filtration of purified HCMV particles was attempted with four commercially available sterile filters of different materials.

TABLE 9

HCMV sterile filtration experiment #1

| Filter | Viral particle yield | Infectious particle yield |
| --- | --- | --- |
| A (Millipore PES. 0.2 µm nominal size) | <1% | <3% |
| B (Millipore PVDF. 0.2 µm, nominal size) | 60% | 73% |
| C (Sartorius Sartobran ® P) - Cellulose acetate, 0.2 µm nominal size | 75% | 90% |

TABLE 10

HCMV sterile filtration experiment #2

| Filter | Viral particle yield | Infectious particle yield |
| --- | --- | --- |
| Sartorius Sartobran ® P Cellulose acetate, 0.2 µm nominal size | 82% | 66% |

TABLE 10-continued

HCMV sterile filtration experiment #2

| Filter | Viral particle yield | Infectious particle yield |
|---|---|---|
| Pall SuporLife ® PES, 0.2 μm nominal size | 80% | 52% |

The data shows that (a) HCMV particles can be sterile filtered at >70% yield with certain sterile filtration membranes, including the cellulose acetate Sartobran® P membrane and the Pall SuporLife® PES membrane; and (b) it is not obvious that HCMV particles can be sterile filtered, as some common sterile filtration membranes give very low yield, including the Millipore PES. In a wider screen of commercially available sterile filtration membranes (data not shown), approximately one third of 25 membranes screened delivered an HCMV particle yield of >70%.

Example 7

Demonstration of Purification Process Including Sterile Filtration

The use of sterile filtration at the end of a HCMV vaccine purification process allows for the use of non-sterile technologies (e.g. packed Capto™ Core polishing chromatography columns). The following data is for a purification of HCMV bioreactor harvest (3 L bioreactor volume) using an exemplary embodiment: (1) Nuclease digestion (with Benzonase®) in the bioreactor prior to harvest; (2) harvest of cell culture medium from microcarrier beads; (3) clarification of harvested medium by a 1.2-micron glass-fiber filter (Sartorius Sartopore® GF+); (4) capture of viral particles by AEX membrane chromatography (Sartorius Sartobind® Q); (5) polishing purification by Capto™ Core 700 chromatography (GE Healthcare) operated in in flow through mode using a packed chromatography column; (6) concentration and buffer exchange by 750-kDa hollow fiber TFF (GE Healthcare), and (7) Sterile filtration using Sartobran® P.

The results of the purification are shown in Table 11.

TABLE 11

Purification process using sterile filtration

| Process Yield (virus particles) | 46% |
| Protein Purity (Mass Spec) | 99% HCMV |
| BSA/dose | 16 ng/dose |

The results indicate that comparable yield, and purity are achieved by this process compared to the process earlier shown for 50-500 L scale harvests.

Additional data was generated from larger batches which incorporate sterile filtration and therefore use non-sterile chromatography technologies (membrane cassettes and packed chromatography columns).

Both batches (100 L and 2000 L) included the following steps:
 1. Benzonase® digestion by addition to bioreactor;
 2. Removal of microcarriers using a 50 μm mesh;
 3. Batch clarification by 1.2 μm filtration (Sartorius Sartopure® GF Plus capsules)
 4. AEX membrane capture using Sartorius Sartobind® Q membranes
 5. Capto™ Core chromatography using a packed column;
 6. TFF concentration and diafiltration.

A sterile filtration step with Sartobran® P was incorporated either before (2000 L batch) or after the TFF step (100 L batch).

Table 12 summarizes the results for the purification.

TABLE 12

Sterile purification process

| | Target/ Claimed Value | Batch | |
|---|---|---|---|
| | | Batch #1 | Batch #2 |
| Purification Scale (Harvested Bioreactor Volume) | N/A | 100 L | 2000 L |
| Location of sterile filtration | N/A | Following TFF (final purification step) | Following Capto ™ Core, prior to TFF |
| Protein Purity (Mass Spec) | >80% HCMV | 87% | ~90%* |
| Residual DNA (ng/dose) (qPCR/ELISA) | <10 ng/dose | 0.02 | 0.22 |
| Residual BSA (ng/dose) (ELISA BSA/ELISA dose) | <50 ng/dose | 43 | 8.3 |
| Product yield (Viral Particles or HCMV glycoprotein Western) | >40% | 50% | 56% |
| Product Yield (infectious Particles) | >30% | 42% | 55% |

*Protein purity estimated for this sample based on surrogate SDS-PAGE analysis. Mass Spec data not available.

Similar to the aseptic process, the results show that at 100 and 2000 L scale, the process was able to achieve >80% HCMV (protein purity), <50 ng per dose BSA, <10 ng per dose residual DNA, >40% viral particle yield, and >30% infectious particle yield.

Example 8

Improved AEX Protein Purity Using Histidine Based Wash

In one version of the purification process, the AEX membrane was washed by increasing NaCl concentration at a constant histidine concentration to remove impurities. In another version, the AEX membrane was washed by increasing histidine concentration at a constant NaCl concentration and a lower pH. This was found to provide a higher purity AEX product as shown in Table 13.

TABLE 13

AEX protein purity comparison using salt based AEX wash versus a histidine based AEX wash

| Process Description | Salt Based AEX Wash | Histidine based AEX Wash |
|---|---|---|
| AEX Equilibration Buffer | 25 mM Histidine, 150 mM NaCl, pH 7 | 25 mM Histidine, 150 mM NaCl, pH 7 |
| AEX Wash Buffer | 25 mM Histidine, 225 mM NaCl, pH 7 | 100 mM Histidine, 150 mM NaCl, pH 6 |
| AEX Product protein purity measure (percent HCMV tegument by SDS-PAGE) | 25% | 41% |
| AEX Product BSA Concentration (μg/mL) | 5.9 | 1.1 |

Other embodiments are within the following claims. While several embodiments have been shown and described, various modifications may be made without departing from the spirit and scope of the present invention.

What is claimed is:

1. A method for the purification of HCMV from a cell culture medium comprising the steps of:
    a) harvesting cell culture medium from a culture of ARPE-19 cells infected with HCMV;
    b) subjecting the cell culture medium to nuclease treatment using an endonuclease at a concentration of 10-160 U/mL;
    c) clarifying the nuclease-treated cell culture medium using a 1.2 µm glass fiber filter to obtain a clarified cell culture medium;
    d) contacting the clarified cell culture medium comprising HCMV with an anion exchange chromatography membrane under conditions that allow the HCMV to bind to the anion exchange chromatography membrane and then eluting the HCMV from the anion exchange chromatography membrane to obtain an eluate;
    e) contacting the eluate with a mixed-mode chromatography resin which is a hydrophobic anion exchange chromatography resin having a molecular weight exclusion of about 700 kDa and then collecting the HCMV from the mixed mode chromatography resin to obtain purified HCMV; and
    f) performing tangential flow filtration on the purified HCMV collected from step e) to adjust to the desired concentration and buffer
    wherein the cells are grown on microcarriers;
    wherein the purified HCMV has at least 80% HCMV protein purity and/or a process yield of at least 40%; and
    wherein the HCMV is a recombinant genetically modified HCMV having a genomic sequence of SEQ ID NO: 1.

2. The method of claim 1, wherein step b) is run prior to step a) by addition of nuclease to the cell culture medium prior to harvesting.

3. The method of claim 1, wherein step b) is run following step a).

4. The method of claim 1, wherein the purified HCMV contains 10 ng or less hcDNA per dose.

* * * * *